United States Patent [19]
Burton et al.

[11] Patent Number: 5,804,440
[45] Date of Patent: Sep. 8, 1998

[54] HUMAN NEUTRALIZING MONOCLONAL ANTIBODIES TO HUMAN IMMUNODEFICIENCY VIRUS

[75] Inventors: Dennis R. Burton, La Jolla; Carlos F. Barbas, San Diego; Richard A. Lerner, La Jolla, all of Calif.

[73] Assignee: The Scripps Research Institute, La Jolla, Calif.

[21] Appl. No.: 899,575

[22] Filed: Jul. 24, 1997

Related U.S. Application Data

[60] Division of Ser. No. 276,852, Jul. 18, 1994, Pat. No. 5,652,138, which is a continuation-in-part of Ser. No. 178,302, filed as PCT/US93/09328, Sep. 30, 1993, abandoned, which is a continuation-in-part of Ser. No. 954,148, Sep. 30, 1992, abandoned.

[51] Int. Cl.$^6$ .............................. C12N 5/10; C12N 5/24; C07H 21/04; C07K 16/10
[52] U.S. Cl. ...................................... 435/339.1; 424/142.1; 424/148.1; 435/328; 435/252.3; 435/252.33; 435/320.1; 530/388.15; 530/388.35; 536/23.53
[58] Field of Search .............................. 424/133.1, 135.1, 424/142.1, 148.1, 160.1; 435/69.6, 70.21, 172.2, 172.3, 328, 339.1, 252.3, 252.33, 320.1; 530/387.3, 388.15, 388.35, 389.4; 536/23.53

[56] References Cited

U.S. PATENT DOCUMENTS 5,652,138   7/1997   Burton et al. ..................... 435/252.33

*Primary Examiner*—Robert D. Budens
*Attorney, Agent, or Firm*—Thomas Fitting; Emily Holmes

[57] ABSTRACT

The present invention describes human monoclonal antibodies which immunoreact with and neutralize human immunodeficiency virus (HIV). Also disclosed are immunotherapeutic and diagnostic methods of using the monoclonal antibodies, as well as cell line for producing the monoclonal antibodies.

8 Claims, 56 Drawing Sheets

```
                                    SHINE-DALGARNO  MET
         GGCCGCAAATTCTATTTCAAGGAGACAGTCATAATG
         CGTTTAAGATAAAGTTCCTCTGTCAGTATTAC

LEADER SEQUENCE

AAATACCTATTGCCTACGGCAGCCGCT
              TTTATGGATAACGGATGCCGTCGGCGA

LEADER SEQUENCE

GGATTGTTATTACTCGCTGCCCAACCAG
              CCTAACAATAATGAGCGACGGGTTGGTC

LINKER                    LINKER

| NCOI   | V_H BACKBONE | XHOI              SPEI |
         CCATGGCCCAGGTGAAACTGCTCGAGATTTCTAGACTAGT
         GGTACCGGGTCCACTTTGACGAGCTCTAAAGATCTGATCA

STOP    LINKER
         TyrProTyrAspValProAspTyrAlaSer
         TACCCGTACGACGTTCCGGACTACGGTTCTTAATAGAATTCG
         ATGGGCATGCTGCAAGGCCTGATGCCAAGAATTATCTTAAGCAGCT

FIG.1
```

```
              ECOR I              SHINE-DALGARNO    MET
         ┌─────────────┐                        ┌─────
         TGAATTCTAAACTAGTCGCCAAGGAGACAGTCATAATGAAAT
         ACTTAAGATTTGATCAGCGGTTCCTCTGTCAGTATTACTTTA

LEADER SEQUENCE

ACCTATTGCCTACGGCCAGCCGCTGGATTGTTATTACTCGCTGCCCAACCAG
TGGATAACGGATGCCGGTCGGCGACCTAACAATAATGAGCGACGGGTTGGTC

NCO I   SAC I         XBA I       Not I
   ┌──────────────┐     ┌────────────┐┌─────────┐
   CCATGGCCGAGCTCGTCAGTTCTAGAGTTAAGCGGCCG
   GGTACCGGCTCGAGCAGTCAAGATCTCAATTCGCCGGCAGCT

FIG.3
```

| CLONE NO. | FAB CONCT (μg/ml) | ELISA TITER | p24 ASSAY MN | p24 ASSAY IIIB | SYNCYTIA ASSAY MN |
|---|---|---|---|---|---|
| 1 | 1.8 | 1:8 | - | - | - |
| 2 | 3.1 | 1:64 | - | - | - |
| 3 | 4.1 | 1:32 | - | - | - |
| 4 | 25.0 | 1:16 | 40 | 80 | >128 |
| 5 | 2.4 | 1:128 | - | - | - |
| 6 | 4.0 | 1:64 | - | - | - |
| 7 | 4.5 | 1:64 | 20 | 20 | 32 |
| 8 | 14.0 | 1:256 | 20 | 20 | - |
| 11 | 11.0 | 1:128 | - | - | - |
| 12 | 6.0 | 1:64 | 80 | 40 | >128 |
| 13 | 6.1 | 1:128 | 80 | 80 | - |
| 18 | 0.9 | 1:128 | - | 20 | - |
| 20 | 6.9 | 1:256 | - | - | 32 |
| 21 | 8.5 | 1:32 | 20 | 20 | 32 |
| 22 | 8.6 | 1:64 | 20 | 20 | - |
| 24 | 0.7 | 1:32 | - | - | - |
| 27 | 10.0 | 1:64 | 20 | 20 | 32 |
| 29 | 16.0 | 1:1024 | - | - | - |
| 31 | 9.3 | 1:128 | - | - | - |
| 35 | 8.9 | 1:64 | - | - | - |
| 2F5mAb | 10.0 | | 40 | 160 | |
| 2F5Fab | 5.0 | | 40 | 20 | |
| F58mAb | 10.0 | | 160 | 40 | |
| F58F(ab')$_2$ | 200.0 | | 40 | 20 | |

FIG. 6

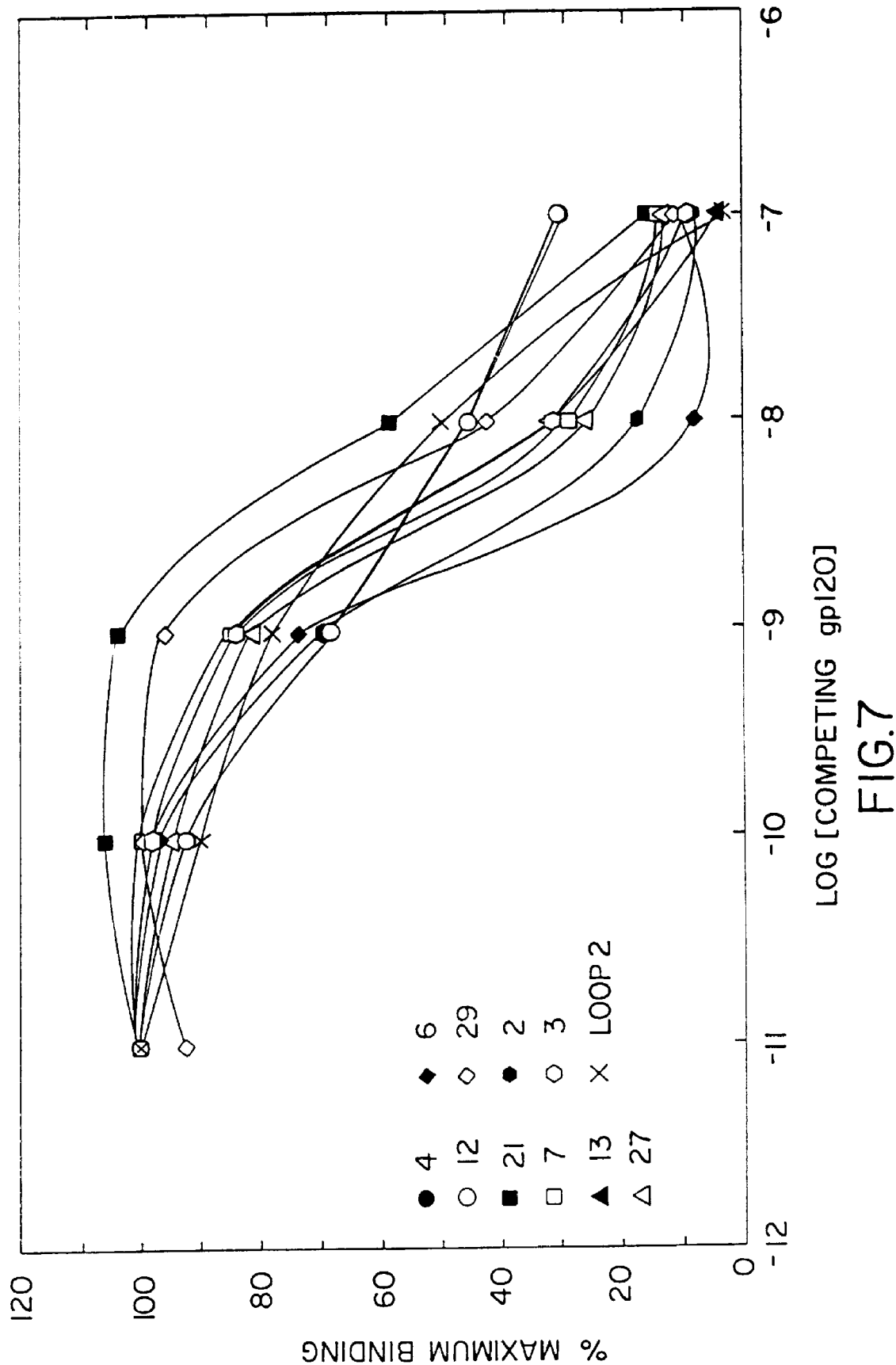

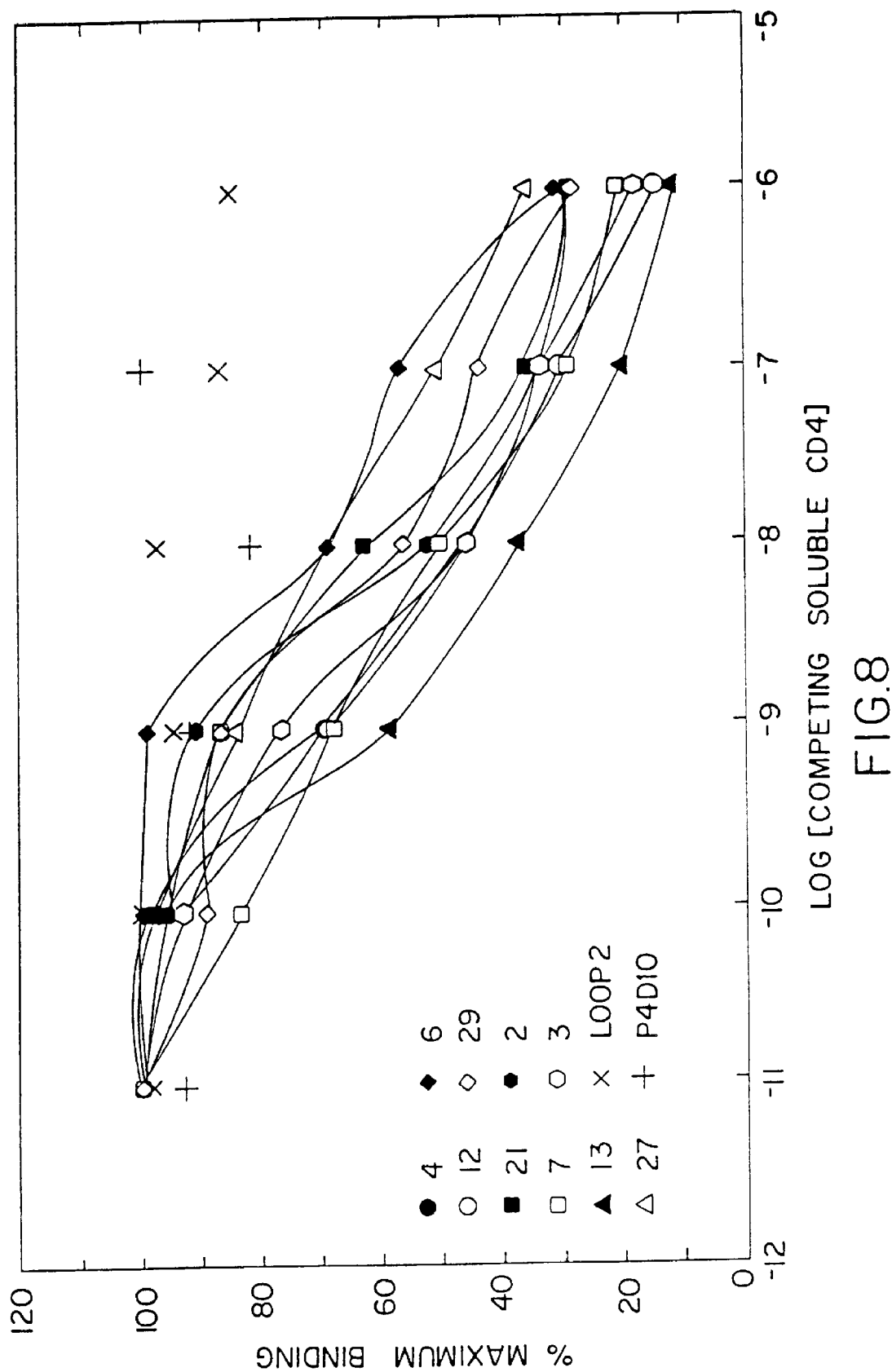

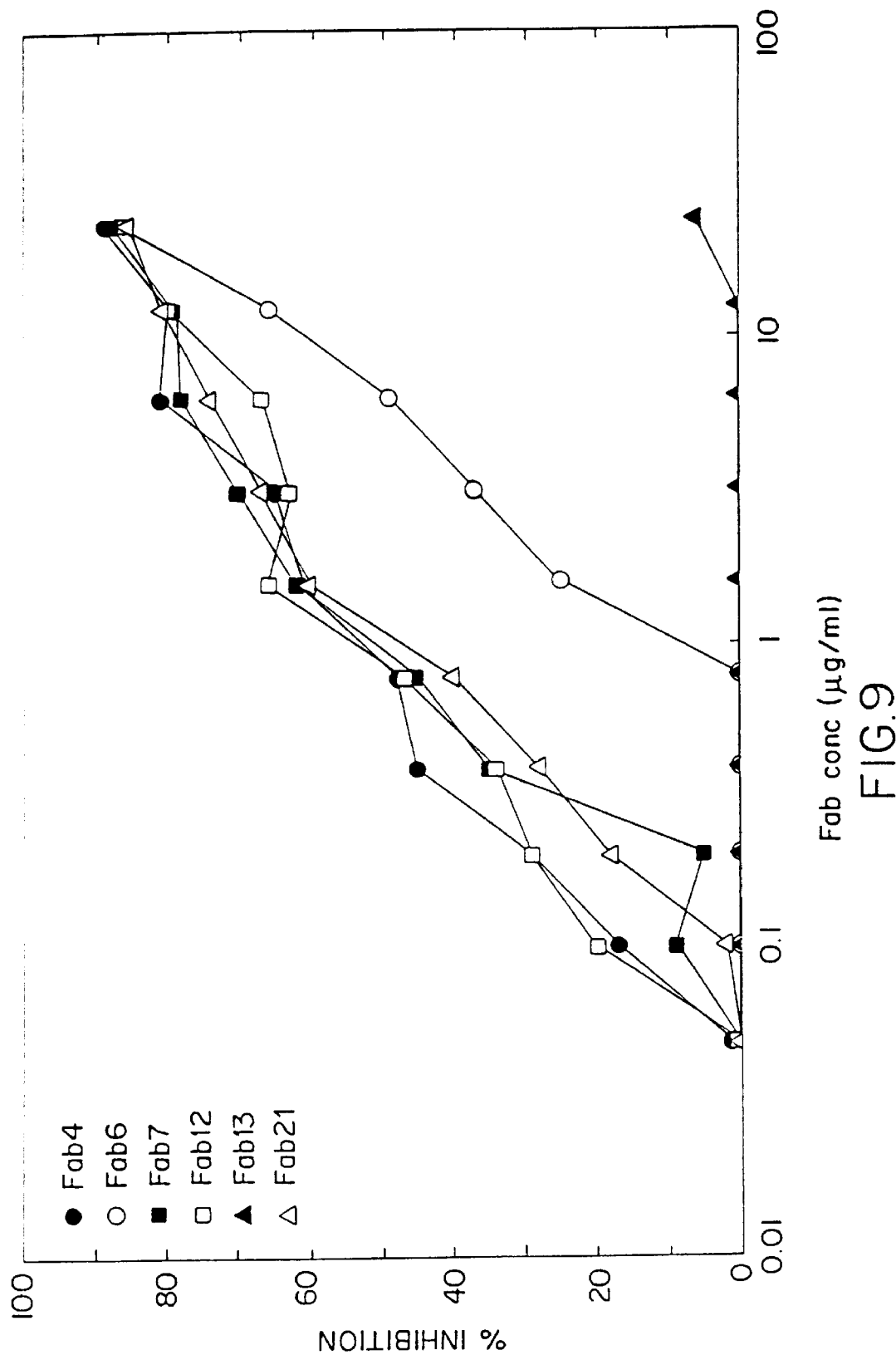

```
Clone          FR1                    CDR1          FR2              CDR2
HIV-H12/L12    ELTQAPGTLSLSPGERATFSC  RSSHSIRSRRVR  WYQHKPGQAPRLVIH  GVSNRAS HIV-H12/LC11   ....S........D.......  .....N......A  ...............  .......
HIV-H12/LC24   ....S........D.......  .....N......A  ...............  .......
HIV-H12/LC22   ....S................  .....N......A  ...............  ......T HIV-H12/LC1    ....S.D...NV......L..  .A..R.S...LA  ....R.......L.Y  ...S..G
HIV-H12/LC7    ....S.D...NA......L..  .A..R.S...LA  ....R.......L.Y  ......G
HIV-H12/LC28   ....S.D...NT......L..  .A..R.G...LA  ....RR......L.Y  ......G HIV-H12/LC13   ....S.....T......IL..  KT..N.W...LA  ...L.S......L.Y  ...K..G
HIV-H12/LC3    ....S.....T......IL..  KT..N.W...LA  ...L.S......L.Y  ...K..G
HIV-H12/LC5    ....S.....T......IL..  KT..N.W...LA  ...L.S......L.Y  ...K..G HIV-H12/LC26   ....S....ST......IL..  KT..N.W...LA  ...V.S.LP...L..  ...R..G
HIV-H12/LC25   ....S....N.......VL..  .T.RN.W...LA  ...VRR......L..  ...K..G

HIV-H12/L12    ELTQAPGTLSLSPGERATFSC  RSSHSIRSRRVR  WYQHKPGQAPRLVIH  GVSNRAS
```

| FR3 | CDR3 | FR4 | SEQ ID NO |
|---|---|---|---|
| GISDRFSGSGSGTDFTLTITRVEPEDFALYYC | QVYGASSYT | FGQGTKI FRKR | 97 |
| .............L.................. | ......... | ........... | 114 |
| .............L.................. | ......... | ........... | 114 |
| .............L.................. | ......... | ......DF... | 115 |
| ............................... | ......... | ......DF... | |
| ......S...S.L.........M......... | .T..G.... | ......DF... | 116 |
| ......S...S.L.........I......... | .T..G.... | ......DF... | 117 |
| ..........S.L.........I......... | .T..G.... | ......DF... | 118 |
| ..P...A......S........V......... | .T..G.A.. | .....VDI... | 119 |
| ..P...A......S........V......... | .T..G.A.. | ....TVDI... | 119 |
| ..P...A......S........V......... | .T..G.A.. | .....VDI... | 120 |
| ..P......AR....S.L..A...V....... | .T..G...S | ........DI... | 121 |
| .VP......AR....S.L......V.F..... | .T..G.... | .....N..DIR. | 122 |
| GISDRFSGSGSGTDFTLTITRVEPEDFALYYC | QVYGASSYT | FGQGTKLERKR | 97 |

FIG. 12B

```
              FR1                          CDR1    FR2              CDR2
H12/L12   LEQSGAEVKKPGASVKVSCQASGYRFS      NFVIH   WVRQAPGQRFEWMG   WINPYNGNKEFSAKFQD

HC1       QVKL.......................      ...L.   .A.....H.P....   ....A..VT.IPP....
HC2       QVKL.......................      ...L.   .A.....H.P....   ....A..VT.I.P....
HC3       QVKL.......................      ...L.   .A.....H.P....   ....A..VT.I.P....
HC7       QVKL..............I........      ...L.   .A.......P....   .F..A..I..I.P....
HC9       QVKL................T......      ...L.   .A.....H.P....   ....A..VT.I.P....
HC10      QVKL...........L...........      ...L.   .A.....H.P....   ....A..VT.I.P....
HC11      QVKL....T.......I..K......T      ..PL.   .A.......P....   ..KIV.E.KY.Q..V..
HC12      QVKL.......................      .....   ..............   .................
HC13      QVKL.......................      ...L.   .A....T.DL....   ....A...V..I.P...
HC14      QVKL.......................      ...L.   .A.....H.P....   ....A..VT.IPP...R.

H12-L12   LEQSGAEVKKPGASVKVSCQASGYRFS      NFVIH   WVRQAPGQRFEWMG   WINPYNGNKEFSAKFQD
```

FIG. 13A

| FR3 | CDR3 | FR4 | SEQ ID NO |
|---|---|---|---|
| RVTFTADTSANTAYMELRSLRSADTAVYYCAR | VGPYSWDDSPQDNYYMDV | WGKGTTVIVSS | 66 |
| ..SL.R....G.V.L..TN..F......... | ..EWT............. | .......T. | 123 |
| ..SL.G....S.V.L....N..F......... | ..EWT............. | ....R...T | 124 |
| ..SL.G....S.V.L......F......... | ..EWT............. | ......... | 125 |
| ..S..G....S...V...N............ | ..PWT............. | ......... | 126 |
| ..SL.G....S.V.L....N..F......... | ..EWT...F......... | ......... | 127 |
| ..SL.G....S.V.L....N..F......... | ..EWT............. | ........T | 128 |
| ......T.........V.G............ | ..EWT..MD..A...... | ........T | 129 |
| ..........D.................... | .....T............ | ......... | 130 |
| .................I............ | ..EWT............. | ......... | 131 |
| ..SL.G....S.V.L......F......... | ..EWT............. | ......... | 131 |
| ..SL.R....G.V.L..TN..F......... | ..EWT............. | ......... | 132 |
| RVTFTADTSANTAYMELRSLRSADTAVYYCAR | VGPYSWDDSPQDNYYMDV | WGKGTTVIVSS | 66 |

FIG. 13B

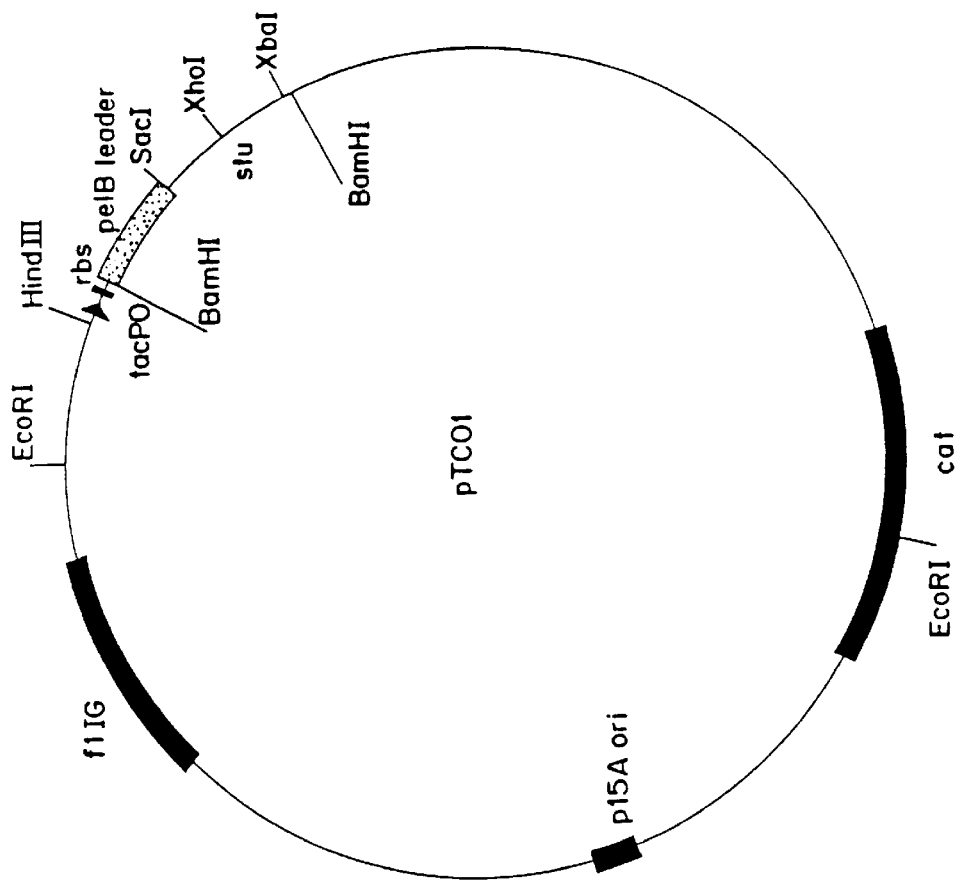
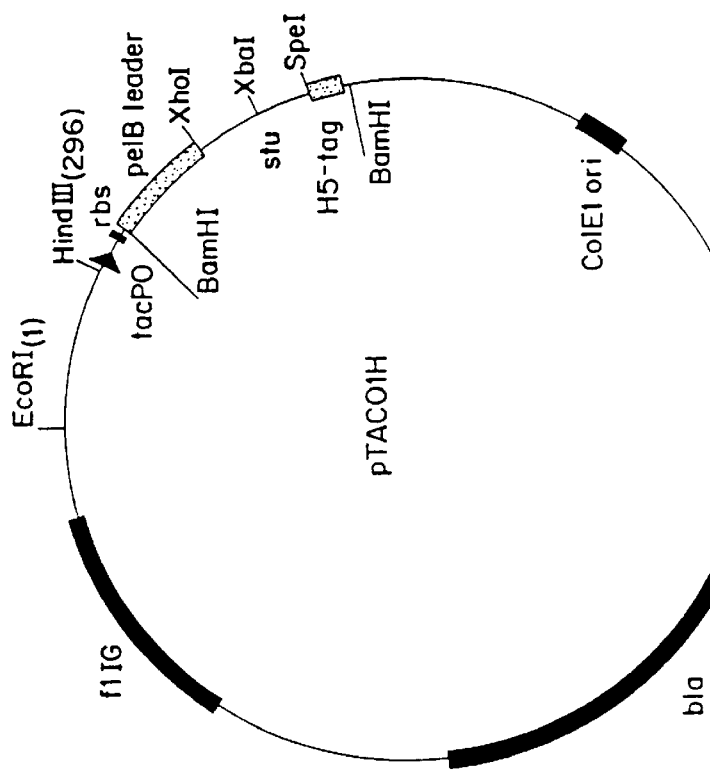
FIG.14B
FIG.14A

FIG. 15A

```
tac promoter                                      rbs         BamHI         pelB leader
                                                                            MetLysTyrLeuLeuProThrAlaAlaAlaGly
TGTTGACAATTAATCATCGGCTCGTATAATGTGTGGAATTGTGAGCGGATAACAATTTCACACAGGAGGAAGGATCCATGAAATACCTATTGCCTACGGCAGCCGCTGGA
ACAACTGTTAATTAGTAGCCGAGCATATTACACACCTTAACACTCGCCTATTGTTAAAGTGTGTCCTCCTTCCTAGGTACTTTATGGATAACGGATGCCGTCGGCGACCT SacI                  XhoI
                                                                STOP
LeuLeuLeuLeuAlaAlaGlnProAlaMetAlaGluLeu
TTGTTATTACTCGCTGCCAACCAGCCATGGCCGAGCTCGGTCGGTCGGTCTCGAGGGTCGGTCGGTCTCTAGAGTTAAGCGGCGC
AACAATAATGAGCGACGGTTGGTCGGTACCGGCTCGAGCCAGCAGCCAGAGCTCCCAGCAGCCAGAGATCTCAATTCGCCGGCG
```

FIG. 15B

```
tac promoter                                      rbs         BamHI         pelB leader
                                                                            MetLysTyrLeuLeuProThrAlaAlaAlaGly
TGTTGACAATTAATCATCGGCTCGTATAATGTGTGGAATTGTGAGCGGATAACAATTTCACACAGGAGGAAGGATCCATGAAATACCTATTGCCTACGGCAGCCGCTGGA
ACAACTGTTAATTAGTAGCCGAGCATATTACACACCTTAACACTCGCCTATTGTTAAAGTGTGTCCTCCTTCCTAGGTACTTTATGGATAACGGATGCCGTCGGCGACCT XhoI                                        XbaI             SpeI      (His)₅-tail
                                                                                         ThrSerHisHisHisHisHisSTOP
LeuLeuLeuLeuAlaAlaGlnProAlaMetAlaGlnValLysLeuLeuGlu
TTGTTATTACTCGCTGCCAACCAGCCATGGCCGAGCTGGAAACTGCTGGAGGGTCGGTCGGTCTCGAGACGGTCGGTCGGTCTCTAGACGGTCGGTCGGTCTCTAGACGGTCGGTCACTAGTCATCATCATCATCATTAAGCTA
AACAATAATGAGCGACGGGTTGGTCGGTACCGGCTCGACCTTTGACGACCTCCCAGCAGCTCTGCCAGCCAGCAGTCTGCCAGCCAGCAGTCTGCCAGCCAGCAGTCAGTGATCAGTAGTAGTAGTAATTCGAT
```

| | b11 | b6 | b4 | b12 | b7 | b21 | b3 | b13 | b22 | B26 | b8 | b18 | b27 | B8 | B35 | s4 | b1 | b14 | b24 | s8 | p35 |
|---|---|---|---|---|---|---|---|---|---|---|---|---|---|---|---|---|---|---|---|---|---|
| b11 | + | + | + | + | + | − | + | w | + | w | + | + | + | + | + | + | + | w | + | w | + |
| b6 | + | + | + | + | + | + | + | w | + | + | + | + | + | + | + | + | + | + | + | + | + |
| b4 | w | + | + | + | + | − | − | + | + | + | + | + | + | + | + | + | + | + | + | + | + |
| b12 | + | + | + | + | + | + | + | + | + | + | + | + | + | + | + | + | + | + | + | + | + |
| b7 | + | + | + | + | + | + | + | + | + | + | + | + | + | + | + | + | + | + | + | + | + |
| b21 | − | − | + | + | + | − | − | − | − | − | − | − | − | − | − | − | − | w | − | − | − |
| b3 | + | + | + | + | + | + | − | + | + | w | + | + | + | + | + | − | − | + | w | + |
| b13 | + | + | + | + | + | − | + | + | + | + | + | + | + | + | + | + | + | + | + | w |
| b22 | − | − | − | − | − | − | + | + | + | + | + | + | + | + | w | − | + | w | w |
| B26 | + | − | − | − | − | − | + | + | + | + | + | + | + | + | + | + | w | w | + |
| b8 | − | − | − | − | − | − | w | + | + | + | + | + | + | + | w | − | − | w | w |
| b18 | − | − | − | − | − | − | + | + | + | + | + | + | + | w | − | − | w | w |
| b27 | − | − | − | − | − | − | + | + | + | + | + | + | + | + | − | − | + | w |
| B8 | − | − | − | − | − | − | + | + | + | + | + | + | + | + | − | − | + | w |
| B35 | − | − | − | − | − | − | + | + | + | + | + | + | + | + | − | − | + | w |
| s4 | − | − | − | − | − | − | − | + | + | + | + | + | + | + | + | − | − | + | + |
| b1 | + | + | − | − | w | + | − | − | − | − | − | + | − | − | − | + | + | + | − | w |
| b14 | − | + | − | − | − | − | − | − | − | − | − | − | − | − | − | + | + | + | − | − |
| b24 | − | + | − | − | − | − | − | − | − | w | − | w | − | + | + | + | − | − |
| s8 | − | − | − | − | w | − | − | w | − | − | − | − | − | − | − | + | − |
| p35 | − | − | − | − | − | − | − | − | − | − | − | − | − | − | − | − | − | + |

FIG. 16

| CLONE | FR1 | CDR1 | FR2 | CDR2 |
|---|---|---|---|---|
| DL 41 19 | LLESGPGLVKPSETLSLTCTVSGGSLS | SFDWN | WIRQPAGKGLEWIG | RIYPSGNTHYNPSLRS |
| DO 41 11 | LLKSGGGLVKPGGSLRLSCVISAFSFS | GYNIN | WVRQAPGKGLEWVS | SISMSTGSLSYADSMKG |
| GL 41 1 | LLESGGGLVKPGGSLRLSCSASGFTFS | SYGMN | WVRQAPGKGPEWVA | YISSSRKYTEYADSVKG |
| MT 41 12 | LLEQSGGGLVQPGGSLRISCVASGDIFYSYAMS | | WVRQAPGKGLEWVA | SISGTGGSNYYADSVKG |
| SS 41 8 | LLESGGGLVQPGGSLRLSCAASGFLYS | SFAMS | WVRQAPGKGLAWVS | TISASGGSTKYADSVKG |

FIG.18A

| FR3 | CDR3 | FR4 |
|---|---|---|
| RVTMSRDTSKNQFSVKLTSVTAADTALYYCAR | ENTGRTIEEIGNFFDI | WGQGTLVTVSSASTKG |
| RFTISRDNAKNSVYLEMSSLTAEDTAMYYCAA | RTPLVGRALDI | WGQGTVVTVSSASTKG |
| RFTISRENAKYSVFLQLDSLTAEDTAIYYCAR | GRDFYSGFGRRDDFHLHYMDV | WGKGTTVTVSSASTKG |
| RFTISRDNSKSTLYLQMNSLRAEDTALYYCAR | DRGPRIGIRGWFDS | WGQGTLVTVSSASTKG |
| RFIISRDNSKNTIYLQMDSLRAEDTAVYYCAK | NFRAFARDPWGD | WGQGTLVTVSSASASTK |

FIG.18B

| CLONE | FR1 | CDR1 | FR2 | CDR2 |
|---|---|---|---|---|
| DL 41 19 | MAELTQSPGTLSLSPGERVIVSC | RASQSVSSNYLA | WYQQKPGQAPRLLIY | GASNRAT |
| DO 41 11 | MAELTQSPGTLSLSPGERATFSC | RSSHSIHTRRVA | WYQHKPGQAPRLVIH | GVSNRAS |
| GL 41 1 | MAELTQSPGTLSLSPGERATLSC | RASQSVSNGYLA | WYQQKPGQAPRLLIY | GASTRAT |
| MT 41 12 | MAELTQSPSSLSASVGDRVTITC | RPSQGIGRFFN | WYQQKPGKAPNLLIY | AADILQS |
| SS 41 8 | MAELTQSPSSLSASVGDRVTITC | RASQGVSSSYLA | WYQQKPGQAPRLVIF | GAYSRAT |

FIG. 19A

| | FR3 | CDR3 | FR4 |
|---|---|---|---|
| | GIPDRFSGSGSGTDFTLTISRLEPEDFAVYYC | QQYGSSGT | FGQGTKVEIKRT |
| | GISDRFSGSGSGTDFTLTITRVEPEDFALYYC | QVYGASSYT | FGQGTKLERKRTVV |
| | DIPDRFSGSGSGADFTLAISRLEPEDFAVYYC | QQYAGSHT | FGQGTKLEIKRTVA |
| | GVPSRFSGSGSGTDFTLTISSLQPEDFATYYC | QQSYSTPYT | FGQGTRLDIKRTVA |
| | GIPDRFSGSGSGTDFTLTISRLEPEDFAVYYC | QQYGSSPIT | FGPGTKVDIKRTVA |

FIG. 19B

```
         5        10        15        20        25        30        35        40        45        50        55        60
         *                  *                   *                   *                   *                   *
AGCTTACCAT GGGTGTGCCC ACTCAGGTCC TGGGGTTGCT GCTGCTGTGG CTTACAGATG
TCGAATGGTA CCCACACGGG TGAGTCCAGG ACCCCAACGA CGACGACACC GAATGTCTAC
           M  G  V  P  T  Q  V  L  G  L  L  L  L  W  L  T  D>

65        70        75        80        85        90        95       100       105       110       115       120
         *                  *                   *                   *                   *                   *
CCAGATGTGA GATCGTTCTC ACGCAGTCTC CAGGCACCCT GTCTCTGTCT CCAGGGGAAA
GGTCTACACT CTAGCAAGAG TGCGTCAGAG GTCCGTGGGA CAGAGACAGA GGTCCCCTTT
 A  R  C  E  I  V  L  T  Q  S  P  G  T  L  S  L  S  P  G  E>

125       130       135       140       145       150       155       160       165       170       175       180
         *                  *                   *                   *                   *                   *
GAGCCACCTT CTCCTGTAGG TCCAGTCACA GCATTCGCAG CCGCCGCGTA GCCTGGTACC
CTCGGTGGAA GAGGACATCC AGGTCAGTGT CGTAAGCGTC GGCGGCGCAT CGGACCATGG
 R  A  T  F  S  C  R  S  S  H  S  I  R  S  R  R  V  A  W  Y>

185       190       195       200       205       210       215       220       225       230       235       240
         *                  *                   *                   *                   *                   *
AGCACAAACC TGGCCAGGCT CCAAGGCTGG TCATACATGG TGTTTCCAAT AGGGCCTCTG
TCGTGTTTGG ACCGGTCCGA GGTTCCGACC AGTATGTACC ACAAAGGTTA TCCCGGAGAC
 Q  H  K  P  G  Q  A  P  R  L  V  I  H  G  V  S  N  R  A  S>

245       250       255       260       265       270       275       280       285       290       295       300
         *                  *                   *                   *                   *                   *
GCATCTCAGA CAGGTTCAGC GGCAGTGGGT CTGGGACAGA CTTCACTCTC ACCATCACCA
CGTAGAGTCT GTCCAAGTCG CCGTCACCCA GACCCTGTCT GAAGTGAGAG TGGTAGTGGT
 G  I  S  D  R  F  S  G  S  G  S  G  T  D  F  T  L  T  I  T>

305       310       315       320       325       330       335       340       345       350       355       360
         *                  *                   *                   *                   *                   *
GAGTGGAGCC TGAAGACTTT GCACTGTACT ACTGTCAGGT CTATGGTGCC TCCTCGTACA
CTCACCTCGG ACTTCTGAAA CGTGACATGA TGACAGTCCA GATACCACGG AGGAGCATGT
 R  V  E  P  E  D  F  A  L  Y  Y  C  Q  V  Y  G  A  S  S  Y>

365       370       375       380       385       390       395       400       405       410       415       420
         *                  *                   *                   *                   *                   *
CTTTTGGCCA GGGGACCAAA CTGGAGAGGA AACGAACTGT GCCTGCACCA TCTGTCTTCA
GAAAACCGGT CCCCTGGTTT GACCTCTCCT TTGCTTGACA CGGACGTGGT AGACAGAAGT
 T  F  G  Q  G  T  K  L  E  R  K  R  T  V  P  A  P  S  V  F>

425       430       435       440       445       450       455       460       465       470       475       480
         *                  *                   *                   *                   *                   *
TCTTCCCGCC ATCTGATGAG CAGTTGAAAT CTGGGACTGC CTCTGTTGTG TGCCTGCTGA
AGAAGGGCGG TAGACTACTC GTCAACTTTA GACCCTGACG GAGACAACAC ACGGACGACT
 I  F  P  P  S  D  E  Q  L  K  S  G  T  A  S  V  V  C  L  L>

485       490       495       500       505       510       515       520       525       530       535       540
         *                  *                   *                   *                   *                   *
ATAACTTCTA TCCCAGAGAG GCCAAAGTAC AGTGGAAGGT GGATAACGCC CTCCAATCGG
TATTGAAGAT AGGGTCTCTC CGGTTTCATG TCACCTTCCA CCTATTGCGG GAGGTTAGCC
 N  N  F  Y  P  R  E  A  K  V  Q  W  K  V  D  N  A  L  Q  S>

545       550       555       560       565       570       575       580       585       590       595       600
         *                  *                   *                   *                   *                   *
GTAACTCCCA GGAGAGTGTC ACAGAGCAGG ACAGCAAGGA CAGCACCTAC AGCCTCAGCA
CATTGAGGGT CCTCTCACAG TGTCTCGTCC TGTCGTTCCT GTCGTGGATG TCGGAGTCGT
 G  N  S  Q  E  S  V  T  E  Q  D  S  K  D  S  T  Y  S  L  S>
```

FIG. 25A

```
       605      610       615      620       625      630       635      640       645      650       655      660
                *                   *                  *                   *                   *                  *
       GCACCCTGAC GCTGAGCAAA GCAGACTACG AGAAACACAA AGTCTACGCC TGCGAAGTCA
       CGTGGGACTG CGACTCGTTT CGTCTGATGC TCTTTGTGTT TCAGATGCGG ACGCTTCAGT
       S  T  L  T   L  S  K    A  D  Y    E  K  H  K    V  Y  A    C  E  V>

665      670       675      680       685      690       695      700       705      710       715      720
                *                   *                  *                   *                   *                  *
       CCCATCAGGG CCTGAGTTCG CCCGTCACAA AGAGCTTCAA CAGGGGAGAG TGTTAATTCT
       GGGTAGTCCC GGACTCAAGC GGGCAGTGTT TCTCGAAGTT GTCCCCTCTC ACAATTAAGA
       T  H  Q  G    L  S  S    P  V  T    K  S  F    N  R  G  E    C  *>

725
       AGAGAATTC
       TCTCTTAAG
```

FIG. 25B

```
      5    10       15   20       25    30      35   40       45   50       55   60
      *             *             *              *             *              *
AATTCGCCGC  CACCATGGAA  TGGAGCTGGG  TCTTTCTCTT  CTTCCTGTCA  GTAACTACAG
TTAAGCGGCG  GTGGTACCTT  ACCTCGACCC  AGAAAGAGAA  GAAGGACAGT  CATTGATGTC
             M   E      W   S   W   V   F   L   F   F   L   S   V   T   T>

65   70       75   80       85   90       95  100      105  110      115  120
      *             *             *              *             *              *
GTGTCCACTC  CCAGGTTCAG  CTGGTTCAGT  CCGGGGCTGA  GGTGAAGAAG  CCTGGGGCCT
CACAGGTGAG  GGTCCAAGTC  GACCAAGTCA  GGCCCCGACT  CCACTTCTTC  GGACCCCGGA
G   V   H   S   Q   V   Q   L   V   Q   S   G   A   E   V   K   K   P   G   A>

125  130      135  140      145  150      155  160      165  170      175  180
      *             *             *              *             *              *
CAGTGAAGGT  TTCTTGTCAG  GCTTCTGGAT  ACAGATTCAG  TAACTTTGTT  ATTCATTGGG
GTCACTTCCA  AAGAACAGTC  CGAAGACCTA  TGTCTAAGTC  ATTGAAACAA  TAAGTAACCC
S   V   K   V   S   C   Q   A   S   G   Y   R   F   S   N   F   V   I   H   W>

185  190      195  200      205  210      215  220      225  230      235  240
      *             *             *              *             *              *
TGCGCCAGGC  CCCCGGACAG  AGGTTTGAGT  GGATGGGATG  GATCAATCCT  TACAACGGAA
ACGCGGTCCG  GGGGCCTGTC  TCCAAACTCA  CCTACCCTAC  CTAGTTAGGA  ATGTTGCCTT
V   R   Q   A   P   G   Q   R   F   E   W   M   G   W   I   N   P   Y   N   G>

245  250      255  260      265  270      275  280      285  290      295  300
      *             *             *              *             *              *
ACAAAGAATT  TTCAGCGAAG  TTCCAGGACA  GAGTCACCTT  TACCGCGGAC  ACATCCGCGA
TGTTTCTTAA  AAGTCGCTTC  AAGGTCCTGT  CTCAGTGGAA  ATGGCGCCTG  TGTAGGCGCT
N   K   E   F   S   A   K   F   Q   D   R   V   T   F   T   A   D   T   S   A>

305  310      315  320      325  330      335  340      345  350      355  360
      *             *             *              *             *              *
ACACAGCCTA  CATGGAGTTG  AGGAGCCTCA  GGTCTGCAGA  CACGGCTGTT  TATTATTGTG
TGTGTCGGAT  GTACCTCAAC  TCCTCGGAGT  CCAGACGTCT  GTGCCGACAA  ATAATAACAC
N   T   A   Y   M   E   L   R   S   L   R   S   A   D   T   A   V   Y   Y   C>

365  370      375  380      385  390      395  400      405  410      415  420
      *             *             *              *             *              *
CGAGAGTGGG  GCCATATAGT  TGGGATGATT  CTCCCCAGGA  CAATTATTAT  ATGGACGTCT
GCTCTCACCC  CGGTATATCA  ACCCTACTAA  GAGGGGTCCT  GTTAATAATA  TACCTGCAGA
A   R   V   G   P   Y   S   W   D   D   S   P   Q   D   N   Y   Y   M   D   V>

425  430      435  440      445  450      455  460      465  470      475  480
      *             *             *              *             *              *
GGGGCAAAGG  AACCACGGTC  ATCGTGAGCT  CAGCTTCCAC  CAAGGGCCCA  TCGGTCTTCC
CCCCGTTTCC  TTGGTGCCAG  TAGCACTCGA  GTCGAAGGTG  GTTCCCGGGT  AGCCAGAAGG
W   G   K   G   T   T   V   I   V   S   S>

485  490      495  500      505  510      515  520      525  530      535  540
      *             *             *              *             *              *
CCCTGGCACC  CTCCTCCAAG  AGCACCTCTG  GGGGCACAGC  GGCCCTGGGC  TGCCTGGTCA
GGGACCGTGG  GAGGAGGTTC  TCGTGGAGAC  CCCCGTGTCG  CCGGGACCCG  ACGGACCAGT 545  550      555  560      565  570      575  580      585  590      595  600
      *             *             *              *             *              *
AGGACTACTT  CCCCGAACCG  GTGACGGTGT  CGTGGAACTC  AGGCGCCCTG  ACCAGCGGCG
TCCTGATGAA  GGGGCTTGGC  CACTGCCACA  GCACCTTGAG  TCCGCGGGAC  TGGTCGCCGC
```

FIG. 27A

```
     605       610       615       620       625       630       635       640       645       650       655       660
      *                   *                   *                   *                   *                   *
TGCACACCTT CCCGGCTGTC CTACAGTCCT CAGGACTCTA CTCCCTCAGC AGCGTGGTGA
ACGTGTGGAA GGGCCGACAG GATGTCAGGA GTCCTGAGAT GAGGGAGTCG TCGCACCACT 665       670       675       680       685       690       695       700       705       710       715       720
      *                   *                   *                   *                   *                   *
CCGTGCCCTC CAGCAGCTTG GGCACCCAGA CCTACATCTG CAACGTGAAT CACAAGCCCA
GGCACGGGAG GTCGTCGAAC CCGTGGGTCT GGATGTAGAC GTTGCACTTA GTGTTCGGGT 725       730       735       740       745       750       755       760       765       770       775       780
      *                   *                   *                   *                   *                   *
GCAACACCAA GGTGGACAAG AAAGTTGGTG AGAGGCCAGC ACAGGGAGGG AGGGTGTCTG
CGTTGTGGTT CCACCTGTTC TTTCAACCAC TCTCCGGTCG TGTCCCTCCC TCCCACAGAC 785       790       795       800       805       810       815       820       825       830       835       840
      *                   *                   *                   *                   *                   *
CTGGAAGCCA GGCTCAGCGC TCCTGCCTGG ACGCATCCCG GCTATGCAGC CCCAGTCCAG
GACCTTCGGT CCGAGTCGCG AGGACGGACC TGCGTAGGGC CGATACGTCG GGGTCAGGTC 845       850       855       860       865       870       875       880       885       890       895       900
      *                   *                   *                   *                   *                   *
GGCAGCAAGG CAGGCCCCGT CTGCCTCTTC ACCCGGAGGC CTCTGCCCGC CCCACTCATG
CCGTCGTTCC GTCCGGGGCA GACGGAGAAG TGGGCCTCCG GAGACGGGCG GGGTGAGTAC 905       910       915       920       925       930       935       940       945       950       955       960
      *                   *                   *                   *                   *                   *
CTCAGGGAGA GGGTCTTCTG GCTTTTTCCC CAGGCTCTGG GCAGGCACAG GCTAGGTGCC
GAGTCCCTCT CCCAGAAGAC CGAAAAAGGG GTCCGAGACC CGTCCGTGTC CGATCCACGG 965       970       975       980       985       990       995      1000      1005      1010      1015      1020
      *                   *                   *                   *                   *                   *
CCTAACCCAG GCCCTGCACA CAAAGGGGCA GGTGCTGGGC TCAGACCTGC CAAGAGCCAT
GGATTGGGTC CGGGACGTGT GTTTCCCCGT CCACGACCCG AGTCTGGACG GTTCTCGGTA 1025      1030      1035      1040      1045      1050      1055      1060      1065      1070      1075      1080
      *                   *                   *                   *                   *                   *
ATCCGGGAGG ACCCTGCCCC TGACCTAAGC CCACCCCAAA GGCCAAACTC TCCACTCCCT
TAGGCCCTCC TGGGACGGGG ACTGGATTCG GGTGGGGTTT CCGGTTTGAG AGGTGAGGGA 1085      1090      1095      1100      1105      1110      1115      1120      1125      1130      1135      1140
      *                   *                   *                   *                   *                   *
CAGCTCGGAC ACCTTCTCTC CTCCCAGATT CGAGTAACTC CCAATCTTCT CTCTGCAGAG
GTCGAGCCTG TGGAAGAGAG GAGGGTCTAA GCTCATTGAG GGTTAGAAGA GAGACGTCTC 1145      1150      1155      1160      1165      1170      1175      1180      1185      1190      1195      1200
      *                   *                   *                   *                   *                   *
CCCAAATCTT GTGACAAAAC TCACACATGC CCACCGTGCC CAGGTAAGCC AGCCCAGGCC
GGGTTTAGAA CACTGTTTTG AGTGTGTACG GGTGGCACGG GTCCATTCGG TCGGGTCCGG 1205      1210      1215      1220      1225      1230      1235      1240      1245      1250      1255      1260
      *                   *                   *                   *                   *                   *
TCGCCCTCCA GCTCAAGGCG GGACAGGTGC CCTAGAGTAG CCTGCATCCA GGGACAGGCC
AGCGGGAGGT CGAGTTCCGC CCTGTCCACG GGATCTCATC GGACGTAGGT CCCTGTCCGG 1265      1270      1275      1280      1285      1290      1295      1300      1305      1310      1315      1320
      *                   *                   *                   *                   *                   *
CCAGCCGGGT GCTGACACGT CCACCTCCAT CTCTCCCTCA GCACCTGAGG CCGCGGGAGG
GGTCGGCCCA CGACTGTGCA GGTGGAGGTA GAGAGGGAGT CGTGGACTCC GGCGCCCTCC
```

FIG. 27B

```
1325 1330   1335 1340   1345 1350   1355 1360   1365 1370   1375 1380
         *           *           *           *           *           *
ACCATCAGTC  TTCCTCTTCC  CCCCAAAACC  CAAGGACACC  CTCATGATCT  CCCGGACCCC
TGGTAGTCAG  AAGGAGAAGG  GGGGTTTTGG  GTTCCTGTGG  GAGTACTAGA  GGGCCTGGGG 1385 1390   1395 1400   1405 1410   1415 1420   1425 1430   1435 1440
         *           *           *           *           *           *
TGAGGTCACA  TGCGTGGTGG  TGGACGTGAG  CCACGAAGAC  CCTGAGGTCA  AGTTCAACTG
ACTCCAGTGT  ACGCACCACC  ACCTGCACTC  GGTGCTTCTG  GGACTCCAGT  TCAAGTTGAC 1445 1450   1455 1460   1465 1470   1475 1480   1485 1490   1495 1500
         *           *           *           *           *           *
GTACGTGGAC  GGCGTGGAGG  TGCATAATGC  CAAGACAAAG  CCGCGGGAGG  AGCAGTACAA
CATGCACCTG  CCGCACCTCC  ACGTATTACG  GTTCTGTTTC  GGCGCCCTCC  TCGTCATGTT 1505 1510   1515 1520   1525 1530   1535 1540   1545 1550   1555 1560
         *           *           *           *           *           *
CAGCACGTAC  CGTGTGGTCA  GCGTCCTCAC  CGTCCTGCAC  CAGGACTGGC  TGAATGGCAA
GTCGTGCATG  GCACACCAGT  CGCAGGAGTG  GCAGGACGTG  GTCCTGACCG  ACTTACCGTT 1565 1570   1575 1580   1585 1590   1595 1600   1605 1610   1615 1620
         *           *           *           *           *           *
GGAGTACAAG  TGCAAGGTCT  CCAACAAAGC  CCTCCCAGCC  CCCATCGAGA  AAACCATCTC
CCTCATGTTC  ACGTTCCAGA  GGTTGTTTCG  GGAGGGTCGG  GGGTAGCTCT  TTTGGTAGAG 1625 1630   1635 1640   1645 1650   1655 1660   1665 1670   1675 1680
         *           *           *           *           *           *
CAAAGCCAAA  GGTGGGACCC  GTGGGGTGCG  AGGGCCACAT  GGACAGAGGC  CGGCTCGGCC
GTTTCGGTTT  CCACCCTGGG  CACCCCACGC  TCCCGGTGTA  CCTGTCTCCG  GCCGAGCCGG 1685 1690   1695 1700   1705 1710   1715 1720   1725 1730   1735 1740
         *           *           *           *           *           *
CACCCTCTGC  CCTGAGAGTG  ACCGCTGTAC  CAACCTCTGT  CCCTACAGGG  CAGCCCCGAG
GTGGGAGACG  GGACTCTCAC  TGGCGACATG  GTTGGAGACA  GGGATGTCCC  GTCGGGGCTC 1745 1750   1755 1760   1765 1770   1775 1780   1785 1790   1795 1800
         *           *           *           *           *           *
AACCACAGGT  GTACACCCTG  CCCCCATCCC  GGGATGAGCT  GACCAAGAAC  CAGGTCAGCC
TTGGTGTCCA  CATGTGGGAC  GGGGGTAGGG  CCCTACTCGA  CTGGTTCTTG  GTCCAGTCGG 1805 1810   1815 1820   1825 1830   1835 1840   1845 1850   1855 1860
         *           *           *           *           *           *
TGACCTGCCT  GGTCAAAGGC  TTCTATCCCA  GCGACATCGC  CGTGGAGTGG  GAGAGCAATG
ACTGGACGGA  CCAGTTTCCG  AAGATAGGGT  CGCTGTAGCG  GCACCTCACC  CTCTCGTTAC 1865 1870   1875 1880   1885 1890   1895 1900   1905 1910   1915 1920
         *           *           *           *           *           *
GGCAGCCGGA  GAACAACTAC  AAGACCACGC  CTCCCGTGCT  GGACTCCGAC  GGCTCCTTCT
CCGTCGGCCT  CTTGTTGATG  TTCTGGTGCG  GAGGGCACGA  CCTGAGGCTG  CCGAGGAAGA 1925 1930   1935 1940   1945 1950   1955 1960   1965 1970   1975 1980
         *           *           *           *           *           *
TCCTCTACAG  CAAGCTCACC  GTGGACAAGA  GCAGGTGGCA  GCAGGGGAAC  GTCTTCTCAT
AGGAGATGTC  GTTCGAGTGG  CACCTGTTCT  CGTCCACCGT  CGTCCCCTTG  CAGAAGAGTA 1985 1990   1995 2000   2005 2010   2015 2020   2025 2030   2035 2040
         *           *           *           *           *           *
GCTCCGTGAT  GCATGAGGCT  CTGCACAACC  ACTACACGCA  GAAGAGCCTC  TCCCTGTCTC
CGAGGCACTA  CGTACTCCGA  GACGTGTTGG  TGATGTGCGT  CTTCTCGGAG  AGGGACAGAG
```

FIG. 27C

```
      2045 2050  2055 2060  2065 2070  2075 2080  2085 2090  2095 2100
         *          *          *          *          *          *
      CGGGTAAATG AGTGCGACGG CCGGCAAGCC CCCGCTCCCC GGGCTCTCGC GGTCGCACGA
      GCCCATTTAC TCACGCTGCC GGCCGTTCGG GGGCGAGGGG CCCGAGAGCG CCAGCGTGCT 2105 2110  2115 2120  2125 2130  2135 2140  2145 2150  2155 2160
         *          *          *          *          *          *
      GGATGCTTGG CACGTACCCC CTGTACATAC TTCCCGGGCG CCCAGCATGG AAATAAAGCA
      CCTACGAACC GTGCATGGGG GACATGTATG AAGGGCCCGC GGGTCGTACC TTTATTTCGT 2165 2170  2175 2180  2185 2190  2195 2200  2205 2210  2215 2220
         *          *          *          *          *          *
      CCCAGCGCTG CCCTGGGCCC CTGCGAGACT GTGATGGTTC TTTCCACGGG TCAGGCCGAG
      GGGTCGCGAC GGGACCCGGG GACGCTCTGA CACTACCAAG AAAGGTGCCC AGTCCGGCTC 2225 2230  2235 2240  2245 2250  2255 2260  2265 2270  2275 2280
         *          *          *          *          *          *
      TCTGAGGCCT GAGTGGCATG AGGGAGGCAG AGCGGGTCCC ACTGTCCCCA CACTGGCCCA
      AGACTCCGGA CTCACCGTAC TCCCTCCGTC TCGCCCAGGG TGACAGGGGT GTGACCGGGT 2285 2290  2295 2300  2305 2310  2315 2320  2325 2330  2335 2340
         *          *          *          *          *          *
      GGCTGTGCAG GTGTGCCTGG GCCGCCTAGG GTGGGGCTCA GCCAGGGGCT GCCCTCGGCA
      CCGACACGTC CACACGGACC CGGCGGATCC CACCCCGAGT CGGTCCCCGA CGGGAGCCGT 2345 2350  2355 2360  2365 2370  2375 2380  2385 2390  2395 2400
         *          *          *          *          *          *
      GGGTGGGGGA TTTGCCAGCG TTGCCCTCCC TCCAGCAGCA CCTGCCCTGG GCTGGGCCAC
      CCCACCCCCT AAACGGTCGC AACGGGAGGG AGGTCGTCGT GGACGGGACC CGACCCGGTG 2405 2410  2415 2420  2425 2430  2435 2440  2445 2450  2455 2460
         *          *          *          *          *          *
      GGGAAGCCCT AGGAGCCCCT GGGGACAGAC ACACAGCCCC TGCCTCTGTA GGAGACTGTC
      CCCTTCGGGA TCCTCGGGGA CCCCTGTCTG TGTGTCGGGG ACGGAGACAT CCTCTGACAG 2465 2470  2475 2480  2485 2490  2495 2500  2505 2510  2515 2520
         *          *          *          *          *          *
      CTGTTCTGTG AGCGCCCTGT CCTCCGACCT CCATGCCCAC TCGGGGGCAT GCCTAGTCCA
      GACAAGACAC TCGCGGGACA GGAGGCTGGA GGTACGGGTG AGCCCCCGTA CGGATCAGGT 2525 2530  2535 2540  2545 2550  2555 2560  2565 2570  2575 2580
         *          *          *          *          *          *
      TGTGCGTAGG GACAGGCCCT CCCTCACCCA TCTACCCCCA CGGCACTAAC CCCTGGCTGT
      ACACGCATCC CTGTCCGGGA GGGAGTGGGT AGATGGGGGT GCCGTGATTG GGGACCGACA 2585 2590  2595 2600  2605 2610  2615 2620  2625 2630  2635 2640
         *          *          *          *          *          *
      CCTGCCCAGC CTCGCACCCG CATGGGGACA CAACCGACTC CGGGGACATG CACTCTCGGG
      GGACGGGTCG GAGCGTGGGC GTACCCCTGT GTTGGCTGAG GCCCCTGTAC GTGAGAGCCC 2645 2650  2655 2660  2665 2670  2675 2680  2685 2690  2695 2700
         *          *          *          *          *          *
      CCCTGTGGAG GGACTGGTGC AGATGCCCAC ACACACACTC AGTCCAGACC CGTTCAACAA
      GGGACACCTC CCTGACCACG TCTACGGGTG TGTGTGTGAG TCAGGTCTGG GCAAGTTGTT 2705 2710  2715 2720  2725 2730  2735 2740  2745 2750  2755 2760
         *          *          *          *          *          *
      AACCCCCGCA CTGAGGTTGG CCGGCACAC GGCCACCACA CACACACGTG CACGCCTCAC
      TTGGGGGCGT GACTCCAACC GGCCGGTGTG CCGGTGGTGT GTGTGTGCAC GTGCGGAGTG
```

FIG. 27D

```
        2765 2770   2775 2780   2785 2790   2795 2800   2805 2810   2815 2820
           *           *           *           *           *           *
        ACACGGAGCC  TCACCCGGGC  GAACTGCACA  GCACCCAGAC  CAGAGCAAGG  TCCTCGCACA
        TGTGCCTCGG  AGTGGGCCCG  CTTGACGTGT  CGTGGGTCTG  GTCTCGTTCC  AGGAGCGTGT 2825 2830   2835 2840   2845 2850   2855 2860   2865 2870   2875 2880
           *           *           *           *           *           *
        CGTGAACACT  CCTCGGACAC  AGGCCCCCAC  GAGCCCCACG  CGGCACCTCA  AGGCCCACGA
        GCACTTGTGA  GGAGCCTGTG  TCCGGGGGTG  CTCGGGGTGC  GCCGTGGAGT  TCCGGGTGCT 2885 2890   2895 2900   2905 2910   2915 2920   2925 2930   2935 2940
           *           *           *           *           *           *
        GCCTCTCGGC  AGCTTCTCCA  CATGCTGACC  TGCTCAGACA  AACCCAGCCC  TCCTCTCACA
        CGGAGAGCCG  TCGAAGAGGT  GTACGACTGG  ACGAGTCTGT  TTGGGTCGGG  AGGAGAGTGT 2945 2950   2955 2960   2965 2970   2975 2980   2985 2990   2995 3000
           *           *           *           *           *           *
        AGGGTGCCCC  TGCAGCCGCC  ACACACACAC  AGGGGATCAC  ACACCACGTC  ACGTCCCTGG
        TCCCACGGGG  ACGTCGGCGG  TGTGTGTGTG  TCCCCTAGTG  TGTGGTGCAG  TGCAGGGACC 3005 3010   3015 3020   3025 3030   3035 3040   3045 3050   3055 3060
           *           *           *           *           *           *
        CCCTGGCCCA  CTTCCCAGTG  CCGCCCTTCC  CTGCAGGGCG  GATCATAATC  AGCCATACCA
        GGGACCGGGT  GAAGGGTCAC  GGCGGGAAGG  GACGTCCCGC  CTAGTATTAG  TCGGTATGGT 3065 3070   3075 3080   3085 3090   3095 3100   3105 3110   3115 3120
           *           *           *           *           *           *
        CATTTGTAGA  GGTTTTACTT  GCTTTAAAAA  ACCTCCCACA  CCTCCCCCTG  AACCTGAAAC
        GTAAACATCT  CCAAAATGAA  CGAAATTTTT  TGGAGGGTGT  GGAGGGGGAC  TTGGACTTTG 3125 3130   3135 3140   3145 3150   3155 3160   3165 3170   3175 3180
           *           *           *           *           *           *
        ATAAAATGAA  TGCAATTGTT  GTTGTTAACT  TGTTTATTGC  AGCTTATAAT  GGTTACAAAT
        TATTTTACTT  ACGTTAACAA  CAACAATTGA  ACAAATAACG  TCGAATATTA  CCAATGTTTA 3185 3190   3195 3200   3205 3210   3215 3220   3225 3230   3235 3240
           *           *           *           *           *           *
        AAAGCAATAG  CATCACAAAT  TTCACAAATA  AAGCATTTTT  TTCACTGCAT  TCTAGTTGTG
        TTTCGTTATC  GTAGTGTTTA  AAGTGTTTAT  TTCGTAAAAA  AAGTGACGTA  AGATCAACAC 3245 3250   3255 3260   3265 3270   3275 3280
           *           *           *           *
        GTTTGTCCAA  ACTCATCAAT  GTATCTTATC  ATGTCTAGAT  CC
        CAAACAGGTT  TGAGTAGTTA  CATAGAATAG  TACAGATCTA  GG
```

FIG. 27E

```
          5         10         15         20         25         30         35         40         45         50         55         60
          *                    *                    *                    *                    *                    *
TTCATTGATC ATTAATCAGC CATACCACAT TTGTAGAGGT TTTACTTGCT TTAAAAAACC
AAGTAACTAG TAATTAGTCG GTATGGTGTA AACATCTCCA AAATGAACGA AATTTTTTGG 65         70         75         80         85         90         95        100        105        110        115        120
          *                    *                    *                    *                    *                    *
TCCCACACCT CCCCCTGAAC CTGAAACATA AAATGAATGC AATTGTTGTT GTTAACTTGT
AGGGTGTGGA GGGGGACTTG GACTTTGTAT TTTACTTACG TTAACAACAA CAATTGAACA 125        130        135        140        145        150        155        160        165        170        175        180
          *                    *                    *                    *                    *                    *
TTATTGCAGC TTATAATGGT TACAAATAAA GCAATAGCAT CACAAATTTC ACAAATAAAG
AATAACGTCG AATATTACCA ATGTTTATTT CGTTATCGTA GTGTTTAAAG TGTTTATTTC 185        190        195        200        205        210        215        220        225        230        235        240
          *                    *                    *                    *                    *                    *
CATTTTTTC  ACTGCATTCT AGTTGTGGTT TGTCCAAACT CATCAATGTA TCTTATCATG
GTAAAAAAAG TGACGTAAGA TCAACACCAA ACAGGTTTGA GTAGTTACAT AGAATAGTAC 245        250        255        260        265        270        275        280        285        290        295        300
          *                    *                    *                    *                    *                    *
TCTGGATCTC TAGCTTCGTG TCAAGGACGG TGACTGCAGT GAATAATAAA ATGTGTGTTT
AGACCTAGAG ATCGAAGCAC AGTTCCTGCC ACTGACGTCA CTTATTATTT TACACACAAA 305        310        315        320        325        330        335        340        345        350        355        360
          *                    *                    *                    *                    *                    *
GTCCGAAATA CGCGTTTTGA GATTTCTGTC GCCGACTAAA TTCATGTCGC GCGATAGTGG
CAGGCTTTAT GCGCAAAACT CTAAAGACAG CGGCTGATTT AAGTACAGCG CGCTATCACC 365        370        375        380        385        390        395        400        405        410        415        420
          *                    *                    *                    *                    *                    *
TGTTTATCGC CGATAGAGAT GGCGATATTG GAAAAATCGA TATTTGAAAA TATGGCATAT
ACAAATAGCG GCTATCTCTA CCGCTATAAC CTTTTTAGCT ATAAACTTTT ATACCGTATA 425        430        435        440        445        450        455        460        465        470        475        480
          *                    *                    *                    *                    *                    *
TGAAAATGTC GCCGATGTGA GTTTCTGTGT AACTGATATC GCCATTTTTC CAAAAGTGAT
ACTTTTACAG CGGCTACACT CAAAGACACA TTGACTATAG GCCTAAAAAG GTTTTCACTA 485        490        495        500        505        510        515        520        525        530        535        540
          *                    *                    *                    *                    *                    *
TTTTGGGCAT ACGCGATATC TGGCGATAGC GCTTATATCG TTTACGGGGG ATGGCGATAG
AAAACCCGTA TGCGCTATAG ACCGCTATCG CGAATATAGC AAATGCCCCC TACCGCTATC 545        550        555        560        565        570        575        580        585        590        595        600
          *                    *                    *                    *                    *                    *
ACGACTTTGG TGACTTGGGC GATTCTGTGT GTCGCAAATA TCGCAGTTTC GATATAGGTG
TGCTGAAACC ACTGAACCCG CTAAGACACA CAGCGTTTAT AGCGTCAAAG CTATATCCAC 605        610        615        620        625        630        635        640        645        650        655        660
          *                    *                    *                    *                    *                    *
ACAGACGATA TGAGGCTATA TCGCCGATAG AGGCGACATC AAGCTGGCAC ATGGCCAATG
TGTCTGCTAT ACTCCGATAT AGCGGCTATC TCCGCTGTAG TTCGACCGTG TACCGGTTAC 665        670        675        680        685        690        695        700        705        710        715        720
          *                    *                    *                    *                    *                    *
CATATCGATC TATACATTGA ATCAATATTG GCCATTAGCC ATATTATTCA TTGGTTATAT
GTATAGCTAG ATATGTAACT TAGTTATAAC CGGTAATCGG TATAATAAGT AACCAATATA
```

FIG. 29A

```
        725       730       735       740       745       750       755       760       765       770       775       780
                   *                   *                   *                   *                   *                   *
        AGCATAAATC AATATTGGCT ATTGGCCATT GCATACGTTG TATCCATATC ATAATATGTA
        TCGTATTTAG TTATAACCGA TAACCGGTAA CGTATGCAAC ATAGGTATAG TATTATACAT 785       790       795       800       805       810       815       820       825       830       835       840
                   *                   *                   *                   *                   *                   *
        CATTTATATT GGCTCATGTC CAACATTACC GCCATGTTGA CATTGATTAT TGACTAGTTA
        GTAAATATAA CCGAGTACAG GTTGTAATGG CGGTACAACT GTAACTAATA ACTGATCAAT 845       850       855       860       865       870       875       880       885       890       895       900
                   *                   *                   *                   *                   *                   *
        TTAATAGTAA TCAATTACGG GGTCATTAGT TCATAGCCCA TATATGGAGT TCCGCGTTAC
        AATTATCATT AGTTAATGCC CCAGTAATCA AGTATCGGGT ATATACCTCA AGGCGCAATG 905       910       915       920       925       930       935       940       945       950       955       960
                   *                   *                   *                   *                   *                   *
        ATAACTTACG GTAAATGGCC CGCCTGGCTG ACCGCCCAAC GACCCCGCC CATTGACGTC
        TATTGAATGC CATTTACCGG GCGGACCGAC TGGCGGGTTG CTGGGGCGG GTAACTGCAG 965       970       975       980       985       990       995      1000      1005      1010      1015      1020
                   *                   *                   *                   *                   *                   *
        AATAATGACG TATGTTCCCA TAGTAACGCC AATAGGGACT TTCCATTGAC GTCAATGGGT
        TTATTACTGC ATACAAGGGT ATCATTGCGG TTATCCCTGA AAGGTAACTG CAGTTACCCA 1025      1030      1035      1040      1045      1050      1055      1060      1065      1070      1075      1080
                   *                   *                   *                   *                   *                   *
        GGAGTATTTA CGGTAAACTG CCCACTTGGC AGTACATCAA GTGTATCATA TGCCAAGTAC
        CCTCATAAAT GCCATTTGAC GGGTGAACCG TCATGTAGTT CACATAGTAT ACGGTTCATG 1085      1090      1095      1100      1105      1110      1115      1120      1125      1130      1135      1140
                   *                   *                   *                   *                   *                   *
        GCCCCCTATT GACGTCAATG ACGGTAAATG GCCCGCCTGG CATTATGCCC AGTACATGAC
        CGGGGGATAA CTGCAGTTAC TGCCATTTAC CGGGCGGACC GTAATACGGG TCATGTACTG 1145      1150      1155      1160      1165      1170      1175      1180      1185      1190      1195      1200
                   *                   *                   *                   *                   *                   *
        CTTATGGGAC TTTCCTACTT GGCAGTACAT CTACGTATTA GTCATCGCTA TTACCATGGT
        GAATACCCTG AAAGGATGAA CCGTCATGTA GATGCATAAT CAGTAGCGAT AATGGTACCA 1205      1210      1215      1220      1225      1230      1235      1240      1245      1250      1255      1260
                   *                   *                   *                   *                   *                   *
        GATGCGGTTT TGGCAGTACA TCAATGGGCG TGGATAGCGG TTTGACTCAC GGGGATTTCC
        CTACGCCAAA ACCGTCATGT AGTTACCCGC ACCTATCGCC AAACTGAGTG CCCCTAAAGG 1265      1270      1275      1280      1285      1290      1295      1300      1305      1310      1315      1320
                   *                   *                   *                   *                   *                   *
        AAGTCTCCAC CCCATTGACG TCAATGGGAG TTTGTTTTGG CACCAAAATC AACGGGACTT
        TTCAGAGGTG GGGTAACTGC AGTTACCCTC AAACAAAACC GTGGTTTTAG TTGCCCTGAA 1325      1330      1335      1340      1345      1350      1355      1360      1365      1370      1375      1380
                   *                   *                   *                   *                   *                   *
        TCCAAAATGT CGTAACAACT CCGCCCCATT GACGCAAATG GGCGGTAGGC GTGTACGGTG
        AGGTTTTACA GCATTGTTGA GGCGGGGTAA CTGCGTTTAC CCGCCATCCG CACATGCCAC 1385      1390      1395      1400      1405      1410      1415      1420      1425      1430      1435      1440
                   *                   *                   *                   *                   *                   *
        GGAGGTCTAT ATAAGCAGAG CTCGTTTAGT GAACCGTCAG ATCGCCTGGA GACGCCATCC
        CCTCCAGATA TATTCGTCTC GAGCAAATCA CTTGGCAGTC TAGCGGACCT CTGCGGTAGG
```

FIG. 29B

```
1445 1450   1455 1460   1465 1470   1475 1480   1485 1490   1495 1500
    *           *           *           *           *           *
ACGCTGTTTT  GACCTCCATA  GAAGACACCG  GGACCGATCC  AGCCTCCGCG  GCCGGGAACG
TGCGACAAAA  CTGGAGGTAT  CTTCTGTGGC  CCTGGCTAGG  TCGGAGGCGC  CGGCCCTTGC 1505 1510   1515 1520   1525 1530   1535 1540   1545 1550   1555 1560
    *           *           *           *           *           *
GTGCATTGGA  ACGCGGATTC  CCCGTGCCAA  GAGTGACGTA  AGTACCGCCT  ATAGAGTCTA
CACGTAACCT  TGCGCCTAAG  GGGCACGGTT  CTCACTGCAT  TCATGGCGGA  TATCTCAGAT 1565 1570   1575 1580   1585 1590   1595 1600   1605 1610   1615 1620
    *           *           *           *           *           *
TAGGCCCACC  CCCTTGGCTT  CTTATGCATG  CTATACTGTT  TTTGGCTTGG  GGTCTATACA
ATCCGGGTGG  GGGAACCGAA  GAATACGTAC  GATATGACAA  AAACCGAACC  CCAGATATGT 1625 1630   1635 1640   1645 1650   1655 1660   1665 1670   1675 1680
    *           *           *           *           *           *
CCCCCGCTTC  CTCATGTTAT  AGGTGATGGT  ATAGCTTAGC  CTATAGGTGT  GGGTTATTGA
GGGGGCGAAG  GAGTACAATA  TCCACTACCA  TATCGAATCG  GATATCCACA  CCCAATAACT 1685 1690   1695 1700   1705 1710   1715 1720   1725 1730   1735 1740
    *           *           *           *           *           *
CCATTATTGA  CCACTCCCCT  ATTGGTGACG  ATACTTTCCA  TTACTAATCC  ATAACATGGC
GGTAATAACT  GGTGAGGGGA  TAACCACTGC  TATGAAAGGT  AATGATTAGG  TATTGTACCG 1745 1750   1755 1760   1765 1770   1775 1780   1785 1790   1795 1800
    *           *           *           *           *           *
TCTTTGCCAC  AACTCTCTTT  ATTGGCTATA  TGCCAATACA  CTGTCCTTCA  GAGACTGACA
AGAAACGGTG  TTGAGAGAAA  TAACCGATAT  ACGGTTATGT  GACAGGAAGT  CTCTGACTGT 1805 1810   1815 1820   1825 1830   1835 1840   1845 1850   1855 1860
    *           *           *           *           *           *
CGGACTCTGT  ATTTTTACAG  GATGGGGTCT  CATTTATTAT  TTACAAATTC  ACATATACAA
GCCTGAGACA  TAAAAATGTC  CTACCCCAGA  GTAAATAATA  AATGTTTAAG  TGTATATGTT 1865 1870   1875 1880   1885 1890   1895 1900   1905 1910   1915 1920
    *           *           *           *           *           *
CACCACCGTC  CCCAGTGCCC  GCAGTTTTTA  TTAAACATAA  CGTGGGATCT  CCACGCGAAT
GTGGTGGCAG  GGGTCACGGG  CGTCAAAAAT  AATTTGTATT  GCACCCTAGA  GGTGCGCTTA 1925 1930   1935 1940   1945 1950   1955 1960   1965 1970   1975 1980
    *           *           *           *           *           *
CTCGGGTACG  TGTTCCGGAC  ATGGGCTCTT  CTCCGGTAGC  GGCGGAGCTT  CTACATCCGA
GAGCCCATGC  ACAAGGCCTG  TACCCGAGAA  GAGGCCATCG  CCGCCTCGAA  GATGTAGGCT 1985 1990   1995 2000   2005 2010   2015 2020   2025 2030   2035 2040
    *           *           *           *           *           *
GCCCTGCTCC  CATGCCTCCA  GCGACTCATG  GTCGCTCGGC  AGCTCCTTGC  TCCTAACAGT
CGGGACGAGG  GTACGGAGGT  CGCTGAGTAC  CAGCGAGCCG  TCGAGGAACG  AGGATTGTCA 2045 2050   2055 2060   2065 2070   2075 2080   2085 2090   2095 2100
    *           *           *           *           *           *
GGAGGCCAGA  CTTAGGCACA  GCACGATGCC  CACCACCACC  AGTGTGCCGC  ACAAGGCCGT
CCTCCGGTCT  GAATCCGTGT  CGTGCTACGG  GTGGTGGTGG  TCACACGGCG  TGTTCCGGCA 2105 2110   2115 2120   2125 2130   2135 2140   2145 2150   2155 2160
    *           *           *           *           *           *
GGCGGTAGGG  TATGTGTCTG  AAAATGAGCT  CGGGGAGCGG  GCTTGCACCG  CTGACGCATT
CCGCCATCCC  ATACACAGAC  TTTTACTCGA  GCCCCTCGCC  CGAACGTGGC  GACTGCGTAA
```

FIG. 29C

```
2165 2170   2175 2180   2185 2190   2195 2200   2205 2210   2215 2220
    *           *           *           *           *           *
TGGAAGACTT  AAGGCAGCGG  CAGAAGAAGA  TGCAGGCAGC  TGAGTTGTTG  TGTTCTGATA
ACCTTCTGAA  TTCCGTCGCC  GTCTTCTTCT  ACGTCCGTCG  ACTCAACAAC  ACAAGACTAT 2225 2230   2235 2240   2245 2250   2255 2260   2265 2270   2275 2280
    *           *           *           *           *           *
AGAGTCAGAG  GTAACTCCCG  TTGCGGTGCT  GTTAACGGTG  GAGGGCAGTG  TAGTCTGAGC
TCTCAGTCTC  CATTGAGGGC  AACGCCACGA  CAATTGCCAC  CTCCCGTCAC  ATCAGACTCG 2285 2290   2295 2300   2305 2310   2315 2320   2325 2330   2335 2340
    *           *           *           *           *           *
AGTACTCGTT  GCTGCCGCGC  GCGCCACCAG  ACATAATAGC  TGACAGACTA  ACAGACTGTT
TCATGAGCAA  CGACGGCGCG  CGCGGTGGTC  TGTATTATCG  ACTGTCTGAT  TGTCTGACAA 2345 2350   2355 2360   2365 2370   2375 2380   2385 2390   2395 2400
    *           *           *           *           *           *
CCTTTCCATG  GGTCTTTTCT  GCAGTCACCG  TCCTTGACAC  GAAGCTTGGG  CTGCAGGTCG
GGAAAGGTAC  CCAGAAAAGA  CGTCAGTGGC  AGGAACTGTG  CTTCGAACCC  GACGTCCAGC 2405 2410   2415 2420   2425 2430   2435 2440   2445 2450   2455 2460
    *           *           *           *           *           *
ATCGACTCTA  GAGGATCGAT  CCCCGGGCGA  GCTCGAATTC  GCCGCCACCA  TGGAATGGAG
TAGCTGAGAT  CTCCTAGCTA  GGGGCCCGCT  CGAGCTTAAG  CGGCGGTGGT  ACCTTACCTC 2465 2470   2475 2480   2485 2490   2495 2500   2505 2510   2515 2520
    *           *           *           *           *           *
CTGGGTCTTT  CTCTTCTTCC  TGTCAGTAAC  TACAGGTGTC  CACTCCCAGG  TTCAGCTGGT
GACCCAGAAA  GAGAAGAAGG  ACAGTCATTG  ATGTCCACAG  GTGAGGGTCC  AAGTCGACCA 2525 2530   2535 2540   2545 2550   2555 2560   2565 2570   2575 2580
    *           *           *           *           *           *
TCAGTCCGGG  GCTGAGGTGA  AGAAGCCTGG  GGCCTCAGTG  AAGGTTTCTT  GTCAGGCTTC
AGTCAGGCCC  CGACTCCACT  TCTTCGGACC  CCGGAGTCAC  TTCCAAAGAA  CAGTCCGAAG 2585 2590   2595 2600   2605 2610   2615 2620   2625 2630   2635 2640
    *           *           *           *           *           *
TGGATACAGA  TTCAGTAACT  TTGTTATTCA  TTGGGTGCGC  CAGGCCCCCG  GACAGAGGTT
ACCTATGTCT  AAGTCATTGA  AACAATAAGT  AACCCACGCG  GTCCGGGGGC  CTGTCTCCAA 2645 2650   2655 2660   2665 2670   2675 2680   2685 2690   2695 2700
    *           *           *           *           *           *
TGAGTGGATG  GGATGGATCA  ATCCTTACAA  CGGAAACAAA  GAATTTTCAG  CGAAGTTCCA
ACTCACCTAC  CCTACCTAGT  TAGGAATGTT  GCCTTTGTTT  CTTAAAAGTC  GCTTCAAGGT 2705 2710   2715 2720   2725 2730   2735 2740   2745 2750   2755 2760
    *           *           *           *           *           *
GGACAGAGTC  ACCTTTACCG  CGGACACATC  CGCGAACACA  GCCTACATGG  AGTTGAGGAG
CCTGTCTCAG  TGGAAATGGC  GCCTGTGTAG  GCGCTTGTGT  CGGATGTACC  TCAACTCCTC 2765 2770   2775 2780   2785 2790   2795 2800   2805 2810   2815 2820
    *           *           *           *           *           *
CCTCAGGTCT  GCAGACACGG  CTGTTTATTA  TTGTGCGAGA  GTGGGGCCAT  ATAGTTGGGA
GGAGTCCAGA  CGTCTGTGCC  GACAAATAAT  AACACGCTCT  CACCCCGGTA  TATCAACCCT 2825 2830   2835 2840   2845 2850   2855 2860   2865 2870   2875 2880
    *           *           *           *           *           *
TGATTCTCCC  CAGGACAATT  ATTATATGGA  CGTCTGGGGC  AAAGGAACCA  CGGTCATCGT
ACTAAGAGGG  GTCCTGTTAA  TAATATACCT  GCAGACCCCG  TTTCCTTGGT  GCCAGTAGCA
```

FIG. 29D

```
2885 2890   2895 2900   2905 2910   2915 2920   2925 2930   2935 2940
    *           *           *           *           *           *
GAGCTCAGCT  TCCACCAAGG  GCCCATCGGT  CTTCCCCCTG  GCACCCTCCT  CCAAGAGCAC
CTCGAGTCGA  AGGTGGTTCC  CGGGTAGCCA  GAAGGGGGAC  CGTGGGAGGA  GGTTCTCGTG 2945 2950   2955 2960   2965 2970   2975 2980   2985 2990   2995 3000
    *           *           *           *           *           *
CTCTGGGGGC  ACAGCGGCCC  TGGGCTGCCT  GGTCAAGGAC  TACTTCCCCG  AACCGGTGAC
GAGACCCCCG  TGTCGCCGGG  ACCCGACGGA  CCAGTTCCTG  ATGAAGGGGC  TTGGCCACTG 3005 3010   3015 3020   3025 3030   3035 3040   3045 3050   3055 3060
    *           *           *           *           *           *
GGTGTCGTGG  AACTCAGGCG  CCCTGACCAG  CGGCGTGCAC  ACCTTCCCGG  CTGTCCTACA
CCACAGCACC  TTGAGTCCGC  GGGACTGGTC  GCCGCACGTG  TGGAAGGGCC  GACAGGATGT 3065 3070   3075 3080   3085 3090   3095 3100   3105 3110   3115 3120
    *           *           *           *           *           *
GTCCTCAGGA  CTCTACTCCC  TCAGCAGCGT  GGTGACCGTG  CCCTCCAGCA  GCTTGGGCAC
CAGGAGTCCT  GAGATGAGGG  AGTCGTCGCA  CCACTGGCAC  GGGAGGTCGT  CGAACCCGTG 3125 3130   3135 3140   3145 3150   3155 3160   3165 3170   3175 3180
    *           *           *           *           *           *
CCAGACCTAC  ATCTGCAACG  TGAATCACAA  GCCCAGCAAC  ACCAAGGTGG  ACAAGAAAGT
GGTCTGGATG  TAGACGTTGC  ACTTAGTGTT  CGGGTCGTTG  TGGTTCCACC  TGTTCTTTCA 3185 3190   3195 3200   3205 3210   3215 3220   3225 3230   3235 3240
    *           *           *           *           *           *
TGGTGAGAGG  CCAGCACAGG  GAGGGAGGGT  GTCTGCTGGA  AGCCAGGCTC  AGCGCTCCTG
ACCACTCTCC  GGTCGTGTCC  CTCCCTCCCA  CAGACGACCT  TCGGTCCGAG  TCGCGAGGAC 3245 3250   3255 3260   3265 3270   3275 3280   3285 3290   3295 3300
    *           *           *           *           *           *
CCTGGACGCA  TCCCGGCTAT  GCAGCCCCAG  TCCAGGGCAG  CAAGGCAGGC  CCCGTCTGCC
GGACCTGCGT  AGGGCCGATA  CGTCGGGGTC  AGGTCCCGTC  GTTCCGTCCG  GGGCAGACGG 3305 3310   3315 3320   3325 3330   3335 3340   3345 3350   3355 3360
    *           *           *           *           *           *
TCTTCACCCG  GAGGCCTCTG  CCCGCCCCAC  TCATGCTCAG  GGAGAGGGTC  TTCTGGCTTT
AGAAGTGGGC  CTCCGGAGAC  GGGCGGGGTG  AGTACGAGTC  CCTCTCCCAG  AAGACCGAAA 3365 3370   3375 3380   3385 3390   3395 3400   3405 3410   3415 3420
    *           *           *           *           *           *
TTCCCCAGGC  TCTGGGCAGG  CACAGGCTAG  GTGCCCCTAA  CCCAGGCCCT  GCACACAAAG
AAGGGGTCCG  AGACCCGTCC  GTGTCCGATC  CACGGGGATT  GGGTCCGGGA  CGTGTGTTTC 3425 3430   3435 3440   3445 3450   3455 3460   3465 3470   3475 3480
    *           *           *           *           *           *
GGGCAGGTGC  TGGGCTCAGA  CCTGCCAAGA  GCCATATCCG  GGAGGACCCT  GCCCCTGACC
CCCGTCCACG  ACCCGAGTCT  GGACGGTTCT  CGGTATAGGC  CCTCCTGGGA  CGGGGACTGG 3485 3490   3495 3500   3505 3510   3515 3520   3525 3530   3535 3540
    *           *           *           *           *           *
TAAGCCCACC  CCAAAGGCCA  AACTCTCCAC  TCCCTCAGCT  CGGACACCTT  CTCTCCTCCC
ATTCGGGTGG  GGTTTCCGGT  TTGAGAGGTG  AGGGAGTCGA  GCCTGTGGAA  GAGAGGAGGG 3545 3550   3555 3560   3565 3570   3575 3580   3585 3590   3595 3600
    *           *           *           *           *           *
AGATTCGAGT  AACTCCCAAT  CTTCTCTCTG  CAGAGCCCAA  ATCTTGTGAC  AAAACTCACA
TCTAAGCTCA  TTGAGGGTTA  GAAGAGAGAC  GTCTCGGGTT  TAGAACACTG  TTTTGAGTGT
```

FIG. 29E

```
3605 3610  3615 3620  3625 3630  3635 3640  3645 3650  3655 3660
     *          *          *          *          *          *
CATGCCCACC GTGCCCAGGT AAGCCAGCCC AGGCCTCGCC CTCCAGCTCA AGGCGGGACA
GTACGGGTGG CACGGGTCCA TTCGGTCGGG TCCGGAGCGG GAGGTCGAGT TCCGCCCTGT 3665 3670  3675 3680  3685 3690  3695 3700  3705 3710  3715 3720
     *          *          *          *          *          *
GGTGCCCTAG AGTAGCCTGC ATCCAGGGAC AGGCCCCAGC CGGGTGCTGA CACGTCCACC
CCACGGGATC TCATCGGACG TAGGTCCCTG TCCGGGGTCG GCCCACGACT GTGCAGGTGG 3725 3730  3735 3740  3745 3750  3755 3760  3765 3770  3775 3780
     *          *          *          *          *          *
TCCATCTCTC CCTCAGCACC TGAGGCCGCG GGAGGACCAT CAGTCTTCCT CTTCCCCCCA
AGGTAGAGAG GGAGTCGTGG ACTCCGGCGC CCTCCTGGTA GTCAGAAGGA GAAGGGGGGT 3785 3790  3795 3800  3805 3810  3815 3820  3825 3830  3835 3840
     *          *          *          *          *          *
AAACCCAAGG ACACCCTCAT GATCTCCCGG ACCCCTGAGG TCACATGCGT GGTGGTGGAC
TTTGGGTTCC TGTGGGAGTA CTAGAGGGCC TGGGGACTCC AGTGTACGCA CCACCACCTG 3845 3850  3855 3860  3865 3870  3875 3880  3885 3890  3895 3900
     *          *          *          *          *          *
GTGAGCCACG AAGACCCTGA GGTCAAGTTC AACTGGTACG TGGACGGCGT GGAGGTGCAT
CACTCGGTGC TTCTGGGACT CCAGTTCAAG TTGACCATGC ACCTGCCGCA CCTCCACGTA 3905 3910  3915 3920  3925 3930  3935 3940  3945 3950  3955 3960
     *          *          *          *          *          *
AATGCCAAGA CAAAGCCGCG GGAGGAGCAG TACAACAGCA CGTACCGTGT GGTCAGCGTC
TTACGGTTCT GTTTCGGCGC CCTCCTCGTC ATGTTGTCGT GCATGGCACA CCAGTCGCAG 3965 3970  3975 3980  3985 3990  3995 4000  4005 4010  4015 4020
     *          *          *          *          *          *
CTCACCGTCC TGCACCAGGA CTGGCTGAAT GGCAAGGAGT ACAAGTGCAA GGTCTCCAAC
GAGTGGCAGG ACGTGGTCCT GACCGACTTA CCGTTCCTCA TGTTCACGTT CCAGAGGTTG 4025 4030  4035 4040  4045 4050  4055 4060  4065 4070  4075 4080
     *          *          *          *          *          *
AAAGCCCTCC CAGCCCCCAT CGAGAAAACC ATCTCCAAAG CCAAAGGTGG GACCCGTGGG
TTTCGGGAGG GTCGGGGTA GCTCTTTTGG TAGAGGTTTC GGTTTCCACC CTGGGCACCC 4085 4090  4095 4100  4105 4110  4115 4120  4125 4130  4135 4140
     *          *          *          *          *          *
GTGCGAGGGC CACATGGACA GAGGCCGGCT CGGCCCACCC TCTGCCCTGA GAGTGACCGC
CACGCTCCCG GTGTACCTGT CTCCGGCCGA GCCGGGTGGG AGACGGGACT CTCACTGGCG 4145 4150  4155 4160  4165 4170  4175 4180  4185 4190  4195 4200
     *          *          *          *          *          *
TGTACCAACC TCTGTCCCTA CAGGGCAGCC CCGAGAACCA CAGGTGTACA CCCTGCCCCC
ACATGGTTGG AGACAGGGAT GTCCCGTCGG GGCTCTTGGT GTCCACATGT GGGACGGGGG 4205 4210  4215 4220  4225 4230  4235 4240  4245 4250  4255 4260
     *          *          *          *          *          *
ATCCCGGGAT GAGCTGACCA AGAACCAGGT CAGCCTGACC TGCCTGGTCA AAGGCTTCTA
TAGGGCCCTA CTCGACTGGT TCTTGGTCCA GTCGGACTGG ACGGACCAGT TTCCGAAGAT 4265 4270  4275 4280  4285 4290  4295 4300  4305 4310  4315 4320
     *          *          *          *          *          *
TCCCAGCGAC ATCGCCGTGG AGTGGGAGAG CAATGGGCAG CCGGAGAACA ACTACAAGAC
AGGGTCGCTG TAGCGGCACC TCACCCTCTC GTTACCCGTC GGCCTCTTGT TGATGTTCTG
```

FIG. 29F

```
        4325 4330   4335 4340   4345 4350   4355 4360   4365 4370   4375 4380
           *           *           *           *           *           *
        CACGCCTCCC  GTGCTGGACT  CCGACGGCTC  CTTCTTCCTC  TACAGCAAGC  TCACCGTGGA
        GTGCGGAGGG  CACGACCTGA  GGCTGCCGAG  GAAGAAGGAG  ATGTCGTTCG  AGTGGCACCT 4385 4390   4395 4400   4405 4410   4415 5520   4425 4430   4435 4440
           *           *           *           *           *           *
        CAAGAGCAGG  TGGCAGCAGG  GGAACGTCTT  CTCATGCTCC  GTGATGCATG  AGGCTCTGCA
        GTTCTCGTCC  ACCGTCGTCC  CCTTGCAGAA  GAGTACGAGG  CACTACGTAC  TCCGAGACGT 4445 4450   4455 4460   4465 4470   4475 4480   4485 4490   4495 4500
           *           *           *           *           *           *
        CAACCACTAC  ACGCAGAAGA  GCCTCTCCCT  GTCTCCGGGT  AAATGAGTGC  GACGGCCGGC
        GTTGGTGATG  TGCGTCTTCT  CGGAGAGGGA  CAGAGGCCCA  TTTACTCACG  CTGCCGGCCG 4505 4510   4515 4520   4525 4530   4535 4540   4545 4550   4555 4560
           *           *           *           *           *           *
        AAGCCCCCGC  TCCCCGGGCT  CTCGCGGTCG  CACGAGGATG  CTTGGCACGT  ACCCCCTGTA
        TTCGGGGGCG  AGGGGCCCGA  GAGCGCCAGC  GTGCTCCTAC  GAACCGTGCA  TGGGGGACAT 4565 4570   4575 4580   4585 4590   4595 4600   4605 4610   4615 4620
           *           *           *           *           *           *
        CATACTTCCC  GGGCGCCCAG  CATGGAAATA  AAGCACCCAG  CGCTGCCCTG  GCCCCTGCG
        GTATGAAGGG  CCCGCGGGTC  GTACCTTTAT  TTCGTGGGTC  GCGACGGGAC  CCGGGGACGC 4625 4630   4635 4640   4645 4650   4655 4660   4665 4670   4675 4680
           *           *           *           *           *           *
        AGACTGTGAT  GGTTCTTTCC  ACGGGTCAGG  CCGAGTCTGA  GGCCTGAGTG  GCATGAGGGA
        TCTGACACTA  CCAAGAAAGG  TGCCCAGTCC  GGCTCAGACT  CCGGACTCAC  CGTACTCCCT 4685 4690   4695 4700   4705 4710   4715 4720   4725 4730   4735 4740
           *           *           *           *           *           *
        GGCAGAGCGG  GTCCCACTGT  CCCCACACTG  GCCCAGGCTG  TGCAGGTGTG  CCTGGGCCGC
        CCGTCTCGCC  CAGGGTGACA  GGGGTGTGAC  CGGGTCCGAC  ACGTCCACAC  GGACCCGGCG 4745 4750   4755 4760   4765 4770   4775 4780   4785 4790   4795 4800
           *           *           *           *           *           *
        CTAGGGTGGG  GCTCAGCCAG  GGGCTGCCCT  CGGCAGGGTG  GGGGATTTGC  CAGCGTTGCC
        GATCCCACCC  CGAGTCGGTC  CCCGACGGGA  GCCGTCCCAC  CCCCTAAACG  GTCGCAACGG 4805 4810   4815 5820   4825 4830   4835 4840   4845 4850   4855 4860
           *           *           *           *           *           *
        CTCCCTCCAG  CAGCACCTGC  CCTGGGCTGG  GCCACGGGAA  GCCCTAGGAG  CCCCTGGGGA
        GAGGGAGGTC  GTCGTGGACG  GGACCCGACC  CGGTGCCCTT  CGGGATCCTC  GGGGACCCCT 4865 4870   4875 4880   4885 4890   4895 4900   4905 4910   4915 4920
           *           *           *           *           *           *
        CAGACACACA  GCCCCTGCCT  CTGTAGGAGA  CTGTCCTGTT  CTGTGAGCGC  CCTGTCCTCC
        GTCTGTGTGT  CGGGGACGGA  GACATCCTCT  GACAGGACAA  GACACTCGCG  GGACAGGAGG 4925 4930   4935 4940   4945 4950   4955 4960   4965 4970   4975 4980
           *           *           *           *           *           *
        GACCTCCATG  CCCACTCGGG  GGCATGCCTA  GTCCATGTGC  GTAGGGACAG  GCCCTCCCTC
        CTGGAGGTAC  GGGTGAGCCC  CCGTACGGAT  CAGGTACACG  CATCCCTGTC  CGGGAGGGAG 4985 4990   4995 5000   5005 5010   5015 5020   5025 5030   5035 5040
           *           *           *           *           *           *
        ACCCATCTAC  CCCCACGGCA  CTAACCCCTG  GCTGTCCTGC  CCAGCCTCGC  ACCCGCATGG
        TGGGTAGATG  GGGGTGCCGT  GATTGGGGAC  CGACAGGACG  GGTCGGAGCG  TGGGCGTACC
```

FIG. 29G

```
      5045 5050   5055 5060   5065 5070   5075 5080   5085 5090   5095 5100
           *           *           *           *           *           *
      GGACACAACC  GACTCCGGGG  ACATGCACTC  TCGGGCCCTG  TGGAGGGACT  GGTGCAGATG
      CCTGTGTTGG  CTGAGGCCCC  TGTACGTGAG  AGCCCGGGAC  ACCTCCCTGA  CCACGTCTAC 5105 5110   5115 5120   5125 5130   5135 5140   5145 5150   5155 5160
           *           *           *           *           *           *
      CCCACACACA  CACTCAGTCC  AGACCCGTTC  AACAAAACCC  CCGCACTGAG  GTTGGCCGGC
      GGGTGTGTGT  GTGAGTCAGG  TCTGGGCAAG  TTGTTTTGGG  GGCGTGACTC  CAACCGGCCG 5165 5170   5175 5180   5185 5190   5195 5200   5205 5210   5215 5220
           *           *           *           *           *           *
      CACACGGCCA  CCACACACAC  ACGTGCACGC  CTCACACACG  GAGCCTCACC  CGGGCGAACT
      GTGTGCCGGT  GGTGTGTGTG  TGCACGTGCG  GAGTGTGTGC  CTCGGAGTGG  GCCCGCTTGA 5225 5230   5235 5240   5245 5250   5255 5260   5265 5270   5275 5280
           *           *           *           *           *           *
      GCACAGCACC  CAGACCAGAG  CAAGGTCCTC  GCACACGTGA  ACACTCCTCG  GACACAGGCC
      CGTGTCGTGG  GTCTGGTCTC  GTTCCAGGAG  CGTGTGCACT  TGTGAGGAGC  CTGTGTCCGG 5285 5290   5295 5300   5305 5310   5315 5320   5325 5330   5335 5340
           *           *           *           *           *           *
      CCCACGAGCC  CCACGCGGCA  CCTCAAGGCC  CACGAGCCTC  TCGGCAGCTT  CTCCACATGC
      GGGTGCTCGG  GGTGCGCCGT  GGAGTTCCGG  GTGCTCGGAG  AGCCGTCGAA  GAGGTGTACG 5345 5350   5355 5360   5365 5370   5375 5380   5385 5390   5395 5400
           *           *           *           *           *           *
      TGACCTGCTC  AGACAAACCC  AGCCCTCCTC  TCACAAGGGT  GCCCCTGCAG  CCGCCACACA
      ACTGGACGAG  TCTGTTTGGG  TCGGGAGGAG  AGTGTTCCCA  CGGGGACGTC  GGCGGTGTGT 5405 5410   5415 5420   5425 5430   5435 5440   5445 5450   5455 5460
           *           *           *           *           *           *
      CACACAGGGG  ATCACACACC  ACGTCACGTC  CCTGGCCCTG  GCCCACTTCC  CAGTGCCGCC
      GTGTGTCCCC  TAGTGTGTGG  TGCAGTGCAG  GGACCGGGAC  CGGGTGAAGG  GTCACGGCGG 5465 5470   5475 5480   5485 5490   5495 5500   5505 5510   5515 5520
           *           *           *           *           *           *
      CTTCCCTGCA  GGGCGGATCA  TAATCAGCCA  TACCACATTT  GTAGAGGTTT  TACTTGCTTT
      GAAGGGACGT  CCCGCCTAGT  ATTAGTCGGT  ATGGTGTAAA  CATCTCCAAA  ATGAACGAAA 5525 5530   5535 5540   5545 5550   5555 5560   5565 5570   5575 5580
           *           *           *           *           *           *
      AAAAAACCTC  CCACACCTCC  CCCTGAACCT  GAAACATAAA  ATGAATGCAA  TTGTTGTTGT
      TTTTTTGGAG  GGTGTGGAGG  GGGACTTGGA  CTTTGTATTT  TACTTACGTT  AACAACAACA 5585 5590   5595 5600   5605 5610   5615 5620   5625 5630   5635 5640
           *           *           *           *           *           *
      TAACTTGTTT  ATTGCAGCTT  ATAATGGTTA  CAAATAAAGC  AATAGCATCA  CAAATTTCAC
      ATTGAACAAA  TAACGTCGAA  TATTACCAAT  GTTTATTTCG  TTATCGTAGT  GTTTAAAGTG 5645 5650   5655 5660   5665 5670   5675 5680   5685 5690   5695 5700
           *           *           *           *           *           *
      AAATAAAGCA  TTTTTTTCAC  TGCATTCTAG  TTGTGGTTTG  TCCAAACTCA  TCAATGTATC
      TTTATTTCGT  AAAAAAAGTG  ACGTAAGATC  AACACCAAAC  AGGTTTGAGT  AGTTACATAG 5750 5710   5715 5720   5725 5730   5735 5740   5745 5750   5755 5760
           *           *           *           *           *           *
      TTATCATGTC  TGAGATCCTC  TACGCCGGAC  GCATCGTGGC  CGGCATCACC  GGCGCCACAG
      AATAGTACAG  ACTCTAGGAG  ATGCGGCCTG  CGTAGCACCG  GCCGTAGTGG  CCGCGGTGTC
```

FIG. 29H

```
       5765 5770  5775 5780  5785 5790  5795 5800  5805 5810  5815 5820
          *          *          *          *          *          *
       GTGCGGTTGC TGGCGCCTAT ATCGCCGACA TCACCGATGG GGAAGATCGG GCTCGCCACT
       CACGCCAACG ACCGCGGATA TAGCGGCTGT AGTGGCTACC CCTTCTAGCC CGAGCGGTGA 5825 5830  5835 5840  5845 5850  5855 5860  5865 5870  5875 5880
          *          *          *          *          *          *
       TCGGGCTCAT GAGCGCTTGT TTCGGCGTGG GTATGGTGGC AGGCCCGTGG CCGGGGGACT
       AGCCCGAGTA CTCGCGAACA AAGCCGCACC CATACCACCG TCCGGGCACC GGCCCCCTGA 5885 5890  5895 5900  5905 5910  5915 5920  5925 5930  5935 5940
          *          *          *          *          *          *
       GTTGGGCGCC ATCTCCTTGC ATGCACCATT CCTTGCGGCG GCGGTGCTCA ACGGCCTCAA
       CAACCCGCGG TAGAGGAACG TACGTGGTAA GGAACGCCGC CGCCACGAGT TGCCGGAGTT 5945 5950  5955 5960  5965 5970  5975 5980  5985 5990  5990 6000
          *          *          *          *          *          *
       CCTACTACTG GGCTGCTTCC TAATGCAGGA GTCGCATAAG GGAGAGCGTC GACCTCGGGC
       GGATGATGAC CCGACGAAGG ATTACGTCCT CAGCGTATTC CCTCTCGCAG CTGGAGCCCG 6005 6010  6015 6020  6025 6030  6035 6040  6045 6050  6055 6060
          *          *          *          *          *          *
       CGCGTTGCTG GCGTTTTTCC ATAGGCTCCG CCCCCCTGAC GAGCATCACA AAAATCGACG
       GCGCAACGAC CGCAAAAAGG TATCCGAGGC GGGGGGACTG CTCGTAGTGT TTTTAGCTGC 6065 6070  6075 6080  6085 6090  6095 6100  6105 6110  6115 6120
          *          *          *          *          *          *
       CTCAAGTCAG AGGTGGCGAA ACCCGACAGG ACTATAAAGA TACCAGGCGT TTCCCCCTGG
       GAGTTCAGTC TCCACCGCTT TGGGCTGTCC TGATATTTCT ATGGTCCGCA AAGGGGGACC 6125 6130  6135 6140  6145 6150  6155 6160  6165 6170  6175 6180
          *          *          *          *          *          *
       AAGCTCCCTC GTGCGCTCTC CTGTTCCGAC CCTGCCGCTT ACCGGATACC TGTCCGCCTT
       TTCGAGGGAG CACGCGAGAG GACAAGGCTG GGACGGCGAA TGGCCTATGG ACAGGCGGAA 6185 6190  6195 6200  6205 6210  6215 6220  6225 6230  6235 6240
          *          *          *          *          *          *
       TCTCCCTTCG GGAAGCGTGG CGCTTTCTCA ATGCTCACGC TGTAGGTATC TCAGTTCGGT
       AGAGGGAAGC CCTTCGCACC GCGAAAGAGT TACGAGTGCG ACATCCATAG AGTCAAGCCA 6245 6250  6255 6260  6265 6270  6275 6280  6285 6290  6295 6300
          *          *          *          *          *          *
       GTAGGTCGTT CGCTCCAAGC TGGGCTGTGT GCACGAACCC CCCGTTCAGC CCGACCGCTG
       CATCCAGCAA GCGAGGTTCG ACCCGACACA CGTGCTTGGG GGGCAAGTCG GGCTGGCGAC 6305 6310  6315 6320  6325 6330  6335 6340  6345 6350  6355 6360
          *          *          *          *          *          *
       CGCCTTATCC GGTAACTATC GTCTTGAGTC CAACCCGGTA AGACACGACT TATCGCCACT
       GCGGAATAGG CCATTGATAG CAGAACTCAG GTTGGGCCAT TCTGTGCTGA ATAGCGGTGA 6365 6370  6375 6380  6385 6390  6395 6400  6405 6410  6415 6420
          *          *          *          *          *          *
       GGCAGCAGCC ACTGGTAACA GGATTAGCAG AGCGAGGTAT GTAGGCGGTG CTACAGAGTT
       CCGTCGTCGG TGACCATTGT CCTAATCGTC TCGCTCCATA CATCCGCCAC GATGTCTCAA 6425 6430  6435 6440  6445 6450  6455 6460  6465 6470  6475 6480
          *          *          *          *          *          *
       CTTGAAGTGG TGGCCTAACT ACGGCTACAC TAGAAGGACA GTATTTGGTA TCTGCGCTCT
       GAACTTCACC ACCGGATTGA TGCCGATGTG ATCTTCCTGT CATAAACCAT AGACGCGAGA
```

FIG. 291

```
     6485 6490   6495 6500   6505 6510   6515 6520   6525 6530   6535 6540
        *           *           *           *           *           *
     GCTGAAGCCA  GTTACCTTCG  GAAAAAGAGT  TGGTAGCTCT  TGATCCGGCA  AACAAACCAC
     CGACTTCGGT  CAATGGAAGC  CTTTTTCTCA  ACCATCGAGA  ACTAGGCCGT  TTGTTTGGTG 6545 6550   6555 6560   6565 6570   6575 6580   6585 6590   6595 6600
        *           *           *           *           *           *
     CGCTGGTAGC  GGTGGTTTTT  TTGTTTGCAA  GCAGCAGATT  ACGCGCAGAA  AAAAAGGATC
     GCGACCATCG  CCACCAAAAA  AACAAACGTT  CGTCGTCTAA  TGCGCGTCTT  TTTTTCCTAG 6605 6610   6615 6620   6625 6630   6635 6640   6645 6650   6655 6660
        *           *           *           *           *           *
     TCAAGAAGAT  CCTTTGATCT  TTTCTACGGG  GTCTGACGCT  CAGTGGAACG  AAAACTCACG
     AGTTCTTCTA  GGAAACTAGA  AAAGATGCCC  CAGACTGCGA  GTCACCTTGC  TTTTGAGTGC 6665 6670   6675 6680   6685 6690   6695 6700   6705 6710   6715 6720
        *           *           *           *           *           *
     TTAAGGGATT  TTGGTCATGA  GATTATCAAA  AAGGATCTTC  ACCTAGATCC  TTTTAAATTA
     AATTCCCTAA  AACCAGTACT  CTAATAGTTT  TTCCTAGAAG  TGGATCTAGG  AAAATTTAAT 6725 6730   6735 6740   6745 6750   6755 6760   6765 6770   6775 6780
        *           *           *           *           *           *
     AAAATGAAGT  TTTAAATCAA  TCTAAAGTAT  ATATGAGTAA  ACTTGGTCTG  ACAGTTACCA
     TTTTACTTCA  AAATTTAGTT  AGATTTCATA  TATACTCATT  TGAACCAGAC  TGTCAATGGT 6785 6790   6795 6800   6805 6810   6815 6820   6825 6830   6835 6840
        *           *           *           *           *           *
     ATGCTTAATC  AGTGAGGCAC  CTATCTCAGC  GATCTGTCTA  TTTCGTTCAT  CCATAGTTGC
     TACGAATTAG  TCACTCCGTG  GATAGAGTCG  CTAGACAGAT  AAAGCAAGTA  GGTATCAACG 6845 6850   6855 6860   6865 6870   6875 6880   6885 6890   6895 6900
        *           *           *           *           *           *
     CTGACTCCCC  GTCGTGTAGA  TAACTACGAT  ACGGGAGGGC  TTACCATCTG  GCCCCAGTGC
     GACTGAGGGG  CAGCACATCT  ATTGATGCTA  TGCCCTCCCG  AATGGTAGAC  CGGGGTCACG 6905 6910   6915 6920   6925 6930   6935 6940   6945 6950   6955 6960
        *           *           *           *           *           *
     TGCAATGATA  CCGCGAGACC  CACGCTCACC  GGCTCCAGAT  TTATCAGCAA  TAAACCAGCC
     ACGTTACTAT  GGCGCTCTGG  GTGCGAGTGG  CCGAGGTCTA  AATAGTCGTT  ATTTGGTCGG 6965 6970   6975 6980   6985 6990   6995 7000   7005 7010   7015 7020
        *           *           *           *           *           *
     AGCCGGAAGG  GCCGAGCGCA  GAAGTGGTCC  TGCAACTTTA  TCCGCCTCCA  TCCAGTCTAT
     TCGGCCTTCC  CGGCTCGCGT  CTTCACCAGG  ACGTTGAAAT  AGGCGGAGGT  AGGTCAGATA 7025 7030   7035 7040   7045 7050   7055 7060   7065 7070   7075 7080
        *           *           *           *           *           *
     TAATTGTTGC  CGGGAAGCTA  GAGTAAGTAG  TTCGCCAGTT  AATAGTTTGC  GCAACGTTGT
     ATTAACAACG  GCCCTTCGAT  CTCATTCATC  AAGCGGTCAA  TTATCAAACG  CGTTGCAACA 7085 7090   7095 7100   7105 7110   7115 7120   7125 7130   7135 7140
        *           *           *           *           *           *
     TGCCATTGCT  ACAGGCATCG  TGGTGTCACG  CTCGTCGTTT  GGTATGGCTT  CATTCAGCTC
     ACGGTAACGA  TGTCCGTAGC  ACCACAGTGC  GAGCAGCAAA  CCATACCGAA  GTAAGTCGAG 7145 7150   7155 7160   7165 7170   7175 7180   7185 7190   7195 7200
        *           *           *           *           *           *
     CGGTTCCCAA  CGATCAAGGC  GAGTTACATG  ATCCCCCATG  TTGTGCAAAA  AAGCGGTTAG
     GCCAAGGGTT  GCTAGTTCCG  CTCAATGTAC  TAGGGGGTAC  AACACGTTTT  TTCGCCAATC
```

FIG. 29J

```
     7205 7210  7215 7220  7225 7230  7235 7240  7245 7250  7255 7260
        *          *          *          *          *          *
     CTCCTTCGGT CCTCCGATCG TTGTCAGAAG TAAGTTGGCC GCAGTGTTAT CACTCATGGT
     GAGGAAGCCA GGAGGCTAGC AACAGTCTTC ATTCAACCGG CGTCACAATA GTGAGTACCA 7265 7270  7275 7280  7285 7290  7295 7300  7305 7310  7315 7320
        *          *          *          *          *          *
     TATGGCAGCA CTGCATAATT CTCTTACTGT CATGCCATCC GTAAGATGCT TTTCTGTGAC
     ATACCGTCGT GACGTATTAA GAGAATGACA GTACGGTAGG CATTCTACGA AAAGACACTG 7325 7330  7335 7340  7345 7350  7355 7360  7365 7370  7375 7380
        *          *          *          *          *          *
     TGGTGAGTAC TCAACCAAGT CATTCTGAGA ATAGTGTATG CGGCGACCGA GTTGCTCTTG
     ACCACTCATG AGTTGGTTCA GTAAGACTCT TATCACATAC GCCGCTGGCT CAACGAGAAC 7385 7390  7395 7400  7405 7410  7415 7420  7425 7430  7435 7440
        *          *          *          *          *          *
     CCCGGCGTCA ACACGGGATA ATACCGCGCC ACATAGCAGA ACTTTAAAAG TGCTCATCAT
     GGGCCGCAGT TGTGCCCTAT TATGGCGCGG TGTATCGTCT TGAAATTTTC ACGAGTAGTA 7445 7450  7455 7460  7465 7470  7475 7480  7485 7490  7495 7500
        *          *          *          *          *          *
     TGGAAAACGT TCTTCGGGGC GAAAACTCTC AAGGATCTTA CCGCTGTTGA GATCCAGTTC
     ACCTTTTGCA AGAAGCCCCG CTTTTGAGAG TTCCTAGAAT GGCGACAACT CTAGGTCAAG 7505 7510  7515 7520  7525 7530  7535 7540  7545 7550  7555 7560
        *          *          *          *          *          *
     GATGTAACCC ACTCGTGCAC CCAACTGATC TTCAGCATCT TTTACTTTCA CCAGCGTTTC
     CTACATTGGG TGAGCACGTG GGTTGACTAG AAGTCGTAGA AAATGAAAGT GGTCGCAAAG 7565 7570  7575 7580  7585 7590  7595 7600  7605 7610  7615 7620
        *          *          *          *          *          *
     TGGGTGAGCA AAAACAGGAA GGCAAAATGC CGCAAAAAAG GGAATAAGGG CGACACGGAA
     ACCCACTCGT TTTTGTCCTT CCGTTTTACG GCGTTTTTTC CCTTATTCCC GCTGTGCCTT 7625 7630  7635 7640  7645 7650  7655 7660  7665 7670  7675 7680
        *          *          *          *          *          *
     ATGTTGAATA CTCATACTCT TCCTTTTTCA ATATTATTGA AGCATTTATC AGGGTTATTG
     TACAACTTAT GAGTATGAGA AGGAAAAAGT TATAATAACT TCGTAAATAG TCCCAATAAC 7685 7690  7695 7700  7705 7710  7715 7720  7725 7730  7735 7740
        *          *          *          *          *          *
     TCTCATGAGC GGATACATAT TTGAATGTAT TTAGAAAAAT AAACAAATAG GGGTTCCGCG
     AGAGTACTCG CCTATGTATA AACTTACATA AATCTTTTTA TTTGTTTATC CCCAAGGCGC 7745 7750  7755 7760  7765 7770  7775 7780  7785 7790  7795 7800
        *          *          *          *          *          *
     CACATTTCCC CGAAAAGTGC CACCTGACGT CTAAGAAACC ATTATTATCA TGACATTAAC
     GTGTAAAGGG GCTTTTCACG GTGGACTGCA GATTCTTTGG TAATAATAGT ACTGTAATTG 7805 7810  7815 7820  7825 7830  7835 7840  7845 7850  7855 7860
        *          *          *          *          *          *
     CTATAAAAAT AGGCGTATCA CGAGGCCCTG ATGGCTCTTT GCGGCACCCA TCGTTCGTAA
     GATATTTTTA TCCGCATAGT GCTCCGGGAC TACCGAGAAA CGCCGTGGGT AGCAAGCATT 7865 7870  7875 7880  7885 7890  7895 7900  7905 7910  7915 7920
        *          *          *          *          *          *
     TGTTCCGTGG CACCGAGGAC AACCCTCAAG AGAAAATGTA ATCACACTGG CTCACCTTGG
     ACAAGGCACC GTGGCTCCTG TTGGGAGTTC TCTTTTACAT TAGTGTGACC GAGTGGAACC
```

FIG. 29K

```
7925 7930   7935 7940   7945 7950   7955 7960   7965 7970   7975 7980
        *           *           *           *           *           *
GGTGGGCCTT  TCTGCGTTTA  TAAGGAGACA  CTTTATGTTT  AAGAAGGTTG  GTAAATTCCT
CCACCCGGAA  AGACGCAAAT  ATTCCTCTGT  GAAATACAAA  TTCTTCCAAC  CATTTAAGGA 7985 7990   7995 8000   8005 8010   8015 8020   8025 8030   8035 8040
        *           *           *           *           *           *
TGCGGCTTTG  GCAGCCAAGC  TAGATCCGGC  TGTGGAATGT  GTGTCAGTTA  GGGTGTGGAA
ACGCCGAAAC  CGTCGGTTCG  ATCTAGGCCG  ACACCTTACA  CACAGTCAAT  CCCACACCTT 8045 8050   8055 8060   8065 8070   8075 8080   8085 8090   8095 8100
        *           *           *           *           *           *
AGTCCCCAGG  CTCCCCAGCA  GGCAGAAGTA  TGCAAAGCAT  GCATCTCAAT  TAGTCAGCAA
TCAGGGGTCC  GAGGGGTCGT  CCGTCTTCAT  ACGTTTCGTA  CGTAGAGTTA  ATCAGTCGTT 8105 8110   8115 8120   8125 8130   8135 8140   8145 8150   8155 8160
        *           *           *           *           *           *
CCAGGCTCCC  CAGCAGGCAG  AAGTATGCAA  AGCATGCATC  TCAATTAGTC  AGCAACCATA
GGTCCGAGGG  GTCGTCCGTC  TTCATACGTT  TCGTACGTAG  AGTTAATCAG  TCGTTGGTAT 8165 8170   8175 8180   8185 8190   8195 8200   8205 8210   8215 8220
        *           *           *           *           *           *
GTCCCGCCCC  TAACTCCGCC  CATCCCGCCC  CTAACTCCGC  CCAGTTCCGC  CCATTCTCCG
CAGGGCGGGG  ATTGAGGCGG  GTAGGGCGGG  GATTGAGGCG  GGTCAAGGCG  GGTAAGAGGC 8225 8230   8235 8240   8245 8250   8255 8260   8265 8270   8275 8280
        *           *           *           *           *           *
CCCCATGGCT  GACTAATTTT  TTTTATTTAT  GCAGAGGCCG  AGGCCGCCTC  GGCCTCTGAG
GGGGTACCGA  CTGATTAAAA  AAAATAAATA  CGTCTCCGGC  TCCGGCGGAG  CCGGAGACTC 8285 8290   8295 8300   8305 8310   8315 8320   8325 8330   8335 8340
        *           *           *           *           *           *
CTATTCCAGA  AGTAGTGAGG  AGGCTTTTTT  GGAGGCCTAG  GCTTTTGCAA  AAACTAGCTT
GATAAGGTCT  TCATCACTCC  TCCGAAAAAA  CCTCCGGATC  CGAAAACGTT  TTTGATCGAA 8345 8350   8355 8360   8365 8370   8375 8380   8385 8390   8395 8400
        *           *           *           *           *           *
GGGGCCACCG  CTCAGAGCAC  CTTCCACCAT  GGCCACCTCA  GCAAGTTCCC  ACTTGAACAA
CCCCGGTGGC  GAGTCTCGTG  GAAGGTGGTA  CCGGTGGAGT  CGTTCAAGGG  TGAACTTGTT 8405 8410   8415 8420   8425 8430   8435 8440   8445 8550   8455 8460
        *           *           *           *           *           *
AAACATCAAG  CAAATGTACT  TGTGCCTGCC  CCAGGGTGAG  AAAGTCCAAG  CCATGTATAT
TTTGTAGTTC  GTTTACATGA  ACACGGACGG  GGTCCCACTC  TTTCAGGTTC  GGTACATATA 8465 8470   8475 8480   8485 8490   8495 8500   8505 8510   8515 8520
        *           *           *           *           *           *
CTGGGTTGAT  GGTACTGGAG  AAGGACTCCG  CTGCAAAACC  CGCACCCTGG  ACTGTGAGCC
GACCCAACTA  CCATGACCTC  TTCCTGAGGC  GACGTTTTGG  GCGTGGGACC  TGACACTCGG 8525 8530   8535 8540   8545 8550   8555 8560   8565 8570   8575 8580
        *           *           *           *           *           *
CAAGTGTGTA  GAAGAGTTAC  CTGAGTGGAA  TTTTGATGGC  TCTAGTACCT  TTCAGTCTGA
GTTCACACAT  CTTCTCAATG  GACTCACCTT  AAAACTACCG  AGATCATGGA  AAGTCAGACT 8585 8690   8595 9600   8605 8610   8615 8620   8625 8630   8635 8640
        *           *           *           *           *           *
GGGCTCCAAC  AGTGACATGT  ATCTCAGCCC  TGTTGCCATG  TTTCGGGACC  CCTTCCGCAG
CCCGAGGTTG  TCACTGTACA  TAGAGTCGGG  ACAACGGTAC  AAAGCCCTGG  GGAAGGCGTC
```

FIG. 29L

```
       8645 8650   8655 8660   8665 8670   8675 8680   8685 8690   8695 8700
            *           *           *           *           *           *
       AGATCCCAAC  AAGCTGGTGT  TCTGTGAAGT  TTTCAAGTAC  AACCGGAAGC  CTGCAGAGAC
       TCTAGGGTTG  TTCGACCACA  AGACACTTCA  AAAGTTCATG  TTGGCCTTCG  GACGTCTCTG 8705 8710   8715 8720   8725 8730   8735 8740   8745 8750   8755 8760
            *           *           *           *           *           *
       CAATTTAAGG  CACTCGTGTA  AACGGATAAT  GGACATGGTG  AGCAACCAGC  ACCCCTGGTT
       GTTAAATTCC  GTGAGCACAT  TTGCCTATTA  CCTGTACCAC  TCGTTGGTCG  TGGGGACCAA 8765 8770   8775 8780   8785 8790   8795 8800   8805 8810   8815 8820
            *           *           *           *           *           *
       TGGAATGGAA  CAGGAGTATA  CTCTGATGGG  AACAGATGGG  CACCCTTTTG  GTTGGCCTTC
       ACCTTACCTT  GTCCTCATAT  GAGACTACCC  TTGTCTACCC  GTGGGAAAAC  CAACCGGAAG 8825 8830   8835 8840   8845 8850   8855 8860   8865 8870   8875 8880
            *           *           *           *           *           *
       CAATGGCTTT  CCTGGGCCCC  AAGGTCCGTA  TTACTGTGGT  GTGGGCGCAG  ACAAAGCCTA
       GTTACCGAAA  GGACCCGGGG  TTCCAGGCAT  AATGACACCA  CACCCGCGTC  TGTTTCGGAT 8885 8890   8895 8900   8905 8910   8915 8920   8925 8930   8935 8940
            *           *           *           *           *           *
       TGGCAGGGAT  ATCGTGGAGG  CTCACTACCG  CGCCTGCTTG  TATGCTGGGG  TCAAGATTAC
       ACCGTCCCTA  TAGCACCTCC  GAGTGATGGC  GCGGACGAAC  ATACGACCCC  AGTTCTAATG 8945 8950   8955 8960   8965 8970   8975 8980   8985 8990   8995 9000
            *           *           *           *           *           *
       AGGAACAAAT  GCTGAGGTCA  TGCCTGCCCA  GTGGGAACTC  CAAATAGGAC  CCTGTGAAGG
       TCCTTGTTTA  CGACTCCAGT  ACGGACGGGT  CACCCTTGAG  GTTTATCCTG  GGACACTTCC 9005 9010   9015 9020   9025 9030   9035 9040   9045 9050   9055 9060
            *           *           *           *           *           *
       AATCCGCATG  GGAGATCATC  TCTGGGTGGC  CCGTTTCATC  TTNCATCGAG  TATGTGAAGA
       TTAGGCGTAC  CCTCTAGTAG  AGACCCACCG  GGCAAACTAG  AANGTAGCTC  ATACACTTCT 9065 9070   9075 9080   9085 9090   9095 9100   9105 9110   9115 9120
            *           *           *           *           *           *
       CTTTGGGGTA  ATAGCAACCT  TTGACCCCAA  GCCCATTCCT  GGGAACTGGA  ATGGTGCAGG
       GAAACCCCAT  TATCGTTGGA  AACTGGGGTT  CGGGTAAGGA  CCCTTGACCT  TACCACGTCC 9125 9130   9135 9140   9145 9150   9155 9160   9165 9170   9175 9180
            *           *           *           *           *           *
       CTGCCATACC  AACTTTAGCA  CCAAGGCCAT  GCGGGAGGAG  AATGGTCTGA  AGCACATCGA
       GACGGTATGG  TTGAAATCGT  GGTTCCGGTA  CGCCCTCCTC  TTACCAGACT  TCGTGTAGCT 9185 9190   9195 9200   9205 9210   9215 9220   9225 9230   9235 9240
            *           *           *           *           *           *
       GGAGGCCATC  GAGAAACTAA  GCAAGCGGCA  CCGGTACCAC  ATTCGAGCCT  ACGATCCCAA
       CCTCCGGTAG  CTCTTTGATT  CGTTCGCCGT  GGCCATGGTG  TAAGCTCGGA  TGCTAGGGTT 9245 9250   9255 9260   9265 9270   9275 9280   9285 9290   9295 9300
            *           *           *           *           *           *
       GGGGGGCCTG  GACAATGCCC  GTGGTCTGAC  TGGGTTCCAC  GAAACGTCCA  ACATCAACGA
       CCCCCCGGAC  CTGTTACGGG  CACCAGACTG  ACCCAAGGTG  CTTTGCAGGT  TGTAGTTGCT 9305 9310   9315 9320   9325 9330   9335 9340   9345 9350   9355 9360
            *           *           *           *           *           *
       CTTTTCTGCT  GGTGTCGCCA  ATCGCAGTGC  CAGCATCCGC  ATTCCCCGGA  CTGTCGGCCA
       GAAAAGACGA  CCACAGCGGT  TAGCGTCACG  GTCGTAGGCG  TAAGGGGCCT  GACAGCCGGT
```

FIG. 29M

```
9365 9370   9375 9380   9385 9390   9395 9400   9405 9410   9415 9420
         *           *           *           *           *           *
GGAGAAGAAA  GGTTACTTTG  AAGACCGCGG  CCCCTCTGCC  AATTGTGACC  CCTTTGCAGT
CCTCTTCTTT  CCAATGAAAC  TTCTGGCGCC  GGGGAGACGG  TTAACACTGG  GGAAACGTCA 9425 9430   9435 9440   9445 9450   9455 9460   9465 9470   9475 9480
         *           *           *           *           *           *
GACAGAAGCC  ATCGTCCGCA  CATGCCTTCT  CAATGAGACT  GGCCACGAGC  CCTTCCAATA
CTGTCTTCGG  TAGCAGGCGT  GTACGGAAGA  GTTACTCTGA  CCGGTGCTCG  GGAAGGTTAT 9485 9490   9495 9500   9505 9510   9515 9520   9525 9530   9535 9540
         *           *           *           *           *           *
CAAAAACTAA  TTAGACTTTG  AGTGATCTTG  AGCCTTTCCT  AGTTCATCCC  ACCCCGCCCC
GTTTTTGATT  AATCTGAAAC  TCACTAGAAC  TCGGAAAGGA  TCAAGTAGGG  TGGGGCGGGG 9545 9550   9555 9560   9565 9570   9575 9580   9585 9590   9595 9600
         *           *           *           *           *           *
AGAGAGATCT  TTGTGAAGGA  ACCTTACTTC  TGTGGTGTGA  CATAATTGGA  CAAACTACCT
TCTCTCTAGA  AACACTTCCT  TGGAATGAAG  ACACCACACT  GTATTAACCT  GTTTGATGGA 9605 9610   9615 9620   9625 9630   9635 9640   9645 9650   9655 9660
         *           *           *           *           *           *
ACAGAGATTT  AAAGCTCTAA  GGTAAATATA  AAATTTTTAA  GTGTATAATG  TGTTAAACTA
TGTCTCTAAA  TTTCGAGATT  CCATTTATAT  TTTAAAAATT  CACATATTAC  ACAATTTGAT 9665 9670   9675 9680   9685 9690   9695 9700   9705 9710   9715 9720
         *           *           *           *           *           *
CTGATTCTAA  TTGTTTGTGT  ATTTTAGATT  CCAACCTATG  GAACTGATGA  ATGGGAGCAG
GACTAAGATT  AACAAACACA  TAAAATCTAA  GGTTGGATAC  CTTGACTACT  TACCCTCGTC 9725 9730   9735 9740   9745 9750   9755 9760   9765 9770   9775 9780
         *           *           *           *           *           *
TGGTGGAATG  CCTTTAATGA  GGAAAACCTG  TTTTGCTCAG  AAGAAATGCC  ATCTAGTGAT
ACCACCTTAC  GGAAATTACT  CCTTTTGGAC  AAAACGAGTC  TTCTTTACGG  TAGATCACTA 9785 9790   9795 9800   9805 9810   9815 9820   9825 9830   9835 9840
         *           *           *           *           *           *
GATGAGGCTA  CTGCTGACTC  TCAACATTCT  ACTCCTCCAA  AAAAGAAGAG  AAAGGTAGAA
CTACTCCGAT  GACGACTGAG  AGTTGTAAGA  TGAGGAGGTT  TTTTCTTCTC  TTTCCATCTT 9845 9850   9855 9860   9865 9870   9875 9880   9885 9890   9895 9900
         *           *           *           *           *           *
GACCCCAAGG  ACTTTCCTTC  AGAATTGCTA  AGTTTTTTGA  GTCATGCTGT  GTTTAGTAAT
CTGGGGTTCC  TGAAAGGAAG  TCTTAACGAT  TCAAAAAACT  CAGTACGACA  CAAATCATTA 9905 9910   9915 9920   9925 9930   9935 9940   9945 9950   9955 9960
         *           *           *           *           *           *
AGAACTCTTG  CTTGCTTTGC  TATTTACACC  ACAAAGGAAA  AAGCTGCACT  GCTATACAAG
TCTTGAGAAC  GAACGAAACG  ATAAATGTGG  TGTTTCCTTT  TTCGACGTGA  CGATATGTTC 9965 9970   9975 9980   9985 9990   999610000   1000510010  1001510020
         *           *           *           *           *           *
AAAATTATGG  AAAAATATTC  TGTAACCTTT  ATAAGTAGGC  ATAACAGTTA  TAATCATAAC
TTTTAATACC  TTTTTATAAG  ACATTGGAAA  TATTCATCCG  TATTGTCAAT  ATTAGTATTG 1002510030  1003510040  1004510050  1005510060  1006510070  1007510080
         *           *           *           *           *           *
ATACTGTTTT  TTCTTACTCC  ACACAGGCAT  AGAGTGTCTG  CTATTAATAA  CTATGCTCAA
TATGACAAAA  AAGAATGAGG  TGTGTCCGTA  TCTCACAGAC  GATAATTATT  GATACGAGTT
```

FIG. 29N

```
         1008510090  1009510100  1010510110  1011510120  1012510130  1013510140
              *           *           *           *           *           *
         AAATTGTGTA  CCTTTAGCTT  TTTAATTTGT  AAAGGGGTTA  ATAAGGAATA  TTTGATGTAT
         TTTAACACAT  GGAAATCGAA  AAATTAAACA  TTTCCCCAAT  TATTCCTTAT  AAACTACATA 1014510150  1015510160  1016510170  1017510180  1018510190  1019510200
              *           *           *           *           *           *
         AGTGCCTTGA  CTAGAGATCA  TAATCAGCCA  TACCACATTT  GTAGAGGTTT  TACTTGCTTT
         TCACGGAACT  GATCTCTAGT  ATTAGTCGGT  ATGGTGTAAA  CATCTCCAAA  ATGAACGAAA 1020510210  1021510220  1022510230  1023510240  1024510250  1025510260
              *           *           *           *           *           *
         AAAAAACCTC  CCACACCTCC  CCCTGAACCT  GAAACATAAA  ATGAATGCAA  TTGTTGTTGT
         TTTTTTGGAG  GGTGTGGAGG  GGGACTTGGA  CTTTGTATTT  TACTTACGTT  AACAACAACA 1026510270  1027510280  1028510290  1029510300  1030510310  1031510320
              *           *           *           *           *           *
         TAACTTGTTT  ATTGCAGCTT  ATAATGGTTA  CAAATAAAGC  AATAGCATCA  CAAATTTCAC
         ATTGAACAAA  TAACGTCGAA  TATTACCAAT  GTTTATTTCG  TTATCGTAGT  GTTTAAAGTG 1032510330  1033510340  1034510350  1035510360  1036510370  1037510380
              *           *           *           *           *           *
         AAATAAAGCA  TTTTTTTCAC  TGCATTCTAG  TTGTGGTTTG  TCCAAACTCA  TCAATGTATC
         TTTATTTCGT  AAAAAAAGTG  ACGTAAGATC  AACACCAAAC  AGGTTTGAGT  AGTTACATAG 1038510390  1039510400  1040510410  1041510420  1042510430  1043510440
              *           *           *           *           *           *
         TTATCATGTC  TGGATCTCTA  GCTTCGTGTC  AAGGACGGTG  ACTGCAGTGA  ATAATAAAT
         AATAGTACAG  ACCTAGAGAT  CGAAGCACAG  TTCCTGCCAC  TGACGTCACT  TATTATTTA 1044510450  1045510460  1046510470  1047510480  1048510490  1049510500
              *           *           *           *           *           *
         GTGTGTTTGT  CCGAAATACG  CGTTTTGAGA  TTTCTGTCGC  CGACTAAATT  CATGTCGCGC
         CACACAAACA  GGCTTTATGC  GCAAAACTCT  AAAGACAGCG  GCTGATTTAA  GTACAGCGCG 1050510510  1051510520  1052510530  1053510540  1054510550  1055510560
              *           *           *           *           *           *
         GATAGTGGTG  TTTATCGCCG  ATAGAGATGG  CGATATTGGA  AAAATCGATA  TTTGAAAATA
         CTATCACCAC  AAATAGCGGC  TATCTCTACC  GCTATAACCT  TTTTAGCTAT  AAACTTTTAT 1056510570  1057510580  1058510590  1059510600  1060510610  1061510620
              *           *           *           *           *           *
         TGGCATATTG  AAAATGTCGC  CGATGTGAGT  TTCTGTGTAA  CTGATATCGC  CATTTTTCCA
         ACCGTATAAC  TTTTACAGCG  GCTACACTCA  AAGACACATT  GACTATAGCG  GTAAAAAGGT 1062510630  1063510640  1064510650  1065510660  1066510670  1067510680
              *           *           *           *           *           *
         AAAGTGATTT  TTGGGCATAC  GCGATATCTG  GCGATAGCGC  TTATATCGTT  TACGGGGGAT
         TTTCACTAAA  AACCCGTATG  CGCTATAGAC  CGCTATCGCG  AATATAGCAA  ATGCCCCCTA 1068510690  1069510700  1070510710  1071510720  1072510730  1073510740
              *           *           *           *           *           *
         GGCGATAGAC  GACTTTGGTG  ACTTGGGCGA  TTCTGTGTGT  CGCAAATATC  GCAGTTTCGA
         CCGCTATCTG  CTGAAACCAC  TGAACCCGCT  AAGACACACA  GCGTTTATAG  CGTCAAAGCT 1074510750  1075510760  1076510770  1077510780  1078510790  1079510800
              *           *           *           *           *           *
         TATAGGTGAC  AGACGATATG  AGGCTATATC  GCCGATAGAG  GCGACATCAA  GCTGGCACAT
         ATATCCACTG  TCTGCTATAC  TCCGATATAG  CGGCTATCTC  CGCTGTAGTT  CGACCGTGTA
```

FIG. 290

```
       1080510810  1081510820  1082510830  1083510840  1084510850  1085510860
            *           *           *           *           *           *
       GGCCAATGCA  TATCGATCTA  TACATTGAAT  CAATATTGGC  CATTAGCCAT  ATTATTCATT
       CCGGTTACGT  ATAGCTAGAT  ATGTAACTTA  GTTATAACCG  GTAATCGGTA  TAATAAGTAA 1086510870  1087510880  1088510890  1089510900  1090510910  1091510920
            *           *           *           *           *           *
       GGTTATATAG  CATAAATCAA  TATTGGCTAT  TGGCCATTGC  ATACGTTGTA  TCCATATCAT
       CCAATATATC  GTATTTAGTT  ATAACCGATA  ACCGGTAACG  TATGCAACAT  AGGTATAGTA 1092510930  1093510940  1094510950  1095510960  1096510970  1097510980
            *           *           *           *           *           *
       AATATGTACA  TTTATATTGG  CTCATGTCCA  ACATTACCGC  CATGTTGACA  TTGATTATTG
       TTATACATGT  AAATATAACC  GAGTACAGGT  TGTAATGGCG  GTACAACTGT  AACTAATAAC 1098510990  1099511000  1100511010  1101511020  1102511030  1103511040
            *           *           *           *           *           *
       ACTAGTTATT  AATAGTAATC  AATTACGGGG  TCATTAGTTC  ATAGCCCATA  TATGGAGTTC
       TGATCAATAA  TTATCATTAG  TTAATGCCCC  AGTAATCAAG  TATCGGGTAT  ATACCTCAAG 1104511050  1105511060  1106511070  1107511080  1108511090  1109511100
            *           *           *           *           *           *
       CGCGTTACAT  AACTTACGGT  AAATGGCCCG  CCTGGCTGAC  CGCCCAACGA  CCCCCGCCCA
       GCGCAATGTA  TTGAATGCCA  TTTACCGGGC  GGACCGACTG  GCGGGTTGCT  GGGGGCGGGT 1110511110  1111511120  1112511130  1113511140  1114511150  1115511160
            *           *           *           *           *           *
       TTGACGTCAA  TAATGACGTA  TGTTCCCATA  GTAACGCCAA  TAGGGACTTT  CCATTGACGT
       AACTGCAGTT  ATTACTGCAT  ACAAGGGTAT  CATTGCGGTT  ATCCCTGAAA  GGTAACTGCA 1116511170  1117511180  1118511190  1119511220  1120511210  1121511220
            *           *           *           *           *           *
       CAATGGGTGG  AGTATTTACG  GTAAACTGCC  CACTTGGCAG  TACATCAAGT  GTATCATATG
       GTTACCCACC  TCATAAATGC  CATTTGACGG  GTGAACCGTC  ATGTAGTTCA  CATAGTATAC 1122511230  1123511240  1124511250  1125511260  1126511270  1127511280
            *           *           *           *           *           *
       CCAAGTACGC  CCCCTATTGA  CGTCAATGAC  GGTAAATGGC  CCGCCTGGCA  TTATGCCCAG
       GGTTCATGCG  GGGGATAACT  GCAGTTACTG  CCATTTACCG  GGCGGACCGT  AATACGGGTC 1128511290  1129511300  1130511310  1131511320  1132511330  1133511340
            *           *           *           *           *           *
       TACATGACCT  TATGGGACTT  TCCTACTTGG  CAGTACATCT  ACGTATTAGT  CATCGCTATT
       ATGTACTGGA  ATACCCTGAA  AGGATGAACC  GTCATGTAGA  TGCATAATCA  GTAGCGATAA 1134511350  1135511360  1136511370  1137511380  1138511390  1139511400
            *           *           *           *           *           *
       ACCATGGTGA  TGCGGTTTTG  GCAGTACATC  AATGGGCGTG  GATAGCGGTT  TGACTCACGG
       TGGTACCACT  ACGCCAAAAC  CGTCATGTAG  TTACCCGCAC  CTATCGCCAA  ACTGAGTGCC 1140511410  1141511420  1142511430  1143511440  1144511450  1145511460
            *           *           *           *           *           *
       GGATTTCCAA  GTCTCCACCC  CATTGACGTC  AATGGGAGTT  TGTTTTGGCA  CCAAAATCAA
       CCTAAAGGTT  CAGAGGTGGG  GTAACTGCAG  TTACCCTCAA  ACAAAACCGT  GGTTTTAGTT 1146511470  1147511480  1148511490  1149511500  1150511510  1151511520
            *           *           *           *           *           *
       CGGGACTTTC  CAAAATGTCG  TAACAACTCC  GCCCCATTGA  CGCAAATGGG  CGGTAGGCGT
       GCCCTGAAAG  GTTTTACAGC  ATTGTTGAGG  CGGGGTAACT  GCGTTTACCC  GCCATCCGCA
```

FIG. 29P

```
          11525 11530   11535 11540   11545 11550   11555 11560   11565 11570   11575 11580
              *             *             *             *             *             *
          GTACGGTGGG    AGGTCTATAT    AAGCAGAGCT    CGTTTAGTGA    ACCGTCAGAT    CGCCTGGAGA
          CATGCCACCC    TCCAGATATA    TTCGTCTCGA    GCAAATCACT    TGGCAGTCTA    GCGGACCTCT 11585 11590   11595 11600   11605 11610   11615 11620   11625 11630   11635 11640
              *             *             *             *             *             *
          CGCCATCCAC    GCTGTTTTGA    CCTCCATAGA    AGACACCGGG    ACCGATCCAG    CCTCCGCGGC
          GCGGTAGGTG    CGACAAAACT    GGAGGTATCT    TCTGTGGCCC    TGGCTAGGTC    GGAGGCGCCG 11645 11650   11655 11660   11665 11670   11675 11680   11685 11690   11695 11700
              *             *             *             *             *             *
          CGGGAACGGT    GCATTGGAAC    GCGGATTCCC    CGTGCCAAGA    GTGACGTAAG    TACCGCCTAT
          GCCCTTGCCA    CGTAACCTTG    CGCCTAAGGG    GCACGGTTCT    CACTGCATTC    ATGGCGGATA 11705 11710   11715 11720   11725 11730   11735 11740   11745 11750   11755 11760
              *             *             *             *             *             *
          AGAGTCTATA    GGCCCACCCC    CTTGGCTTCT    TATGCATGCT    ATACTGTTTT    TGGCTTGGGG
          TCTCAGATAT    CCGGGTGGGG    GAACCGAAGA    ATACGTACGA    TATGACAAAA    ACCGAACCCC 11765 11770   11775 11780   11785 11790   11795 11800   11805 11810   11815 11820
              *             *             *             *             *             *
          TCTATACACC    CCCGCTTCCT    CATGTTATAG    GTGATGGTAT    AGCTTAGCCT    ATAGGTGTGG
          AGATATGTGG    GGGCGAAGGA    GTACAATATC    CACTACCATA    TCGAATCGGA    TATCCACACC 11825 11830   11835 11840   11845 11850   11855 11860   11865 11870   11875 11880
              *             *             *             *             *             *
          GTTATTGACC    ATTATTGACC    ACTCCCTAT     TGGTGACGAT    ACTTCCATT     ACTAATCCAT
          CAATAACTGG    TAATAACTGG    TGAGGGATA     ACCACTGCTA    TGAAAGGTAA    TGATTAGGTA 11885 11890   11895 11900   11905 11910   11915 11920   11925 11930   11935 11940
              *             *             *             *             *             *
          AACATGGCTC    TTTGCCACAA    CTCTCTTTAT    TGGCTATATG    CCAATACACT    GTCCTTCAGA
          TTGTACCGAG    AAACGGTGTT    GAGAGAAATA    ACCGATATAC    GGTTATGTGA    CAGGAAGTCT 11945 11950   11955 11960   11965 11970   11975 11980   11985 11990   11995 12000
              *             *             *             *             *             *
          GACTGACACG    GACTCTGTAT    TTTTACAGGA    TGGGGTCTCA    TTTATTATTT    ACAAATTCAC
          CTGACTGTGC    CTGAGACATA    AAAATGTCCT    ACCCCAGAGT    AAATAATAAA    TGTTTAAGTG 12005 12010   12015 12020   12025 12030   12035 12040   12045 12050   12055 12060
              *             *             *             *             *             *
          ATATACAACA    CCACCGTCCC    CAGTGCCCGC    AGTTTTTATT    AAACATAACG    TGGGATCTCC
          TATATGTTGT    GGTGGCAGGG    GTCACGGGCG    TCAAAAATAA    TTTGTATTGC    ACCCTAGAGG 12065 12070   12075 12080   12085 12090   12095 12100   12105 12110   12115 12120
              *             *             *             *             *             *
          ACGCGAATCT    CGGGTACGTG    TTCCGGACAT    GGGCTCTTCT    CCGGTAGCGG    CGGAGCTTCT
          TGCGCTTAGA    GCCCATGCAC    AAGGCCTGTA    CCCGAGAAGA    GGCCATCGCC    GCCTCGAAGA 12125 12130   12135 12140   12145 12150   12155 12160   12165 12170   12175 12180
              *             *             *             *             *             *
          ACATCCGAGC    CCTGCTCCCA    TGCCTCCAGC    GACTCATGGT    CGCTCGGCAG    CTCCTTGCTC
          TGTAGGCTCG    GGACGAGGGT    ACGGAGGTCG    CTGAGTACCA    GCGAGCCGTC    GAGGAACGAG 12185 12190   12195 12200   12205 12210   12215 12220   12225 12230   12235 12240
              *             *             *             *             *             *
          CTAACAGTGG    AGGCCAGACT    TAGGCACAGC    ACGATGCCCA    CCACCACCAG    TGTGCCGCAC
          GATTGTCACC    TCCGGTCTGA    ATCCGTGTCG    TGCTACGGGT    GGTGGTGGTC    ACACGGCGTG
```

FIG. 29Q

```
         1224512250  1225512260  1226512270  1227512280  1228512290  1229512300
                  *           *           *           *           *           *
         AAGGCCGTGG  CGGTAGGGTA  TGTGTCTGAA  AATGAGCTCG  GGGAGCGGGC  TTGCACCGCT
         TTCCGGCACC  GCCATCCCAT  ACACAGACTT  TTACTCGAGC  CCCTCGCCCG  AACGTGGCGA 1230512310  1231512320  1232512330  1233512340  1234512350  1235512360
                  *           *           *           *           *           *
         GACGCATTTG  GAAGACTTAA  GGCAGCGGCA  GAAGAAGATG  CAGGCAGCTG  AGTTGTTGTG
         CTGCGTAAAC  CTTCTGAATT  CCGTCGCCGT  CTTCTTCTAC  GTCCGTCGAC  TCAACAACAC 1236512370  1237512380  1238512390  1239512400  1240412410  1241512420
                  *           *           *           *           *           *
         TTCTGATAAG  AGTCAGAGGT  AACTCCCGTT  GCGGTGCTGT  TAACGGTGGA  GGGCAGTGTA
         AAGACTATTC  TCAGTCTCCA  TTGAGGGCAA  CGCCACGACA  ATTGCCACCT  CCCGTCACAT 1242512430  1243512440  1244512450  1245512460  1246512470  1247512480
                  *           *           *           *           *           *
         GTCTGAGCAG  TACTCGTTGC  TGCCGCGCGC  GCCACCAGAC  ATAATAGCTG  ACAGACTAAC
         CAGACTCGTC  ATGAGCAACG  ACGGCGCGCG  CGGTGGTCTG  TATTATCGAC  TGTCTGATTG 1248512490  1249512500  1250512510  1251512520  1252512530  1253512540
                  *           *           *           *           *           *
         AGACTGTTCC  TTTCCATGGG  TCTTTTCTGC  AGTCACCGTC  CTTGACACGA  AGCTTACCAT
         TCTGACAAGG  AAAGGTACCC  AGAAAAGACG  TCAGTGGCAG  GAACTGTGCT  TCGAATGGTA 1254512550  1255512560  1256512570  1257512580  1258512590  1259512600
                  *           *           *           *           *           *
         GGGTGTGCCC  ACTCAGGTCC  TGGGGTTGCT  GCTGCTGTGG  CTTACAGATG  CCAGATGTGA
         CCCACACGGG  TGAGTCCAGG  ACCCCAACGA  CGACGACACC  GAATGTCTAC  GGTCTACACT 1260512610  1261512620  1262512630  1263512640  1264512650  1265512660
                  *           *           *           *           *           *
         GATCGTTCTC  ACGCAGTCTC  CAGGCACCCT  GTCTCTGTCT  CCAGGGGAAA  GAGCCACCTT
         CTAGCAAGAG  TGCGTCAGAG  GTCCGTGGGA  CAGAGACAGA  GGTCCCCTTT  CTCGGTGGAA 1266512670  1267512680  1268512690  1269512700  1270512710  1271512720
                  *           *           *           *           *           *
         CTCCTGTAGG  TCCAGTCACA  GCATTCGCAG  CCGCCGCGTA  GCCTGGTACC  AGCACAAACC
         GAGGACATCC  AGGTCAGTGT  CGTAAGCGTC  GGCGGCGCAT  CGGACCATGG  TCGTGTTTGG 1272512730  1273512740  1274512750  1275512760  1276512770  1277512780
                  *           *           *           *           *           *
         TGGCCAGGCT  CCAAGGCTGG  TCATACATGG  TGTTTCCAAT  AGGGCCTCTG  GCATCTCAGA
         ACCGGTCCGA  GGTTCCGACC  AGTATGTACC  ACAAAGGTTA  TCCCGGAGAC  CGTAGAGTCT 1278512790  1279512800  1280512810  1281512820  1282512830  1283512840
                  *           *           *           *           *           *
         CAGGTTCAGC  GGCAGTGGGT  CTGGGACAGA  CTTCACTCTC  ACCATCACCA  GAGTGGAGCC
         GTCCAAGTCG  CCGTCACCCA  GACCCTGTCT  GAAGTGAGAG  TGGTAGTGGT  CTCACCTCGG 1284512850  1285512860  1286512870  1287512880  1288512890  1289512900
                  *           *           *           *           *           *
         TGAAGACTTT  GCACTGTACT  ACTGTCAGGT  CTATGGTGCC  TCCTCGTACA  CTTTTGGCCA
         ACTTCTGAAA  CGTGACATGA  TGACAGTCCA  GATACCACGG  AGGAGCATGT  GAAAACCGGT 1290512910  1291512920  1292512930  1293512940  1294512950  1295512960
                  *           *           *           *           *           *
         GGGGACCAAA  CTGGAGAGGA  AACGAACTGT  GCCTGCACCA  TCTGTCTTCA  TCTTCCCGCC
         CCCCTGGTTT  GACCTCTCCT  TTGCTTGACA  CGGACGTGGT  AGACAGAAGT  AGAAGGGCGG
```

FIG. 29R

```
     12965 12970  12975 12980  12985 12990  12995 13000  13005 13010  13015 13020
         *              *              *              *              *              *
     ATCTGATGAG CAGTTGAAAT CTGGGACTGC CTCTGTTGTG TGCCTGCTGA ATAACTTCTA
     TAGACTACTC GTCAACTTTA GACCCTGACG GAGACAACAC ACGGACGACT TATTGAAGAT 13025 13030  13035 13040  13045 13050  13055 13060  13065 13070  13075 13080
         *              *              *              *              *              *
     TCCCAGAGAG GCCAAAGTAC AGTGGAAGGT GGATAACGCC CTCCAATCGG GTAACTCCCA
     AGGGTCTCTC CGGTTTCATG TCACCTTCCA CCTATTGCGG GAGGTTAGCC CATTGAGGGT 13085 13090  13095 13100  13105 13110  13115 13120  13125 13130  13135 13140
         *              *              *              *              *              *
     GGAGAGTGTC ACAGAGCAGG ACAGCAAGGA CAGCACCTAC AGCCTCAGCA GCACCCTGAC
     CCTCTCACAG TGTCTCGTCC TGTCGTTCCT GTCGTGGATG TCGGAGTCGT CGTGGGACTG 13145 13150  13155 13160  13165 13170  13175 13180  13185 13190  13195 13200
         *              *              *              *              *              *
     GCTGAGCAAA GCAGACTACG AGAAACACAA AGTCTACGCC TGCGAAGTCA CCCATCAGGG
     CGACTCGTTT CGTCTGATGC TCTTTGTGTT TCAGATGCGG ACGCTTCAGT GGGTAGTCCC 13205 13210  13215 13220  13225 13230  13235 13240  13245 13250  13255
         *              *              *              *              *              *
     CCTGAGATCG CCCGTCACAA AGAGCTTCAA CAGGGGAGAG TGTTAATTCT AGAGAA
     GGACTCTAGC GGGCAGTGTT TCTCGAAGTT GTCCCCTCTC ACAATTAAGA TCTCTT
```

FIG. 29S

HUMAN NEUTRALIZING MONOCLONAL ANTIBODIES TO HUMAN IMMUNODEFICIENCY VIRUS

This is a divisional of application Ser. No. 08/276,852, filed Jul. 18, 1994, now U.S. Pat. No. 5,652,138, which is a continuation-in-part of application Ser. No. 08/178,302, filed Jan. 6, 1994, now abandoned, which is a U.S. national stage filing pursuant to 35 USC 371 based on PCT application Ser. No. US93/09328, filed Sep. 30, 1993, which is a continuation-in-part of application Ser. No. 07/954,148, filed Sep. 30, 1992, now abandoned, whose disclosures are incorporated herein by reference.

TECHNICAL FIELD

The present invention relates generally to the field of immunology and specifically to human monoclonal antibodies which bind and neutralize human immunodeficiency virus (HIV).

BACKGROUND

1. HIV Immunotherapy

HIV is the focus of intense studies as it is the causative agent for acquired immunodeficiency syndrome (AIDS). Immunotherapeutic methods are one of several approaches to prevention, cure or remediation of HIV infection and HIV-induced diseases. Specifically, the use of neutralizing antibodies in passive immunotherapies is of central importance to the present invention.

Passive immunization of HIV-1 infected humans using human sera containing polyclonal antibodies immunoreactive with HIV has been reported. See for example, Jackson et al., *Lancet*, September 17:647–652, (1988); Karpas et al., *Proc. Natl. Acad. Sci., USA*, 87:7613–7616 (1990).

Numerous groups have reported the preparation of human monoclonal antibodies that neutralize HIV isolates in vitro. The described antibodies typically have immunospecificities for epitopes on the HIV glycoprotein gp120 or the related external surface envelope glycoprotein gp120 or the transmembrane glycoprotein gp41. See, for example Levy, *Micro. Rev.*, 57:183–289 (1993); Karwowska et al., *Aids Research and Human Retroviruses*, 8:1099–1106 (1992); Takeda et al., *J. Clin. Invest.*, 89:1952–1957 (1992); Tilley et al., *Aids Research and Human Retroviruses*, 8:461–467 (1992); Laman et al., *J. Virol.*, 66:1823–1831 (1992); Thali et al., *J. Virol.*, 65:6188–6193 (1991); Ho et al., *Proc. Natl. Acad. Sci. USA*, 88:8949–8952 (1991); D'Souza et al., *AIDS*, 5:1061–1070 (1991); Tilley et al., *Res. Virol.*, 142:247–259 (1991); Broliden et al., *Immunol.*, 73:371–376. (1991); Matour et al., *J. Immunol.*, 146:4325–4332 (1991); and Gorny et al., *Proc. Natl. Acad. Sci., USA*, 88:3238–3242 (1991).

To date, none of the reported human monoclonal antibodies have been shown to be effective in passive immunization therapies. Further, as monoclonal antibodies, they all each react with an individual epitope on the HIV envelope glycoprotein, gp120 or gp160. The epitope against which an effective neutralizing antibody immunoreacts has not been identified.

There continues to be a need to develop human monoclonal antibody preparations with significant HIV neutralization activity. In addition, there is a need for monoclonal antibodies immunoreactive with additional and diverse neutralizing epitopes on HIV gp120 and gp41 in view of recent studies suggesting that gp120 and gp41 are involved in both binding of the HIV virus to the cell as well as in post binding events including envelope shedding and cleavage. See, for review, Levy, *Micro. Rev.*, 57:183–289 (1993). Additional (new) epitope specificities are required because, upon passive immunization, the administered patient can produce an immune response against the administered antibody, thereby inactivating the particular therapeutic antibody.

2. Human Monoclonal Antibodies Produced From Combinatorial Phagemid Libraries

The use of filamentous phage display vectors, referred to as phagemids, has been repeatedly shown to allow the efficient preparation of large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries. Kang et al., *Proc. Natl. Acad. Sci., USA*, 88:4363–4366 (1991). Combinatorial libraries of antibodies have been produced using both the cpVIII membrane anchor (Kang et al., supra) and the cpiii membrane anchor. Barbas et al., *Proc. Natl. Acad. Sci., USA*, 88:7978–7982 (1991).

The diversity of a filamentous phage-based combinatorial antibody library can be increased by shuffling of the heavy and light chain genes (Kang et al., *Proc. Natl. Acad. Sci., USA*, 88:11120–11123 (1991)), by altering the CDR3 regions of the cloned heavy chain genes of the library (Barbas et al., *Proc. Natl. Acad. Sci., USA*, 89:4457–4461 (1992)), and by introducing random mutations into the library by error-prone polymerase chain reactions (PCR) [Gram et al., *Proc. Natl. Acad. Sci., USA*, 89:3576–3580 (1992)].

Filamentous phage display vectors have also been utilized to produce human monoclonal antibodies immunoreactive with hepatitis B virus (HBV) or HIV antigens. See, for example Zebedee et al., *Proc. Natl. Acad. Sci., USA*, 89:3175–3179 (1992); and Burton et al., *Proc. Natl. Acad. Sci., USA*, 88:10134–10137 (1991), respectively. None of the previously described human monoclonal antibodies produced by phagemid vectors that are immunoreactive with HIV have been shown to neutralize HIV.

In particular, none of the previously-described human monoclonal antibodies produced by phagemid vectors are capable of neutralizing a majority of the field isolates of HIV. It is believed that certain of the antibodies described herein are particularly effective at neutralizing HIV because the antibodies immunoreact with an important antigenic determinant present on "mature" gp120 and not present on the HIV precursor protein gp160.

BRIEF DESCRIPTION OF THE INVENTION

Methods have now been discovered using the phagemid vectors to identify and isolate from combinatorial libraries human monoclonal antibodies that neutralize HIV, and allow the rapid preparation of large numbers of neutralizing antibodies of completely human derivation. The identified neutralizing antibodies define new epitopes on the HIV gp120 and gp41 glycoproteins, thereby increasing the availability of new immunotherapeutic human monoclonal antibodies.

The invention provides human monoclonal antibodies that neutralize HIV, and also provides cell lines used to produce these monoclonal antibodies.

Also provided are amino acid sequences which confer neutralization function to the antigen binding domain of a monoclonal antibody, and which can be used immunogenically to identify other antibodies that specifically bind and neutralize HIV. The monoclonal antibodies of the invention find particular utility as reagents for the diagnosis and immunotherapy of HIV-induced disease.

A major advantage of the monoclonal antibodies of the invention derives from the fact that they are encoded by a human polynucleotide sequence. Thus, in vivo use of the monoclonal antibodies of the invention for diagnosis and immunotherapy of HIV-induced disease greatly reduces the problems of significant host immune response to the passively administered antibodies which is a problem commonly encountered when monoclonal antibodies of xenogeneic or chimeric derivation are utilized.

An additional major advantage of a preferred group of monoclonal antibodies described herein derives from the fact that they immunoreact with a is unique determinant present on mature HIV glycoprotein gp120. This class of antibodies is particularly effective at neutralizing field isolates of HIV.

In one embodiment, the invention contemplates a human monoclonal antibody capable of immunoreacting with human immunodeficiency virus (HIV) glycoprotein gp120 and neutralizing HIV. A preferred human monoclonal antibody has the binding specificity of a monoclonal antibody comprising a heavy chain immunoglobulin variable region amino acid residue sequence selected from the group consisting of SEQ ID Nos 66, 67, 68, 70, 72, 73, 74, 75, 78 and 97.

In a particularly preferred embodiment, the invention describes a human monoclonal antibody capable of immunoreacting with human immunodeficiency virus (HIV) glycoprotein gp120 and neutralizing HIV, wherein the monoclonal antibody has the capacity to reduce HIV infectivity titer in an in vitro virus infectivity assay by 50% at a concentration of less than 700 nanograms (ng) of antibody per milliliter (ml).

Preferably, an anti-gp120 monoclonal antibody of this invention binds mature gp120 preferentially over HIV precursor glycoprotein gp160. More preferably, an anti-gp120 monoclonal antibody binds to a V1/V2 loop deficient-variant gp120 substantially less than native gp120, thereby defining a important epitope for the antibody. Human monoclonal antibodies having these properties are particularly useful at neutralizing field isolates, and therefore provide useful information regarding the immunocompetence of an immune response in HIV-infected patients.

Therefore, the invention provides for a screening method to determine whether HIV-infected patients contain antibodies of the class that neutralize field isolates. The method for determining immunocompetence of a human anti-human immunodeficiency virus (HIV) antibody in a sample comprises the steps of:

(1) contacting a sample believed to contain a human anti-HIV antibody with a diagnostically effective amount of the above-described anti-gp120 monoclonal antibody in a competition immunoreaction admixture containing mature gp120 in the solid phase;

(2) maintaining the competition immunoreaction admixture under conditions sufficient for the monoclonal antibody to bind with the gp120 in the solid phase and form a solid phase immunoreactant; and (3) detecting the amount of the immunoreactant present in the solid phase, and thereby the immunocompetence of any human anti-HIV antibody in the sample.

Another preferred human monoclonal antibody has the binding specificity of a monoclonal antibody comprising a light chain immunoglobulin variable region amino acid residue sequence selected from the group consisting of SEQ ID Nos 95, 96, 97, 98, 101, 102, 103, 104, 105, 107, 110, 115, 118, 121, 122, 124 and 132.

In a further embodiment, the invention contemplates a human monoclonal antibody capable of immunoreacting with human immunodeficiency virus (HIV) glycoprotein gp41 and neutralizing HIV. A preferred human monoclonal antibody has the binding specificity of a monoclonal antibody comprising a heavy chain immunoglobulin variable region amino acid residue sequence selected from the group consisting of SEQ ID Nos 142, 143, 144, 145 and 146. Another preferred human monoclonal antibody has the binding specificity of a monoclonal antibody comprising a light chain immunoglobulin variable region amino acid residue sequence selected from the group consisting of SEQ ID NOs 147, 148, 149, 150 and 151.

In another embodiment, the invention describes a polynucleotide sequence encoding a heavy or light chain immunoglobulin variable region amino acid residue sequence portion of a human monoclonal antibody of this invention. Also contemplated are DNA expression vectors containing the polynucleotide, and host cells containing the vectors and polynucleotides of the invention.

The invention also contemplates a method of detecting human immunodeficiency virus (HIV) comprising contacting a sample suspected of containing HIV with a diagnostically effective amount of the monoclonal antibody of this invention, and determining whether the monoclonal antibody immunoreacts with the sample. The method can be practiced in vitro or in vivo, and may include a variety of methods for determining the presence of an immunoreaction product.

In another embodiment, the invention describes a method for providing passive immunotherapy to human immunodeficiency virus (HIV) disease in a human, comprising administering to the human an immunotherapeutically effective amount of the monoclonal antibody of this invention. The administration can be provided prophylactically, and by a parenteral administration. Pharmaceutical compositions containing one or more of the different human monoclonal antibodies are described for use in the therapeutic methods of the invention.

BRIEF DESCRIPTION OF THE DRAWINGS

In the drawings forming a portion of this disclosure:

FIG. 1 illustrates the sequence of the double-stranded synthetic DNA inserted into Lambda Zap to produce a Lambda Hc2 expression vector. The preparation of the double-stranded synthetic DNA insert is described in Example 1a2). The various features required for this vector to express the $V_H$-coding DNA homologs include the Shine-Dalgarno ribosome binding site, a leader sequence to direct the expressed protein to the periplasm as described by Mouva et al., *J. Biol. Chem.*, 255:27, 1980, and various restriction enzyme sites used to operatively link the $V_H$ homologs to the expression vector. The $V_H$ expression vector sequence also contains a short nucleic acid sequence that codes for amino acids typically found in variable regions heavy chain ($V_H$ backbone). This $V_H$ backbone is just upstream and in the proper reading as the $V_H$ DNA homologs that are operatively linked into the Xho I and Spe I cloning sites. The sequences of the top and bottom strands of the double-stranded synthetic DNA insert are listed respectively in SEQ ID NO 1 and SEQ ID NO 2. The ten amino acid sequence comprising the decapeptide tag is listed in SEQ ID NO 5. The synthetic DNA insert is directionally ligated into Lambda Zap II digested with the restriction enzymes Not 1 and Xho I to form Lambda Hc2 expression vector.

FIG. 3 illustrates the sequence of the double-stranded synthetic DNA inserted into Lambda Zap to produce a Lambda Lc2 expression vector. The various features required for this vector to express the $V_L$-coding DNA homologs are described in FIG. 1. The $V_L$-coding DNA homologs are operatively linked into the Lc2 sequence at the Sac I and Xho I restriction sites. The sequences of the top and bottom strands of the double-stranded synthetic DNA insert are listed respectively in SEQ ID NO 3 and SEQ ID NO 4. The synthetic DNA insert is directionally ligated into Lambda Zap II digested with the restriction enzymes Sac I and Not I to form Lambda Lc2 expression vector.

FIG. 6 illustrates the neutralization of HIV-1 by recombinant Fabs. The same supernate preparations were used in p24 and syncytia assays. The figures indicate neutralization titers. Refer to Example 3 for details of the assay procedures and discussion of the results. The ELISA titers and Fab concentrations were determined as described in Example 2b.

FIG. 7 illustrates the relative affinities of Fab fragments for gp120 (IIIB) as illustrated by inhibition ELISA performed as described in Example 2b6). Fabs 27, 6, 29, 2 and 3 are all prototype members of the different groups discussed in Example 9a. Loop 2 is an Fab fragment selected from the same library as the other Fabs but which recognizes the V3 loop. The data is plotted as the percentage of maximum binding on the Y-axis against increasing concentrations ($10^{-11}$M to $10^{-1}$M) of soluble gp120 on the X-axis.

FIG. 8 illustrates the soluble CD4 competition with Fab fragments for gp120 (IIIB). P4D10 and loop2 are controls. P4D10 is a mouse monoclonal antibody reacting with the V3 loop of gp120 (IIIB). The data, discussed in Example 2b6), is plotted as described in FIG. 7.

FIG. 9 illustrates the neutralization of HIV by purified Fabs prepared as described in Example 3. The results shown are derived from the syncytia assay using the MN strain. The data is plotted as percent of inhibition of binding on the Y-axis against increasing Fab concentrations [0.1 to greater than 10 micrograms/milliliter ($\mu$g/ml)] on the X-axis.

FIG. 10 illustrates the amino acid residue sequences of variable heavy ($V_H$) domains of Fabs binding to gp120. Seven distinct groups have been identified as described in Example 9a based on sequence homology. Identity with the first sequence in a group is indicated by dots. The Fab clone names are indicated in the left hand column. The corresponding SEQ ID Nos are indicated in the right hand column. The sequenced regions from right to left are framework region 1 (FR1), complementary determining region 1 (CDR1), framework region 2 (FR2), complementary determining region 2 (CDR2), framework region 3 (FR3), complementary determining region 3 (CDR3), and framework region 4 (FR4). The five amino-terminal residue sequence beginning with LEQ arises from the VH1a while the 5 amino-terminal residue sequence beginning with LEE arises from the VH3a primers. The b11 and b29 sequences are very similar to the b3 group and could be argued to be intraclonal variants within that group; they are placed in their own group because of differences at the the V-D and D-J interface.

FIG. 11 illustrates the amino acid residue sequences of variable light ($V_L$) domains of Fabs binding to gp120. Refer to FIG. 10 for the description of the figure and to Example 9b for analysis of the sequences.

FIG. 12 illustrates the amino acid residue sequences of $V_L$ domains from Fabs binding to gp120 and generated by shuffling the heavy chain from clone b12 against a library of light chains (H12-LCn Fabs) as described in Example 10. Note that the new $V_L$ sequences have designated clone numbers that do not relate to those numbers from the original library. The unique sequences are listed in the Sequence Listing from SEQ ID NO 114 to 122. The new $V_L$ domain sequences are compared to that of the original clone b12 $V_L$ sequence.

FIG. 13 illustrates the amino acid residue sequences of $V_H$ domains from Fabs binding to gp120 and generated by shuffling the light chain from clone b12 against a library of heavy chains (L12-HCn Fabs) as described in Example 10. Note that the new $V_H$ sequences have designated clone numbers that do not relate to those numbers from the original library. The unique sequences are listed in the Sequence Listing from SEQ ID NO 123 to 132. The new $V_H$ domain sequences are compared to that of the original clone b12 $V_H$ sequence.

FIG. 14 illustrates, in two figures, FIGS. 14A and 14B, plasmid maps of the heavy (pTAC01H) and light chain (pTC01) replicon-compatible chain-shuffling vectors, respectively. Both plasmids are very similar in the section containing the promoter and the cloning site. Abbreviations: tacPO, tac promoter/operon; 5 histidine amino acid residue tag (histidine)5-tail; f1IG, intergenic region of f1-phage; stu, stuffer fragment ready for in-frame replacement by light and heavy chain, respectively; cat, chloramphenicol transferase gene; bla, b-lactamase gene; ori, origin of replication. The map is drawn approximately to scale.

FIG. 15 illustrates the nucleotide sequences of the binary shuffling vectors in two FIGS., 15A and 15B. The construction and use of the vectors is described in Example 11. In FIG. 15A, the double-stranded nucleotide sequence of the multiple cloning site in light chain vector, pTC01, is shown. The sequences of the top and bottom nucleotide base strands are listed respectively in SEQ ID NO 8 and SEQ ID NO 9. The amino acid residue sequence comprising the pelB leader ending in the Sac I restriction site is listed in SEQ ID NO 10. In FIG. 15B, the nucleotide sequence of the multiple cloning site in heavy chain vector, pTAC01H, is shown. The sequences of the top and bottom nucleotide base strands are listed respectively in SEQ ID NO 11 and SEQ ID NO 12. The amino acid residue sequence comprising the pelB leader ending in the Xho I restriction site is listed as SEQ ID NO 13. The amino acid residue sequence comprising the histidine tail is listed in SEQ ID NO 14. Relevant restriction sites are underlined. tac promoter and ribosome binding site (rbs) are indicated by boxes.

FIG. 16 illustrates the complete set of directed crosses between heavy and light chains of all Fab fragments isolated from the original library by panning with gp160 (IIIB) (b1–b27), gp120 (IIIB) (B8–B35), gp120 (SF2) (s4–s8), and the loop peptide (p35) assayed by ELISA against IIIB gp120 as described in Example 11. Heavy chains are listed horizontally and light chains are listed vertically. Clones are sorted according to the grouping established in Example 9. Different groups are separated by horizontal and vertical lines. A "–" at the intersection of a particular heavy chain and light chain signifies a clear negative (a signal of 3 times background or less) for that particular cross, a "+" shows a clear positive comparable to the original heavy and light chain combination, and a "w" denotes an intermediate value in the ELISA. "●": the HCp35/LCp35 combination is negative when gp120 (IIIB) is used, but positive when assayed with gp120 (IIIB). Identical chains carry the same identifier (either *, ¶, §, or ¥).

FIG. 18 illustrates the amino acid residue sequences of variable heavy ($V_H$) domains of Fabs binding to gp41. The Fab clone names are indicated in the left hand column. The heavy chain sequences of the five Fabs individually designated DL 41 19, DO 41 11, GL 41 1, MT 41 12 and SS 41 8 have been assigned the respective SEQ ID Nos 142, 143, 144, 145 and 146. The sequenced regions from right to left are framework region 1 (FR1), complementary determining region 1 (CDR1), framework region 2 (FR2)., complementary determining region 2 (CDR2), framework region 3 (FR3), complementary determining region 3 (CDR3), and framework region 4 (FR4).

FIG. 19 illustrates the amino acid residue sequences of variable light ($V_L$) domains of Fabs binding to gp41. Refer to FIG. 18 for the description of the figure. The light chain sequences of the five Fabs individually designated DL 41 19, DO 41 11, GL 41 1, MT 41 12 and SS 41 8 have been assigned the respective SEQ ID NOs 147, 148, 149, 150 and 151.

FIGS. 25A and 25B illustrate the nucleotide and amino acid residue sequences of the b12 light chain gene in the pSG-5 mammalian expression vector described in Example 4b. The b12 light chain has been modified for expression in mammalian cells as described in Example 4b.

FIGS. 27A through 27E illustrate the nucleotide sequences of the b12 heavy chain VH and constant regions in the pEe6HC BM12 mammalian expression vector as described Example 4d. The amino acid residue sequence of the b12 heavy chain VH is given. The b12 VH has been modified for expression in mammalian cells as described in Example 4d.

FIG. 29A through 29S illustrates the nucleotide sequence of the pEE12 mammalian expression vector and the b12 IgG1 heavy and light chain genes, pEe12 Combo BM 12, as described in Example 4f. The VH and light chain genes have been modified for expression in mammalian cells as described in Example 4.

DETAILED DESCRIPTION OF THE INVENTION

A. Definitions

Figure 2:
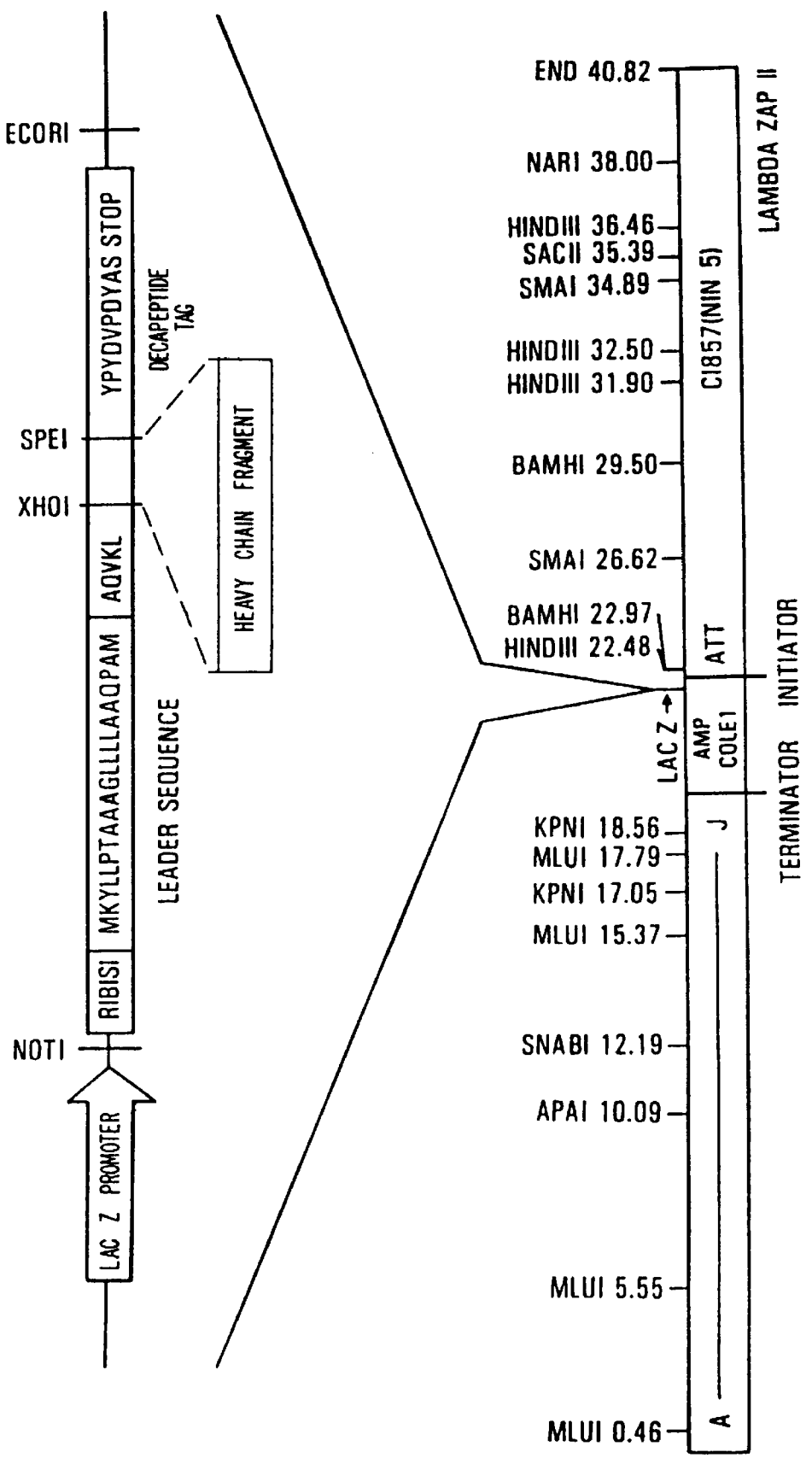
FIG. 2 illustrates the major features of the bacterial expression vector Lambda Hc2 ($V_H$ expression vector). The orientation of the insert in Lambda Zap II is shown. The $V_H$ DNA homologs are inserted into the Xho I and Spe I cloning sites. The read through transcription produces the decapeptide epitope (tag) that is located just 3' of the cloning site. The amino acid residue sequence of the decapeptide tag and the Pel B leader sequence/spacer are respectively listed in SEQ ID NO 5 and 6.

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature (described in *J. Biol. Chem.*, 243:3552–59 (1969) and adopted at 37 CFR §1.822(b)(2)), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left-to-right orientation in the conventional direction of amino terminus to carboxy terminus. In addition, the phrase "amino acid residue" is broadly defined to include the amino acids listed in the Table of Correspondence and modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Recombinant DNA (rDNA) molecule: A DNA molecule produced by operatively linking two DNA segments. Thus, a recombinant DNA molecule is a hybrid DNA molecule comprising at least two nucleotide sequences not normally found together in nature. RDNA'S not having a common biological origin, i.e., evolutionarily different, are said to be "heterologous".

Vector: A RDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors". Particularly important vectors allow cloning of cDNA (complementary DNA) from mRNAs produced using reverse transcriptase.

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')$_2$ and F(v).

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Although historically a monoclonal antibody was produced by immortalization of a clonally pure immunoglobulin secreting cell line, a monoclonally pure population of antibody molecules can also be prepared by the methods of the present invention.

Fusion Polypeptide: A polypeptide comprised of at least two polypeptides and a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Cistron: Sequence of nucleotides in a DNA molecule coding for an amino acid residue sequence and including upstream and downstream DNA expression control elements.

Leader Polypeptide: A short length of amino acid sequence at the amino end of a polypeptide, which carries or directs the polypeptide through the inner membrane and so ensures its eventual secretion into the periplasmic space and perhaps beyond. The leader sequence peptide is commonly removed before the polypeptide becomes active.

Reading Frame: Particular sequence of contiguous nucleotide triplets (codons) employed in translation. The reading frame depends on the location of the translation initiation codon.

B. Human Monoclonal Antibodies

The present invention relates to human monoclonal antibodies which are specific for, and neutralize human immunodeficiency virus (HIV). In a preferred embodiment of the invention, human monoclonal antibodies are disclosed which are capable of binding epitopic polypeptide sequences in glycoprotein gp120 of HIV. A further preferred embodiment are human monoclonal antibodies capable of binding epitopic polypeptide sequences in glycoprotein gp 41 of HIV. Also disclosed is an antibody having a specified amino acid sequence, which sequence confers the ability to bind a specific epitope and to neutralize HIV when the virus is bound by these antibodies. A human monoclonal antibody with a claimed specificity, and like human monoclonal antibodies with like specificity, are useful in the diagnosis and immunotherapy of HIV-induced disease.

The term "HIV-induced disease" means any disease caused, directly or indirectly, by HIV. An example of a HIV-induced disease is acquired autoimmunodeficiency syndrome (AIDS), and any of the numerous conditions associated generally with AIDS which are caused by HIV infection.

Thus, in one aspect, the present invention is directed to human monoclonal antibodies which are reactive with a HIV neutralization site and cell lines which produce such antibodies. The isolation of cell lines producing monoclonal antibodies of the invention is described in great detail further herein, and can be accomplished using the phagemid vector library methods described herein, and using routine screening techniques which permit determination of the elementary immunoreaction and neutralization patterns of the monoclonal antibody of interest. Thus, if human monoclonal antibody being tested binds and neutralizes HIV in a manner similar to a human monoclonal antibody produced by the cell lines of the invention then the tested antibody is considered equivalent to an antibody of the invention.

It is also possible to determine, without undue experimentation, if a human monoclonal antibody has the same (i.e., equivalent) specificity as a human monoclonal antibody of this invention by ascertaining whether the former prevents the latter from binding to HIV. If the human monoclonal antibody being tested competes with the human monoclonal antibody of the invention, as shown by a decrease in binding by the human monoclonal antibody of the invention in standard competition assays for binding to a solid phase antigen, for example to gp120, then it is likely that the two monoclonal antibodies bind to the same, or a closely related, epitope.

Still another way to determine whether a human monoclonal antibody has the specificity of a human monoclonal antibody of the invention is to pre-incubate the human monoclonal antibody of the invention with HIV with which it is normally reactive, and then add the human monoclonal antibody being tested to determine if the human monoclonal antibody being tested is inhibited in its ability to bind HIV. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out utilizing HIV neutralization assays and determining whether the monoclonal antibody neutralizes HIV.

The ability to neutralize HIV at one or more stages of virus infection is a desirable quality of a human monoclonal antibody of the present invention. Virus neutralization can be measured by a variety of in vitro and in vivo methodologies. Exemplary methods described herein for determining the capacity for neutralization are the in vitro assays that measure inhibition of HIV-induced syncytia formation, plaque assays and assays that measure the inhibition of output of core p24 antigen from a cell infected with HIV.

As shown herein, the immunospecificity of a human monoclonal antibody of this invention can be directed to epitopes that are shared across serotypes and/or strains of HIV, or can be specific for a single strain of HIV, depending upon the epitope. Thus, a preferred human monoclonal antibody can immunoreact with HIV-1, HIV-2, or both, and can immunoreact with one or more of the HIV-1 strains IIIB, MN, RF, SF-2, Z2, Z6, CDC4, ELI and the like strains. In addition, a preferred human monoclonal antibody can immunoreact and neutralize a majority of field isolates of HIV, as described further herein.

The immunospecificity of an antibody, its HIV-neutralizing capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin the antibody, and in part by the light chain variable region amino acid residue sequence. Preferred human monoclonal antibodies immunoreact with the CD4 binding site of glycoprotein gp120.

Also disclosed is an antibody having a specified amino acid sequence, which sequence confers the ability to bind a specific unique neutralizing epitope and to neutralize HIV when the virus is bound by these antibodies.

A preferred human monoclonal antibody of this invention has the binding specificity of a monoclonal antibody comprising a heavy chain immunoglobulin variable region amino acid residue sequence selected from the group of sequences consisting of SEQ ID NOs 66, 67, 68, 70, 72, 73, 74, 75, 78 and 97, and conservative substitutions thereof.

Another preferred human monoclonal antibody of this invention has the binding specificity of a monoclonal antibody having a light chain immunoglobulin variable region amino acid residue sequence selected from the group of sequences consisting of SEQ ID NOs 95, 96, 97, 98, 101, 102, 103, 104, 105, 107, 110, 115, 118, 121, 122, 124 and 132, and conservative substitutions thereof.

In a preferred embodiment, a monoclonal antibodies of this invention exhibits a potent capacity to neutralize HIV. The capacity to neutralize HIV is expressed as a concentration of antibody molecules required to reduce the infectivity titer of a suspension of HIV when assayed in an typical in vitro infectivity assay, such as is described herein. A monoclonal antibody of this invention has the capacity to reduce HIV infectivity titer in an in vitro virus infectivity assay by 50% at a concentration of less than 700 nanograms (ng) of antibody per milliliter (ml) of culture medium in the assay, and preferably reduces infectivity titers 50% at a concentration of less than 300 ng/ml, and more preferably at concentrations less than about 10 ng/ml.

Exemplary and preferred monoclonal antibodies described herein are effective at 3–700 ng/ml, and therefore are particularly well suited for inhibiting HIV in vitro and in vivo.

Particularly preferred human monoclonal antibodies of this invention immunoreact with gp120 in its "mature" form, which form is to be distinguished from antigenic determinants present on the HIV envelope precursor glycoprotein designated gp160. gp160 is processed during virus biogenesis by cleavage into two polypeptides, gp41 and gp120. "Mature" gp120 refers to the processed protein that is found in mature HIV virus particles, and can be detected on the surface of HIV-infected cells.

Thus, a preferred antibody of this invention binds mature gp120 preferentially over HIV precursor glycoprotein gp160. By "binds preferentially" is meant that the antibody immunoreacts with (binds) substantially more mature gp120 than gp160 in an immunoreaction admixture. Substantially more typically indicates that at least greater than 50% of the total mass of immunoprecipitated material is gp120, and preferably indicates that at least greater than 75%, more preferably 90%, of the immunoprecipitated material is gp120.

Methods for determining immunoreaction of a subject antibody with gp120 or gp160 are well known in the art, and the invention need not be so limited. However, preferred methods for determining the relative amounts of envelope glycoprotein antigens are described in the Examples, and include radio-immunoprecipitation (RIP) of cell-surface labeled HIV-infected cells, followed by molecular weight analysis of the labeled products by polyacrylamide gel electrophoresis (PAGE).

A preferred human monoclonal antibody also has the ability to immunoreact with native gp120 and comparatively bind substantially less of a variant gp120 produced by recombinant DNA methods in which the V1 and V2 loops have been deleted. The variant gp120, also referred to a V1/V2 loop deficient-variant gp120, is described in the Examples, and is seen to bind substantially less of a preferred antibody, b12, in comparison to native gp120. The term "native gp120" refers to a mature gp120 protein having a normal amino acid residue sequence instead of a variant protein having selected amino acid residue substitutions or deletions, such as the V1/V2 loop deficient-variant in which the V1 and V2 loops were deleted. This preferential binding with native gp120 compared to the V1/V2 loop deficient-variant identifies an important epitope defined by a preferred antibody of this invention. Antibodies having this binding epitope are particularly effective at neutralizing a majority of field isolates of HIV, as described herein.

The ability to bind "substantially less" V1/V2 loop deficient-variant gp120 than native gp120 can be readily measured using various immunoreaction detection methods, although the assay methods described in Example 5c are particularly preferred. In preferred embodiments, substantially less binding to V1/V2 loop deficient-variant gp120 compared to native gp120 is indicated when the comparison is conducted as described as in Example 5c, and the native gp120 exhibits a ratio value deviating from the mean of greater than 2.0 and the variant exhibits a ratio value deviating from the mean of less than 0.5.

A particularly preferred human monoclonal antibody of this invention also has the capacity to neutralize a majority of field isolates as disclosed herein. As is well understood, the field (i.e., clinically isolated) strains of HIV are typically different to some degree antigenically from laboratory strains. Therefor, it is well understood that useful neutralizing antibodies must immunoreact with, and be neutralizing against, field isolates of HIV. Preferably, the useful antibody neutralized a large percentage of field isolates, thereby increasing its effectiveness when new strains are encountered.

The Examples demonstrate that the human monoclonal antibody b12 has the ability to neutralize a majority of the field isolates tested. By majority is meant that in a representative and diverse collection of field isolates, the antibody is capable of neutralizing at least 50% of the strains, and preferably at least 75% of the strains tested. In this context, "neutralizing" means an effect of reducing the HIV infectivity titre in an in vitro virus infectivity assay as described herein at the antibody concentrations described.

Thus, the invention also contemplates a human monoclonal antibody capable of immunoreacting with and neutralizing a first preselected human immunodeficiency virus (HIV), such as the laboratory isolate MN or IIIB, that is further capable of immunoreacting with and neutralizing one or more other (i.e., second) strains of HIV, particularly field strains. In this embodiment, supported by the teachings of the Examples, the antibody has the capacity to reduce HIV infectivity titer in an in vitro virus infectivity assay of the first HIV strain by 50% at a concentration of at least less than 700 nanograms (ng) of antibody per milliliter (ml), and has the capacity to reduce HIV infectivity titer of a second field strain of HIV in the same in vitro virus infectivity assay by 50% at a concentration of less than about 700 nanograms (ng) of antibody per milliliter (ml). In more preferred embodiments and depending upon the particular HIV strain, the capacity to reduce second field strain infectivity titers by 50% can be exhibited at lower antibody concentrations, such as below 300 ng/ml.

A particularly preferred antibody is an antibody having the binding specificity of the b12 monoclonal antibody described herein. The amino acid residue sequence of the heavy chain variable region of b12 is shown in SEQ ID NO 66, and the light chain variable region sequence of b12 is shown in SEQ ID NO 97. Still more preferred are human antibodies having the binding specificity of the immunoglobulin heavy and light chain polypeptides produced by ATCC 69079.

Further preferred human monoclonal antibodies immunoreact with the CD4 binding site of glycoprotein gp41. A preferred human monoclonal antibody of this invention has the binding specificity of a monoclonal antibody comprising a heavy chain immunoglobulin variable region amino acid residue sequence selected from the group of sequences consisting of SEQ ID NOs 142, 143, 144, 145, and 146 and conservative substitutions thereof.

Another preferred human monoclonal antibody of this invention has the gp41 binding specificity of a monoclonal antibody having a light chain immunoglobulin variable region amino acid residue sequence selected from the group of sequences consisting of SEQ ID NOs 147, 148, 149, 150, and 151 and conservative substitutions thereof.

As shown by the present teachings and using the combinatorial library shuffling and screening methods, one can identify new heavy and light chain pairs (H:L) that function as a HIV-neutralizing monoclonal antibody. In particular, one can shuffle a known heavy chain, derived from an HIV-neutralizing human monoclonal antibody, with a library of light chains to identify new H:L pairs that form a functional antibody according to the present invention. Similarly, one can shuffle a known light chain, derived from an HIV-neutralizing human monoclonal antibody, with a library of heavy chains to identify new H:L pairs that form a functional antibody according to the present invention.

Particularly preferred human monoclonal antibodies are those having the gp120 immunoreaction (binding) specificity of a monoclonal antibody having heavy and light chain immunoglobulin variable region amino acid residue sequences in pairs (H:L) selected from the group consisting of SEQ ID NOs 66:95, 67:96, 72:102, 66:97, 73:107, 74:103, 70:101, 68:98, 75:104, 72:105, 78:110, 66:118, 66:122, 66:121, 66:115, 97:124, 97:132 and 66:98, and conservative substitutions thereof. The designation of two SEQ ID NOs with a colon, e.g., 66:95, is to connote a H:L pair formed by the heavy and light chain, respectively, amino acid residue sequences shown in SEQ ID NO 66 and SEQ ID NO 95, respectively.

Further preferred human monoclonal antibodies are those having the gp41 immunoreaction (binding) specificity of a monoclonal antibody having heavy and light chain immunoglobulin variable region amino acid residue sequences in pairs (H:L) selected from the group consisting of SEQ ID NOs 142:147, 143:148, 144:149, 145:150, and 146:151, and conservative substitutions thereof.

Particularly preferred are human monoclonal antibodies having the binding specificity of the monoclonal antibody produced by the *E. coli* microorganisms deposited with the ATCC, as described further herein.

Particularly preferred are human monoclonal antibodies having the binding specificity of the monoclonal antibodies produced by the *E. coli* microorganisms designated ATCC 69078, 69079 and 69080. By "having the binding specificity" is meant equivalent monoclonal antibodies which exhibit the same or similar immunoreaction and neutralization properties, and which compete for binding to an HIV antigen. Preferred are the human monoclonal antibodies produced by ATCC 69078, 69079 and 69080.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also neutralize HIV. Analogously, another preferred embodiment of the invention relates to polynucleotides which encode the above noted heavy and/or light chain polypeptides and to polynucleotide sequences which are complementary to these polynucleotide sequences. Complementary polynucleotide sequences include those sequences which hybridize to the polynucleotide sequences of the invention under stringent hybridization conditions.

By using the human monoclonal antibodies of the invention, it is now possible to produce anti-idiotypic antibodies which can be used to screen human monoclonal antibodies to identify whether the antibody has the same binding specificity as a human monoclonal antibody of the invention and also used for active immunization (Herlyn et al., *Science*, 232:100 (1986)). Such anti-idiotypic antibodies can be produced using well-known hybridoma techniques (Kohler et al., *Nature*, 256:495 (1975)). An anti-idiotypic antibody is an antibody which recognizes unique determinants present on the human monoclonal antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the human monoclonal antibody of the invention produced by a cell line which was used to immunize the second animal, it is now possible to identify other clones with the same idiotype as the antibody of the hybridoma used for immunization. Idiotypic identity between human monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody can be used for immunization, since the anti-idiotype monoclonal antibody binding domain effectively acts as an antigen.

In one preferred embodiment, the invention contemplates a truncated immunoglobulin molecule comprising a Fab fragment derived from a human monoclonal antibody of this invention. The Fab fragment, lacking Fc receptor, is soluble, and affords therapeutic advantages in serum half life, and diagnostic advantages in modes of using the soluble Fab fragment. The preparation of a soluble Fab fragment is generally known in the immunological arts and can be accomplished by a variety of methods. A preferred method of producing a soluble Fab fragment is described herein.

In another preferred embodiment, the invention contemplates an immunoglobulin molecule comprising a Fab fragment derived from a human monoclonal antibody of this invention and the fragment crystallizable (Fc) domain of a human immunoglobulin molecule. The entire (i.e., complete) immunoglobulin (Ig) molecule comprising a Fab fragment with the Fc domain may afford therapeutic and diagnostic advantages, and can be any of the several Ig species depending upon the ultimate use, including IgG, IgA, IgD, IgE, IgM, and isotypes thereof. The immunoglobulin molecule would be capable of effector functions associated with the Fc domain when used in passive immunotherapy. These effector functions include antibody-dependent cellular cytotoxicity (ADCC) and complement-dependent cellular cytotoxicity (CDCC) which promote the death of the cell to which the immunoglobulin molecule is specifically bound. The effector functions may therefore be desirable in therapeutic applications. Diagnostic assays include the ability to detect the presence of the immunoglobulin molecule. These assays rely on the cross-linking of red cells or beads in agglutinations, the activation of complement in plaque assays, or the antigenic properties of the Fc region of the heavy chain as detected by secondary antibodies in ELISA or RIA procedures to detect the presence of the immunoglobulin molecule. Such diagnostic assays can only be performed with the entire immunoglobulin molecule. The isolation of the immunoglobulin molecule is also facilitated by the presence of the Fc domain in that commonly used methods of immunoglobulin purification are based upon interaction of reagents with the Fc domain. The preparation of a Fab fragment with the Fc domain is generally known in the immunological arts and can be accomplished by a variety of methods. A preferred method of producing a Fab fragment with the Fc domain is described herein.

Particularly preferred is the immunoglobulin IgG1 human antibody described herein that is comprised of the b12 antibody Fab fragment and human Fc domain derived from an IgG1 subtype, designated b12 IgG1. The structure and preparation of this preferred human monoclonal antibody is described herein, and is prepared using the recombinant DNA expression vector pEE12. The complete nucleotide sequence of the vector for expression the complete heavy and light chains in the form of b12 IgG1 is shown in FIG. 27 and also in SEQ ID NOS 156 and 170. Accordingly, the amino acid residue and nucleotide sequences, respectively, for a preferred complete heavy chain are shown in SEQ ID NOs 155 and 154, respectively, and for a preferred light chain are shown in SEQ ID NOs 153, and 152, respectively. The nucleotide sequences for preferred heavy and light chains are also shown in SEQ ID NOs 169 and 168, respectively.

C. Immunotherapeutic Methods and Compositions

The human monoclonal antibodies can also be used immunotherapeutically for HIV disease. The term "immunotherapeutically" or "immunotherapy" as used herein in conjunction with the monoclonal antibodies of the invention denotes both prophylactic as well as therapeutic administration. Thus, the monoclonal antibodies can be administered to high-risk patients in order to lessen the likelihood and/or severity of HIV-induced disease, administered to patients already evidencing active HIV infection, or administered to patients at risk of HIV infection.

1. Therapeutic Compositions

The present invention therefore contemplates therapeutic compositions useful for practicing the therapeutic methods described herein. Therapeutic compositions of the present invention contain a physiologically tolerable carrier together with at least one species of human monoclonal antibody as described herein, dissolved or dispersed therein as an active ingredient. In a preferred embodiment, the therapeutic composition is not immunogenic when administered to a human patient for therapeutic purposes, unless that purpose is to induce an immune response, as described elsewhere herein.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like.

The preparation of a pharmacological composition that contains active ingredients dissolved or dispersed therein is well understood in the art. Typically such compositions are prepared as sterile injectables either as liquid solutions or suspensions, aqueous or non-aqueous, however, solid forms suitable for solution, or suspensions, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains an HIV-neutralizing of a human monoclonal antibody of the present invention, typically an amount of at least 0.1 weight percent of antibody per weight of total therapeutic composition. A weight percent is a ratio by weight of antibody to total composition. Thus, for example, 0.1 weight percent is 0.1 grams of antibody per 100 grams of total composition.

2. Therapeutic Methods

In view of the demonstrated HIV neutralizing ability of the human monoclonal antibodies of the present invention, the present disclosure provides for a method for neutralizing HIV in vitro or in vivo. The method comprises contacting a sample believed to contain HIV with a composition comprising a therapeutically effective amount of a human monoclonal antibody of this invention.

For in vivo modalities, the method comprises administering to the patient a therapeutically effective amount of a physiologically tolerable composition containing a human monoclonal antibody of the invention. Thus, the present invention describes in one embodiment a method for providing passive immunotherapy to HIV disease in a human comprising administering to the human an immunotherapeutically effective amount of the monoclonal antibody of this invention.

A representative patient for practicing the present passive immunotherapeutic methods is any human exhibiting symptoms of HIV-induced disease, including AIDS or related conditions believed to be caused by HIV infection, and humans at risk of HIV infection. Patients at risk of infection by HIV include babies of HIV-infected pregnant mothers, recipients of transfusions known to contain HIV, users of HIV contaminated needles, individuals who have participated in high risk sexual activities with known HIV-infected individuals, and the like risk situations.

In one embodiment, the passive immunization method comprises administering a composition comprising more than one species of human monoclonal antibody of this invention, preferably directed to non-competing epitopes or directed to distinct serotypes or strains of HIV, as to afford increased effectiveness of the passive immunotherapy.

A therapeutically (immunotherapeutically) effective amount of a human monoclonal antibody is a predetermined amount calculated to achieve the desired effect, i.e., to neutralize the HIV present in the sample or in the patient, and thereby decrease the amount of detectable HIV in the sample or patient. In the case of in vivo therapies, an effective amount can be measured by improvements in one or more symptoms associated with HIV-induced disease occurring in the patient, or by serological decreases in HIV antigens.

Thus, the dosage ranges for the administration of the monoclonal antibodies of the invention are those large enough to produce the desired effect in which the symptoms of the HIV disease are ameliorated or the likelihood of infection decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art.

The dosage can be adjusted by the individual physician in the event of any complication.

A therapeutically effective amount of an antibody of this invention is typically an amount of antibody such that when administered in a physiologically tolerable composition is sufficient to achieve a plasma concentration of from about 0.1 microgram (ug) per milliliter (ml) to about 100 ug/ml, preferably from about 1 ug/ml to about 5 ug/ml, and usually about 5 ug/ml. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

The human monoclonal antibodies of the invention can be administered parenterally by injection or by gradual infusion over time. Although the HIV infection is typically systemic and therefore most often treated by intravenous administration of therapeutic compositions, other tissues and delivery means are contemplated where there is a likelihood that the tissue targeted contains infectious HIV. Thus, human monoclonal antibodies of the invention can be administered intravenously, intraperitoneally, intramuscularly, subcutaneously, intracavity, transdermally, and can be delivered by peristaltic means.

The therapeutic compositions containing a human monoclonal antibody of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As an aid to the administration of effective amounts of a monoclonal antibody, a diagnostic method for detecting a monoclonal antibody in the subject's blood is useful to characterize the fate of the administered therapeutic composition.

The invention also relates to a method for preparing a medicament or pharmaceutical composition comprising the human monoclonal antibodies of the invention, the medicament being used for immunotherapy of HIV disease.

D. Diagnostic Assay Methods

The present invention contemplates various assay methods for determining the presence, and preferably amount, of HIV in a sample such as a biological fluid or tissue sample using a human monoclonal antibody of this invention as an immunochemical reagent to form an immunoreaction product whose amount relates, either directly or indirectly, to the amount of HIV in the sample.

In a related embodiment, the present invention contemplates various assay methods for determining the presence, and preferably amount, of an anti-HIV antibody present in a sample such as a biological fluid or tissue sample from a HIV-infected individual using a human monoclonal antibody of this invention as an immunochemical reagent to form an immunoreaction product whose amount relates, either directly or indirectly, to the amount of anti-HIV antibody in the sample.

Those skilled in the art will understand that there are numerous well known clinical diagnostic chemistry procedures in which an immunochemical reagent of this invention can be used to form an immunoreaction product whose amount relates to the amount of HIV or anti-HIV antibody present in a body sample. Thus, while exemplary assay methods are described herein, the invention is not so limited.

Various heterogenous and homogeneous protocols, either competitive or noncompetitive, can be employed in performing an assay method of this invention. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay.

Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of HIV. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

For purposes of the invention, HIV may be detected by the monoclonal antibodies of the invention when present in samples of biological fluids and tissues. Any sample containing a detectable amount of HIV can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

The monoclonal antibodies of the invention are suited for use in vitro, for example, in immunoassays in which they can be utilized in liquid phase or bound to a solid phase carrier for the detection of HIV in samples, as described above. The monoclonal antibodies in these immunoassays can be detectably labeled in various ways for in vitro use.

In using the human monoclonal antibodies of the invention for the in vivo detection of antigen, the detectably labeled human monoclonal antibody is given in a dose which is diagnostically effective. The term "diagnostically effective" means that the amount of detectably labeled human monoclonal antibody is administered in sufficient quantity to enable detection of the site having the HIV antigen for which the monoclonal antibodies are specific.

The concentration of detectably labeled human monoclonal antibody which is administered should be sufficient such that the binding to HIV is detectable compared to the background. Further, it is desirable that the detectably labeled monoclonal antibody be rapidly cleared from the circulatory system in order to give the best target-to-background signal ratio.

As a rule, the dosage of detectably labeled human monoclonal antibody for in vivo diagnosis will vary depending on such factors as age, sex, and extent of disease of the individual. The dosage of human monoclonal antibody can vary from about 0.01 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tissue, and other factors known to those of skill in the art.

For in vivo diagnostic imaging, the type of detection instrument available is a major factor in selecting a given radioisotope. The radioisotope chosen must have a type or decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The human monoclonal antibodies of the invention can be used in vitro and in vivo to monitor the course of HIV disease therapy. Thus, for example, by measuring the increase or decrease in the number of cells infected with HIV or changes in the concentration of HIV present in the body or in various body fluids, it would be possible to determine whether a particular therapeutic regimen aimed at ameliorating the HIV disease is effective.

In a related diagnostic embodiment, the invention contemplates screening HIV-infected patients for the presence of circulating anti-HIV antibodies immunoreactive with gp120 that have a similar epitope immunospecificity when compared to a neutralizing antibody of this invention. Such a screening method indicates that the HIV-infected patient is exhibiting a significant immune response to the virus, and provides useful information regarding disease status and prognosis. The presence of anti-HIV antibodies cross-reactive with a neutralizing antibody of this invention indicates that the patient has some degree of HIV neutralizing activity, as defined herein.

The diagnostic assay involves determining whether the patient contains human anti-HIV antibodies immunoreactive with the same, similar or overlapping epitopes as a neutralizing antibody of the invention, such that there is a likelihood that there is a useful neutralizing immune response in the patient. There are a variety of immunological assay formats that can be utilized to determine cross-reactivity of test and control antibodies, and the invention need not be so limiting. Particularly preferred are competition assays for a common antigen, preferably in the solid phase.

A preferred embodiment of the competition immunoassay method comprises the steps of:

(1) contacting a sample believed to contain a human anti-HIV antibody with a diagnostically effective amount of the monoclonal antibody described herein that binds mature gp120 in a competition immunoreaction admixture containing mature gp120 in the solid phase;

(2) maintaining said competition immunoreaction admixture under conditions sufficient for said monoclonal antibody to bind with said gp120 in the solid phase and form a solid phase immunoreactant; and (3) detecting the amount of said immunoreactant present in said solid phase, and thereby the immunocompetence of any human anti-HIV antibody in said sample.

A diagnostically effective amount, in this context, is a amount relative to the solid phase gp120, preferably "mature" gp120 as defined herein, sufficient to produce a detectable solid phase immunoreaction product between the solid phase gp120 and the control anti-gp120 antibody of this invention. Exemplary competition assays are described herein using the preferred b12 antibody.

Conditions for conducting the competition immunoreaction are well known in the art and can be varied according to recognized parameters in the contacting, the reaction admixtures, the maintenance step, the immunoreaction conditions and the detecting step. For example, the detection step can be conducted by use of a labeled antibody of this invention, by use of a second, labeled anti-human antibody, and the like, as described herein.

E. Diagnostic Systems

The present invention also describes a diagnostic system, preferably in kit form, for assaying for the presence of HIV or an anti-HIV antibody in a sample according to the diagnostic methods described herein. A diagnostic system includes, in an amount sufficient to perform at least one assay, a subject human monoclonal antibody, as a separately packaged reagent.

In another embodiment, a diagnostic system is contemplated for assaying for the presence of an anti-HIV monoclonal antibody in a body fluid sample such as for monitoring the fate of therapeutically administered antibody. The system includes, in an amount sufficient for at least one assay, a subject antibody as a control reagent, and preferably a preselected amount of HIV antigen, each as separately packaged immunochemical reagents.

Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In embodiments for detecting HIV or anti-HIV antibody in a body fluid, a diagnostic system of the present invention can include a label or indicating means capable of signaling the formation of an immunocomplex containing a human monoclonal antibody of the present invention.

The word "complex" as used herein refers to the product of a specific binding reaction such as an antibody-antigen reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}$I, $^{125}$I, $^{128}$I, $^{132}$I and $^{51}$Cr represent one class of gamma ray emission-producing radioactive element indicating groups. Particularly preferred is $^{125}$I. Another group of useful labeling means are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such $^{111}$ indium of $^{3}$H.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of an antigen or antibody of this invention in a vascular fluid sample such as blood, serum, or plasma. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, in some embodiments, a human monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems.

The term "package" refers to a solid matrix or material such as glass, plastic (e.g., polyethylene, polypropylene and polycarbonate), paper, foil and the like capable of holding within fixed limits a diagnostic reagent such as a monoclonal antibody of the present invention. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by an antibody or polypeptide to be detected.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a human monoclonal antibody of the invention which is, or can be, detectably labelled. The kit may also have containers containing any of the other above-recited immunochemical reagents used to practice the diagnostic methods.

F. Methods for Producing an HIV-Neutralizing Human Monoclonal Antibody

The present invention describes methods for producing novel HIV-neutralizing human monoclonal antibodies. The methods are based generally on the use of combinatorial libraries of antibody molecules which can be produced from a variety of sources, and include naive libraries, modified libraries, and libraries produced directly from human donors exhibiting an HIV-specific immune response.

The combinatorial library production and manipulation methods have been extensively described in the literature, and will not be reviewed in detail herein, except for those feature required to make and use unique embodiments of the present invention. However, the methods generally involve the use of a filamentous phage (phagemid) surface expression vector system for cloning and expressing antibody species of the library. Various phagemid cloning systems to produce combinatorial libraries have been described by others. See, for example the preparation of combinatorial antibody libraries on phagemids as described by Kang et al., *Proc. Natl. Acad. Sci., USA*, 88:4363–4366 (1991); Barbas et al., *Proc. Natl. Acad. Sci., USA*, 88:7978–7982 (1991); Zebedee et al., *Proc. Natl. Acad. Sci., USA*, 89:3175–3179 (1992); Kang et al., *Proc. Natl. Acad. Sci., USA*, 88:11120–11123 (1991); Barbas et al., *Proc. Natl. Acad. Sci., USA*, 89:4457–4461 (1992); and Gram et al., *Proc. Natl. Acad. Sci., USA*, 89:3576–3580 (1992), which references are hereby incorporated by reference.

In one embodiment, the method involves preparing a phagemid library of human monoclonal antibodies by using donor immune cell messenger RNA from HIV-infected donors. The donors can be symptomatic of AIDS, but in preferred embodiments the donor is asymptomatic, as the resulting library contains a substantially higher number of HIV-neutralizing human monoclonal antibodies.

In another embodiment, the donor is naive relative to an immune response to HIV, i.e., the donor is not HIV-infected. Alternatively, the library can be synthetic, or can be derived from a donor who has an immune response to other antigens.

The method for producing a human monoclonal antibody generally involves (1) preparing separate H and L chain-encoding gene libraries in cloning vectors using human immunoglobulin genes as a source for the libraries, (2) combining the H and L chain encoding gene libraries into a single dicistronic expression vector capable of expressing and assembling a heterodimeric antibody molecule, (3) expressing the assembled heterodimeric antibody molecule on the surface of a filamentous phage particle, (4) isolating the surface-expressed phage particle using immunoaffinity techniques such as panning of phage particles against a preselected antigen, thereby isolating one or more species of phagemid containing particular H and L chain-encoding genes and antibody molecules that immunoreact with the preselected antigen.

As described herein the Examples, the resulting phagemid library can be manipulated to increase and/or alter the immunospecificities of the monoclonal antibodies of the library to produce and subsequently identify additional, desirable, human monoclonal antibodies of the present invention.

For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in the complementarity determining region (CDR) of the variable region of the immunoglobulin polypeptide, and subsequently screened for desirable immunoreaction and neutralization capabilities.

In one embodiment, the H and L genes can be cloned into separate, monocistronic expression vectors, referred to as a "binary" system described is further herein. In this method, step (2) above differs in that the combining of H and L chain encoding genes occurs by the co-introduction of the two binary plasmids into a single host cell for expression and assembly of a phagemid having the surface accessible antibody heterodimer molecule.

In one shuffling embodiment, the shuffling can be accomplished with the binary expression vectors, each capable of expressing a single heavy or light chain encoding gene, as described in Example 11.

In the present methods, the antibody molecules are monoclonal because the cloning methods allow for the preparation of clonally pure species of antibody producing cell lines. In addition, the monoclonal antibodies are human because the H and L chain encoding genes are derived from human immunoglobulin producing immune cells, such as spleen, thymus, bone marrow, and the like.

The method of producing a HIV-neutralizing human monoclonal antibody also requires that the resulting antibody library, immunoreactive with a preselected HIV antigen, is screened for the presence of antibody species which have the capacity to neutralize HIV in one or more of the assays described herein for determining neutralization capacity. Thus, a preferred library of antibody molecules is first produced which binds to an HIV antigen, preferably gp160, gp120, gp41, the V3 loop region of gp160, or the CD4 binding site of gp120 and gp41, and then is screened for the presence of HIV-neutralizing antibodies as described herein.

Additional libraries can be screened from shuffled libraries for additional HIV-immunoreactive and neutralizing human monoclonal antibodies.

As a further characterization of the present invention the nucleotide and corresponding amino acid residue sequence of the antibody molecule's H or L chain encoding gene is determined by nucleic acid sequencing. The primary amino acid residue sequence information provides essential information regarding the antibody molecule's epitope reactivity.

Sequence comparisons of identified HIV-immunoreactive monoclonal antibody variable chain region sequences are shown herein in FIGS. 10–13. The sequences are aligned based on sequence homology, and groups of related antibody molecules are identified thereby in which heavy chain or light chain genes share substantial sequence homology.

An exemplary preparation of a human monoclonal antibody is described in the Examples. The isolation of a particular vector capable of expressing an antibody of interest involves the introduction of the dicistronic expression vector into a host cell permissive for expression of filamentous phage genes and the assembly of phage particles. Where the binary vector system is used, both vectors are introduced in the host cell. Typically, the host is E. coli. Thereafter, a helper phage genome is introduced into the host cell containing the immunoglobulin expression vector (s) to provide the genetic complementation necessary to allow phage particles to be assembled. The resulting host cell is cultured to allow the introduced phage genes and immunoglobulin genes to be expressed, and for phage particles to be assembled and shed from the host cell. The shed phage particles are then harvested (collected) from the host cell culture media and screened for desirable immunoreaction and neutralization properties. Typically, the harvested particles are "panned" for immunoreaction with a preselected antigen. The strongly immunoreactive particles are then collected, and individual species of particles are clonally isolated and further screened for HIV neutralization. Phage which produce neutralizing antibodies are selected and used as a source of a human HIV neutralizing monoclonal antibody of this invention.

Human monoclonal antibodies of this invention can also be produced by altering the nucleotide sequence of a polynucleotide sequence that encodes a heavy or light chain of a monoclonal antibody of this invention. For example, by site directed mutagenesis, one can alter the nucleotide sequence of an expression vector and thereby introduce changes in the resulting expressed amino acid residue sequence. Thus one can take the polynucleotide of SEQ ID NO 66, for example, and convert it into the polynucleotide of SEQ ID NO 67. Similarly, one can take a known polynucleotide and randomly alter it by random mutagenesis, reintroduce the altered polynucleotide into an expression system and subsequently screen the product H:L pair for HIV-neutralizing activity.

Site-directed and random mutagenesis methods are well known in the polynucleotide arts, and are not to be construed as limiting as methods for altering the nucleotide sequence of a subject polynucleotide.

Due to the presence of the phage particle in an immunoaffinity isolated antibody, one embodiment involves the manipulation of the resulting cloned genes to truncate the immunoglobulin-coding gene such that a soluble Fab fragment is secreted by the host E. coli cell containing the phagemid vector. Thus, the resulting manipulated cloned immunoglobulin genes produce a soluble Fab which can be readily characterized in ELISA assays for epitope binding studies, in competition assays with known anti-HIV antibody molecules, and in HIV neutralization assays. The solubilized Fab provides a reproducible and comparable antibody preparation for comparative and characterized studies.

The preparation of soluble Fab is generally described in the immunological arts, and can be conducted as described herein in Example 2b6), or as described by Burton et al., *Proc. Natl. Acad. Sci., USA*, 88:10134–10137 (1991).

G. Expression Vectors and Polynucleotides for Expressing Anti-HIV Monoclonal Antibodies The preparation of human monoclonal antibodies of this invention depends, in one embodiment, on the cloning and expression vectors used to prepare the combinatorial antibody libraries described herein. The cloned immunoglobulin heavy and light chain genes can be shuttled between lambda vectors, phagemid vectors and plasmid vectors at various stages of the methods described herein.

The phagemid vectors produce fusion proteins that are expressed on the surface of an assembled filamentous phage particle.

A preferred phagemid vector of the present invention is a recombinant DNA (rDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide defining an immunoglobulin heavy or light chain variable region, and (3) a filamentous phage membrane anchor domain. The vector includes DNA expression control sequences for expressing the fusion polypeptide, preferably prokaryotic control sequences.

The filamentous phage membrane anchor is preferably a domain of the cpIII or cpVIII coat protein capable of associating with the matrix of a filamentous phage particle, thereby incorporating the fusion polypeptide onto the phage surface.

The secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from Erwinia carotova are described in Lei et al., *Nature*, 331:543–546 (1988).

The leader sequence of the pelB protein has previously been used as a secretion signal for fusion proteins (Better et al., *Science*, 240:1041–1043 (1988); Sastry et al., *Proc. Natl. Acad. Sci., USA*, 86:5728–5732 (1989); and Mullinax et al., *Proc. Natl. Acad. Sci., USA*, 87:8095–8099 (1990)). Amino acid residue sequences for other secretion signal polypeptide domains from *E. coli* useful in this invention as described in Oliver, *Escherichia coli* and *Salmonella Typhimurium*, Neidhard, F. C. (ed.), American Society for Microbiology, Washington, D.C., 1:56–69 (1987).

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane.

In the phage f1, gene VIII coat protein's membrane spanning region comprises residue Trp-26 through Lys-40, and the cytoplasmic region comprises the carboxy-terminal 11 residues from 41 to 52 (Ohkawa et al., *J. Biol. Chem.*, 256:9951–9958 (1981)). An exemplary membrane anchor would consist of residues 26 to 40 of cpVIII. Thus, the amino acid residue sequence of a preferred membrane anchor domain is derived from the M13 filamentous phage gene VIII coat protein (also designated cpVIII or CP 8). Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpIII). Gene III coat protein is present on a mature filamentous phage at one end of the phage particle with typically about 4 to 6 copies of the coat protein.

For detailed descriptions of the structure of filamentous phage particles, their coat proteins and particle assembly, see the reviews by Rached et al., *Microbiol. Rev.*, 50:401–427 (1986); and Model et al., in "*The Bacteriophages*: Vol. 2", R. Calendar, ed. Plenum Publishing Co., pp. 375–456 (1988).

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3–9 nucleotides long located 3–11 nucleotides upstream from the initiation codon (Shine et al., *Nature*, 254:34 (1975). The sequence, AGGAGGU, which is called the Shine-Dalgarno (SD) sequence, is complementary to the 3' end of *E. coli* 16S rRNA. Binding of the ribosome to mRNA and the sequence at the 3' end of the mRNA can be affected by several factors:

(i) The degree of complementarity between the SD sequence and 3' end of the 16S rRNA.

(ii) The spacing and possibly the DNA sequence lying between the SD sequence and the AUG. Roberts et al., *Proc. Natl. Acad. Sci., USA*, 76:760, (1979a); Roberts et al., *Proc. Natl. Acad. Sci. USA*, 76:5596 (1979b); Guarente et al., *Science*, 209:1428 (1980); and Guarente et al., *Cell*, 20:543 (1980). Optimization is achieved by measuring the level of expression of genes in plasmids in which this spacing is systematically altered. Comparison of different mRNAs shows that there are statistically preferred sequences from positions −20 to +13 (where the A of the AUG is position 0). Gold et al., *Annu. Rev. Microbiol.*, 35:365 (1981). Leader sequences have been shown to influence translation dramatically. Roberts et al., 1979 a, b supra.

(iii) The nucleotide sequence following the AUG, which affects ribosome binding. Taniguchi et al.,*J. Mol. Biol.*, 118:533 (1978).

The 3' control sequences define at least one termination (stop) codon in frame with and operatively linked to the heterologous fusion polypeptide.

In preferred embodiments, the vector utilized includes a prokaryotic origin of replication or replicon, i.e., a DNA sequence having the ability to direct autonomous replication and maintenance of the recombinant DNA molecule extra chromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColE1 found in pBR322 and a variety of other common plasmids. Also preferred is the p15A origin of replication found on pACYC and its derivatives. The ColE1 and p15A replicon have been extensively utilized in molecular biology, are available on a variety of plasmids and are described at least by Sambrook et al., in "Molecular Cloning: a Laboratory Manual", 2nd edition, Cold Spring Harbor Laboratory Press (1989).

The ColE1 and p15A replicons are particularly preferred for use in one embodiment of the present invention where two "binary" plasmids are utilized because they each have the ability to direct the replication of plasmid in *E. coli* while the other replicon is present in a second plasmid in the same *E. coli* cell. In other words, ColE1 and p15A are non-interfering replicons that allow the maintenance of two plasmids in the same host (see, for example, Sambrook et al., supra, at pages 1.3–1.4). This feature is particularly important in the binary vectors embodiment of the present invention because a single host cell permissive for phage replication must support the independent and simultaneous replication of two separate vectors, namely a first vector for expressing a heavy chain polypeptide, and a second vector for expressing a light chain polypeptide.

In addition, those embodiments that include a prokaryotic replicon can also include a gene whose expression confers a selective advantage, such as drug resistance, to a bacterial host transformed therewith. Typical bacterial drug resistance genes are those that confer resistance to ampicillin, tetracycline, neomycin/kanamycin or cholamphenicol. Vectors typically also contain convenient restriction sites for insertion of translatable DNA sequences. Exemplary vectors are the plasmids pUC8, pUC9, pBR322, and pBR329 available from BioRad Laboratories, (Richmond, Calif.) and pPL and pKK223 available from Pharmacia, (Piscataway, N.J.).

A vector for expression of a monoclonal antibody of the invention on the surface of a filamentous phage particle is a recombinant DNA (rDNA) molecule adapted for receiving and expressing translatable first and second DNA sequences in the form of first and second polypeptides wherein one of the polypeptides is fused to a filamentous phage coat protein membrane anchor. That is, at least one of the polypeptides is a fusion polypeptide containing a filamentous phage membrane anchor domain, a prokaryotic secretion signal domain, and an immunoglobulin heavy or light chain variable domain.

A DNA expression vector for expressing a heterodimeric antibody molecule provides a system for independently cloning (inserting) the two translatable DNA sequences into two separate cassettes present in the vector, to form two separate cistrons for expressing the first and second polypeptides of the antibody molecule, or the ligand binding portions of the polypeptides that comprise the antibody molecule (i.e., the H and L variable regions of an immunoglobulin molecule). The DNA expression vector for expressing two cistrons is referred to as a dicistronic expression vector.

The vector comprises a first cassette that includes upstream and downstream translatable DNA sequences operatively linked via a sequence of nucleotides adapted for directional ligation to an insert DNA. The upstream translatable sequence encodes the secretion signal as defined herein. The downstream translatable sequence encodes the filamentous phage membrane anchor as defined herein. The cassette preferably includes DNA expression control sequences for expressing the receptor polypeptide that is produced when an insert translatable DNA sequence (insert DNA) is directionally inserted into the cassette via the sequence of nucleotides adapted for directional ligation. The filamentous phage membrane anchor is preferably a domain of the cpIII or cpVIII coat protein capable of binding the matrix of a filamentous phage particle, thereby incorporating the fusion polypeptide onto the phage surface.

The receptor expressing vector also contains a second cassette for expressing a second receptor polypeptide. The second cassette includes a second translatable DNA sequence that encodes a secretion signal, as defined herein, operatively linked at its 3' terminus via a sequence of nucleotides adapted for directional ligation to a downstream DNA sequence of the vector that typically defines at least one stop codon in the reading frame of the cassette. The second translatable DNA sequence is operatively linked at its 5' terminus to DNA expression control sequences forming the 5' elements. The second cassette is capable, upon insertion of a translatable DNA sequence (insert DNA), of expressing the second fusion polypeptide comprising a receptor of the secretion signal with a polypeptide coded by the insert DNA.

An upstream translatable DNA sequence encodes a prokaryotic secretion signal as described earlier. The upstream translatable DNA sequence encoding the pelB secretion signal is a preferred DNA sequence for inclusion in a receptor expression vector. A downstream translatable DNA sequence encodes a filamentous phage membrane anchor as described earlier. Thus, a downstream translatable DNA sequence encodes an amino acid residue sequence that corresponds, and preferably is identical, to the membrane anchor domain of either a filamentous phage gene III or gene VIII coat polypeptide.

A cassette in a DNA expression vector of this invention is the region of the vector that forms, upon insertion of a translatable DNA sequence (insert DNA), a sequence of nucleotides capable of expressing, in an appropriate host, a fusion polypeptide. The expression-competent sequence of nucleotides is referred to as a cistron. Thus, the cassette comprises DNA expression control elements operatively linked to the upstream and downstream translatable DNA sequences. A cistron is formed when a translatable DNA sequence is directionally inserted (directionally ligated) between the upstream and downstream sequences via the sequence of nucleotides adapted for that purpose. The resulting three translatable DNA sequences, namely the upstream, the inserted and the downstream sequences, are all operatively linked in the same reading frame.

Thus, a DNA expression vector for expressing an antibody molecule provides a system for cloning translatable DNA sequences into the cassette portions of the vector to produce cistrons capable of expressing the first and second polypeptides, i.e., the heavy and light chains of a monoclonal antibody.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form. The choice of vector to which transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

A sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication (see, for example, Rasched et al., *Microbiol. Rev.,* 50:401–427 (1986); and Horiuchi, *J. Mol. Biol.,* 188:215–223 (1986)).

A preferred filamentous phage origin of replication for use in the present invention is an M13, f1 or fd phage origin of replication (Short et al., *Nucl. Acids Res.,* 16:7583–7600 (1988)). Preferred DNA expression vectors for cloning and expression a human monoclonal antibody of this invention are the dicistronic expression vectors pComb8, pComb2-8, pComb3, pComb2-3 and pComb2-3', described herein.

A particularly preferred vector of the present invention includes a polynucleotide sequence that encodes a heavy or light chain variable region of a human monoclonal antibody of the present invention. Particularly preferred are vectors that include a nucleotide sequence that encodes a heavy or light chain amino acid residue sequence shown in FIGS. 10–13, that encodes a heavy or light chain having the binding specificity of those sequences shown in FIGS. 10–13, or that encodes a heavy or light chain having conservative substitutions relative to a sequence shown in FIGS. 10–13, and complementary polynucleotide sequences thereto.

Insofar as polynucleotides are component parts of a DNA expression vector for producing a human monoclonal antibody heavy or light chain immunoglobulin variable region amino acid residue sequence, the invention also contemplates isolated polynucleotides that encode such heavy or light chain sequences.

It is to be understood that, due to the genetic code and its attendant redundancies, numerous polynucleotide sequences can be designed that encode a contemplated heavy or light chain immunoglobulin variable region amino acid residue sequence. Thus, the invention contemplates such alternate polynucleotide sequences incorporating the features of the redundancy of the genetic code.

Insofar as the expression vector for producing a human monoclonal antibody of this invention is carried in a host cell compatible with expression of the antibody, the invention contemplates a host cell containing a vector or polynucleotide of this invention. A preferred host cell is *E. coli*, as described herein.

*E. coli* cultures containing preferred expression vectors that produce a human monoclonal antibody of this invention were deposited pursuant to Budapest Treaty requirements with the American Type Culture Collection (ATCC), Rockville, Md., as described herein.

EXAMPLES

The following examples are intended to illustrate, but not limit, the scope of the invention.

1. Construction of a Dicistronic Expression Vector for Producing a Heterodimeric Receptor on Phage Particles To obtain a vector system for generating a large number of Fab antibody fragments that can be screened directly, expression libraries in bacteriophage Lambda have previously been constructed as described in Huse et al., *Science,* 246:1275–1281 (1989). These systems did not contain design features that provide for the expressed Fab to be targeted to the surface of a filamentous phage particle.

The main criterion used in choosing a vector system was the necessity of generating the largest number of Fab fragments which could be screened directly. Bacteriophage Lambda was selected as the starting point to develop an expression vector for three reasons. First, in vitro packaging of phage DNA was the most efficient method of reintroducing DNA into host cells. Second, it was possible to detect protein expression at the level of single phage plaques. Finally, the screening of phage libraries typically involved less difficulty with nonspecific binding. The alternative, plasmid cloning vectors, are only advantageous in the analysis of clones after they have been identified. This advantage was not lost in the present system because of the use of a dicistronic expression vector such as pCombVIII, thereby permitting a plasmid containing the heavy chain, light chain, or Fab expressing inserts to be excised.

a. Construction of Dicistronic Expression Vector pCOMB

1) Preparation of Lambda Zap™II

Lambda Zap™ II is a derivative of the original Lambda Zap (ATCC Accession No. 40,298) that maintains all of the characteristics of the original Lambda Zap including 6 unique cloning sites, fusion protein expression and the ability to rapidly excise the insert in the form of a phagemid (Bluescript SK–), but lacks the SAM 100 mutation, allowing growth on many Non-Sup F strains, including XL1-Blue. The Lambda Zap™ II was constructed as described in Short et al., *Nuc. Acids Res.,* 16:7583–7600, 1988, by replacing the Lambda S gene contained in a 4254 base pair (bp) DNA fragment produced by digesting Lambda Zap with the restriction enzyme Nco I. This 4254 bp DNA fragment was replaced with the 4254 bp DNA fragment containing the Lambda S gene isolated from Lambda gtlo (ATCC # 40,179) after digesting the vector with the restriction enzyme Nco I. The 4254 bp DNA fragment isolated from lambda gt10 was ligated into the original Lambda Zap vector using T4 DNA ligase and standard protocols such as those described in *Current Protocols in Molecular Biology,* Ausubel et al., eds., John Wiley and Sons, New York, 1987, to form Lambda Zap™ II.

2) Preparation of Lambda Hc2

To express a plurality of $V_H$-coding DNA homologs in an *E. coli* host cell, a vector designated Lambda Hc2 was constructed. The vector provided the following: the capacity to place the $V_H$-coding DNA homologs in the proper reading frame; a ribosome binding site as described by Shine et al., *Nature,* 254:34 (1975); a leader sequence directing the expressed protein to the periplasmic space designated the pelB secretion signal; a polynucleotide sequence that coded for a known epitope (epitope tag); and also a polynucleotide that coded for a spacer protein between the $V_H$-coding DNA homolog and the polynucleotide coding for the epitope tag. Lambda Hc2 has been previously described by Huse et al., *Science,* 246:1275–1281 (1989).

To prepare Lambda Hc2, a synthetic DNA sequence containing all of the above features was constructed by designing single stranded polynucleotide segments of 20–40 bases that would hybridize to each other and form the double stranded synthetic DNA sequence shown in FIG. 1. The individual single-stranded polynucleotide segments are shown in Table 1.

Polynucleotides N2, N3, N9-4, N11, N10-5, N6, N7 and N8 (Table 1) were kinased by adding 1 $\mu$l of each polynucleotide 0.1 micrograms/microliter ($\mu$g/$\mu$l) and 20 units of $T_4$ polynucleotide kinase to a solution containing 70 mM Tris-HCl (Tris[hydroxymethyl]aminomethane hydrochloride) at pH 7.6, 10 mM MgCl$_2$, 5 mM dithiothreitol (DTT), 10 mM beta-mercaptoethanol, 500 micrograms per milliliter (µg/ml) bovine serum albumin (BSA). The solution was maintained at 37 degrees Centigrade (37° C.) for 30 minutes and the reaction stopped by maintaining the solution at 65° C. for 10 minutes. The two end polynucleotides, 20 nanograms (ng) of polynucleotides N1 and polynucleotides N12, were added to the above kinasing reaction solution together with 1/10 volume of a solution containing 20 mM Tris-HCl at pH 7.4, 2.0 mM MgCl$_2$ and 50 mM NaCl. This solution was heated to 70° C. for 5 minutes and allowed to cool to room temperature, approximately 25° C., over 1.5 hours in a 500 ml beaker of water. During this time period all 10 polynucleotides annealed to form the double stranded synthetic DNA insert shown in FIG. 1. The individual polynucleotides were covalently linked to each other to stabilize the synthetic DNA insert by adding 40 µl of the above reaction to a solution containing 50 mM Tris-HCl at pH 7.5, 7 mM MgCl$_2$, 1 mM DTT, 1 mM adenosine triphosphate (ATP) and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 µl of the above reaction, 4 µl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

each strand (top and bottom) of Lambda Hc2 is listed in the Sequence Listing as SEQ ID NO 1 and SEQ ID NO 2, respectively. The resultant Lambda Hc2 expression vector is shown in FIG. 2.

3) Preparation of Lambda Lc2

To express a plurality of V$_L$-coding DNA homologs in an E. coli host cell, a vector designated Lambda Lc2 was constructed having the capacity to place the V$_L$-coding DNA homologs in the proper reading frame, provided a ribosome binding site as described by Shine et al., Nature, 254:34 (1975), provided the pelB gene leader sequence secretion signal that has been previously used to successfully secrete Fab fragments in E. coli by Lei et al., J. Bac., 169:4379 (1987) and Better et al., Science, 240:1041 (1988), and also provided a polynucleotide containing a restriction endonuclease site for cloning. Lambda Lc2 has been previously described by Huse et al., Science, 246:1275–1281 (1989).

A synthetic DNA sequence containing all of the above features was constructed by designing single stranded polynucleotide segments of 20–60 bases that would hybridize to each other and form the double stranded synthetic DNA sequence shown in FIG. 3. The sequence of each individual single-stranded polynucleotide segment (01–08) within the double stranded synthetic DNA sequence is shown in Table 2.

Polynucleotides 02, 03, 04, 05, 06 and 07 (Table 2) were kinased by adding 1 µl (0.1 µg/µl) of each polynucleotide and 20 units of T$_4$ polynucleotide kinase to a solution containing 70 mM Tris-HCl at pH 7.6, 10 mM MgCl$_2$, 5 mM DTT, 10 mM beta-mercaptoethanol, 500 µg/ml of BSA. The

TABLE 1

| SEQ ID NO | | |
|---|---|---|
| (15) | N1) | 5' GGCCGCAAATTCTATTTCAAGGAGACAGTCAT 3' |
| (16) | N2) | 5' AATGAAATACCTATTGCCTACGGCAGCCGCTGGATT 3' |
| (17) | N3) | 5' GTTATTACTCGCTGCCCAACCAGCCATGGCCC 3' |
| (18) | N6) | 5' CAGTTTCACCTGGGCCATGGCTGGTTGGG 3' |
| (19) | N7) | 5' CAGCGAGTAATAACAATCCAGCGGCTGCCGTAGGCAATAG 3' |
| (20) | N8) | 5' GTATTTCATTATGACTGTCTCCTTGAAATAGAATTTGC 3' |
| (21) | N9-4) | 5' AGGTGAAACTGCTCGAGATTTCTAGACTAGTTACCCGTAC 3' |
| (22) | N10-5) | 5' CGGAACGTCGTACGGGTAACTAGTCTAGAAATCTCGAG 3' |
| (23) | N11) | 5' GACGTTCCGGACTACGGTTCTTAATAGAATTCG 3' |
| (24) | N12) | 5' TCGACGAATTCTATTAAGAACCGTAGTC 3' |

The completed synthetic DNA insert was ligated directly into the Lambda Zap™ II vector described in Example 1a1) that had been previously digested with the restriction enzymes, Not I and Xho I. The ligation mixture was packaged according to the manufacture's instructions using Gigapack II Gold packing extract available from Stratagene, La Jolla, Calif. The packaged ligation mixture was plated on XL1-Blue cells (Stratagene). Individual lambda plaques were cored and the inserts excised according to the in vivo excision protocol for Lambda Zap™ II provided by the manufacturer (Stratagene). This in vivo excision protocol moved the cloned insert from the Lambda Hc2 vector into a phagemid vector to allow easy for manipulation and sequencing. The accuracy of the above cloning steps was confirmed by sequencing the insert using the Sanger dideoxy method described in by Sanger et al., Proc. Natl. Acad. Sci., USA, 74:5463–5467 (1977) and using the manufacture's instructions in the AMV Reverse Transcriptase $^{35}$S-ATP sequencing kit (Stratagene). The sequence of the resulting double-stranded synthetic DNA insert in the V$_H$ expression vector (Lambda Hc2) is shown in FIG. 1. The sequence of solution was maintained at 37° C. for 30 minutes and the reaction stopped by maintaining the solution at 65° C. for 10 minutes. The 20 ng each of the two end polynucleotides, 01 and 08, were added to the above kinasing reaction solution together with 1/10 volume of a solution containing 20.0 mM Tris-HCl at pH 7.4, 2.0 mM MgCl$_2$ and 15.0 mM sodium chloride (NaCl). This solution was heated to 70° C. for 5 minutes and allowed to cool to room temperature, approximately 25° C., over 1.5 hours in a 500 ml beaker of water. During this time period all 8 polynucleotides annealed to form the double stranded synthetic DNA insert shown in FIG. 3. The individual polynucleotides were covalently linked to each other to stabilize the synthetic DNA insert by adding 40 µl of the above reaction to a solution containing 50 mM Tris-HCl at pH 7.5, 7 mM MgCl$_2$, 1 mM DTT, 1 mM ATP and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 µl of the above reaction, 4 µl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

ends which are ligated together to result in Lambda Lc3 lacking a Spe I site. Lambda Lc3 is a preferred vector for use in constructing a combinatorial vector as described below.

TABLE 2

| SEQ ID NO | | |
|---|---|---|
| (25) | 01) | 5' TGAATTCTAAACTAGTCGCCAAGGAGACAGTCAT 3' |
| (26) | 02) | 5' AATGAAATACCTATTGCCTACGGCAGCCGCTGGATT 3' |
| (27) | 03) | 5' GTTATTACTCGCTGCCCAACCAGCCATGGCC 3' |
| (28) | 04) | 5' GAGCTCGTCAGTTCTAGAGTTAAGCGGCCG 3' |
| (29) | 05) | 5' GTATTTCATTATGACTGTCTCCTTGGCGACTAGTTTAGAATTCAAGCT 3' |
| (30) | 06) | 5' CAGCGAGTAATAACAATCCAGCGGCTGCCGTAGGCAATAG 3' |
| (31) | 07) | 5' TGACGAGCTCGGCCATGGCTGGTTGGG 3' |
| (32) | 08) | 5' TCGACGGCCGCTTAACTCTAGAAC 3' |

Figure 4:
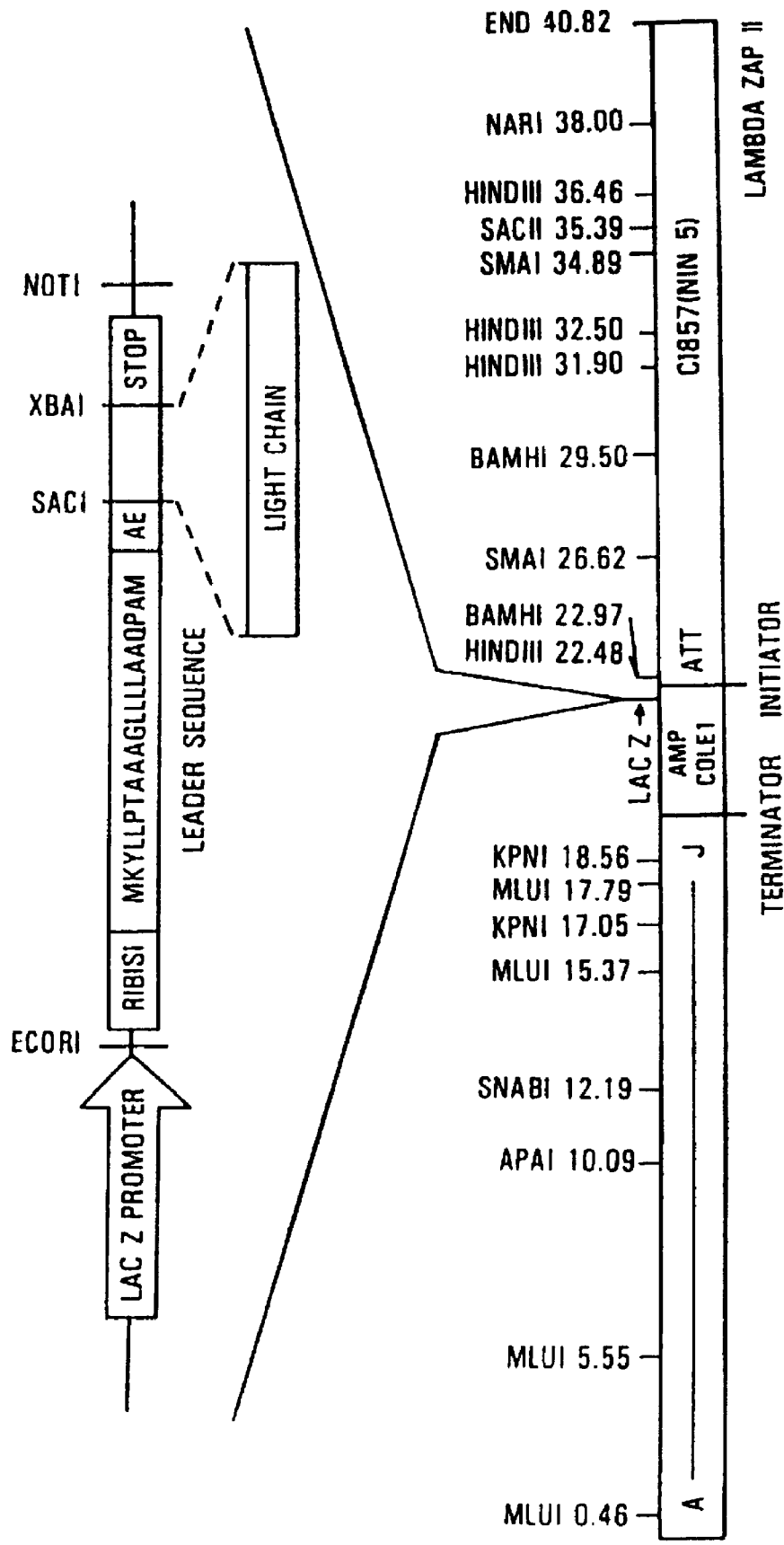
FIG. 4 illustrates the major features of the bacterial expression vector Lc2 ($V_L$ expression vector). The synthetic DNA sequence from FIG. 3 is shown at the top along with the LacZ promoter from Lambda Zap II. The orientation of the insert in Lambda Zap II is shown. The $V_L$ DNA homologs are inserted into the Sac I and Xho I cloning sites. The amino acid residue sequence of the Pel B leader sequence/spacer is listed in SEQ ID NO 7.

The completed synthetic DNA insert was ligated directly into the Lambda Zap™ II vector described in Example 1a1) that had been previously digested with the restriction enzymes Sac I and Xho I. The ligation mixture was packaged according to the manufacture's instructions using Gigapack II Gold packing extract (Stratagene). The packaged ligation mixture was plated on XL1-Blue cells (Stratagene). Individual lambda plaques were cored and the inserts excised according to the in vivo excision protocol for Lambda Zap™ II provided by the manufacturer (Stratagene). This in vivo excision protocol moved the cloned insert from the Lambda Lc2 vector into a plasmid phagemid vector allow for easy manipulation and sequencing. The accuracy of the above cloning steps was confirmed by sequencing the insert using the manufacture's instructions in the AMV Reverse Transcriptase $^{35}$S-DATP sequencing kit (Stratagene). The sequence of the resulting Lc2 expression vector (Lambda Lc2) is shown in FIG. 3. Each strand is separately listed in the Sequence Listing as SEQ ID NO 3 and SEQ ID NO 4. The resultant Lc2 vector is schematically diagrammed in FIG. 4.

A preferred vector for use in this invention, designated Lambda Lc3, is a derivative of Lambda Lc2 prepared above. Lambda Lc2 contains a Spe I restriction site located 3' to the EcoR I restriction site and 5' to the Shine-Dalgarno ribosome binding site as shown in the sequence in FIG. 3 and in SEQ ID NO 3. A Spe I restriction site is also present in Lambda Hc2 as shown in FIGS. 1 and 2 and in SEQ ID NO 1. A combinatorial vector, designated pComb, was constructed by combining portions of Lambda Hc2 and Lc2 together as described in Example 1a4) below. The resultant combinatorial pComb vector contained two Spe I restriction sites, one provided by Lambda Hc2 and one provided by Lambda Lc2, with an EcoR I site in between. Despite the presence of two Spe I restriction sites, DNA homologs having Spe I and EcoR I cohesive termini were successfully directionally ligated into a pComb expression vector previously digested with Spe I and EcoR I as described in Example 1b below. The proximity of the EcoR I restriction site to the 3' Spe I site, provided by the Lc2 vector, inhibited the complete digestion of the 3' Spe I site. Thus, digesting pComb with Spe I and EcoR I did not result in removal of the EcoR I site between the two Spe I sites.

The presence of a second Spe I restriction site may be undesirable for ligations into a pComb vector digested only with Spe I as the region between the two sites would be eliminated. Therefore, a derivative of Lambda Lc2 lacking the second or 3' Spe I site, designated Lambda Lc3, was produced by first digesting Lambda Lc2 with Spe I to form a linearized vector. The ends were filled in to form blunt 4) Preparation of pComb Phagemids were excised from the expression vectors Lambda Hc2 or Lambda Lc2 using an in vivo excision protocol described above. Double stranded DNA was prepared from the phagemid-containing cells according to the methods described by Holmes et al., Anal. Biochem., 114:193 (1981). The phagemids resulting from in vivo excision contained the same nucleotide sequences for antibody fragment cloning and expression as did the parent vectors, and are designated phagemid Hc2 and Lc2, corresponding to Lambda Hc2 and Lc2, respectively.

For the construction of combinatorial phagemid vector pComb, produced by combining portions of phagemid Hc2 and phagemid Lc2, phagemid Hc2 was first digested with Sac I to remove the restriction site located 5' to the LacZ promoter. The linearized phagemid was then blunt ended with T4 polymerase and ligated to result in a Hc2 phagemid lacking a Sac I site. The modified Hc2 phagemid and the Lc2 phagemid were then separately restriction digested with Sca I and EcoR I to result in a Hc2 fragment having from 5' to 3' Sca I, Not I, Xho I, Spe I and EcoR I restriction sites and a Lc2 fragment having from 5' to 3' EcoR I, Sac I, Xba I and Sac I restriction sites. The linearized phagemids were then ligated together at their respective cohesive ends to form pComb, a circularized phagemid having a linear arrangement of restriction sites of Not I, Xho I, Spe I, EcoR I, Sac I, Xba I, Not I, Apa I and Sca I. The ligated phagemid vector was then inserted into an appropriate bacterial host and transformants were selected on the antibiotic ampicillin.

Figure 5:
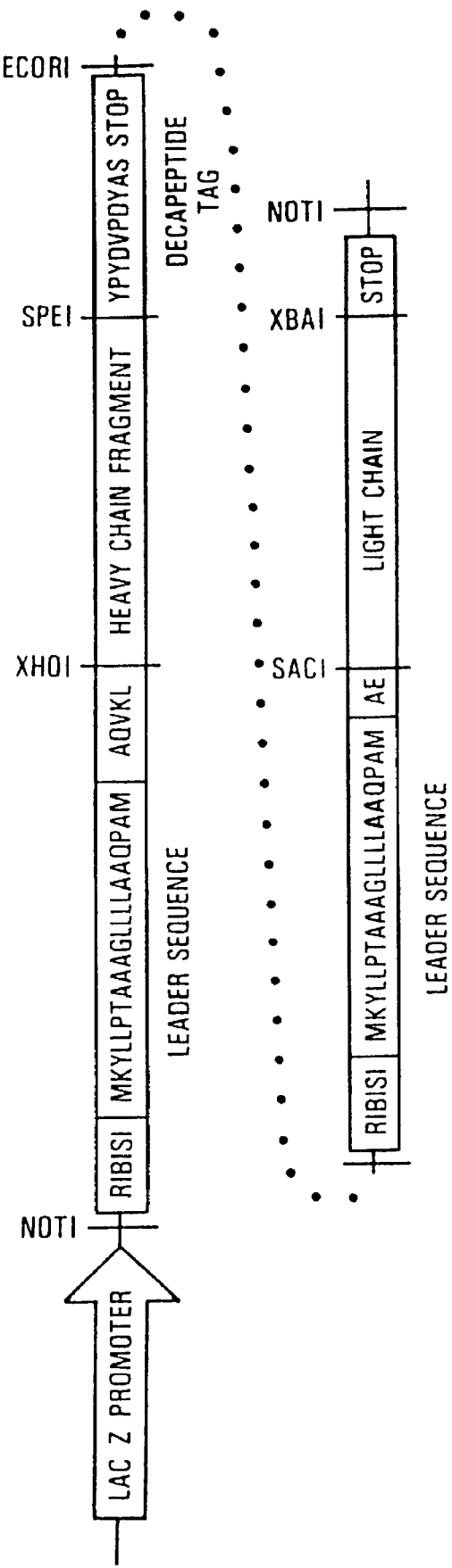
FIG. 5 illustrates the dicistronic expression vector, pComb, in the form of a phagemid expression vector.

Selected ampicillin resistant transformants were screened for the presence of two Not I sites. The resulting ampicillin resistant combinatorial phagemid vector was designated pComb, the schematic organization of which is shown in FIG. 5. The resultant combinatorial vector, pComb, consisted of a DNA molecule having two cassettes to express two fusion proteins and having nucleotide residue sequences for the following operatively linked elements listed in a 5' to 3' direction: a first cassette consisting of an inducible LacZ promoter upstream from the LacZ gene; a Not I restriction site; a ribosome binding site; a pelB leader; a spacer; a cloning region bordered by a 5' Xho and 3' Spe I restriction site; a decapeptide tag followed by expression control stop sequences; an EcoR I restriction site located 5' to a second cassette consisting of an expression control ribosome binding site; a pelB leader; a spacer region; a cloning region bordered by a 5' Sac I and a 3' Xba I restriction site followed by expression control stop sequences and a second Not I restriction site.

A preferred combinatorial vector for use in this invention, designated pComb2, is constructed by combining portions of phagemid Hc2 and phagemid Lc3 as described above for preparing pComb. The resultant combinatorial vector, pComb2, consists of a DNA molecule having two cassettes identical to pComb to express two fusion proteins identically to pComb except that a second Spe I restriction site in the second cassette is eliminated.

b. Construction of the pCombIII Vector for Expressing Fusion Proteins Having a Bacteriophage Coat Protein Membrane Anchor Because of the multiple endonuclease restriction cloning sites, the pComb phagemid expression vector prepared above is a useful cloning vehicle for modification for the preparation of an expression vector for use in this invention. To that end, pComb was digested with EcoR I and Spe I followed by phosphatase treatment to produce linearized pComb.

1) Preparation of pCombIII

A separate phagemid expression vector was constructed using sequences encoding bacteriophage cpIII membrane anchor domain. A PCR product defining the DNA sequence encoding the filamentous phage coat protein,cpIII, membrane anchor containing a LacZ promotor region sequence 3' to the membrane anchor for expression of the light chain and Spe I and EcoR I cohesive termini was prepared from M13mp18, a commercially available bacteriophage vector (Pharmacia, Piscataway, N.J.).

To prepare a modified cpIII, replicative form DNA from M13mp18 was first isolated. Briefly, into 2 ml of LB (Luria-Bertani medium), 50 µl of a culture of a bacterial strain carrying an F' episome (JM107, JM109 or TG1) was admixed with a one tenth suspension of bacteriophage particles derived from a single plaque. The admixture was incubated for 4 to 5 hours at 37° C. with constant agitation. The admixture was then centrifuged at 12,000×g for 5 minutes to pellet the infected bacteria. After the supernatant was removed, the pellet was resuspended by vigorous vortexing in 100 µl of ice-cold solution I. Solution I was prepared by admixing 50 mM glucose, 10 mM EDTA (disodium ethylenediaminetetraacetic acid) and 25 mM Tris-HCl at pH 8.0, and autoclaving for 15 minutes.

To the bacterial suspension, 200 µl of freshly prepared Solution II was admixed and the tube was rapidly inverted five times. Solution II was prepared by admixing 0.2N NaOH and ok SDS. To the bacterial suspension, 150 µl of ice-cold Solution III was admixed and the tube was vortexed gently in an inverted position for 10 seconds to disperse Solution III through the viscous bacterial lysate. Solution III was prepared by admixing 60 ml of 5M potassium acetate, 11.5 ml of glacial acetic acid and 28.5 ml of water. The resultant bacterial lysate was then stored on ice for 5 minutes followed by centrifugation at 12,000×g for 5 minutes at 4° C. in a microfuge. The resultant supernatant was recovered and transferred to a new tube. To the supernatant was added an equal volume of phenol/chloroform and the admixture was vortexed. The admixture was then centrifuged at 12,000×g for 2 minutes in a microfuge. The resultant supernatant was transferred to a new tube and the double-stranded bacteriophage DNA was precipitated with 2 volumes of ethanol at room temperature. After allowing the admixture to stand at room temperature for 2 minutes, the admixture was centrifuged to pellet the DNA. The supernatant was removed and the pelleted replicative form DNA was resuspended in 25 µl of Tris-HCl at pH 7.6, and 10 mM EDTA (TE).

An alternative Lac-B primer for use in constructing the cpIII membrane anchor and LacZ promotor region was Lac-B' as shown in Table 3. The amplification reactions were performed as described above with the exception that in the second PCR amplification, Lac-B' was used with Lac-F instead of Lac-B. The product from the amplification reaction is listed in the sequence listing as SEQ ID NO 41 from nucleotide position 1 to nucleotide position 172. The use of Lac-B' resulted in a LacZ region lacking 29 nucleotides on the 3' end but was functionally equivalent to the longer fragment produced with the Lac-F and Lac-B primers.

The products of the first and second PCR amplifications using the primer pairs G-3(F) and G-3(B) and Lac-F and Lac-B were then recombined at the nucleotides corresponding to cpIII membrane anchor overlap and Nhe I restriction site and subjected to a second round of PCR using the G-3(F) (SEQ ID NO 35) and Lac-B (SEQ ID NO 38) primer pair to form a recombined PCR DNA fragment product consisting of the following: a 5' Spe I restriction site; a cpIII DNA membrane anchor domain beginning at the nucleotide residue sequence which corresponds to the amino acid residue 198 of the entire mature cpIII protein; an endogenous stop site provided by the membrane anchor at amino acid residue number 112; a Nhe I restriction site, a LacZ promoter, operator and Cap-binding site sequence; and a 3' EcoR I restriction site.

To construct a phagemid vector for the coordinate expression of a heavy chain-cpIII fusion protein as prepared in Example 2 with kappa light chain, the recombined PCR modified cpIII membrane anchor domain DNA fragment was then restriction digested with Spe I and EcoR I to produce a DNA fragment for directional ligation into a similarly digested pComb2 phagemid expression vector having only one Spe I site prepared in Example 1a4) to form a pComb2-III (also referred to as pComb2-III) phagemid expression vector. Thus, the resultant ampicillin resistance conferring pComb2-3 vector, having only one Spe I restriction site, contained separate LacZ promoter/operator sequences for directing the separate expression of the heavy chain (Fd)-cpIII fusion product and the light chain protein. The expressed proteins were directed to the periplasmic space by pelB leader sequences for functional assembly on the membrane. Inclusion of the phage F1 intergenic region in the vector allowed for packaging of single stranded phagemid with the aid of helper phage. The use of helper phage superinfection lead to expression of two forms of cpIII. Thus, normal phage morphogenesis was perturbed by competition between the Fab-cpIII fusion and the native cpIII of the helper phage for incorporation into the virion for Fab-cpVIII fusions. In addition, also contemplated for use in this invention are vectors conferring chloramphenicol resistance and the like.

A more preferred phagemid expression vector for use in this invention having additional restriction enzyme cloning sites, designated pComb-III' or pComb2-3', was prepared as described above for pComb2-3 with the addition of a 51 base pair fragment from pBluescript as described by Short et al., Nuc. Acids Res., 16:7583–7600 (1988) and commercially available from Stratagene. To prepare pComb2-3', pComb2-3 was first digested with Xho I and Spe I restriction enzymes to form a linearized pComb2-3. The vector pBluescript was digested with the same enzymes releasing a 51 base pair fragment containing the restriction enzyme sites Sal I, Acc I, Hinc II, Cla I, Hind III, EcoR V, Pst I, Sma I and BamH I. The 51 base pair fragment was ligated into the linearized pComb2-3 vector via the cohesive Xho I and Spe I termini to form pComb2-3'.

TABLE 3

| SEQ ID NO | Primer | | |
|---|---|---|---|
| (35)[1] | G-3 | (F) | 5' GAGACGACTAGTGGTGGCGGTGGCTCTCCATTCGTTTGTGAATATCAA 3' |
| (36)[2] | G-3 | (B) | 5' TTACTAGCTAGCATAATAACGGAATACCCAAAAGAACTGG 3' |
| (37)[3] | LAC-F | | 5' TATGCTAGCTAGTAACACGACAGGTTTCCCGACTGG 3' |
| (38)[4] | LAC-B | | 5' ACCGAGCTCGAATTCGTAATCATGGTC 3' |
| (39)[5] | LAC-B' | | 5' AGCTGTTGAATTCGTGAAATTGTTATCCGCT 3' |

F Forward Primer
B Backward Primer
[1]From 5' to 3': Spe I restriction site sequence is single underlined; the overlapping sequence with the 5' end of cpIII is double underlined
[2]From 5' to 3': Nhe I restriction site sequence is single underlined; the overlapping sequence with 3' end of cpIII is double underlined.
[3]From 5' to 3': overlapping sequence with the 3' end of cpIII is double underlined; Nhe I restriction sequence begins with the nucleotide residue "G" at position 4 and extends 5 more residues = GCTAGC.
[4]EcoR I restriction site sequence is single underlined.
[5]Alternative backwards primer for amplifying LacZ; EcoR I restriction site sequence is single underlined.

2. Isolation of HIV-1-Specific Monoclonal Antibodies Produced from the Dicistronic Expression Vector, pComb2-3

In practicing this invention, the heavy (Fd consisting of $V_H$ and $C_H1$) and light (kappa) chains ($V_L$, $C_L$) of antibodies are first targeted to the periplasm of E. coli for the assembly of heterodimeric Fab molecules. In order to obtain expression of antibody Fab libraries on a phage surface, the nucleotide residue sequences encoding either the Fd or light chains must be operatively linked to the nucleotide residue sequence encoding a filamentous bacteriophage coat protein membrane anchor. A coat protein for use in this invention in providing a membrane anchor is III (cpIII or cp3). In the Examples described herein, methods for operatively linking a nucleotide residue sequence encoding a Fd chain to a cpIII membrane anchor in a fusion protein of this invention are described.

In a phagemid vector, a first and second cistron consisting of translatable DNA sequences are operatively linked to form a dicistronic DNA molecule. Each cistron in the dicistronic DNA molecule is linked to DNA expression control sequences for the coordinate expression of a fusion protein, Fd-cpIII, and a kappa light chain.

The first cistron encodes a periplasmic secretion signal (pelB leader) operatively linked to the fusion protein, Fd-cpIII. The second cistron encodes a second pelB leader operatively linked to a kappa light chain. The presence of the pelB leader facilitates the coordinated but separate secretion of both the fusion protein and light chain from the bacterial cytoplasm into the periplasmic space.

In this process, the phagemid expression vector carries an ampicillin selectable resistance marker gene (beta lactamase or bla) in addition to the Fd-cpIII fusion and the kappa chain. The f1 phage origin of replication facilitates the generation of single stranded phagemid. The isopropyl thiogalactopyranoside (IPTG) induced expression of a dicistronic message encoding the Fd-cpIII fusion ($V_H$, $C_{H1}$, cpIII) and the light chain ($V_L$, $C_L$) leads to the formation of heavy and light chains. Each chain is delivered to the periplasmic space by the pelB leader sequence, which is subsequently cleaved. The heavy chain is anchored in the membrane by the cpIII membrane anchor domain while the light chain is secreted into the periplasm. The heavy chain in the presence of light chain assembles to form Fab molecules. This same result can be achieved if, in the alternative, the light chain is anchored in the membrane via a light chain fusion protein having a membrane anchor and heavy chain is secreted via a pelB leader into the periplasm.

With subsequent infection of E. coli with a helper phage, as the assembly of the filamentous bacteriophage progresses, the coat protein III is incorporated on the tail of the bacteriophage.

a. Preparation of Lymphocyte RNA

Five milliliters of bone marrow was removed by aspiration from HIV-1 asymptomatic seropositive individuals. Total cellular RNA was prepared from the bone marrow lymphocytes as described above using the RNA preparation methods described by Chomczynski et al., Anal Biochem., 162:156–159 (1987) and using the RNA isolation kit (Stratagene) according to the manufacturer's instructions. Briefly, for immediate homogenization of the cells in the isolated bone marrow, 10 ml of a denaturing solution containing 3.0M guanidinium isothiocyanate containing 71 μl of beta-mercaptoethanol was admixed to the isolated bone marrow. One ml of sodium acetate at a concentration of 2M at pH 4.0 was then admixed with the homogenized cells. One ml of phenol that had been previously saturated with $H_2O$ was also admixed to the denaturing solution containing the homogenized spleen. Two ml of a chloroform:isoamyl alcohol (24:1 v/v) mixture was added to this homogenate. The homogenate was mixed vigorously for ten seconds and maintained on ice for 15 minutes. The homogenate was then transferred to a thick-walled 50 ml polypropylene centrifuged tube (Fisher Scientific Company, Pittsburgh, Pa.). The solution was centrifuged at 10,000×g for 20 minutes at 4° C. The upper RNA-containing aqueous layer was transferred to a fresh 50 ml polypropylene centrifuge tube and mixed with an equal volume of isopropyl alcohol. This solution was maintained at −20° C. for at least one hour to precipitate the RNA. The solution containing the precipitated RNA was centrifuged at 10,000×g for twenty minutes at 4° C. The pelleted total cellular RNA was collected and dissolved in 3 ml of the denaturing solution described above. Three ml of isopropyl alcohol was added to the re-suspended total cellular RNA and vigorously mixed. This solution was maintained at −20° C. for at least 1 hour to precipitate the RNA. The solution containing the precipitated RNA was centrifuged at 10,000×g for ten minutes at 4° C. The pelleted RNA was washed once with a solution containing 75% ethanol. The pelleted RNA was dried under vacuum for 15 minutes and then re-suspended in dimethyl pyrocarbonate-treated (DEPC-$H_2O$) $H_2O$.

Messenger RNA (mRNA) enriched for sequences containing long poly A tracts was prepared from the total cellular RNA using methods described in Molecular Cloning: A Laboratory Manual, Maniatis et al., eds., Cold Spring Harbor, N.Y., (1982). Briefly, one half of the total RNA isolated from a single donor prepared as described above was resuspended in one ml of DEPC-$H_2O$ and maintained at 65° C. for five minutes. One ml of 2× high salt loading buffer consisting of 100 mM Tris-HCl, 1M NaCl, 2.0 mM EDTA at pH 7.5, and 0.2% SDS was admixed to the resuspended RNA and the mixture allowed to cool to room temperature.

The total purified mRNA was then used in PCR amplification reactions as described in Example 2c. Alternatively, the mRNA was further purified to poly A+ RNA by the following procedure. The total mRNA was applied to an oligo-dT (Collaborative Research Type 2 or Type 3) column that was previously prepared by washing the oligo-dT with a solution containing 0.1M sodium hydroxide and 5 mM EDTA and then equilibrating the column with DEPC-$H_2O$. The eluate was collected in a sterile polypropylene tube and reapplied to the same column after heating the eluate for 5 minutes at 65° C. The oligo-dT column was then washed with 2 ml of high salt loading buffer consisting of 50 mM Tris-HCl at pH 7.5, 500 mM sodium chloride, 1 mM EDTA at pH 7.5 and 0.1% SDS. The oligo dT column was then washed with 2 ml of 1× medium salt buffer consisting of 50 mM Tris-HCl, pH 7.5, 100 mM, 1 mM EDTA and 0.1% SDS. The messenger RNA was eluted from the oligo-dT column with 1 ml of buffer consisting of 10 mM Tris-HCl at pH 7.5, 1 mM EDTA at pH 7.5, and 0.05% SDS. The messenger RNA was purified by extracting this solution with phenol/chloroform followed by a single extraction with 100% chloroform. The messenger RNA was concentrated by ethanol precipitation and resuspended in DEPC $H_2O$.

The resultant purified mRNA contained a plurality of anti-HIV encoding $V_H$ and $V_L$ sequences for preparation of an anti-HIV-1 Fab DNA library.

b. Construction of a Combinatorial HIV-1 Antibody Library

1) Selection of Oligonucleotide Primers

The nucleotide sequences encoding the immunoglobulin protein CDR's are highly variable. However, there are several regions of conserved sequences that flank the V region domains of either the light or heavy chain, for instance, and that contain substantially conserved nucleotide sequences, i.e., sequences that will hybridize to the same primer sequence. Therefore, polynucleotide synthesis (amplification) primers that hybridize to the conserved sequences and incorporate restriction sites into the DNA homolog produced that are suitable for operatively linking the synthesized DNA fragments to a vector were constructed. More specifically, the primers were designed so that the resulting DNA homologs produced can be inserted into an expression vector of this invention in reading frame with the upstream translatable DNA sequence at the region of the vector containing the directional ligation means.

For amplification of the $V_H$ domains, primers were designed to introduce cohesive termini compatible with directional ligation into the unique Xho I and Spe I sites of the pComb2-3 expression vector. In all cases, the 5' primers VH1a (5' CAGGTGCAG<u>CTCGAG</u>CAGTCTGGG 3' SEQ ID NO 42) and VH3a (5' GAGGTGCAG<u>CTCGAG</u>GAGTCTGGG 3' SEQ ID NO 43) were designed to maximize homology with the $V_H1$ and $V_H3$ subgroup families, respectively, although considerable cross-priming of other subgroups was expected. The Xho I restriction site for cloning into the pComb2-3 vector is underlined. The 3' primer CG1z having the nucleotide sequence 5' GCATGT <u>ACTAGT</u>TTTGTCACAAGATTTGGG 3' (SEQ ID NO 44) used in conjunction with the 5' primers is the primer for the heavy chain corresponding to part of the hinge region. The Spe I site for cloning into the pComb2-3 vector is underlined.

The nucleotide sequences encoding the $V_L$ domain are highly variable. However, there are several regions of conserved sequences that flank the $V_L$ domains including the $J_L$, $V_L$ framework regions and $V_L$ leader/promotor. Therefore, amplification primers were constructed that hybridized to the conserved sequences and incorporate restriction sites that allow cloning the amplified fragments into the pComb2-3 expression vector cut with Sac I and Xba I.

For amplification of the kappa $V_L$ domains analogous to the heavy chain primers listed above, the 5' primers, VK1a (5' GACATC<u>GAGCTC</u>ACCCAGTCTCCA 3' SEQ ID NO 45) and VK3a (5' GAAATT<u>GAGCTC</u>ACGCAGTCTCCA 3' SEQ ID NO 46), were used. These primers also introduced a Sac I restriction endonuclease site indicated by the underlined nucleotides to allow the $V_L$ DNA homolog to be cloned into the pComb2-3 expression vector. The 3' $V_L$ amplification primer, CK1a having a nucleotide sequence 5' GCGCCG<u>TCTAGA</u>ACTAACACTCTCCCCTGTTGAAG CTCTTTGTGACGGGCAAG 3' (SEQ ID NO 47) corresponding to the 3' end of the light chain was used to amplify the light chain while incorporating the underlined Xba I restriction endonuclease site required to insert the $V_L$ DNA homolog into the pComb2-3 expression vector.

All primers and synthetic polynucleotides described herein, were either purchased from Research Genetics in Huntsville, Ala. or synthesized on an Applied Biosystems DNA synthesizer, model 381A, using the manufacturer's instruction.

2) PCR Amplification of $V_H$ and $V_L$ DNA Homologs

In preparation for PCR amplification, mRNA prepared above was used as a template for cDNA synthesis by a primer extension reaction. First, 20–50 µg of total mRNA in water was first hybridized (annealed) at 70° C. for 10 minutes with 600 ng (60.0 pmol) of either the heavy or light chain 3' primers listed above. Subsequently, the hybridized admixture was used in a typical 50 µl reverse transcription reaction containing 200 µM each of DATP, dCTP, dGTP and dTTP, 40 mM Tris-HCl at pH 8.0, 8 mM $MgCl_2$, 50 mM NaCl, 2 mM spermidine and 600 units of reverse transcriptase (SuperScript, BRL). The reaction admixture was then maintained for one hour at 37° C. to form an RNA-cDNA admixture.

Three µl of the resultant RNA-cDNA admixture was then used in PCR amplification in a reaction volume of 100 µl containing a mixture of all four dNTPs at a concentration of 60 µM, 50 mM KCl, 10 mM Tris-HCl at pH 8.3, 15 mM $MgCl_2$, 0.1% gelatin and 5 units of *Thermus aquaticus* (Taq) DNA polymerase (Perkin-Elmer-Cetus, Emeryville, Calif.), and 60 pmol of the appropriate 5' and 3' primers listed above. The separate reaction admixtures were overlaid with mineral oil and subjected to 35 cycles of amplification. Each amplification cycle included denaturation at 91° C. for 1 minute, annealing at 52° C. for 2 minutes and polynucleotide synthesis by primer extension (elongation) at 72° C. for 1.5 minutes, followed by a final maintenance period of 10 minutes at 72° C. An aliquot of the reaction admixtures were then separately electrophoresed on a 2% agarose gel. After successful amplification as determined by gel electrophoretic migration, the remainder of the RNA-cDNA was amplified after which the PCR products of a common 3' primer were pooled into separate $V_H$- and $V_L$-coding DNA homolog-containing samples and were then extracted twice with phenol/chloroform, once with chloroform, ethanol precipitated and were stored at −70° C. in 10 mM Tris-HCl at pH 7.5, and 1 mM EDTA.

3) Insertion of $V_H$ and $V_L$-Coding DNA Homologs into pComb2-3 Expression Vector The $V_H$-coding DNA homologs (heavy chain) prepared above were then digested with an excess of Xho I and Spe I for subsequent ligation into a similarly digested and linearized pComb2-3 in a total volume of 150 µl with 10 units of ligase at 16° C. overnight. The construction of the library was performed as described by Burton et al., *Proc. Natl. Acad. Sci. USA*, 88:10134–10137 (1991). Briefly, following ligation, the pComb2-3 vector containing heavy chain DNA was then transformed by electroporation into 300 µl of XL1-Blue cells. After transformation and culturing, library size was determined by plating aliquots of the culture. Typically the library had about $10^7$ members. An overnight culture was then prepared from which phagemid DNA containing the heavy chain library was prepared.

For the cloning of the $V_L$-coding DNA homologs (light chain), 10 µg of phagemid DNA containing the heavy chain library was then digested with Sac I and SbaI. The resulting linearized vector was treated with phosphatase and purified by agarose gel electrophoresis. The desired fragment, 4.7 kb in length, was excised from the gel. Ligation of this vector with prepared light chain PCR DNA proceeded as described above for heavy chain. A library of approximately $10^7$ members having heavy chain fragments operatively linked to the cpIII anchor sequence (Fd-cpIII) and light chain fragments was thus produced.

4) Preparation of Phage Expressing Fab Heterodimers

Following transformation of the resultant library produced above into XL1-Blue cells, phage were prepared to allow for isolation of HIV-1 specific Fabs by panning on target antigens. To isolate phage on which heterodimer expression has been induced, 3 ml of SOC medium (SOC was prepared by admixture of 20 g bacto-tryptone, 5 g yeast extract and 0.5 g NaCl in one liter of water, adjusting the pH to 7.5 and admixing 20 ml of glucose just before use to induce the expression of the Fd-cpIII and light chain heterodimer) was admixed and the culture was shaken at 220 rpm for one hour at 37° C., after which time 10 ml of SB (SB was prepared by admixing 30 g tryptone, 20 g yeast extract, and 10 g Mops buffer per liter with pH adjusted to 7) containing 20 µg/ml carbenicillin and 10 µg/ml tetracycline and the admixture was shaken at 300 rpm for an additional hour. This resultant admixture was admixed to 100 ml SB containing 50 µg/ml carbenicillin and 10 µg/ml tetracycline and shaken for one hour, after which time helper phage VCSM13 ($10^{12}$ pfu) were admixed and the admixture was shaken for an additional two hours. After this time, 70 µg/ml kanamycin was admixed and maintained at 30° C. overnight. The lower temperature resulted in better heterodimer incorporation on the surface of the phage. The supernatant was cleared by centrifugation (4000 rpm for 15 minutes in a JA10 rotor at 4° C.). Phage were precipitated by admixture of 4% (w/v) polyethylene glycol 8000 and 3% (w/v) NaCl and maintained on ice for 30 minutes, followed by centrifugation (9000 rpm for 20 minutes in a JA10 rotor at 4° C.). Phage pellets were resuspended in 2 ml of PBS and microcentrifuged for three minutes to pellet debris, transferred to fresh tubes and stored at −20° C. for subsequent screening as described below.

For determining the titering colony forming units (cfu), phage (packaged phagemid) were diluted in SB and 1 µl was used to infect 50 µl of fresh (OD600=1) XL1-Blue cells grown in SB containing 10 µg/ml tetracycline. Phage and cells were maintained at room temperature for 15 minutes and then directly plated on LB/carbenicillin plates.

5) Selection of Anti-HIV-1 Heterodimers on Phage Surfaces

(a) Multiple Pannings of the Phaae Library

The phage library produced in Example 2b4) was panned against recombinant gp120 of HIV-1 strain IIIb as described herein on coated microtiter plate to select for anti-gp120 heterodimers. A second phage library was panned S against recombinant gp41 (American Biotechnologies, Boston, Mass.) as described below to select for anti-gp41 heterodimers.

The panning procedure used was a modification of that originally described by Parmley and Smith (Parmley et al., *Gene*, 73:305–318 (1988). Four rounds of panning were performed to enrich for specific antigen-binding clones. For this procedure, four wells of a microtiter plate (Costar 3690) were coated overnight at 4° C. with 25 µl of 40 µg/ml gp120 or gp41 (American Biotechnologies) prepared above in 0.1M bicarbonate, pH 8.6. The wells were washed twice with water and blocked by completely filling the well with 3% (w/v) BSA in PBS and maintaining the plate at 37° C. for one hour. After the blocking solution was shaken out, 50 µl of the phage library prepared above (typically $10^{11}$ cfu) were admixed to each well, and the plate was maintained for two hours at 37° C.

Phage were removed and the plate was washed once with water. Each well was then washed ten times with TBS/Tween (50 mM Tris-HCl at pH 7.5, 150 mM NaCl, 0.5% Tween 20) over a period of one hour at room temperature where the washing consisted of pipetting up and down to wash the well, each time allowing the well to remain completely filled with TBS/Tween between washings. The plate was washed once more with distilled water and adherent phage were eluted by the addition of 50 µl of elution buffer (0.1M HCl, adjusted to pH 2.2 with solid glycine, containing 1 mg/ml BSA) to each well followed by maintenance at room temperature for 10 minutes. The elution buffer was pipetted up and down several times, removed, and neutralized with 3 µl of 2M Tris base per 50 µl of elution buffer used.

Eluted phage were used to infect 2 ml of fresh ($OD_{600}$=1) *E. coli* XL1-Blue cells for 15 minutes at room temperature, after which time 10 ml of SB containing 20 µg/ml carbenicillin and 10 µg/ml tetracycline was admixed. Aliquots of 20, 10, and 1/10 µl were removed from the culture for plating to determine the number of phage (packaged phagemids) that were eluted from the plate. The culture was shaken for one hour at 37° C., after which it was added to 100 ml of SB containing 50 µg/ml carbenicillin and 10 µg/ml tetracycline and shaken for one hour. Helper phage VCSM13 ($10^{12}$ pfu) were then added and the culture was shaken for an additional two hours. After this time, 70 µg/ml kanamycin was added and the culture was incubated at 37° C. overnight. Phage preparation and further panning were repeated as described above.

Following each round of panning, the percentage yield of phage were determined, where % yield—(number of phage eluted/number of phage applied)×100. The initial phage input ratio was determined by titering on selective plates to be approximately $10^{11}$ cfu for each round of panning. The final phage output ratio was determined by infecting two ml of logarithmic phase XL1-Blue cells as described above and plating aliquots on selective plates. In the first panning for gp120-reactive phage, 4.6×$10^{11}$ phage were applied to four wells and 7.7×$10^5$ phage were eluted. After the fourth panning 1.0×$10^6$ phage were eluted. From this procedure, 20 clones were selected from the Fab library for their ability to bind to glycosylated recombinant gp120 from the IIIB strain of HIV-1. Five clones were selected from the Fab library specific for binding to gp41. The panned phage surface libraries were then converted into ones expressing soluble Fab fragments for further screening by ELISA as described below.

In addition to panning on gp120 of strain IIIB and gp41, also contemplated as antigens for panning of combinatorial libraries is recombinant gp120 (IIIB strain) produced in baculovirus and recombinant gp120 (SF2 strain) produced in Chinese Hamster Ovary cells obtained as described by Steimer et al., *Science*, 254:105–108 (1991). Another antigen, a synthetic cyclic peptide, $N=CH-(CH_2)_3CO$ [SISGPGRAFYTG]$NCH_2CO$-Cys-NH2 (SEQ ID NO 48) prepared as described by Satterthwait et al., *Bulletin of the World Health Organization*, 68: Suppl., 17–25 (1990) corresponding to the central most conserved part of the V3 loop of gp120 was coupled to maleimide-activated BSA. The library was panned using 1, 2 or 4 ELISA wells coated with 1 $\mu$g of protein antigen or 10 $\mu$g BSA-peptide per well. Four rounds of panning were carried out for each antigen as described above. Eluted phage from the final round were used to infect XL1-Blue cells. Four rounds of panning against the four antigens produced an amplification in eluted phage of between 100 and 1000 fold. The panned phage surface libraries were then converted into ones expressing soluble Fab fragments for further screening by ELISA as described below.

6) Preparation of Soluble Heterodimers and Characterization of Binding Specificity to HIV-1 Antigens In order to further characterize the specificity of the mutagenized heterodimers expressed on the surface of phage as described above, soluble Fab heterodimers from acid eluted phage were prepared and analyzed in ELISA assays on HIV-1 derived antigen-coated plates and by competitive ELISA.

To prepare soluble heterodimers, phagemid DNA from the 20 gp120 positive clones and the 5 gp41 positive clones prepared above was isolated and digested with Spe I and Nhe I. Digestion with these enzymes produced compatible cohesive ends. The 4.7 kb DNA fragment lacking the gene III portion was gel-purified (0.6% agarose) and self-ligated. Transformation of *E. coli* XL1-Blue afforded the isolation of recombinants lacking the cpIII fragment. Clones were examined for removal of the cpIII fragment by Xho I-Xba I digestion, which should yield an 1.6-kb fragment. Clones were grown in 100 ml SB containing 50 $\mu$g/ml carbenicillin and 20 mM $MgCl_2$ at 37° C. until an $OD_{600}$ of 0.2 was achieved. IPTG (1 mM) was added and the culture grown overnight at 30° C. (growth at 37° C. provides only a light reduction in heterodimer yield). Cells were pelleted by centrifugation at 4000 rpm for 15 minutes in a JA10 rotor at 4° C. Cells were resuspended in 4 ml PBS containing 34 $\mu$g/ml phenylmethylsulfonyl fluoride (PMSF) and lysed by sonication on ice (2–4 minutes at 50% duty). Debris was pelleted by centrifugation at 14,000 rpm in a JA20 rotor at 4° C. for 15 minutes. The supernatant was used directly for ELISA analysis as described below and was stored at $-20°$ C. For the study of a large number of clones, 10 ml cultures provided sufficient heterodimer for analysis. In this case, sonications were performed in 2 ml of buffer.

Assays as described above were also performed for the gp41-specific clones.

a) Screeninc by ELISA

The soluble heterodimers prepared above were assayed by ELISA. For this assay, gp120 and gp41 were separately admixed to individual wells of a microtiter plate as described above for the panning procedure and maintained at 4° C. overnight to allow the protein solution to adhere to the walls of the well. After the maintenance period, the wells were washed five times with water and thereafter maintained for one hour at 37° C. with 100 $\mu$l solution of 1% BSA diluted in PBS to block nonspecific sites on the wells. Afterwards, the plates were inverted and shaken to remove the BSA solution. Twenty-five $\mu$l of soluble heterodimers prepared above reactive with the specific glycoprotein substrate were then admixed to each well and maintained at 37° C. for one hour to form immunoreaction products. Following the maintenance period, the wells were washed ten times with water to remove unbound soluble antibody and then maintained with a 25 $\mu$l of a 1:1000 dilution of secondary goat anti-human IgG F(ab')$_2$ conjugated to alkaline phosphatase diluted in PBS containing 1% BSA. The wells were maintained at 37° C. for one hour after which the wells were washed ten times with water followed by development with 50 $\mu$l of p-nitrophenyl phosphate (PNPP). Color development was monitored at 405 nm. Positive clones gave A405 values of >1 (mostly >1.5) after 10 minutes, whereas negative clones gave values of 0.1 to 0.2.

Approximate concentrations of gp120-reactive Fab were determined by ELISA using a sandwich ELISA as described by Zebedee et al., *Proc. Natl. Acad. Sci. USA*, 89:3175–3179 (1992) and are presented in the first column of FIG. 6. In addition, since Fabs are expressed in *E. coli* and the fraction of correctly assemble protein can vary, the amount of Fab reacting with gp120 was also assessed by ELISA titration. That data is also presented in FIG. 6 in the second column.

For the clones panned against the HIV-1 derived antigens, after conversion of the panned phage surface libraries to ones expressing soluble Fab fragments, 30–40 colonies were used to transform XL1-Blue cells and the supernates screened in ELISA assays against the antigen used in panning. Generally greater than 80% of the supernates tested positive. A representative number of positives were then selected from each antigen panning for further analysis.

(b) Competitive ELISA with Soluble gp120 and CD4

Immunoreactive heterodimers as determined in the above ELISA were then analyzed by competition ELISA to determine the affinity of the selected heterodimers. The ELISA was performed as described above on microtiter wells separately coated with 5 $\mu$g/ml of gp120 or soluble CD4 (American Biotechnologies) in 0.1M bicarbonate buffer at pH 8.6. Increasing concentrations of soluble or free gp120 ranging in concentration from $10^{-11}$M up to $10^{-7}$M diluted in 0.5% BSA/0.025% Tween 20/PBS were admixed with soluble heterodimers, the dilutions of which were determined in titration experiments that resulted in substantial reduction of OD values after a 2-fold dilution. For the CD4 competition assays, increasing concentrations of soluble or free CD4 ranging in concentration from $10^{-11}$M up to $10^{-6}$M diluted in 0.5% BSA/0.025% Tween 20/PBS were admixed with soluble heterodimers. The plates were maintained for 90–120 minutes at 37° C. and carefully washed ten times with 0.05% Tween 20/PBS before admixture of alkaline phosphatase-labelled goat anti-human IgG F(ab')2 at a dilution of 1:500 followed by maintenance for 1 hour at 37° C. Development was performed as described for ELISA.

To establish the relationship between neutralizing ability as described in Example 3 below could be related to antigen binding affinity of HIV-1-specific Fabs, competition ELISAs were carried out where soluble gp120 was competed with gp120 coated on ELISA plates for Fab binding. FIG. 7 shows that all Fabs were competed from binding to gp120 with a $IC_{50}$ of approximately $10^{-9}M$ free gp120. In addition as shown in Example 3, there is no correlation between antigen affinity and neutralization. The Fabs tested included Fabs 4, 12, 21 and 7 that are members of the same groups as determined by sequence analysis and comparison as described in Example 9. Fabs 13, 27, 6, 29, 2 and 3 are all members of the different groups as determined by sequence analysis and comparison as described in Example 9. Loop 2 is an Fab fragment selected from the same library as the other Fabs but which recognizes the V3 loop. Only with the V3 loop peptide was competition carried out with gp120 from the SF2 strain.

To investigate whether neutralization could be associated with blocking of the gp120-CD4 interaction, competition ELISAs were carried out with soluble CD4 competing with Fabs for binding to gp120-coated ELISA wells. The results are shown in FIG. 8. P4D10 and loop 2 are controls not expected to be competed by CD4. P4D10 is a mouse monoclonal antibody reacting with the V3 loop of gp120 (IIIB). Loop 2 Fab competition was carried out using gp120 (SF2). As shown in FIG. 8 the binding of all Fabs with the exception of the controls was inhibited with an $IC_{50}$ of approximately $10^{-8}M$ of soluble CD4. In addition, no difference was detected between the neutralizing and non-neutralizing Fabs to gp120 inhibited by CD4.

This implies that blocking of the CD4-gp120 interaction is unlikely to be an important factor in Fab neutralization of the HIV-1 virus.

Similar competition assays were performed with the Fabs panned against the four HIV-1 derived antigens. The 19 Fabs derived from panning against gp120 (IIIB) showed apparent affinities (1/concentration at 50% inhibition) for gp120 (IIIB) in the range $10^7$–$10^{-9}M$ with most being $1$–$3\times10^{-8}M$. The panning procedure tends to select strongly for tight binders so a grouping into a relatively narrow band of affinities was expected. Of 16 Fabs derived from panning against gp160 (IIIB), 6 were also reactive with gp120 (IIIB) and competition ELISAs showed they had similar apparent affinities as the gp120-panned Fabs. The non-gp120 reactive clones from the gp160 panning showed a lower ELISA reactivity with gp160 and could not be satisfactorily competed with gp160. They may be directed against gp41 but were not pursued here. Eight Fabs derived from panning against gp120 (SF2) also showed strong ELISA reactivity with gp120 (IIIB) and gave similar apparent binding affinities. Four Fabs were derived from panning against the V3 loop peptide. Of these Fabs, 2 reacted in ELISA with gp120 (SF2) but none with gp120 (IIIB). The apparent binding affinity of these loop binders to gp120 (SF2) was $10^{-8}M$.

To complete the survey in terms of strain cross-reactivity of Fabs, those derived from the gp120 and gp160 (IIIB) pannings were examined for ELISA reactivity with gp120 (SF2). All were reactive. Therefore, all the Fabs examined, with the exception of those selected by panning against the V3 loop peptide, bound to gp120 from IIIB and SF2 strains.

The Fabs were screened for CD4 inhibition of their binding to gp120 (IIIB) immobilized on ELISA wells. All, again with the exception of the V3 loop binders, showed sensitivity to CD4 inhibition. The inhibition constants were in the range $10^{-7}$ to $10^{-9}M$.

c) Binding Affinity Determination Using Surface Plasmon Resonance

Binding affinities were determined for six of the Fabs using surface plasmon resonance. Surface plasmon resonance was performed as it is a more accurate method for measuring affinity than competition ELISA. The six Fabs were chosen based upon sequence analysis which revealed that the heavy chains could be organized into 7 groups (Example 9). Each group contained members with identical V-D and D-J joining regions, implying a common clonal origin with varying numbers of differences elsewhere in the VH domain. Six Fabs were chosen as a representative of each respective group for further study as described herein. The single member of the seventh group was not included in these studies. The binding affinities of the six Fabs that are directed against the CD4 binding site of the gp120 envelope glycoprotein were determined using surface plasmon resonance as follows.

A Pharmacia BIAcore machine was used for the binding affinity determinations as previously described in Malmborg, et al., *J. Immunol.*, 35:643–650 (1992) and Mattsson, et al., *J. Immunol. Meth.*, 145:229–240 (1991). Optimization for the Fab fragments involved a number of steps. Two separate channels on a biosensor chip were coated with gp120 derived from the HIV-1 strain LAI (Repligen, Cambridge Mass.) such that one channel could be used for the determination of on-rate constants ($k_{on}$) and the other for the determination of off-rate constants ($k_{off}$).

For immobilization of antigen on the sensor surfaces, a flow rate of 5 $\mu$l/min of PBS, pH 7.4 was established over the biosensor chip. The chip was then activated by injecting 30 $\mu$l of activation solution (Pharmacia Biosensor, 50% 0.2M N-ethyl-N'-(3-diethylaminopropyl)-carbodiimide, 50% N-hydroxysuccinimide). The flow rate was then adjusted to 10 $\mu$l/min and the gp120 was injected in 10 mM sodium acetate buffer, pH 4.5. When association rates were to be determined, 25 $\mu$l of gp120 at 10 $\mu$g/ml was injected (a final level of 4000 Response Units (RU)). Twenty $\mu$l of gp120 at 2 $\mu$g/ml were injected for the determination of dissociation constants (a final level of 800 RU). In both cases, a flow rate of 5 $\mu$l/min was reestablished following the gp120 injection and the chip was blocked from any further immobilization by the injection of 30 $\mu$l of 1M ethanolamine, pH 8.5 (Pharmacia Biosensor).

For determination of on-rate constants ($k_{on}$), a series of dilutions were made for each Fab to give final concentrations in the range of 1 to 20 $\mu$g/ml. 30 $\mu$l of each Fab solution was injected in separate experiments over the immobilized gp120 at a flow rate of 5 $\mu$l/min. The change in response per unit time (dR/dt) was plotted against time (t) for each concentration. The slopes of each of these graphs were then plotted against their corresponding concentrations to give a final graph from which the on-rate constant could be read.

For determination of off-rate constants ($k_{off}$), 30 $\mu$l of each Fab solution at 150 $\mu$g/ml were injected over the immobilized antigen at a flow rate of 5 $\mu$l/min. Once the reaction had reached equilibrium, the Fab was removed from the antigen at a constant flow rate of 50 $\mu$l/min. A plot was then made of $\ln(R_t/R_0)$ against $t_t$–$t_0$ for the dissociation phase. $R_t$ is the response at time $t_t$ and $R_0$ is the initial response at time $t_0$. The slope of this graph was taken to be the off-rate constant. Affinities ($K_a$) were then calculated and expressed as $k_{on}/k_{off}$.

The apparent affinities of the panel of recombinant Fabs isolated from the donor as determined in competition ELISA and surface plasmon resonance were compared. Values of approximately $10^8 M^{-1}$ were obtained by competition ELISA as described in Example 2b6c in which the soluble and immobilized gp120 competed for binding to Fab in bacterial supernatants. Such a methodology only gives an approximate measure of affinity. Therefore, the affinities of six of these Fabs were measured using real-time biospecific interaction analysis (surface plasmon resonance) in order to obtain more accurate affinity constant values. The results are reproducible with a standard deviation from the mean of approximately 5% as determined by calculating a number of the affinity constants in triplicate. All Fabs examined have affinities in the range of $5 \times 10^7$ to $1 \times 10^8 M^{-1}$ as determined in surface plasmon resonance (Table 4). These values are in broad agreement with those derived from competition ELISA. These values imply no correlation between affinity for recombinant gp120 derived from LAI and the ability to neutralize the HXBc2 clone of HIV-1 derived from LAI as assessed in Example 3c.

TABLE 4

| Fab | $k_{on}$ (M$^{-1}$S$^{-1}$) | $k_{off}$ (S$^{-1}$) | $K_{a\,(M-1)}$ |
|---|---|---|---|
| b3  | $9.6 \times 10^3$ | $1.8 \times 10^{-4}$ | $5.1 \times 10^7$ |
| b6  | $1.6 \times 10^4$ | $1.6 \times 10^{-4}$ | $9.7 \times 10^7$ |
| b11 | $5.6 \times 10^4$ | $4.3 \times 10^{-4}$ | $1.3 \times 10^8$ |
| b12 | $4.5 \times 10^4$ | $4.3 \times 10^{-4}$ | $1.1 \times 10^8$ |
| b13 | $1.1 \times 10^4$ | $1.4 \times 10^{-4}$ | $7.9 \times 10^7$ |
| b14 | $6.0 \times 10^4$ | $6.5 \times 10^{-4}$ | $9.2 \times 10^7$ |

Also contemplated are competition ELISA and surface plasmon resonance assays where the binding of HIV-1 recombinant Fabs of this invention is performed in the presence of excess Fabs of this invention as well as those HIV-1 antibodies, polyclonal or monoclonal, present in patient sera, either asymptomatic or symptomatic, or obtained by other means such as EBV transformation and the like. The ability of an exogenously admixed antibody to compete for the binding of a characterized Fab of this invention will allow for the determination of equivalent antibodies in addition to unique epitopes and binding specificities.

3. Neutralizing Activity of Recombinant Human Fab Fragments Against HIV-1 In Vitro Binding of antibodies to viruses can result in loss of infectivity or neutralization and, although not the only defense mechanism against viruses, it is widely accepted that antibodies have an important role to play. However, understanding of the molecular principles underlying antibody neutralization is limited and lags behind that of the other effector functions of antibody. Such understanding is required for the rational design of vaccines and for the most effective use of passive antibody for prophylaxis or therapy. This is particularly urgent for the human immunodeficiency viruses.

A number of studies have led to the general conclusion that viruses are neutralized by more than one mechanism and the one employed will depend on factors such as the nature of the virus, the epitope recognized, the isotype of the antibody, the cell receptor used for viral entry and the virus:antibody ratio. The principle mechanisms of neutralization can be considered as aggregation of virions, inhibition of attachment of virus to cell receptor and inhibition of events following attachment such as fusion of viral and cellular membranes and secondary uncoating of the virion. One of the important features of the third mechanism is that it may require far less than the approximately stoichiometric amounts of antibody expected for the first two mechanisms since occupation of a small number of critical sites on the virion may be sufficient for neutralization. For instance it has been shown that neutralization of the influenza A virion obeys single hit kinetics as described by Outlaw et al., *Epidemiol. Infect.*, 106:205–220 (1992).

Intensive studies have been carried out on antibody neutralization of HIV-1. For review, see Nara et al., *FASEB J.*, 5:2437–2455 (1991). Most have focussed on a single linear epitope in the third hypervariable domain of the viral envelope glycoprotein gp120 known as the V3 loop. Antibodies to this loop are suggested to neutralize by inhibiting fusion of viral and cell membranes. Binding to the loop resulting in neutralization can occur prior to virus-cell interaction or following gp120 binding to CD4. See, Nara, In Retroviruses of Human Aids and Related Animal Diseases, eds. Girard et al., pp. 138–150 (1988); Linsely et al., *J. Virol.*, 62:3695–3702 (1988); and Skinner et al., *J. Virol.*, 67:4195–4200 (1988). Features of the V3 loop are sequence variability within the loop [Goudsmit et al., *FASEB J.*, 5:2427–2436 (1991) and Albert et al., *AIDS*, 4:107–112 (1990)] and sensitivity of neutralizing antibodies against the loop to sequence variations outside the loop [Nara et al., *FASEB J.*, 5:2437–2455 (1991); Albert et al., supra; McKeating et al., *AIDS*, 3:777–784 (1989); and Wahlberg et al., *AIDS Res. Hum. Retroviruses*, 7:983–990 (1991). Hence anti-V3 loop antibodies are often strain specific and mutations in the loop in vivo may provide a mechanism for viral escape from antibody neutralization.

Recently considerable interest has focused on antibodies capable of blocking CD4 binding to gp120. A number of groups have described the features of these antibodies as (a) reacting with conformational i.e., non-linear epitopes, (b) reacting with a wide range of virus isolates and (c) being the predominant neutralizing antibodies in humans after longer periods of infection. See, Berkower,et al., *J. Virol.*, 65:5983–5990 (1991); Steimer et al., *Science*, 254:105–108 (1991); Ho et al., *J. Virol.*, 65:489–493 (1991); Kang et al., *Proc. Natl. Acad. Sci., USA*, 88:6171–6175 (1991); Posner et al., *J. Immunol.*, 146:4325–4332 (1991); and Tilley et al., *Res. Virol.*, 142:247–259 (1991). Neutralizing antibodies of this type would appear to present a promising target for potential therapeutics. The mechanism(s) of neutralization of these antibodies is unknown although there is some indication that this may not be blocking of virus attachment since a number of mouse monoclonal antibodies inhibiting CD4 binding to gp120 are either non-neutralizing or only weakly neutralizing.

The generation of human monoclonal antibodies against the envelope of HIV-1 as described by Burton et al., *Proc. Natl. Acad. Sci. USA*, 88:10134–10137 (1991) using combinatorial libraries allows a novel approach to the problem of neutralization. Given the lack of a three-dimensional structure for gp120 and the complexity of the virus, the approach seeks to explore neutralization at the molecular level through the behavior of related antibodies. This is possible for the following reasons: (1) the combinatorial approach allows the rapid generation of large numbers of human antibodies; (2) the antibodies (Fab fragments) are expressed in *E. coli* and can readily be sequenced; and (3) antibodies have similar sequences and common structural motifs allowing functional differences to be meaningfully correlated with primary structure.

Neutralization studies were performed as described herein on the human recombinant Fab fragments from 20 clones against gp120 prepared as described in Examples 1 and 2, all of which are strain cross-reactive and inhibited by CD4 from binding to gp120. The results presented herein show that neutralization was not effected by virus aggregation or cross-linking of gp120 molecules on the virion surface and was not correlated with blocking of the interaction between soluble CD4 and recombinant gp120.

Neutralization studies were also performed as described herein on the human recombinant Fab fragments from the gp41-reactive clones prepared as described in Examples 1 and 2. The results are presented below.

Two different assays, a p24 ELISA assay and a syncytium assay, were performed to measure neutralization ability of the recombinant human HIV-1 immunoreactive Fabs. An additional assay, a plaque assay, was performed for determining the neutralization effectiveness of the gp41-reactive Fabs. In plaque assays, CD4+ cells were cultured in the presence or absence of soluble gp41-reactive Fabs prior to inoculation with virus. Inhibition of infectivity, also referred to as neutralization, by antibodies was expressed as the percent of plaque formation in the cultures compared to cells exposed to PBS alone.

Neutralization assays were also performed with an antibody molecule consisting of the light chain and the VH region of the Fab 12 and the constant regions (CH1, CH2, and CH3) of an IgG1 molecule. Quantitative infectivity microplaque and syncytial formation assays to measure neutralization were performed with the b12 IgG1 and laboratory isolates MN and IIIB of HIV-1 virus. In the syncytial formation assay, virus was grown in H9 cells and infectivity measured by culturing monolayers of CEM-SS target cells with 100–200 syncytial forming units (SFUs) of virus, in the presence or absence of antibody. p24 ELISA and microplaque formation assays were also performed with primary clinical isolates of the HIV-1 virus.

In addition, the ability of the recombinant human HIV-1 immunoreactive Fabs b3, b6, b12, b13, and b12 to neutralize the HXBc2 molecular clone of gp120 derived from HTLV-IIIB (LAI) was determined in an envelope complementation assay. The supernatant containing recombinant HIV-1 virions from cotransfected COS-1 cells was incubated with the recombinant Fabs prior to incubation with Jurkat cells. The recombinant HIV-1 virions contained the HXBc2 clone of HIV-1 strain LAI which encodes a chloramphenicol acetyltransferase (CAT) gene. Upon infection of Jurkat cells with the recombinant HIV-1 virions, the CAT gene was expressed and CAT activity measured. Activity of the CAT gene was therefore an indication of infectivity of the Jurkat cells with the recombinant HIV-1 virion. Lack of CAT activity indicated the Jurkat cells were not infected with the recombinant HIV-1 virion.

For some of these assays, the recombinant Fabs were first purified. One liter cultures of SB containing 50 $\mu$g/ml carbenicillin and 20 mM $MgCl_2$ were inoculated with appropriate clones and induced 7 hours later with 2 mM IPTG and grown overnight at 30° C. The cell pellets were sonicated and the resultant supernatant were concentrated to a 50 ml volume. The filtered supernatants were loaded on a 25 ml protein G-anti-Fab column, washed with 120 ml buffer at a rate of 3 ml/minute and eluted with citric acid at pH 2.3. The neutralized fractions were then concentrated and exchanged into 50 mM MES at pH 6.0 and loaded onto a 2 ml Mono-S column at a rate of 1 ml/minute. A gradient of 0–500 mM NaCl was run at 1 ml/minute with the Fab eluting in the range of 200–250 mM NaCl. After concentrating, the Fabs were positive when titered on ELISA against gp120 and gave a single band at 50 kD by 10–15% SDS-PAGE. Concentration was determined by absorbance measurement at 280nm using an extinction coefficient (1 mg/ml) of 1.4.

a. Neutralization as Measured by the p24 ELISA Assay

For this assay, diluted tissue culture supernatants of HIV-1 IIIB or MN-infected peripheral blood mononuclear cells (PBMC) ($50TCID_{50}$ (50% tissue culture infectious dose), 100 $\mu$l) were maintained for 2 hours at 37° C. with serial dilutions (1:2), beginning at a dilution of 1:20, of recombinant Fab supernates prepared in Example 2b6). Control Fab supernates were also provided that included human neutralizing sera, a known human neutralizing monoclonal antibody 2F5 and the Fab fragment derived from that antibody by papain digestion, and a known mouse neutralizing monoclonal antibody and its $F(ab')_2$ fragment as described by Broliden et al., J. Virol., 64:936–940 (1990). PBMC ($1 \times 10^5$ cells) were admixed to the virus/antibody admixture and maintained for 1 hour at 37° C. Thereafter, the cells were washed and maintained in RPMI 1640 medium (GIBCO) supplemented with 10% fetal calf serum, 1% glutamine, antibiotics and IL-2. The culture medium was changed at days 1 and 4. At 7 days post-infection, supernates were collected and analyzed by HIV-1 p24 antigen capture ELISA as described by Sundqvist et al., J. Med. Virol., 29:170–175 (1989) the disclosure of which is hereby incorporated by reference. Neutralization was defined as positive if an 80% or greater reduction of optical density at 490 nm in the culture supernatant occurred as compared to negative Fab or negative human serum. Tests with all Fabs, mabs and sera were repeated on at least two occasions.

b. Quantitative Infectivity Assay Based on Syncytial Formation

A quantitative neutralization assay with the MN strain of HIV-1 was performed as described by Nara et al., AIDS Res. Human Retroviruses, 3:283–302 (1987), the disclosure of which is hereby incorporated by reference. Monolayers of CEM-SS target cells were cultured with virus, in the presence or absence of antibody, and the number of syncytia forming units determined 3–5 days later. An equivalent amount of virus was used in the assays to allow direct comparison of the various antibody concentrations tested. The assays were repeatable over a virus-surviving fraction range of 1 to 0.001 within a 2 to 4-fold difference in the concentration of antibody ($P<0.001$).

c. Neutralization as Measured by the Envelope Complementation Assay

The ability of purified recombinant Fabs b3, b6, b11, b12, b13, and b14 to neutralize the HXBc2 gp120 molecular clone of the HIV-1 (LAI) isolate was assessed in an envelope complementation assay (Helseth et al., J. Virol., 65:2119–2123 (1991)). Briefly, COS-1 cells were cotransfected with a plasmid expressing envelope glycoprotein 120 derived from HIV-1 (LAI) and a plasmid containing an env-defective HXBc2 clone and encoding the bacterial CAT gene. Equal fractions of the cell supernatants containing recombinant virions were incubated at 37° C. for 1 hour with varying concentrations of recombinant Fab (0.1–20 $\mu$g/ml) or control monoclonal antibody 110.4 prior to incubation with Jurkat cells. Three days post-infection, the Jurkat cells were lysed and CAT activity measured. Neutralization was expressed as a decrease in the percentage of residual chloramphenicol transferase (CAT) activity. Control monoclonal antibody 110.4 is a strongly neutralizing antibody directed to the V3 loop of the HXBc2 HIV-1 strain.

d. Results of the Neutralization Assays for gp120

Assays were generally repeated at least twice with reproducible results. For the data reported in FIG. 6, the gp120-specific Fab supernates were divided into two parts, one being used in the p24 assay and the other in the syncytia assay. A dash (-) indicates that there was no neutralization at 1:20 dilution in the p24 assay and 1:16 in the syncytial assay (with most clondetecowing no detectable neutralization at a 1:4 dilution). Neutralization titers are indicated in the figure. For the p24 assay, the titer corresponds to the greatest dilution producing >80% reduction in absorbance in ELISA. For the syncytia assay, Fabs 4 and 12 produced >95% neutralization at a 1:4 dilution of supernate and 80 and 70% reduction at 1:128 dilution respectively. These Fabs were effective neutralizers in both types of assays. They have also been shown to neutralize infection by IIIB and RF strains using a PCR-based assay of proviral integration. Fabs 6 and 7 showed no neutralization in the syncytia assay but other supernate preparations showed activity. Fab 13 was consistently effective in the p24 assay but not in the syncytia assay. A number of other clones show lower levels of neutralizing ability.

Fabs were purified from a selection of some of the clones as described above and used in both neutralization assays. As shown in FIG. 9, Fabs 4 and 12 were again effective in both assays at similar levels with for example 50% inhibition of syncytial formation at an Fab concentration of approximately 20 nM (1 µg/ml). The results shown are derived from the syncytia assay using the MN strain. Fabs 7 and 21 were equally effective in the syncytial assay but somewhat less so in the p24 assay. The p24 assay indicated greater than 80% neutralization of HIV-1 MN strain for Fab 4 at 3, Fab 7 at 15, Fab 12 at 3, Fab 13 at 4 and Fab 21 at 7 µg/ml, respectively. Fab 13 however was ineffective in the syncytial assay at 25 µg/ml. For the IIIB strain, greater than 80% neutralization was observed for Fab 4 at 13, Fab 7 at 15, Fab 12 at 7 and Fab 21 at 14 µg/ml, respectively. Although Fab 11 was not effective in neutralization assays when unpurified as shown in FIG. 6, following purification, Fab 11 was equally effective as Fab 12 in neutralizing HIV-1. For this reason, the Fab is being deposited with the ATCC as described in Example 12 along with Fab 12 and Fab 13.

Figure 23:
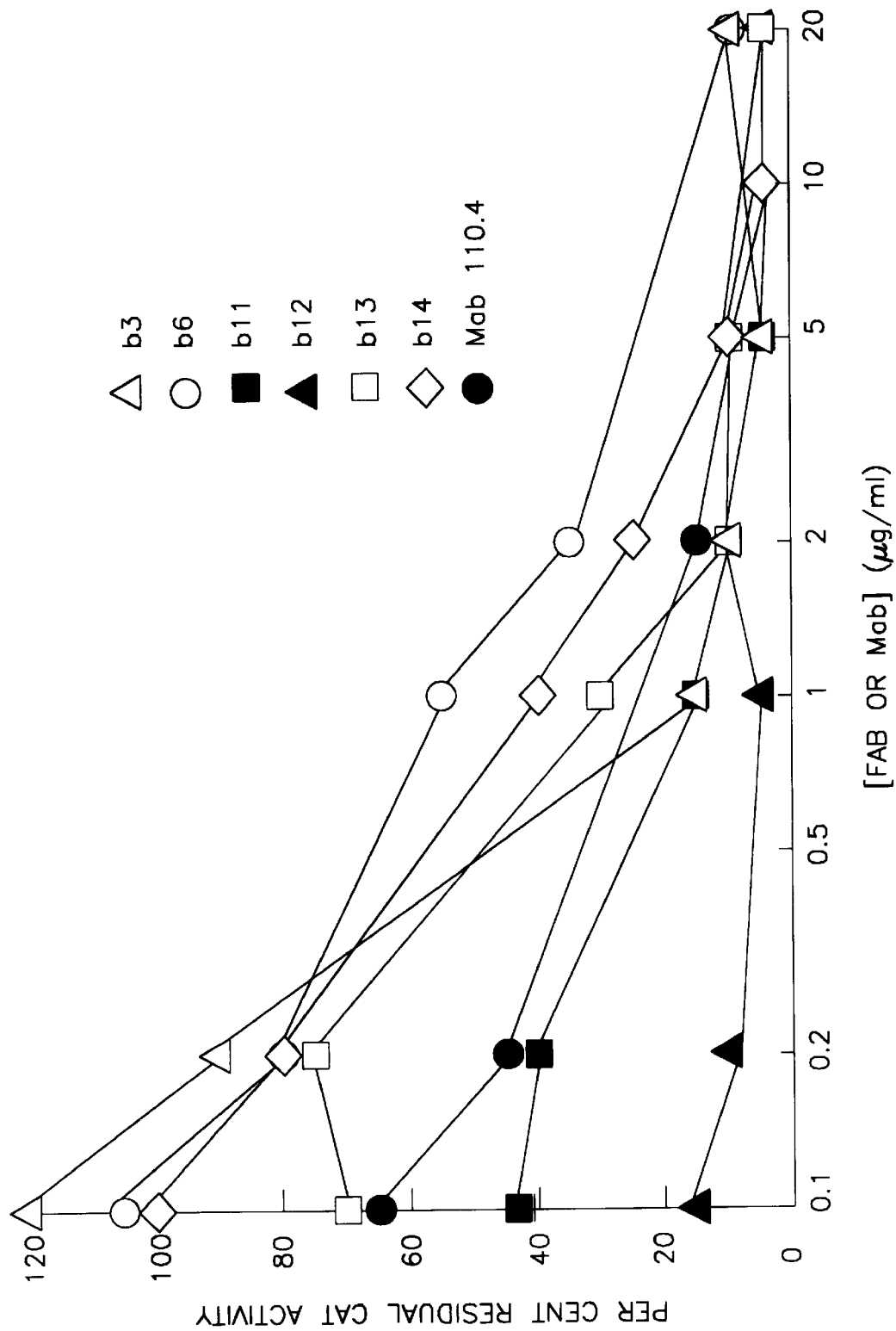
FIG. 23 illustrates the neutralization of the HXBc2 molecular clone of HIV-1 LAI by purified Fabs and a monoclonal antibody 110.4 (Mab 110.4) in an envelope complementation assay as described in Example 3c. Neutralization of HXBc2 infectivity is expressed as a decrease in residual CAT activity. The data is plotted as % residual CAT activity on the Y-axis and increasing concentrations of Fab,and MAb (0.1–20 μg/ml) on the X-axis.

The ability of purified recombinant Fabs b3, b6, b11, b12, b13, and b14 to neutralize the HXBc2 gp120 molecular clone of the HIV-1 (LAI) isolate was assessed in an envelope complementation assay. FIG. 23 shows the concentration dependence of Fab neutralization of the HXBc2 clone in this assay. All of the Fabs neutralize effectively at the highest concentration measured (20 µg/ml). Irrelevant Fabs, Fabs directed to surface glycoproteins on other viruses such as RSV, do not neutralize in this assay. Examination of the lower concentrations clearly reveals that Fab b12 is the most effective neutralizer. The neutralizing potency of Fab b12 was greater than that of the 110.4 whole monoclonal antibody tested in parallel. The 110.4 antibody is one of the most potent antibodies directed against the V3 loop of the HXBc2 HIV-1 strain (Thali, M. and J. Sodroski, unpublished observations). In other studies, Fab b12 has been found to show exceptional neutralizing ability towards laboratory (Example 3 and Barbas et al., *Proc. Natl. Acad. Sci. USA*, 91, in press (1994)) and field isolates of HIV-1 as described in Example 5.

There are a number of conclusions arising from the data shown in the FIGS. 6, 9 and 23. It is apparent that HIV-1 can be neutralized without virion aggregation or cross-linking of gp120 molecules on the virion surface since monovalent Fab fragments are effective. To further confirm this finding, a Fab fragment was produced by papain digestion of a known neutralizing human monoclonal antibody. As shown in FIG. 6, the Fab fragment was approximately equally effective as the whole IgG in neutralization of the MN strain of HIV-1. This is consistent with results on Fabs prepared from two mouse monoclonal antibodies to the V3 loop. An $F(ab')_2$ fragment of a mouse monoclonal antibody was somewhat less effective than the parent IgG in neutralization of the MN strain. Interestingly, the fragments from these control antibodies were relatively poor in neutralizing the IIIB strain of HIV-1. The results also show that there appears to be a difference between the two assays employed since Fab 13 was consistently effective in one assay but not the other. The principal variables were the incubation time of the virus and antibody prior to infection (2 hours for the p24 assay and 0.5 hours for the syncytial assay), the amount of virus used for infection, the cells used to propagate virus (human PBMCs for the former and H9 cells for the latter) and the cells infected (human PBMCs for the former and CEM.SS cells for the latter). Of these, there is a strong possibility that the MN virus used in the two assays, having been passaged through different cells, is critically different.

The Fabs show a spectrum of neutralizing ability for gp120 from a molecular clone HXBc2 derived from the HIV-1 strain LAI in the envelope complementation assay. Fab b12 exhibited the greatest potency of neutralization and was even more effective in this assay than a whole antibody directed to the V3 loop of gp120. Neutralizing ability is not correlated with either the apparent affinity of the Fab for gp120 derived from the recombinant HIV-1 strain LAI as estimated by competition ELISA or the affinity for gp120 derived from HIV-1 strain LAI as determined by surface plasmon resonance. For example, Fabs b6, b12, and b14 have very similar affinities by surface plasmon resonance (Table 4) but different neutralization ability in the envelope complementation assay (FIG. 23). Similarly, neutralization is not correlated with the ability of the Fab to compete with soluble CD4 in a competition ELISA.

e. Results of the Neutralization Assays for gp41

The gp41-reactive Fabs exhibited specificity to the conformation epitope of gp41 including amino acid residues in positions 565–585 and 644–663. The five selected gp41-specific Fabs were designated DL 41 19, DO 41 11, GL 41 1, MT 41 12 and SS 41 8. Neutralization assays were performed as described above for the gp120-reactive Fabs. In the plaque assays, the data shown is the concentration of Fab in micrograms/milliliter required to achieve 50 of neutralization. The data for the other two neutralization assays is also expressed in micrograms/milliliter of Fab required to neutralize infection as defined in the description of the p24 and syncytial assays above. The results of the three neutralization assays, plaque, syncytial and p24, are presented in Table 5. The MN and IIIB HIV strains were used as indicated in Table 5 for the assays. The abbreviation "ND" stands for not determined when indicated in the table.

TABLE 5

| | Assay/Strain | | | | |
|---|---|---|---|---|---|
| | Plaque | | Syncytial | P24 | |
| Fab | MN | IIIB | IIIB | MN | IIIB |
| DL 41 19 | <4 | <40 | 1.4 | ND | ND |
| DO 41 11 | <40 | 7.1 | 2.3 | 0.9 | ND |
| GL 41 1 | <4 | <4 | 1.7 | ND | 3.5 |
| MT 41 12 | <40 | <40 | 5.5 | 4.5 | 4.5 |
| SS 41 8 | <4 | <4 | 2.2 | ND | 7.1 |

As shown in Table 5, all five Fabs were effective at neutralizing both MN and IIIB strains of HIV in either plaque, syncytial or p24 assays. Fabs DL 41 19 and DO 41 11 exhibited strain specificity in the plaque assay where the former was ten-fold more effective at inhibiting plaque formation with the MN strain than with the IIIB strain. The opposite specificity was seen with the DO 41 11 Fab. However, both Fabs exhibited comparable neutralization as measured by the syncytial assay. Two Fabs, GL 41 1 and SS 41 8, were equally effective at inhibiting plaque formation with either MN or IIIB strains. The Fab MT 41 12 was similarly not strain-specific although neutralization required 10 fold more antibody. No strain specificity was evident when Fab MT 41 12 was used in p24 assays where the same amount of antibody was equally effective. All five antibodies were neutralized IIIB as measured in the syncytial assay.

Thus, the five gp41-specific Fabs neutralized HIV-1 MN and IIIB in at least two of the three assays used for measuring neutralizing activity. Moreover, strain specificity was prevalent in two of the five assays as measured by the plaque assay. Based on these differential neutralization characteristics, the gp41-specific Fabs provide useful therapeutic reagents for neutralizing HIV-1.

4. Construction of a Mammalian Expression Vector pEe12 Combo BM 12 for the Expression of an IgG1 Antibody Molecule with the Fab from b12 (b12 IgG1)

Although Fab b12 is capable of neutralizing some primary isolates, the corresponding whole antibody molecule is likely to be more effective. The whole antibody, consisting of the Fab fragment and the Fc domain, participates in the elimination of foreign cells by first binding specifically to the foreign cell via the Fab portion and interacting with other cells in the immune system via the Fc domain. The Fc domain also enables the antibody to bind complement.

Fab b12 was converted to a whole IgG1 molecule (b12 IgG1) by cassetting the variable heavy chain (VH) and light chain genes into a vector created for high-level mammalian expression. b12 IgG1 used in the neutralization studies was prepared by expression in Chinese hamster ovary (CHO) cells and purified by affinity chromatography.

The strategy to convert the Fab b12 to a whole IgG1 molecule was similar to that described previously for the generation of a whole antibody beginning with a phage derived Fab (Bender, et al., *Hum. Antibod. Hybridomas*, 4:74–79 (1992)).

a. Construction of b12 Heavy Chain IgG1 pSG-5 Mammalian Expression Vector

1) Modification of b12 Heavy Chain Variable Region to Introduce a Kozak Secuence, Mammalian Leader Sequence, and Human VH Consensus Sequence First, the b12 VH region was cloned into a pSG-5 expression vector (Green et al., *Nucl. Acids Res.*, 16:369 (1988)) to fuse the b12 VH to the heavy chain constant domains (CH1, CH2, and CH3) of an IgG1 antibody molecule. The double-stranded Fab b12 DNA was used as a template for isolating the gene encoding the VH region of the Fab b12, the amino acid residue sequence of which is listed in SEQ ID NO 66. Fab b12 DNA and mouse B73.2 IgG1 DNA (Whittle, et al., *Protein Eng.*, 1:499 (1987) and Bruggmeman, et al., *J. Exp. Med.*, 166:1351 (1987)) were used as templates for a PCR amplification for the construction of a DNA fragment consisting of the unique Kozak sequence for the control of heavy chain expression, the mouse B72.3 heavy chain leader sequence (MEWSWVFLFFLSVTTGVHS (SEQ ID NO 155 from amino acid residue sequence 1 to 20)), the human VH consensus sequence (QVQLVQ (SEQ ID NO 155 from amino acid residue sequence 21 to 26)), and the VH region of the Fab b12. Altering the beginning of the VH from the mouse consensus sequence to the human consensus sequence also destroyed the original Xho I cloning site. The restriction sites EcoR I and Sst I were introduced in the amplification reaction and were located at the 5' and 3' ends of the fragment, respectively. The procedure for creating the modified VH fragment by combining the products of the two separate PCR amplifications is described below.

The primer pair, HC-1 (SEQ ID NO 157) and HC-2 (SEQ ID NO 158) as shown in Table 10, was used in the first PCR reaction to amplify a portion of the Fab b12 VH gene and incorporate the human heavy chain consensus sequence into the 5' end of the VH fragment and introduce an Sst I cloning site in the 3' end of the VH fragment. In addition, the 5' PCR primer introduces sequences into the VH fragment which form 27 base pairs of homology with the mouse leader sequence fragment prepared below. The 27 base pairs of homology in the fragments is used in a subsequent PCR reaction to fuse the two PCR products (Yon and Fried, *Nucl. Acids Res.*, 17:4895 (1989)) to form a modified VH fragment consisting of the EcoR I cloning site, the mouse leader sequence 72.3, the human consensus sequence, the remaining VH coding sequence, and the Sst I cloning site. For the PCR reactions, 1 $\mu$l containing 100 ng of Fab b12 DNA was admixed with 10 $\mu$l of lOX PCR buffer in a 0.5 ml microfuge tube. To the DNA admixture, 8 $\mu$l of a 2.5 mM solution of dNTPs (DATP, dCTP, dGTP, dTTP) was admixed to result in a final concentration of 200 micromolar ($\mu$M) of each dNTP. 1 $\mu$l (equivalent to 20 picomoles (pM)) of the 5' forward HC-1 primer and 1 $\mu$l (20 pM) of the 3' backward HC-2 primer were admixed into the DNA solution. To the admixture, 73 $\mu$l of sterile water and 2.5 units of Taq DNA polymerase was added. Two drops of mineral oil were placed on top of the admixture and 35 rounds of PCR amplification in a thermocycler were performed. The amplification cycle consisted of 52° C. for 1 minute, 72° C. for 2 minutes and 94° C. for 0.5 minutes.

The primer pair, HC-3 (SEQ ID NO 159) and HC-4 (SEQ ID NO 160) as shown in Table 10, was used in a separate PCR reaction to amplify the mouse B72.3 leader sequence and incorporate an EcoR I cloning site at the 5' end of the fragment and to introduce a 27 base pair sequence which has homology to the modified VH fragment prepared above. Double-stranded DNA encoding the mouse B73.2 IgG1 (Whittle, et al., supra) was used as a template for preparation of the mouse 72.3 leader sequence. The PCR reaction to prepare the mouse leader sequence fragment was performed using the same conditions as described above for the preparation of the modified VH fragment.

The resultant PCR modified b12 VH DNA fragment and mouse leader sequence fragment were purified by electrophoresis in a 2.5% Nu-Sieve agarose gel (FMC). The area in the agarose containing the modified b12 VH DNA fragment and mouse leader sequence fragment were excised from the agarose.

A third PCR amplification using the primer pairs, HC-1 (SEQ ID NO 157) and HC-3 (SEQ ID NO 159) as shown in Table 10, was performed to fuse the mouse leader fragment with the modified VH fragment. The primers used for this amplification were designed to preserve an EcoR I site, a unique Kozak sequence, and the mouse B72.3 heavy chain leader sequence on the 5' end of the amplified fragment and to preserve the Sst I cloning site on the 5' end of the amplified fragment. The templates used in this PCR reaction were the two purified PCR reaction products described above. The PCR reaction and subsequent purification of the PCR product were performed as described above.

2) Modification of b12 Heavy Chain Variable Region to Eliminate a BalII Restriction Site The b12 modified heavy chain fragment prepared in Example 4a1 contained a Bgl II cloning site at amino acid residue 87 which would interfere with the insertion of the heavy chain fragment into the pEE6 mammalian expression vector. The Bgl II restriction site was therefore eliminated in a PCR reaction using primers which destroyed the Bgl II restriction site while preserving the encoded amino acid, arginine at amino acid residue 87 of the modified b12 heavy chain fragment.

The primer pair, HC-1 (SEQ ID NO 157) and HC-6 (SEQ ID NO 162) as shown in Table 10, was used in the first PCR reaction to preserve the 5' region of the modified b12 heavy chain fragment and destroy the Bgl II restriction site at amino acid residue 87 of the heavy chain. The HC-6 primer introduces sequences into the VH fragment which form 32 base pairs of homology with the remaining portion of the VH fragment which will be prepared as described below. The 32 base pairs of homology in the fragments was used in a subsequent PCR reaction to fuse the two PCR products (Yon and Fried, supra) to form a modified VH fragment as described above but without the Bgl II restriction site. The PCR reaction was performed and the PCR products were purified as described in Example 4a1.

The primer pair, HC-2 (SEQ ID NO 142) and HC-5 (SEQ ID NO 145) as shown in Table 10, was used in the second PCR reaction to preserve the 3' region of the modified b12 heavy chain fragment and destroy the Bgl II restriction site. The HC-5 primer introduces sequences into the VH fragment which form 32 base pairs of homology with the remaining portion of the VH fragment which was prepared in the first PCR reaction. PCR products which have incorporated the HC-5 and HC-6 primers contain 32 base pairs of overlapping sequences which are identical. It is the annealing of the two PCR products at these 32 base pairs during the subsequent PCR reaction which fuses the two portions of the VH fragment together to recreate the entire VH fragment as described in Yon and Fried (supra).

A third PCR amplification using the primer pairs, HC-1 (SEQ ID NO 157) and HC-3 (SEQ ID NO 159) as shown in Table 10, was performed to fuse the two VH fragments in which the Bgl II restriction site had been destroyed. The primers used for this amplification were designed to preserve an EcoR I site, a unique Kozak sequence, and the mouse B72.3 heavy chain leader sequence on the 5' end of the amplified fragment and the Sst I cloning site on the 3' end of the amplified fragment. The templates used in this PCR reaction were the two purified PCR reaction products described above. The PCR reaction and subsequent purification of the PCR product were performed as described in Example 4a1.

3) Insertion of Modified b12 Heavy Chain Variable Region into the pSG-5 Mammalian Expression Vector The modified b12 heavy chain variable region PCR product was ligated into a mammalian expression vector (Adair, et al., Hum. Antibod. Hybridomas, in press). The mammalian expression vector consisted of the pSG-5 vector (FIG. 24) with a human IgG1 gene inserted at the EcoR I site. The human IgG1 gene contained a VH insert in the same reading frame as the constant regions of the human IgG1 gene. The VH insert was removed by digestion with EcoR I and Sst I enzymes. The constant regions (CH1, CH2, and CH3) remained in the pSG-5 vector. Transcription of the heavy chain gene in the pSG-5 expression vector is under the control of the SV40 early promoter. Transcriptional termination is signaled by the SV40 polyadenylation signal sequence downstream of the heavy chain sequence. The M13 intergenic region allows for the production of single-stranded DNA for nucleotide sequence determination.

The modified b12 heavy chain variable region PCR product was digested with EcoR I and Sst I and purified on a 2.5% Nu-Sieve agarose gel (FMC). The mammalian expression vector DNA containing the IgG1 sequences was digested in parallel with EcoR I and Sst I enzymes to remove the original VH region. The PCR modified heavy chain variable region was ligated to the constant regions in the mammalian expression vector using T4 DNA ligase under conditions well known to those of skill in the art and transformed into DH5α competent cells following the manufacturer's recommended procedures (GIBCO, BRL Life Technologies, Gaithersburg, Md.). The PCR modified heavy chain variable region was inserted in the same reading frame as the constant regions of the human IgG1 gene in the pSG-5 vector. Miniprep DNAs were analyzed and large scale plasmid preparations performed. The nucleotide sequence of the 5' untranslated region including the Kozak sequence, mouse B72.3 heavy chain leader sequence, heavy chain variable region, heavy chain constant regions, and SV40 signal sequence was determined by the dideoxynucleotide chain termination method (Sanger et al., supra).

TABLE 10

| SEQ ID NO | Primer | | |
|---|---|---|---|
| (141)[1] | HC-1 | (F) | 5' CAGGTTCAGCTGGTTCAGTCCGGGGCT 3' |
| (142)[2] | HC-2 | (B) | 5' CCTTGGAGCTCACGATGACCGTGGTTCCTTGGCCCCAGACGTCC 3' |
| (143)[3] | HC-3 | (F) | 5' GGCCGCGAATTCGCCGCCACCATGGAATGGAGCTGGGTCTTTCTCTTCTTCCTGTCAGTA 3' |
| (144)[2] | HC-4 | (B) | 5' AGCCCCGGACTGAACCAGCTGAACCTG 3' |
| (145)[4] | HC-5 | (F) | 5' GGAGTTGAGGAGCCTCAGGTCTGCAGACACGG 3' |
| (146)[4] | HC-6 | (B) | 5' CCGTGTCTGCAGACCTGTGGCTCCTCAACTCC 3' |
| (147) | LC-1 | (F) | 5' GATGCCAGATGTGAGATCGTTCTCACGCAGTCT 3' |
| (148)[3,5] | LC-2 | (B) | 5' GCGGGATCCGAATTCTCTAGAATTAACACTCTCCCCTGTTGAAGCTCTTTGTGACGGGCGAACTCAG 3' |
| (149)[3] | LC-3 | (F) | 5' GCGCGAATTCACCATGGGTGTGCCCACTCAGGTCCTGGGGTTGCTGCTGC 3' |
| (150) | LC-4 | (B) | 5' AGACTGCGTGAGAACGATCTCACATCTGGCATC 3' |
| (151)[6] | LC-5 | (F) | 5' GCGCAAGCTTACCATGGGTGTGCCCACTCAGGTCCTGGGGTTGCTGCTGC 3' |

F Forward primer
B Backward Primer
[1]the Sst I cloning site is single underlined
[2]the primers, HC-2 and HC-4 contain complementary sequences
[3]the EcoR I cloning site is single underlined
[4]in HC-4, the G that is double underlined was altered from an A to eliminate a Bgl II restriction site; in HC-5, the C that is double underlined was altered from a T to eliminate a Bgl II restriction site
[5]the base A that is double underlined was introduced in the PCR primer to alter the encoded amino acid from an arginine, R, to a serine, S
[6]the HindIII cloning site is single underlined b. Construction of a b12 Light Chain pSG-5 Mammalian Expression Vector 1) Modification of b12 Light Chain to Introduce a Kozak Seauence, Mammalian Leader Seauence, and Human Light Chain Consensus Sequence The b12 light chain was cloned into a separate pSG-5 expression vector (Green et al., supra). The double-stranded Fab b12 DNA was used as a template for isolating the gene encoding the light chain of the Fab b12, the amino acid residue sequence the light chain of Fab b12 is listed in SEQ ID NO 97. Mouse B73.2 IgG1 DNA (Whittle, et al., *Protein Eng.*, 1:499 (1987) and Bruggmeman, et al., *J. Exp. Med.*, 166:1351 (1987)) was used as a template for isolating the mouse B73.2 leader sequence. Fab b12 and mouse B73.2 IgG1 DNA were thus used as templates for a PCR amplification for the construction of a DNA fragment consisting of the unique Kozak sequence for control of light chain expression, the mouse B72.3 light chain leader sequence (MGVPTQLGLLLWLTDARC (SEQ ID NO 153 from amino acid residue sequence 1 to 20)), and the b12 light chain beginning with a human light chain amino acid consensus sequence (EIVLTQSP (SEQ ID NO 153 from amino acid residue sequence 21 to 28). Altering the beginning of the light chain from the mouse amino acid consensus sequence to the human amino acid consensus sequence also destroys the original Sac I cloning site. The restriction site, EcoR I, was introduced in the amplification reactions and was located at both the 5' and 3' ends of the fragment. The procedure for creating this fragment by combining the products of two separate PCR amplifications is described below.

The primer pair, LC-1 (SEQ ID NO 163) and LC-2 (SEQ ID NO 164), was used in the first PCR reaction as performed above to amplify the Fab b12 light chain gene and incorporate the human light chain consensus sequence into the fragment and the EcoR I cloning site into the 3' end of the b12 light chain fragment. For the PCR reaction, 1 μl containing 100 ng of Fab b12 DNA was admixed with 10 μl of 10× PCR buffer in a 0.5 ml microfuge tube. To the DNA admixture, 8 μl of a 2.5 mM solution of dNTPs (DATP, dCTP, dGTP, dTTP) was admixed to result in a final concentration of 200 μM of each DNTP. 1 μl (equivalent to 20 pM) of the LC-1 primer and 1 μl (20 pM) of the 3' backward LC-2 primer was admixed into the DNA solution. To the admixture, 73 μl of sterile water and 2.5 units of Taq DNA polymerase was added. Two drops of mineral oil were placed on top of the admixture and 35 rounds of PCR amplification in a thermocycler were performed. The amplification cycle consisted of 52° C. for 1 minute, 72° C. for 2 minutes and 94° C. for 0.5 minutes.

The primer pair, LC-3 (SEQ ID NO 165) and LC-4 (SEQ ID NO 166) as shown in Table 10, was used in a separate PCR reaction to amplify the mouse light chain B72.3 leader sequence and incorporate an EcoR I cloning site at the 5' end of the fragment and to introduce a 27 base pair sequence which has homology to the modified light chain fragment prepared above. Double-stranded DNA encoding the mouse B73.2 IgG1 (Whittle, et al., supra) was used as a template for preparation of the mouse 72.3 leader sequence. The PCR reaction to prepare the mouse leader sequence fragment was performed using the same conditions as described in Example 4a for the preparation of the modified VH fragment.

The resultant PCR modified b12 light chain DNA fragment and light chain mouse leader sequence fragment were purified by electrophoresis in a 2.5% Nu-Sieve agarose gel (FMC). The area in the agarose containing the modified b12 light chain DNA fragment and light chain mouse leader sequence fragment were excised from the agarose.

A third PCR amplification using the primer pairs, LC-1 (SEQ ID NO 157) and LC-4 (SEQ ID NO 166) as shown in Table 10, was performed to fuse the light chain mouse leader fragment with the modified light chain fragment. The primers used for this amplification were designed to preserve an EcoR I site, a unique Kozak sequence, and the mouse B72.3 light chain leader sequence on the 5' end of the amplified fragment and to preserve the EcoR I cloning site on the 5' end of the amplified fragment. The templates used in this PCR reaction were the two purified PCR reaction products described above. The PCR reaction and subsequent purification of the PCR product were performed as described in Example 4a1.

2) Insertion of Modified b12 Light Chain into pSG-5 Mammalian Expression Vector

Figure 24:
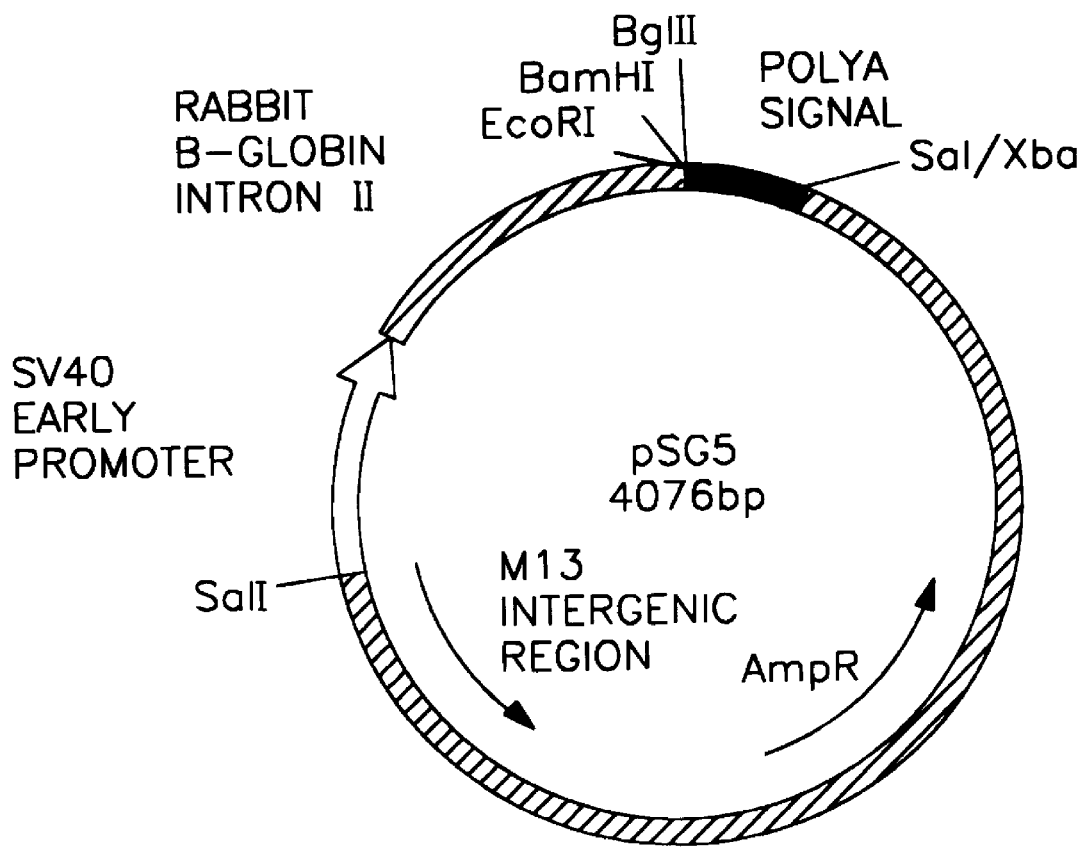
FIG. 24 illustrates the pSG-5 mammalian expression vector as described in Examples 4a and 4b. Transcription of the heavy or light chain gene when inserted in the EcoRI site is under the control of the SV40 early promoter. Transcriptional termination is signaled by the SV40 polyadenylation signal sequence downstream of the heavy chain sequence. The M13 intergenic region allows for the production of single-stranded DNA for nucleotide sequence determination. The amp$^R$ gene is for selection of the vector in bacterial cells.
Figure 26:
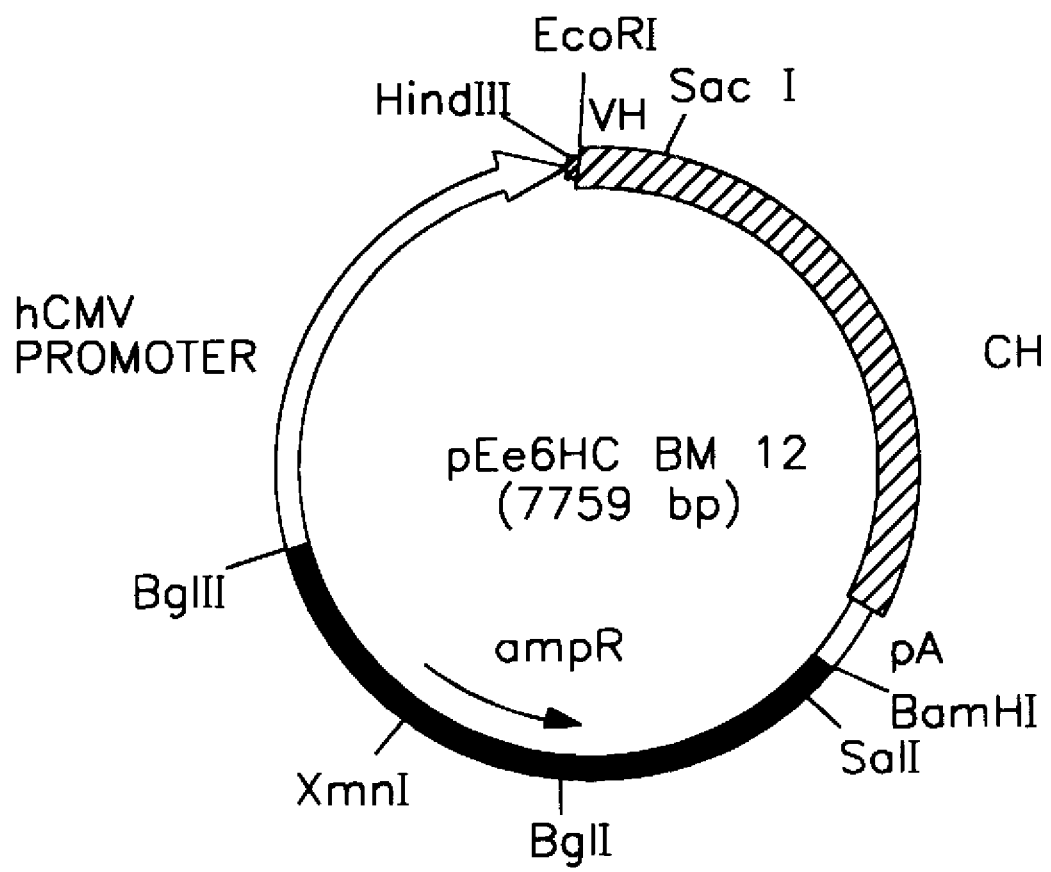
FIG. 26 illustrates pEe6HC BM12, the pEE6 mammalian expression vector with the b12 IgG1 heavy chain gene that has been modified for antibody expression in mammalian cells as described in Example 4d. The VH was originally derived from the Fab b12 and has the same binding specificity as the Fab b12. The pEE6 vector has a human CMV promoter for expression of the heavy chain, a polyadenylation signal for termination of transcription, and an ampicillin gene for selection in bacteria.

The modified b12 light chain PCR product was ligated to a pSG-5 vector (FIG. 24). The pSG-5 vector had the same features described in Example 4a2 but did not contain a human IgG1 gene.

The modified b12 light chain PCR product was digested with EcoR I and purified on a 2.5% Nu-Sieve agarose gel (FMC). The pSG-5 vector DNA was digested in parallel with EcoR I enzyme. The PCR modified light chain was ligated to the pSG-5 vector using T4 DNA ligase (New England Biolabs, Beverly, Mass.) and transformed into DH5α competent cells (GIBCO, BRL Life Technologies, Gaithersburg, Md.) following manufacturer's instructions. Miniprep DNAs were analyzed and isolation of plasmid DNA performed. The nucleotide sequence of the light chain gene was determined using the dideoxy-nucleotide chain termination method (Sanger et al., supra). The nucleotide sequence of the 5' untranslated region, mouse B72.3 light chain leader sequence, light chain variable region, light chain constant region, and SV40 signal sequence was obtained. The nucleotide and amino acid residue sequences are illustrated in FIGS. 25A and 25B and are given in the sequence listing as SEQ ID NOs 152 and 153.

c. Transient Expression of b12 Heavy and Light Chain Genes in DSG-5 Vectors in COS-7 Cells 1) Transient Expression of b12 IgG1 in COS-7 Cells The human heavy and light chains in the separate pSG-5 expression vectors were cotransformed and transiently expressed in COS-7 cells. COS-7 cells (SV40 transformed African Green Monkey Kidney Cells) provide a rapid and convenient method to test the expression and function of the antibody genes. The COS-7 cells constituitively express the SV40 large T antigen which supports the transient replication of episomes carrying the SV40 origin of replication. The pSG-5 expression vector has an SV40 origin of replication. Upon transfection into COS-7 cells, the expression vectors are replicated in the nucleus to a high copy number, resulting in relatively high transient expression levels.

COS-7 cells were obtained from the American Type Culture Collection (CRL 1651) and cultured in Dulbecco's modified Eagle's medium (DMEM), supplemented with 10% fetal bovine serum (GIBCO BRL, Gaithersburg, Md.) and 1% penicillin, and 1% streptomycin. Transfections were performed with 10 μg of plasmid DNA per 100 mm tissue culture plate containing 1×10$^6$ cells. The control plate was transfected with plasmid vector DNA without an insert. The plates were incubated at 37° C. after transfection. The supernatants were harvested at 48 hours and tested for gp120 binding specificity in an ELISA assay.

2) ELISA Assay for the Detection of Binding of b12 IgG1 to gp120

Supernatants from COS-7 transformants were tested for binding to gp120 in an ELISA assay. Briefly, the ELISA plate was coated with recombinant IIIB gp120 antigen at a concentration of 1 μg/ml. The serially diluted supernatant containing the b12 antibody was added to the wells and incubated at 37° C. for 1 hour. After washing the plate to remove unbound antibody, a goat anti-human Ig Fc horse radish peroxidase (HRP) conjugated secondary antibody was added and incubated for an additional hour. An OPD substrate for the HRP conjugated antibody was added and the HRP activity detected by determining the absorbant 490 nm.

d. Insertion of the b12 Heavy Chain IgG1 into the pEE6 Mammalian Expression Vector to Create pEe6HC BM 12

After confirmation that the antibody molecule expressed by the heavy and light chain pSG-5 expression vectors bound gp120 as described in Example 4c, the heavy chain was removed from the pSG-5 vector and ligated into the pEE6 mammalian expression vector (Bebbington et al., *Bio/Technoloay*, 10:169 (1992)). The pEE6 vector (Celltech, England) contains an HCMV promoter and the glutamine synthetase gene (GS). The pEE6 vector was chosen because of the GS gene which serves as a selectable marker. CHO cells are devoid of GS activity and thus are dependent on a supply of glutamine in the culture medium. Cells transfected with the pEE6 vector containing the GS gene are able to synthesize glutamine from glutamate and can survive in the absence of glutamine in the culture medium. For CHO cells, the addition of methyl sulfoxamine (MSX) leads to amplification of the transfected plasmid DNA.

The heavy chain pSG-5 vector was digested with EcoR I and Bgl II to remove the 5' untranslated region including the unique Kozak sequence, mouse heavy chain B72.3 leader sequence, and heavy chain variable and constant regions from the pSG-5 vector. The pEE6 vector was also digested with EcoR I and BamH I. Both the vector and heavy chain DNAs were analyzed on a 0.7% low melting point agarose (LMPA) gel. The 3.5 kb heavy chain band and the 4.68 kb pEE6 vector band were excised from the gel and ligated together in the presence of the LMPA at 15° C. overnight with 1 μl of T4 DNA ligase and 1 μl of 10× ligase buffer (New England Biolabs, Beverly, Mass.). Upon ligation, the EcoR I site is reconstituted but the BamH I and BglII sites are destroyed. Prior to transformation, 5 μl of the ligated DNA in LMPA was diluted with 20 μl of TCM buffer (10 mM tris, 10 mM CaCl$_2$, and 10 mM MgCl$_2$). Only 10 μl of the 25 μl was used for the transformation. The ligated circular plasmid DNA construct was transformed into maximum efficiency DH5α competent cells. The standard protocol for transformation was used, wherein the DNA and 100 μl of the competent bacterial mix (GIBCO BRL, Gaithersburg, Mass.) were incubated on ice for 20 minutes and heat shocked at 42° C. followed by incubation on ice for 2 minutes. About 900 μl of SOC (GIBCO BRL, Gaithersburg, Mass.) was added to the transformation. Only 100 μl of the 1000 μl of the transformed cells was plated on LB with carbenicillin plates (carbenicillin at 50 μg/ml). The plates were incubated at 37° C. overnight. Twelve individual colonies were picked for miniprep analysis. Several diagnostic digests confirmed the presence of the heavy chain insert. Plasmid DNA was isolated on a CsCl gradient (Sambrook et al., supra). The nucleotide and amino acid residue sequences are illustrated in FIGS. 27A through 27E and the nucleotide and amino acid residue sequences are given in the sequence listing as SEQ ID NOs 154 and 155.

e. Insertion of the b12 Light Chain into the pEE12 Mammalian Expression Vector

The light chain was ligated into the pEE12 vector (Celltech, England) from the pSG-5 vector involving similar steps as described in Example 4d for the heavy chain. The pEE12 vector has a human CMV promoter for expression of the light chain, a polylinker to provide cloning sites, and a polyadenylation signal for termination of transcription. The vector also contains the GS selectable marker gene, whose expression is controlled by an SV40 early promoter at the 5' end of the GS gene, an intron, and a polyadenylation signal at the 3' end of the GS gene.

1) Preparation of Modified b12 Light Chain

The 5' PCR primer was designed to replace the EcoR I cloning site with a HindIII cloning site. The 3' PCR primer maintained the EcoR I cloning site.

The primer pair, LC-5 (SEQ ID NO 167) and LC-2 (SEQ ID NO 165), was used in the PCR reaction as described in Example 4a1 to amplify the Fab b12 light chain gene and incorporate HindIII and EcoR I cloning sites into 5' and 3' ends of the fragment, respectively. The b12 pSG-5 vector containing the b12 light chain was used as the template in the PCR reaction. For the PCR reaction, 1 μl containing 100 ng of b12 pSG-5 DNA was admixed with 10 μl of 10× PCR buffer in a 0.5 ml microfuge tube. To the DNA admixture, 8 μl of a 2.5 mM solution of dNTPs (dATP, dCTP, dGTP, dTTP) was admixed to result in a final concentration of 200 micromolar (μM) of each DNTP. 1 μl (equivalent to 20 pM) of the LC-5 primer and 1 μl (20 pM) of the 3' backward LC-2 primer was admixed into the DNA solution. To the admixture, 73 μl of sterile water and 2.5 units of Taq DNA polymerase was added. Two drops of mineral oil were placed on top of the admixture and 35 rounds of PCR amplification in a thermocycler were performed. The amplification cycle consisted of 52° C. for 1 minute, 72° C. for 2 minutes and 94° C. for 0.5 minutes.

The resultant PCR modified b12 light chain DNA fragment was purified by electrophoresis in a 2.5% Nu-Sieve agarose gel (FMC). The area in the agarose containing the modified b12 light chain DNA fragment was isolated from the agarose.

2) Insertion of the Modified b12 Light Chain into the pEE12 Mammalian Expression Vector The modified b12 light chain purified PCR product and the pEE12 vector were digested with HindIII and EcoR I in separate reactions. The digested DNAs were analyzed on an LMPA gel, the DNA excised, and ligated together in the presence of the LMPA gel as described for the heavy chain construct in Example 4d. The ligation products were transformed into DH5α competent cells, minipreps analyzed, and DNA prepared as described for the heavy chain constructs in Example 4d.

f. insertion of the Modified b12 Heavy Chain into the pEE12 Mammalian Expression Vector Containing the b12 Light Chain to Create the Combinatorial Vector pEe12 Combo BM 12

Figure 28:
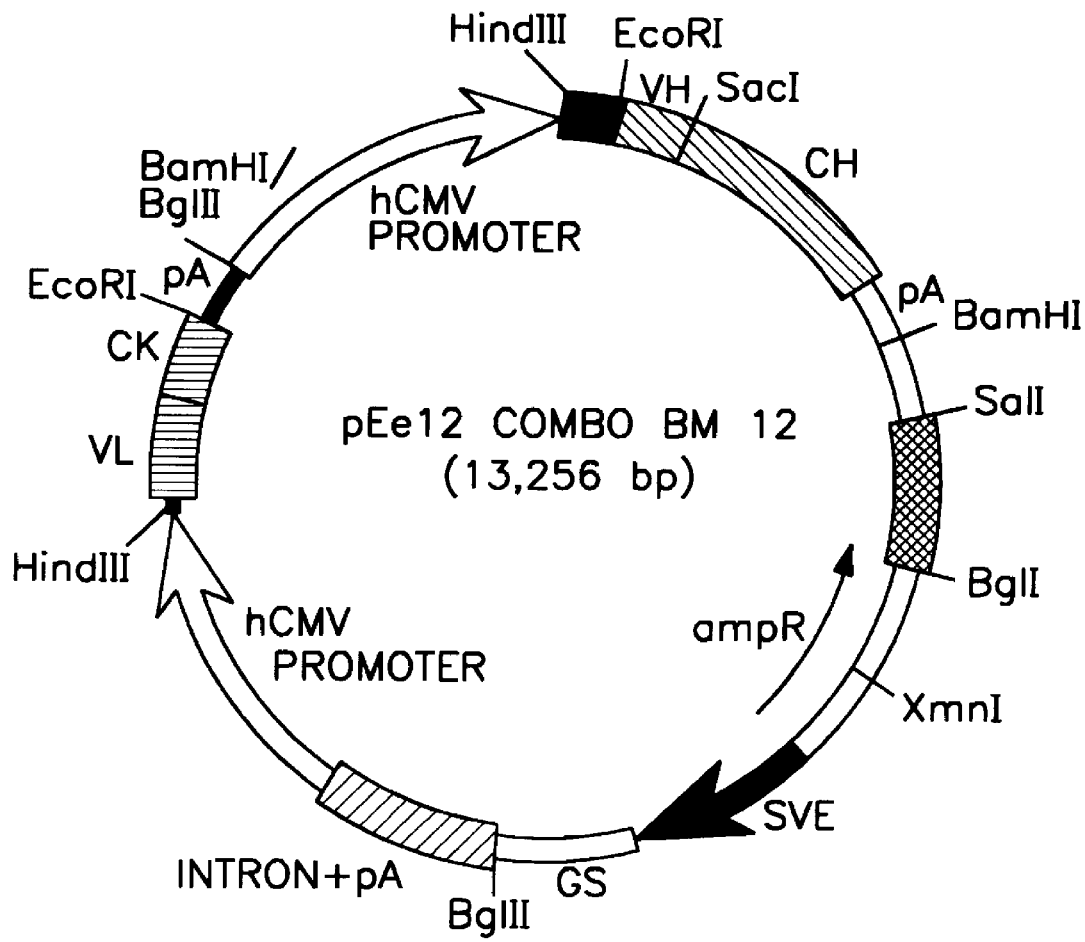
FIG. 28 illustrates pEe12 Combo BM12, the pEE12 mammalian expression vector with b12 IgG1 heavy and light chain genes that have been modified for antibody expression in mammalian cells as described in example 4f. The VH and light chain were originally derived from the Fab b12 and have the same binding specificity as the Fab b12. The pEE12 vector has a human CMV promoter for expression of the light chain, a polylinker to provide cloning sites, and a polyadenylation signal for termination of transcription. The vector also contains the GS selectable marker gene whose expression is controlled an SV40 early promoter at the 5' end of the GS gene, an intron, and a polyadenylation signal at the 3' end of the GS gene. A heavy chain cassette comprising the HCMV promoter, enhancer elements, heavy chain gene, and polyadenylation signal were removed from the pEE6 vector and inserted into the pEE12 vector to generate the combinatorial construct containing both the b12 light and heavy chain genes.

A heavy chain cassette comprising the HCMV promoter, enhancer elements, heavy chain gene, and polyadenylation signal were removed from the pEE6 vector and inserted into the pEE12 vector containing the b12 light chain gene, prepared in Example 4e, to generate the combinatorial construct, pEe12 Combo BM 12, containing both the b12 light and heavy chain genes (FIG. 28).

The heavy chain cassette was removed from the pEE6 vector by digestion with BglII and Sal I. The pEE12 vector containing the light chain gene, prepared in Example 4e, was also digested with BglII and Sal I. The heavy chain cassette and the pEE12 vector containing the light chain gene from Example 4e were ligated together at the BglII and Sal I sites as described in Example 4d. The combinatorial construct was transformed into DH5α competent cells and miniprep DNA was analyzed for the presence of the heavy and light chains as in Example 4d. The nucleotide sequence of the heavy and light chain genes was determined. The nucleotide sequence of pEe12 Combo BM 12, the pEE12 vector containing the b12 heavy and light chain genes is given in the sequence listing as SEQ ID NO 156 and is illustrated in FIGS. 29A through 29R.

gp120 Binding of b12 IgG1 Antibody Expressed from the Heavy and Light Chain Genes in the Combinatorial Vector pEe12 Combo BM 12

The combinatorial pEe12 Combo BM 12 vector containing both the heavy and light chain genes was used to transfect CHO cells. Stable clones were selected in Glasgow Minimal Essential Media (GIBCO) supplemented with 10% dialyzed fetal bovine serum and 50 μM methyl sulfoxamine (MSX). Several clones were isolated and expanded in 6-well cluster dishes. The supernatants of subconfluent cultures were harvested and tested by ELISA for binding to gp120 as described in Example 4c2. The clone producing the highest levels of b12 IgG1 as determined by ELISA with gp120 IIIB was chosen for further study. The antibody was purified by affinity chromatography using protein A as described in Sambrook, et al., supra. The affinity of b12 IgG1 for gp120 IIIB as measured by surface plasmon resonance as described in Example 2b6c is $1.3 \times 10^9 M^{-1}$.

5. Neutralizing Activity of Recombinant b12 Whole IgG1 Antibody (b12 IgG1) Against HIV-1 In Vitro The key issue in producing antibodies to HIV-1 for therapeutic or prophylactic purposes is that they should be highly potent (of high affinity and neutralizing ability) and be cross reactive with a wide range of primary clinical (field) isolates. These are generally two opposing characteristics. The ability of b12 whole IgG1 antibody (b12 IgG1) to neutralize the infectivity of laboratory strains of HIV-1 and a wide variety of primary clinical isolates has been examined in p24 ELISA assays, microplaque assays, and by syncytial formation assays.

The primary clinical isolates used as a source of HIV-1 virus in these assays came from various regions of the world by three organizations: the World Health Organization (WHO), the Henry M. Jackson Foundation for the Advancement of Military Medicine (HMJFAMM), and the National Institute of Allergy and Infectious Diseases (NIAID). Isolates from the WHO Network for HIV-1 Isolation and Characterization were obtained through the AIDS Research and Reference reagent Program, Division of AIDS, NIAID, NIH. Isolates from HMJFAMM were provided by Dr. John Mascola, Walter Reed Army Institute of Research, Rockville, Md. and Dr. Francine McCutchan, Henry M. Jackson Research Laboratory, Rockville Md. Isolates from NIAID were kindly provided by Dr. Jim Bradac, Division of AIDS, NIAID, NIH.

The HIV-1 viruses were collected from various regions of the world, expanded in mitogen-stimulated peripheral blood mononuclear cells (PBMC) (Mascola et al., *J. Infect. Dis.,* 169:48–54 (1994)), and culture supernatants containing infectious virus were stored in central repositories at −70° C. The designation of viruses into clades was made on the basis of sequence information based on the gag gene or on the V2-C5 region of gp120, or in some cases, after heteroduplex mobility analysis (Louwagie et al., *AIDS,* 7:769–772 (1993) and Delwart et al., *Science,* 262:1257–1261 (1993)).

The HIV-1 viruses include a set of 14 primary isolates which contain a high proportion of isolates which are relatively refractory to antibody neutralization by sera from other HIV-1 infected individuals (Wrin et al., *J. Acq. Imm. Def. Synd.,* 7:211–219 (1994)), 12 primary infant isolates obtained at birth or within two weeks of age, and 69 international isolates belonging to 6 different clades.

Several different neutralization assays were performed because HIV-1 neutralization by antibody shows considerable variation depending upon the assay used and the precise experimental conditions such as inoculum size and incubation time of virus and antibody (D'Souza et al., *AIDS,* 8:169–173 (1994)). By performing neutralization assays on a range of laboratory and primary isolates in a number of different laboratories, it has been demonstrated that b12 IgG1 is a highly potent neutralizing antibody effective against a wide breadth of isolates.

a. Quantitative Neutralization of HIV-1 MN and IIIb by b12 IgG1 as Measured in a Plaque Assay b12 IgG1 was initially tested for its ability to neutralize the HIV-1 laboratory strains MN and IIIB in a plaque formation assay in laboratories which recently tested a panel of monoclonal antibodies as part of the NIAID/WHO Antibody Serological Project (D'Souza et al., supra).

b12 IgG1 showed 50% neutralization titers of 3 ng/ml for the MN strain and 7 ng/ml for the IIIB strain using plaque formation (Hanson, et al., *J. Clin. Microbiol.,* 28:2030–2034 (1990)) to determine the ability of the antibody to inhibit infectivity of the HIV-1 strains.

b. Quantitative Neutralization of HIV-1 MN and IIIb by b12 IgG1 as Measured by Syncytial Formation b12 IgG1 showed 50% neutralization titers of 20 ng/ml for both MN and IIIB strains using syncytial formation as the reporter assay as described in Example 3b (Nara et al., *AIDS Res. Human Retroviruses,* 3:283–302 (1987)).

The syncytial formation assay was performed as described in Example 5c. Briefly, virus was grown in H9 cells. For infectivity measurement, monolayers of CEM-SS target cells were cultured with 100–200 syncytial forming units (SFUs) of virus, in the presence or absence of antibody, and the number of syncytia determined after 3–5 days of incubation. The assays were repeatable over a virus-surviving fraction range of 1 to 0.001 within a 2 to 4-fold difference in the concentration of antibody (P<0.001).

c. Neutralization of Primary Virus Isolates by b12 IgG1 as Measured by the D24 ELISA Assay The ability of b12 IgG1 to neutralize infectivity of PBMCs by HIV-1 virus was quantitatively measured in the p24 ELISA assay (Daar et al., *Proc. Natl. Acad. Sci. U.S.A.,* 87:6574–6578 (1990) and Ho et al., *J. Virol.,* 65:489–493 (1991)). The p24 ELISA assay is further described in Example 3a.

1) Neutralization of Ten Primary Virus Isolates by b12 IgG1

HIV-1 viruses were isolated from 10 individuals from various locations in the U.S. and with varying disease status. The HIV-1 viruses had been cultured only once or twice in peripheral blood mononuclear cells (PBMCs). Viral stocks were grown in PBMCs and the assay was performed in PBMCs.

Briefly, HIV-1 virus at 50 $TCID_{50}$ and varying concentrations of b12 IgG1 were incubated together for 30 min at 37° C. before addition to PHA-stimulated PBMCs. HIV-1 virus replication was assessed after incubation for 5 to 7 days by p24 ELISA measurement as described in Example 3a. HIV-1 virus positive controls used in this assay were the molecularly cloned HIV-1 virus JR-CSF and the HIV-1 isolate JR-FL (O'Brien et al., *J. Virol.,* 66:3125–3130 (1992), O'Brien et al., *Nature,* 348:69–73 (1990), and O'Brien et al., *J. Virol.*, in press (1994)). Stocks of JR-CSF were prepared by infection of PBMC with supernatants initially obtained by DNA transfection. HIV-1 IIIB and HIV-1 MN are viruses with an extensive history of passage in transformed T-cell lines (Robert-Guroff et al., *Nature*, 316:72–74 (1985)). Stocks of these strains grown in H9 cells were passaged in mitogen-stimulated PBMC to prepare viruses that had been grown in the same cells as the primary viruses, to eliminate the influence of any host cell-dependent epigenic factors on virus neutralization (Wrin, et al., *J. Acq. Imm. Def. Synd.*, 7:211–219 (1994)). The stock of PBMC-grown MN was a gift from A. N. Conley (Merck Research Labs).

2) Neutralization of 12 Primary Infant Isolates by b12 IgG1 b12 IgG1 was also tested for the ability to neutralize infectivity of a panel of 12 primary infant isolates in the p24 ELISA assay. Virus isolates were obtained from 12 infants born to HIV-1 seropositive mothers; 7 were obtained at birth and 5 between birth and 14 days of age. All the infants were from California. Virus was isolated from patient PBMCs by coculture with PBMCs from healthy seronegative donors. Viral stocks were prepared by passaging the last positive culture dilution once into PBMCs. All of the isolates, except one (isolate 7), were non-syncytial inducing in MT2 cells and therefore could not be assayed in the syncytial forming assay as herein described. HIV-1 virus from these stocks was grown in PBMCs and neutralization assessed using PHA-stimulated PBMCs as indicator cells and determination of extracellular p24 as the reporter assay essentially as described in Example 3a (AIDS Clinical Trials Group Virology manual for HIV Laboratories, Department of AIDS Research, NIAID, NIH, version 2.0 (1993)).

Serial dilutions of b12 IgG1 (0.3 to 20 $\mu$g/ml) were incubated with 20 TCID$_{50}$ or 100 TCID$_{50}$ virus in triplicate for 2 hours at 37° C. before addition to PHA-stimulated PBMCs. Virus replication was assessed after 5 days by p24 ELISA measurement. Neutralization was expressed as either a 50% or 90% reduction in p24 antigen as compared to values observed in the absence of antibody (Table 6).

d. Neutralization of Primary Virus Isolates by b12 IgG1 as Measured in a Microplaque Assay A quantitative microplaque assay to measure the reduction of infectivity of primary clinical isolates of HIV-1 in the presence of the b12 IgG1 and pooled human plasma was performed as described in Hanson et al., *J. of Clin. Microb.*, 2030–2034 (1990). The set of primary clinical isolates was chosen to contain a high proportion of isolates which are relatively refractory to antibody neutralization by sera from other HIV-1 infected individuals (Wrin et al., *J. Acq. Imm. Def. Synd.*, 7:211–219 (1994)). Viruses were grown in PBMCs and the assay carried out in MT2 cells. This limits study to viruses which grow in this cell line but provides an additional measure of neutralization.

Primary clinical isolates of HIV-1 were isolated from frozen peripheral blood lymphocytes obtained from seropositive donors as described in Gallo et al., *J. of Clin. Microb.*, 1291–1294 (1987) and cultivated in peripheral blood mononuclear cells (PBMC). Briefly, HIV isolates were obtained by incubating frozen HIV-infected patient PBMCs with seronegative donor PBMCs in RPMI-1640 medium containing 20% heat-inactivated fetal bovine serum, 2 $\mu$g/ml polybrene, 5% interleukin-2, and 0.1% anti-human leukocyte interferon. The cultures were fed with fresh donor PBMCs once a week, and the supernatants were assayed for the presence of reverse transcriptase (RT) activity beginning at day 11. The cultures were considered positive if, for 2 consecutive weeks, the RT counts were >10-fold higher than those in the cultures of the seronegative donor PBMCs alone.

The resultant RT-positive virus isolates were tested for cytolysis in the MT4 ($\alpha$-4 clone) (Hanson et al., supra). Cytolysis in MT4 is a requirement for viruses to be usable in the subsequent MT2 microplaque assay system. Supernatant fluids from the primary PBMC isolation cultures were used to infect expanded cultures of phytohemagglutinin (PHA)-stimulated PBMCs from healthy seronegative blood donors. These infected PBMC cultures were grown in RPMI-1640 medium supplemented with 15% fetal bovine serum, 5% interleukin-2, 0.1% anti-$\alpha$ interferon, 2 $\mu$g/ml polybrene, 50 $\mu$g/ml gentamicin, 100 U/ml penicillin, and 100 $\mu$g/ml streptomycin. The crude supernatants were harvested after 7 days and frozen as viral stocks at −70° C.

Figure 21:
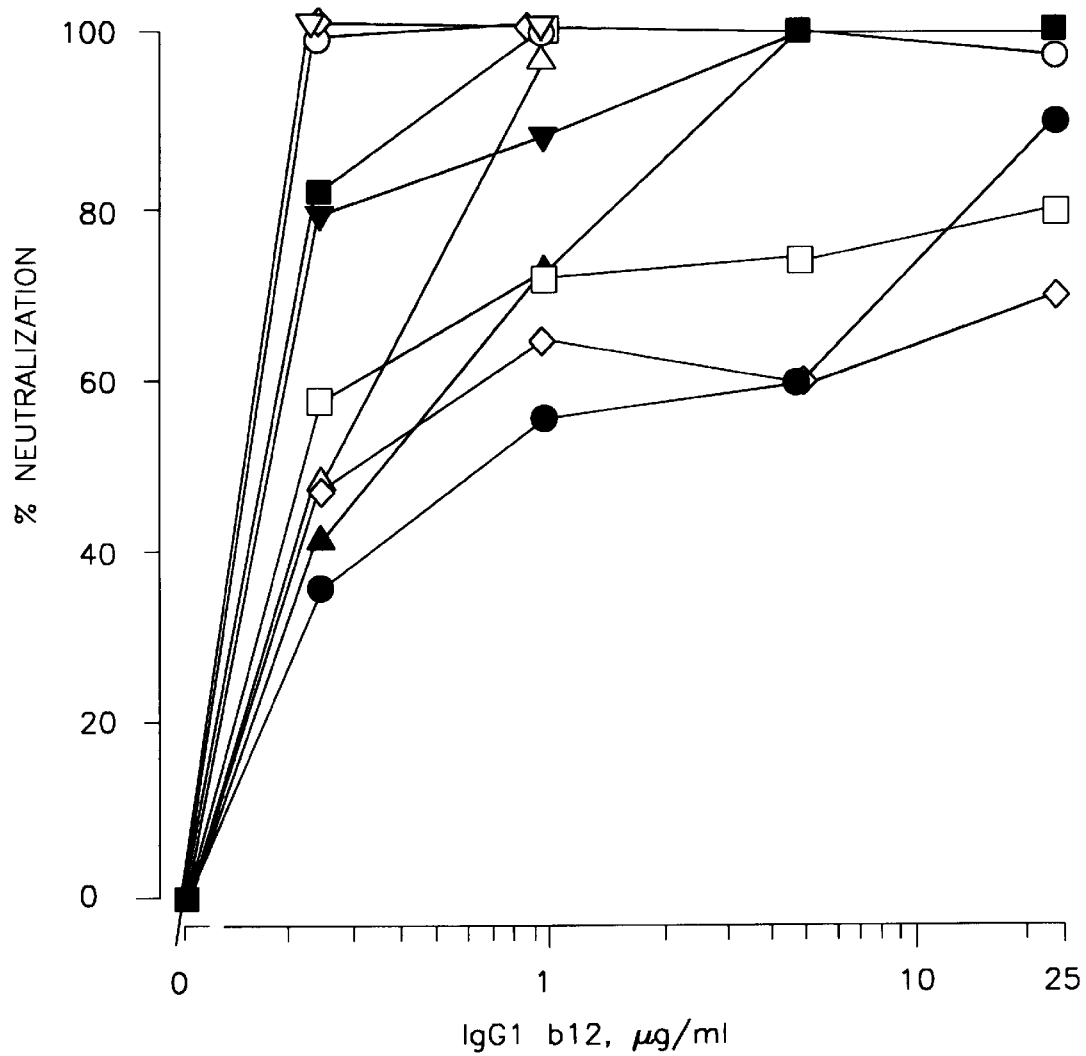
FIG. 21 illustrates the neutralization of HIV-1 by b12 IgG1 as assessed using PHA-stimulated PBMCs as indicator cells and determination of extracellular p24 as the reporter assay. Refer to Example 5d for details of the assay procedures and discussion of the results. The designation, location, and disease status of the virus donors were as follows: ■, VS (New York, acute), ▼, N70-2 (New Orleans, asymptomatic), ▲, AC (San Diego, AIDS), ●, LS (Los Angeles, AIDS), □, NYC-A (New York, unknown), ▽, WM (Los Angeles, AIDS), △, RA (New York, acute), ◇, JP (New York, acute). The molecularly cloned HIV-1 virus JR-CSF (◆) and HIV-1 isolate JR-FL (○) were also assayed for neutralization. The data is plotted as % neutralization on the Y-axis against increasing concentrations of b12 IgG1 (0–25 μg/ml) on the X-axis.

The primary clinical isolates of HIV-1 used in this microplaque assay are given in Table 6. VL134, VL648, and VL025 are viruses isolated from infected mothers in New York in 1992; UG266 and UG274 are clade D isolates which were a gift from John Mascola the Division of Retrovirology, Walter Reed Army Institute of Research; the remaining viruses were isolated from homosexual males in California in 1992. The pooled human plasma preparation, containing neutralizing antibody, was derived from 13 HIV-1 positive individuals selected for high neutralization titer against the MN isolate. The laboratory HIV-1 strains MN and IIIb were propagated in H9 cells as controls in the microplaque assay.

b12 IgG1 and a pool of human plasma from 13 HIV-1 seropositive patients were used as the source of neutralizing antibodies in a 96-well microtiter plaque reduction assay as described by Hanson et al., supra. Briefly, 3-fold serial dilutions of the b12 IgG1 or heat-inactivated pooled patients' plasma were combined in quadruplicate with an equal volume containing 20 plaque-forming units (PFU) of HIV-1 virus per well and incubated for 18 hours at 37° C. Negative control wells also contained 50% normal human serum pool with no patient immune serum. After the 18 hour incubation of Fabs or serum and virus, 90,000 MT2 cells were added per well and incubated at 37° C. for 1 hour. SeaPlaque Agarose in assay medium at 39.5° C. was then added to a final concentration of 0.8%. While the warm agarose was still molten, the microtiter plates were centrifuged at 20° C. for 20 minutes at 500×g to form cell monolayers. The plates were incubated for 6 days at 37° C. and then stained 18 to 24 hours with 50 $\mu$g/ml propidium iodide. The fluorescent plaques were counted with transillumination by a 304 nm ultraviolet light source using a low-power stereo zoom microscope. Inhibition of infectivity, or neutralization titer, is defined as the $\mu$g/ml of Fab or the plasma dilution giving 50% inhibition of plaque count as compared with controls without antibody. This dilution was interpolated between data points.

e. Results of the Neutralization Assays by b12 IgG1 with Laboratory Virus Isolates Results of the ability of the b12 IgG1 to neutralize laboratory virus isolates in both the plaque and syncytial formation assays suggest the antibody is approximately two orders of magnitude more potent than other CD4 site antibodies in the WHO/NIAID Project and comparable to the best antibodies directed to the V3 loop of gp120. However, whereas antibodies directed to the V3 loop of gp120 are strongly strain specific, b12 IgG1 is roughly equally effective against MN and IIIB. The b12 IgG1 antibody is comparable in potency to a CD4-IgG molecule in these assays (Example 3c). In a separate assay using p24 production to determine infectivity (Daar et al., *Proc. Natl. Acad. Sci. U.S.A.*, 87:6574–6580 (1990) and Ho et al., *J. Virol.*, 65:489–493 (1991)), 50% neutralization titers of less than 40 ng/ml were found for both the MN and IIIB laboratory strains.

f. Results of the Neutralization Assays by b12 IgG1 with Primary Virus Isolates b12 IgG1 showed essentially complete neutralization of 7 of 10 isolates at 5 µg/ml with all the isolates showing 50% neutralization at 51 µg/ml as determined in the p24 reporter assay (FIG. 21).

The inhibition of infectivity, or neutralization titer, for b12 IgG1 and the pooled HIV seropositive human plasma from 13 donors is given in Table 6. The neutralization titer for each of the viral isolates is expressed as the minimum µg/ml of b12 IgG1 required for 50% inhibition of plaque count as compared to the controls. The neutralization titer for each of the viral isolates is expressed as the minimum titer of the pooled HIV seropositive human plasma from 13 donors required for 50% inhibition of plaque count as compared to the controls.

TABLE 6

| virus | host cell | b12 IgG1 50% neutralization titer (µg/ml) | pooled human plasma: dilution for 50% neutralization |
|---|---|---|---|
| IIIB | H9 | 0.007 | 1:767 |
| MN | H9 | 0.003 | 1:24,000 |
| VL135 | PBMC | 10 | 1:44 |
| UG274 | PBMC | 0.7 | 1:37 |
| VL134 | PBMC | 5.6 | 1:30 |
| VL596 | PBMC | 8.5 | 1:17 |
| UG266 | PBMC | 3.8 | 1:12 |
| VL434 | PBMC | 22 | 1:10 |
| VL172 | PBMC | >200 | 1:10 |
| VL750 | PBMC | >200 | 1:10 |
| VL069 | PBMC | >50 | <1:10 |
| VL077 | PBMC | >200 | <1:10 |
| VL114 | PBMC | <7.4 | <1:10 |
| VL263 | PBMC | 5.0 | <1:10 |
| VL648 | PBMC | 16.7 | <1:10 |
| VL025 | PBMC | 16.7 | <1:10 |

The b12 IgG1 was able to neutralize ten of the fourteen primary clinical isolates assayed at concentrations of ≦50 µg/ml as measured as the µg/ml required for 50% inhibition of plaque count as compared to the controls (Table 6). Pooled human plasma was able to neutralize 5 of the 14 primary clinical isolates assayed at >1:10 dilution as measured as the dilution required for 50% inhibition of plaque count as compared to the controls without antibody.

Table 6 shows that four isolates, which were not neutralized even by a 1:10 dilution of pooled human plasma, were neutralized by b12 IgG1. Most of the viruses reported in Table 6 were isolated from U. S. donors although two, both of which are neutralized by b12 IgG1, were from Ugandan donors and assigned to clade D.

Results of neutralization of 12 infant primary isolates with b12 IgG1 as determined by p24 ELISA measurements are given in Table 7.

TABLE 7

| | b12 IgG1 Antibody Concentration (µg/ml) | |
|---|---|---|
| Infant Isolate | 50% inhibition | >90% inhibition |
| 1 | 20 | >20 |
| 2 | 1.25 | >20 |
| 3 | <0.3 | 0.3 |
| 4 | <0.3 | 0.6 |
| 5 | 2.5 | 20 |
| 6 | 5 | >20 |
| 7 | 5 | >20 |
| 8 | <0.3 | 0.3 |
| 9 | 0.3 | 5 |
| 10 | 0.3 | 2.5 |
| 11 | <0.3 | 0.6 |
| 12 | <0.3 | 0.3 |

As shown in Table 7, b12 IgG1 achieved 90% neutralization for 8 of 12 infant isolates at concentrations of ≦20 µg/ml in the p24-based assay. All 12 isolates were 50 neutralized in the range of 0.3 to 20 µg/ml with the majority being neutralized at <5 µg/ml. In contrast, a pooled hyperimmune globulin product HIVIG achieved 90% neutralization of only 3 or 12 isolates within a concentration range up to 100 µg/ml. HIVIG is a hyperimmune IgG preparation obtained from the pooled plasma of selected HIV-1 asymptomatic seropositive donors meeting the following criteria: presence of p24 serum antibody titers >128, CD4 lymphocyte count ≧400 cells/µl and the absence of p24 and hepatitis B surface antigen by enzyme immunoassay (Cummins et al., *Blood*, 77:1111–1114 (1991)). The HIVIG used in these experiments was lot number IHV-50-101 (North American Biologicals).

HIV-1 neutralization by antibody shows considerable variation depending upon the assay used and precise experimental conditions such as inoculum size and incubation time of virus and antibody (D'Souza et al., supra). However, by carrying out neutralization on a range of laboratory and primary isolates in a number of assays in different laboratories, we have shown that b12 IgG1 is a highly potent neutralizing antibody effective against a wide breadth of primary isolates. The results clearly demonstrate that, although primary isolates may be more difficult to neutralize by antibody than laboratory strains, they are not intrinsically resistant (Conley et al., *Proc. Natl. Acad. Sci. U.S.A.*, 91:3348–3353 (1994)). The potency of b12 IgG1 against the majority of U. S. isolates is in a concentration range (≦5 µg/ml) which could be achieved in vivo in passive immunotherapy. Furthermore, the affinities of recombinant antibodies displayed on phage can be enhanced by mutagenesis and selection in vitro and this strategy has been used to considerably improve the potency and breadth of reactivity of Fab b12 (Barbas et al., *Proc. Natl. Acad. Sci. U.S.A.*, 91:3809–3812 (1994)). For optimal potency and strain cross-reactivity for passive immunization, a cocktail of in vitro improved antibodies may be most appropriate.

The results have implications for passive immunization and vaccine design. The ability of b12 IgG1 to neutralize a range of primary isolates implies conservation of a structural feature associated with the CD4 binding site of gp120 which is accessible to antibody and important for neutralization. A vaccine might seek to present this feature to the immune system. Clearly, the feature is present on recombinant gp120 since b12 was affinity selected from a library using this molecule. However, b12 and related antibodies formed only a small part of the repertoire affinity selected from this library by recombinant gp120. Most of the antibodies obtained were far less potent in neutralization even though they were also directed to the CD4 binding site, were cross-competitive with b12 for binding to recombinant gp120 and had similar affinities to b12 (Barbas et al., *Proc. Natl. Acad. Sci., U.S.A.*, 89:9339–9343 (1992), Barbas et al., *J. Mol. Biol.*, 230:812–823 (1993), and Example 2b6(c). Therefore, recombinant gp120 appears to present the b12 epitope in conjunction with several other weakly neutralizing and overlapping epitopes and its efficacy as a vaccine may suffer. Interestingly, evidence from antibody binding to infected cells suggests that b12 does recognize a native conformation of gp120 more effectively than other CD4 binding site antibodies (Example 7). In any case, b12 IgG1 and the library approach could be useful in vaccine and passive immunization evaluation. The ability of a candidate vaccine to preferentially bind b12 and/or preferentially select potent neutralizing antibodies from libraries should be positive indicators for vaccine development.

5. Determination of the Relationship Between the Epitopes Recognized by Fabs with Purified HIV-1 Antigens The Fabs show a spectrum of neutralizing abilities as described in Example 5. It was therefore sought to determine if the epitopes recognized by individual Fabs could be distinguished from each other, and if possible, determine how the epitopes recognized by the individual Fabs related to neutralization.

a. Competitive ELISA between Fabs and b13 Whole IgG1 Antibody for Binding to gp120

The first method to distinguish between the epitopes bound by the Fabs of this invention was to compare the epitope recognized by the Fab b13 with the other Fabs. The Fab b13 had been spliced to the Fc region of IgG1 to generate a whole IgGi molecule and therefore contains the Fc region of the IgG1 antibody. The other Fabs do not contain the Fc region of the IgG1 antibody. The binding of the b13 IgG1 could therefore be distinguished from the binding of other Fabs by using a labeled anti-Fc reagent in competition ELISA. A competition ELISA in which the Fabs b3, b6, b11, b12, and b14 competed with b13 IgG1 for binding to immobilized gp120 was performed.

Competitive ELISAs were performed between the Fabs b3, b6, b11, b12, and b14 and the b13 whole IgG1 antibody. The whole antibody was obtained by splicing constant domain genes with the b13 Fab and expressing the protein in Chinese Hamster Ovary cells (CHO) as described in Example 4 (Bender et al., supra and in Example 4a for the Fab b12). The ELISA was performed as described above in Example 2b6b. Briefly, microtiter wells were coated with 0.1 µg/ml of gp120 derived from the HIV-1 strain LAI in 0.1M bicarbonate buffer at pH 8.6. Soluble or free Fab fragments were serially diluted from 1:100 to 1:32,000 in 0.5% BSA/0.025% Tween 20/PBS. The dilution of b13 IgG1 was held constant at 1:10,000 in 0.5% BSA/0.025% Tween 20/PBS. The b13 IgG1 and Fabs were admixed, added to the gp120-coated microtiter wells and maintained for 120 minutes at 37° C. After maintenance, the wells were carefully washed ten times with 0.05% Tween 20/PBS. The amount of b13 IgG1 antibody bound to the plate after washing was detected using a peroxidase-labeled antibody specific for the Fc portion of IgG1 contained on the b13 antibody.

Results of this assay indicated that the Fabs b3, b6, b11, b12, and b14 are competitive with b13 IgG1 for binding to gp120 indicating that the epitopes recognized by the individual Fabs are probably either proximal or identical to the epitope recognized by the b13 IgG1. A control anti-tetanus toxoid Fab did not compete with IgG1 b13 in this assay.

Competition monitored in an ELISA format showed that all of the Fabs compete with the b13 Fab as a whole IgG. There is also an indication that Fabs b12 and b13 are distinct in that they are somewhat less effective in cross-competition than the other members of the panel.

b. Epitope Similarity Determination Between the Fabs in Binding to gp120 Using BIAcore A more precise method for determining the similarity of epitopes was performed using the BIAcore. The procedure adopted here was to immobilize a polyclonal anti-human F(ab')$_2$ on the sensor chip and use this to capture the individual Fabs. An Fab of this invention was injected and captured by the polyclonal anti-human F(ab')$_2$. The captured Fab was then used to bind gp120 derived from the HIV-1 strain LAI. The captured Fab would thus bind the gp120 at its respective epitope. A second Fab of this invention was then injected. A response in the BIAcore assay after injection of the second Fab indicates that binding has occurred. If the second Fab injected recognizes the same or similar epitope on the gp120 as the first Fab, no response would occur. No response would therefore indicate that the two Fabs tested in the assay competed for binding to the same or similar epitope on gp120. Alternatively, a response in the assay suggests that the epitopes recognized by the two Fabs are distinct from one another and that binding of the second Fab to gp120 to a second epitope is possible in the presence of the first Fab. A response would therefore indicate that the two Fabs tested in the assay did not compete for binding to the same or similar epitope.

The precise epitope similarity determination with the BIAcore was performed as follows. A flow rate of 5 µl/min of PBS, pH 7.4 was established and the biosensor chip was activated by injecting 30 µl of activation solution (Pharmacia Biosensor, 50% 0.2M N-ethyl-N'-(e-diethylaminopropyl)-carbodiimide, 50% N-hydroxysuccinimide). The flow rate was then adjusted to 10 µl/min and the antigen was injected in 10 mM sodium acetate buffer, pH 4.5. Forty µl of goat anti-human F(ab')$_2$ (Pierce) at a concentration of 40 µg/ml in 10 mM sodium acetate buffer, pH 4.5 was injected to give a final immobilization of 10000 Response Units (RU). The chip was then blocked from any further immobilization by injecting 30 µl of 1M ethanolamine, pH 8.5 (Pharmacia Biosensor). The flow rate was adjusted to 1 µl/min and 4 µl of the first Fab at a concentration of 100 µg/ml was injected, immediately followed by 4 µl of an anti-cytomegalovirus Fab at a concentration of 150 µg/ml to block any remaining binding sites on the immobilized goat anti-human F(ab')$_2$. Next, 4 µl of gp120 at a concentration of 10 µg/ml was injected followed by 4 µl of the second Fab at 100 µg/ml. The assay was performed with a combination of all of the Fabs to give a mosaic of binding patterns. The entire surface was regenerated with 25 µl of 60 mM HCl so that the next cycle could be performed.

Table 8b indicates the results of the epitope similarity determination by BIAcore. Table 8a shows the positive and negative controls for the clones used. The positive controls are the RU levels obtained when the first Fab used is the clone indicated and the second Fab is an anti-gp120 V3-loop Fab. The Fabs of this invention compete with soluble CD4 for binding to gp120. The second Fab, an anti-gp120 V3-loop Fab, neither competes with soluble CD4 nor competes with anti-CD4 site Fabs and therefore would react with a different epitope than the Fabs of this invention. As can be seen from the table, all positive controls result in significant values of 125 or more, indicating the validity of the technique to distinguish between non-identical epitopes. The negative controls are the values obtained when the same Fab is injected twice. This gives the background values for each Fab. These values were subtracted from all subsequent experiments in order to give true values.

An epitope map, Table 8b, was then constructed. ND indicates that this combination of Fabs was not performed. It can be seen from this map that Fabs b3, b6, b11, and b14 form a set which compete highly effectively with one another for binding to a similar or the same epitope. For the most part, a member of the set competes for binding as well with another member as it does with itself (RU=0). On the other hand, b12 and b13 appear somewhat different in that while they compete for binding with members of the above set, they do not compete as effectively as the other Fabs within the set. Further, competition for binding to the same or similar epitope between b12 and b13 is incomplete. This suggests that the epitopes of Fabs b12 and b13 are sufficiently dissimilar from those of the other four and from each other, to allow detectable binding when they are used in combination with any of the other Fabs. It may therefore be concluded that clones b3, b6, b11, and b14 bind the same or similar epitopes, with Fabs b12 and b13 bind to epitopes which can be distinguished from the other epitopes in this assay.

TABLE 8a

| Fab | b3 | b6 | b11 | b12 | b13 | b14 |
|---|---|---|---|---|---|---|
| POSITIVE CONTROL (RU) | 129 | 128 | 131 | 125 | 135 | 134 |
| NEGATIVE CONTROL (RU) | 24 | 38 | ND | 17 | 15 | ND |

ND indicates that this combination of Fabs was not performed.

TABLE 8b

|  |  | Fab 1 | | | |
|---|---|---|---|---|---|
|  |  | b13 | b12 | b6 | b3 |
| Fab 2 | b14 | 30 | 24 | 14 | 0 |
|  | b11 | 54 | 28 | 14 | 0 |
|  | b3 | 26 | 29 | 0 | 0 |
|  | b6 | 21 | 17 | 0 | ND |
|  | b12 | 22 | 0 | ND | ND |

ND indicates that this combination of Fabs was not performed.

c. Comparison of Fab Epitopes with Wild-type and Mutant Forms of gp120 Using ELISA with gp120 in the Solid Phase Epitope similarity determinations of the panel of Fabs was performed with a panel of HXBc2 gp120 mutants of the HIV-1 strain LAI. Conserved residues of gp120 were altered to generate the HXBc2 gp120 mutants. The interaction between the mutants and Fabs was investigated to examine binding specificity differences between the Fabs at greater resolution. The HXBc2 gp120 mutants used in this assay had been previously characterized with respect to gp160 precursor processing, gp120-gp41 association, and CD4 binding ability (olshevsky et al., *J. Virol.*, 64: 5701–5707 (1990)). Both wild type and mutant gp120s were tested for their ability to bind a saturating concentration of each Fab.

The epitope determination with wild-type and mutant gp120 was performed with HIV-1 envelope glycoproteins from culture supernatants of COS-1 cells transfected with plasmids expressing either wild-type or mutant gp120 from the HXBc2 clone. Microtiter wells were coated with the antibody D7324 (Aalto BioReagents; Dublin, Ireland) which binds to the conserved 15 amino acid sequence at the carboxy terminus of gp120. The wild-type or mutant gp120 were thus captured onto the surface of microtiter wells by binding to the D7324 antibody. A reference HIV-1 positive human serum pool at a 1:3000 dilution in 0.5% Tween 20 was assayed for binding to the wild-type and mutant gp120s by incubating the serum pool with the immobilized gp120. The bound antibody was detected by a second enzyme conjugated antibody. The reading obtained with the HIV-1 positive human serum pool, N=4, was used as the reference value for each mutant. The Fabs of this invention were then assessed for binding to the wild-type and mutant gp120s and the ratio of the Fab to reference serum was determined for each gp120 mutant (Table 9). The average ratio for the entire panel of Fabs was calculated and any individual ratio deviating from the mean by less than 0.5 times was considered to indicate a gp120 amino acid change that decreased Fab recognition, while those deviating by more than 2.0 times indicated an amino acid change that enhanced Fab recognition. In this way, a map of mutations affecting the binding of the Fab to gp120 was obtained for each clone essentially as previously described (Helseth et al., *J. Virol.*, 65:2119–2123 (1991) and Olshevsky et al., supra).

TABLE 9

| | Fab | | | | | |
|---|---|---|---|---|---|---|
| Mutation | B3 | B6 | B11 | B12 | B13 | B14 |
| 45 W/S | 1.60 | 0.61 | 0.50 | 0.68 | 1.20 | 0.28 |
| 113 D/A | 1.46 | 1.73 | 1.89 | 1.13 | 0.99 | 0.00 |
| 113 D/R | 1.40 | 1.50 | 1.61 | 0.67 | 0.71 | 0.00 |
| NO V1/V2 | 1.07 | 1.48 | 1.42 | 0.23 | 0.86 | 1.68 |
| NO V1/V2/V3 | 2.05 | 1.48 | 1.94 | 0.47 | 0.95 | 1.60 |
| NO V3 | 1.88 | 1.64 | 1.92 | 0.46 | 1.08 | 1.72 |
| 183/184 PI/SG | 0.82 | 0.73 | 0.69 | 0.33 | 0.92 | 0.32 |
| 207 K/W | 1.15 | 1.57 | 1.19 | 2.54 | 1.30 | 1.36 |
| 252 R/W | 1.58 | 1.52 | 1.58 | 1.65 | 1.39 | 2.04 |
| 256 S/Y | 0.64 | 0.14 | 0.33 | 0.82 | 1.15 | 0.00 |
| 257 T/R | 0.08 | 0.59 | 0.00 | 0.76 | 0.22 | 0.00 |
| 257 T/A | 0.86 | 0.93 | 0.75 | 0.99 | 0.68 | 0.40 |
| 257 T/G | 0.91 | 0.70 | 1.14 | 0.74 | 0.75 | 0.00 |
| 262 N/T | 1.06 | 0.64 | 1.19 | 0.62 | 0.72 | 0.24 |
| 269 E/L | 0.73 | 0.48 | 0.45 | 0.78 | 0.83 | 0.20 |
| 314 G/W | 0.59 | 0.36 | 0.39 | 0.65 | 0.71 | 0.28 |
| 356 N/I | 0.67 | 0.66 | 0.39 | 0.92 | 0.80 | 0.52 |
| 368 D/R | 0.19 | 0.18 | 0.00 | 0.04 | 0.00 | 0.00 |
| 368 D/T | 0.28 | 0.20 | 0.00 | 0.03 | 0.02 | 0.00 |
| 370 E/R | 0.01 | 0.25 | 0.17 | 0.07 | 0.00 | 0.00 |
| 370 E/Q | 0.25 | 0.89 | 0.58 | 0.46 | 0.14 | 0.00 |
| 384 Y/E | 1.21 | 1.02 | 1.11 | 0.25 | 0.02 | 0.88 |
| 386 N/Q | 0.88 | 0.59 | 0.31 | 1.05 | 0.01 | 0.36 |
| 395 W/S | 0.92 | 0.59 | 0.47 | 1.00 | 1.05 | 0.12 |
| 427 W/S | 1.57 | 1.11 | 1.53 | 0.63 | 0.98 | 0.00 |
| 435 Y/S | 1.93 | 1.16 | 1.58 | 1.41 | 1.24 | 2.04 |
| 450 T/N | 0.62 | 0.48 | 0.58 | 0.75 | 0.75 | 0.60 |
| 457 D/A | 0.62 | 0.39 | 0.44 | 0.28 | 0.62 | 0.20 |
| 457 D/R | 0.84 | 0.55 | 0.92 | 0.32 | 0.58 | 0.56 |
| 470 P/L | 0.80 | 0.64 | 0.72 | 0.72 | 0.18 | 0.24 |
| 475 M/S | 0.06 | 1.02 | 0.33 | 1.50 | 1.39 | 0.92 |
| 477 D/V | 0.50 | 0.09 | 0.00 | 0.07 | 0.52 | 0.00 |

The general patterns observed are broadly similar to many CD4 site antibodies and of soluble CD4. Fab b12 is distinguished by its decreased binding to a mutant in which the V1 and V2 loops are deleted. This may or may not be related to the enhanced neutralizing ability of Fab b12. However, it is clear that the V1 and V2 loops and the V3 loop can affect antibody binding to the CD4 binding site either by direct contact or by transmitted conformational effects.

Sensitivity to certain mutations in residues, particularly towards the C-terminus of gp120, has previously been associated with CD4 binding site antibodies (Thali et al., *J. Virol.*, 66:5636–5641 (1992) and Thali et al., *J. Virol.*, 65:6188–6193 ((1991)). These mutations include residue 257 mutated from threonine to arginine (257 T/R), 368 D/R, 370 E/R, 457 D/A and 477 D/V. Most of these mutations abrogate Fab binding or reduce it to low levels consistent with the assignment of the recombinant Fabs in this assay as reacting with the CD4 site.

In a particular mutant of gp120, the V1/V2 loop (residues 119–205) is completely removed. This mutation enhances the binding of Fabs b6, b11, and b14 but significantly decreases the binding of Fab b12. Deletion of the V3 loop produces a more modest decrease in Fab b12 binding while generally enhancing the binding of the other Fabs. The 314 G/W change in the V3 loop produces a decrease in binding of all the Fabs. This effect has been observed for other CD4 binding site antibodies (Moore and Sodroski, unpublished observations).

When the binding specificities of each Fab is examined in detail, each Fab has a unique mutant binding profile. For example, Fab b14 binding is eliminated by the 113 D/A change whereas the binding of the other Fabs is unchanged or enhanced; Fab b3 and b11 binding is reduced by the 475 M/S mutation but binding by the other Fabs is unchanged and the 370 E/Q change reduces binding of all the Fabs except for b6 and possibly b11. Fab b12 is distinguished by its decreased binding to a mutant in which the V1 and V2 loops are deleted. This may or may not be related to the enhanced neutralizing ability of Fab b12 and will be the subject of further study. However, it is clear that the V1 and V2 loops and the V3 loop can affect antibody binding to the CD4 binding site either by direct contact or transmitted conformational effects.

The effects on Fab binding of a series of point mutations in gp120 afford the opportunity to look more closely at recognition differences. The general patterns observed are broadly reminiscent of many CD4 site antibodies and of soluble CD4 itself. Fab b12 is distinguished by its decreased binding to a mutant in which the V1 and V2 loops are deleted. This may or may not be related to the enhanced neutralizing ability of Fab b12. It will be necessary to study a number of variants of Fab b12, which could be produced by chain shuffling or mutation, to answer this question. However, it is clear that the V1 and V2 loops and the V3 loop can affect antibody binding to the CD4 binding site either by direct contact or transmitted conformational effects.

Figure 20:
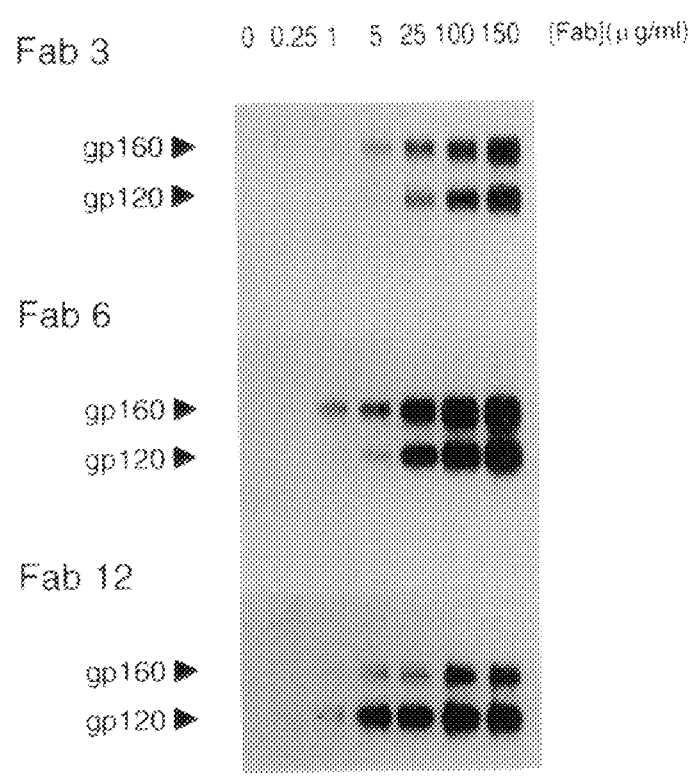
FIG. 20 illustrates the relative binding affinities of b3, b6, and b12 for the total envelope glycoproteins (gp160) and for the gp120 glycoprotein (gp120) expressed on the surface of COS-1 cells as determined by immunoprecipitation and described in Example 6. The signal on the autoradiogram represents the relative amount of envelope glycoproteins bound with increasing concentrations of Fab (0–150 μg/ml).

6. Determination of the Relationship Between the Epytopes Recognized by the Fabs with HIV-1 Antigen Multimeric Complexes a. Comparison of Fab Epitopes with gp120 and gp160 Expressed as Multimeric Complexes on the Surface of COS-1 Cells Given the lack of correlation of Fab neutralization with binding parameters assessed using recombinant gp120, the binding of Fabs b3, b6, and b12 to COS-1 cells expressing the HXBc2 envelope glycoproteins gp160 and gp120 was compared. Fab b3, the poorest neutralizer, Fab b6, also a poor neutralizer, and Fab b12, the most effective neutralizer as determined in Example 5 were used in the assay. The envelope glycoproteins expressed by the COS-1 cells were gp160, the precursor of gp120 and gp41, and the mature gp120. In this assay, different concentrations of Fab were incubated with radiolabeled COS-1 cells which express gp160 and gp120 on their surface. The cells were then washed and lysed. The gp120 and gp160 envelope glycoproteins bound to Fab were precipitated with goat anti-F (ab')$_2$ antibody and analyzed by protein gel electrophoresis and shown in FIG. 20. Since the amount of HIV-1 envelope glycoprotein expressed on the surface of transfected COS-1 cells is small compared with the amount present intracellularly, after cell lysis, the bound Fab is presented with a large excess of both mature gp120 and gp160 precursor forms. The total amount of envelope glycoproteins precipitated thus provides an indication of the amount of Fab bound to the cell surface. Scanning densitometry profiles were derived from the autoradiographs and are expressed in arbitrary densitometric units.

Although the lack of saturation for Fabs b6 and b3 precludes a precise estimate of affinity, it is clear that Fab b3 exhibits a lower affinity for the precursor gp160 than either Fab b6 or b12. When the binding of Fab b12 and b6 are compared, several differences are apparent. Assuming that Fab 6 achieves saturation at concentrations slightly higher than 150 µg/ml, the estimated affinities of Fab b12 and b6 for the total population of envelope glycoproteins recognized differ only marginally. The most striking difference in the binding of Fab b12 and b6 to the multimeric envelope glycoprotein complex is the preferential detection of gp120 relative to gp160 by Fab b12. Using densitometry to estimate amounts, it is seen from FIG. 20 that Fab b12 immunoreacts with an amount of gp120 that is at least about 50% more than the gp160 present in the immunoreaction admixture. The estimated affinities, based on the Fab concentrations at which half-maximal binding to gp120 is observed, are $3 \times 10^7 M^{-1}$ and $<6 \times 10^6 M^{-1}$ for Fabs b12 and b6, respectively.

The binding of the Fabs to the multimeric envelope glycoprotein complex on the transfected COS-1 cell surface provides some insights into the observed differences in neutralization potency. The binding of the most potent neutralizing Fab, Fab b12, achieves saturation at roughly 100 µg/ml, whereas neither of the less potent neutralizing Fabs achieves saturation even at 150 µg/ml. Fab b3 clearly exhibits a lower affinity for the cell surface envelope glycoprotein complex than do the other two Fabs tested, b12 and b6. The most striking difference in the binding of b12 and b6 to the multimeric envelope glycoprotein complex is the preferential precipitation of gp120 relative to gp160 by the bound Fab b12. In addition to these differences in gp120 recognition, it appears that the overall number of cell surface envelope glycoproteins capable of being recognized by the less neutralizing Fabs is greater than that seen for Fab b12. These differences suggest that Fab b12 may recognize a more limited subset of envelope glycoprotein conformations and that these conformations are better approximated by the mature gp120 glycoprotein in the cell lysates. It is known that the gp160 precursor assumes a greater variety of conformations during the maturation process than does the fully folded gp120 product (Thiriart, et al., *J. Immunol.*, 143:1832–1836 (1989) and Fennie and Lasky, *J. Virol.*, 63:639–646 (1989)). The enhanced neutralization ability of Fab b12 could reflect a higher affinity for a restricted gp120 conformation present in the functionally relevant subset of envelope glycoprotein spikes. Such a functionally relevant group of envelope glycoproteins moieties probably represents a small subset of the total population, consistent with the low infectious fraction associated with HIV-1 and other retroviral virus preparations. One caveat to these observations is that the glycosylation of gp120 expressed as a recombinant protein in baculovirus or on the surface of COS-1 cells is likely to differ and this could affect binding of the Fabs of this invention. However, no difference in the affinity for CD4 binding site antibodies between the two forms of gp120 has been observed previously using a range of antibodies (Moore and Sodroski, unpublished observations). In addition, these studies employed a molecular clone of HIV-1 and its extension to primary isolates will need to be studied further.

Fabs derived from combinatorial libraries may be viewed as "artificial". However, as shown here, the recognition properties of a set of antibodies directed to the CD4 site of gp120 show many features in common with those derived by conventional means. They also show many features in common with one another suggesting that, with the caveats inherent in the library approach (Barbas et al., *J. Molec. Biol.*, 230:812–823 (1993) and Burton and Barbas, *Nature*, 359:782–783 (1992)), one individual produces several clearly distinct antibodies directed to a common structural feature, i.e., the CD4 binding site. This is in agreement with observations made on anti-CD4 binding site antibodies using anti-idiotype antibodies (Chamat et al., *J. Immunol.*, 149:649–654 (1992) and Hariharan et al., *J. Virol.*, 67:953–960 (1993)). One advantage of producing several antibodies is that escape (at least in binding terms) is made more difficult. The only mutations in Table 9 which essentially eliminate the binding of all the antibodies also reduce CD4 binding ability.

The observations presented here have significance for vaccine development. The most effective vaccine may need to induce antibodies to the CD4 binding site with properties similar to those of Fab b12. Given the data above, recombinant gp120 offers no special qualities in this regard. Further, the Fab b12 type of antibody formed only about 10% (4/33 Fabs) of the cloned response of the library donor (Barbas et al., *J. Molec. Biol.*, 230:812–823 (1993)) and has not been described amongst the human antibodies derived by other means suggesting it may be a minor component of typical responses. It is clearly of some interest for vaccine design to define more precisely the structure recognized by Fab b12.

7. Recognition of gp120 from Primary HIV-1 Isolates by b12 IgG1 in Vitro

The ability of the b12 IgG1 to recognize the gp120 molecule from HIV-1 virus from 69 primary isolates was determined in an ELISA assay. Recognition of the primary HIV-1 virus isolate with b12 IgG1 is indicative of the prevalence of the b12 epitope in the HIV-1 pandemic. To probe the occurrence of the b12 epitope in the HIV-1 pandemic, binding of the b12 IgG1 to gp120 from 69 international isolates belonging to 6 different clades was examined. Virus isolates assayed were obtained from the WHO, HMJFAMM, and NIAID.

Infectious culture supernatants containing virus and free gp120 were treated with 1%(v/v) Nonidet-P40 (NP40) non-ionic detergent to provide a source of gp120 (Moore et al., *AIDS*, 3:155–160 (1989)). Microplate wells (Immulon II, Dynatech, Ltd.) were first coated with sheep polyclonal antibody D7324. This antibody was raised to the peptide APTKAKRRVVQREKR, derived from the C-terminal 15 amino acids of the clade B IIIB HIV-1 viral isolate. Next, an appropriate volume of inactivated supernatant containing gp120 was diluted with a buffer comprising tris-buffered saline (TBS)/1% (v/v) NP40/10% fetal calf serum (FCS) and a 100 $\mu$l aliquot added to the microplate wells for 2 hours at room temperature. Unbound gp120 was removed by washing with TBS, and bound gp120 was detected with CD4-IgG (1 $\mu$g/ml) or with b12 IgG1 diluted in a buffer comprising TBS/2% (w/v) nonfat dry milk powder/20% (v/v)sheet serum (TMTSS) essentially as previously described (Moore et al., *AIDS*, 4:307–310 (1990)) and Moore et al., *J. Virol.*, 68:469–473 (1994)). CD4-IgG is a fusion molecule which consists of CD4 and IgG. The CD4 portion binds to gp120 and the IgG portion provides the means for detection of the CD4-IgG fusion molecule with labeled anti-IgG reagents. Bound antibody was then detected with an appropriate alkaline-phosphatase conjugated anti-IgG, followed by AMPAK (Dako Diagnostics). Absorbance was determined at 492 nm ($OD_{492}$). Each virus was tested against CD4-IgG in triplicate and against b12 IgG1 in duplicate. All $OD_{492}$ values were corrected for non-specific antibody binding in the absence of added gp120 (buffer blank). The mean, blank-corrected $OD_{492}$ values for CD4-IgG and b12 IgG1 were then calculated, and the $OD_{492}$ ratios of b12 IgG1:CD4-IgG were determined. This normalization procedure enables allowance to be made for the different amounts of gp120 captured onto the solid phase via antibody D7324 when comparing antibody reactivity with a panel of viruses. Binding ratios of 0.50 or greater were deemed to represent strong antibody reactivity; ratios from 0.25–0.50 were considered indicative of moderate reactivity; values of <0.25 were designated as representative of essentially negative monoclonal antibody reactivity.

Figure 22:
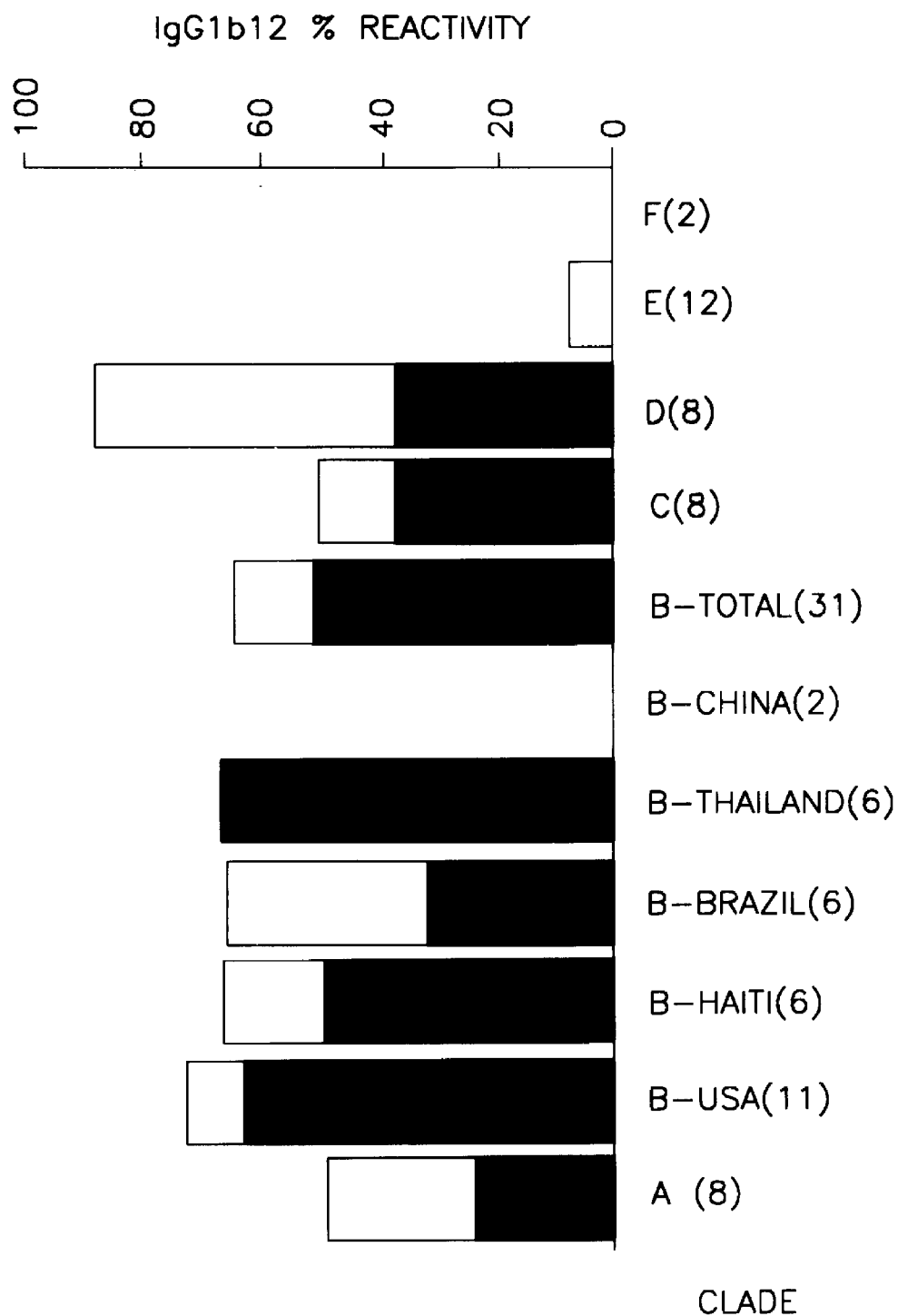
FIG. 22 illustrates the reactivity of b12 IgG1 with a panel of international isolates of HIV-1 as described in Example 8. Reactivity was determined with gp120 isolated from the HIV-1 samples in ELISA with the b12 IgG1 as described in Example 8. Data is plotted as % b12 IgG1 reactivity on the X-axis against clades A-F on the Y-axis. Country names indicate where the HIV-1 virus was originally isolated. The numbers in parenthesis refer to the number of viruses of each clade examined. Reactivity is designated as strong (▓) or moderate (▒).

As shown in FIG. 22, b12 IgG1 reacts with ≧50% of clades A-D but only 1 of 12 isolates from lade E. Reactivity with lade B isolates from the U.S.A. is approximately 75%.

8. Nucleic Acid Sequence Analysis Comparison Between HIV-1 Specific Monoclonal Antibody Fabs and the Corresponding Derived Amino Acid Residue Sequence To explore the relationship between neutralizing and weakly or non-neutralizing Fabs, the variable domains of 32 clones expressing human anti-gp120 Fabs, prepared in Example 2 including the 20 listed in FIG. 6 for which neutralizing activity was assessed, were sequenced. In addition, the five gp41-specific Fabs were also sequenced.

Nucleic acid sequencing was performed on double-stranded DNA using Sequenase 1.0 (USB, Cleveland, Ohio) and the appropriate primers hybridizing to sequences in the Cg1 domain (SEQGb: 5' GTCGTTGACCAGGCAGC-CCAG 3' SEQ ID NO 49) or the Ck domain (SEQKb: 5' ATAGAAGTTGTTCAGCAGGCA 3' SEQ ID NO 50). Alternatively sequencing employed single stranded DNA and the T3 primer (5' ATTAACCCTCACTAAAG 3', SEQ ID NO 51) or one hybridizing to a sequence in the Ck domain (KEF: 5' GAATTCTAAACTAGCTAGTTCG 3' SEQ ID NO 52).

Figure 10A:
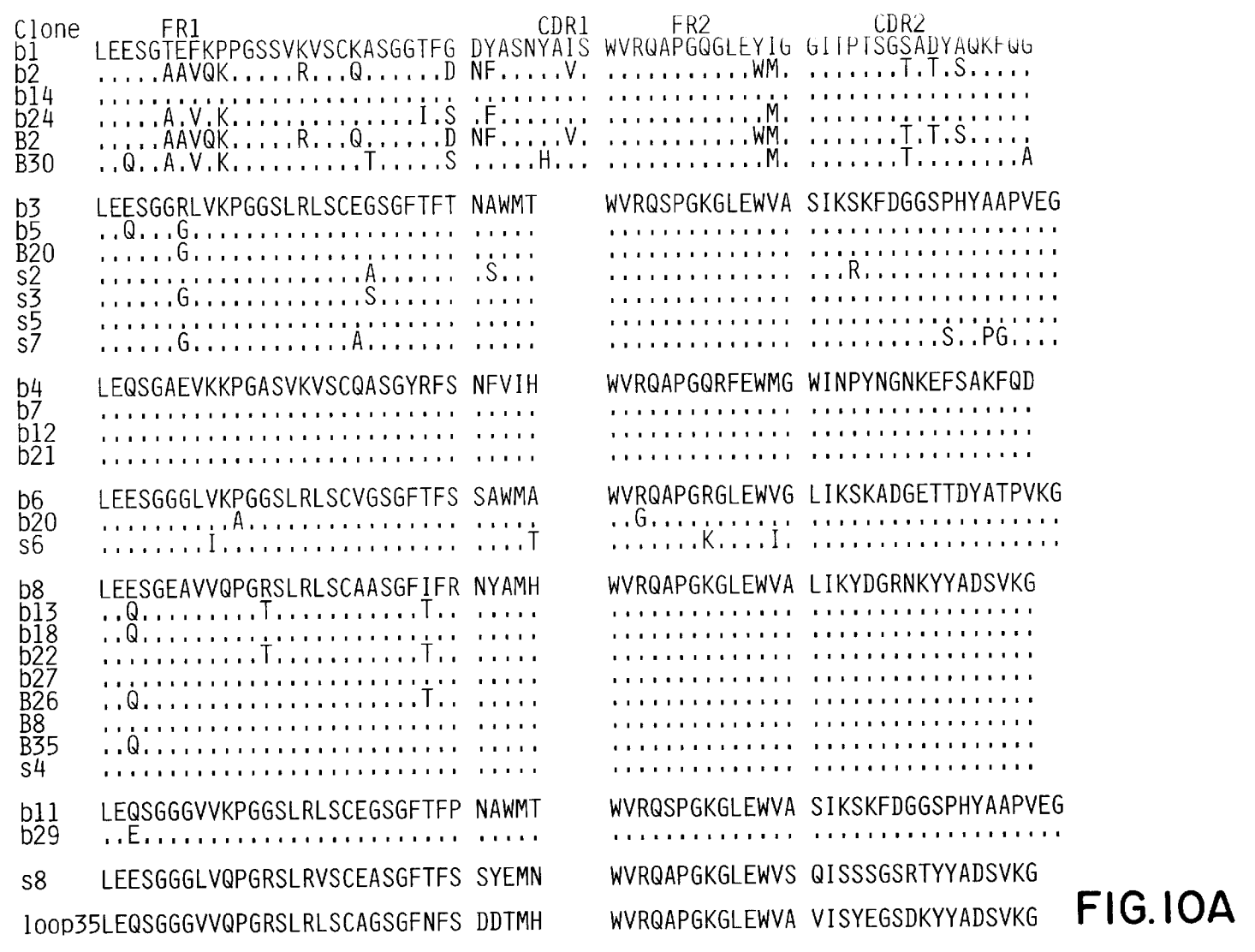
Figure 10B:
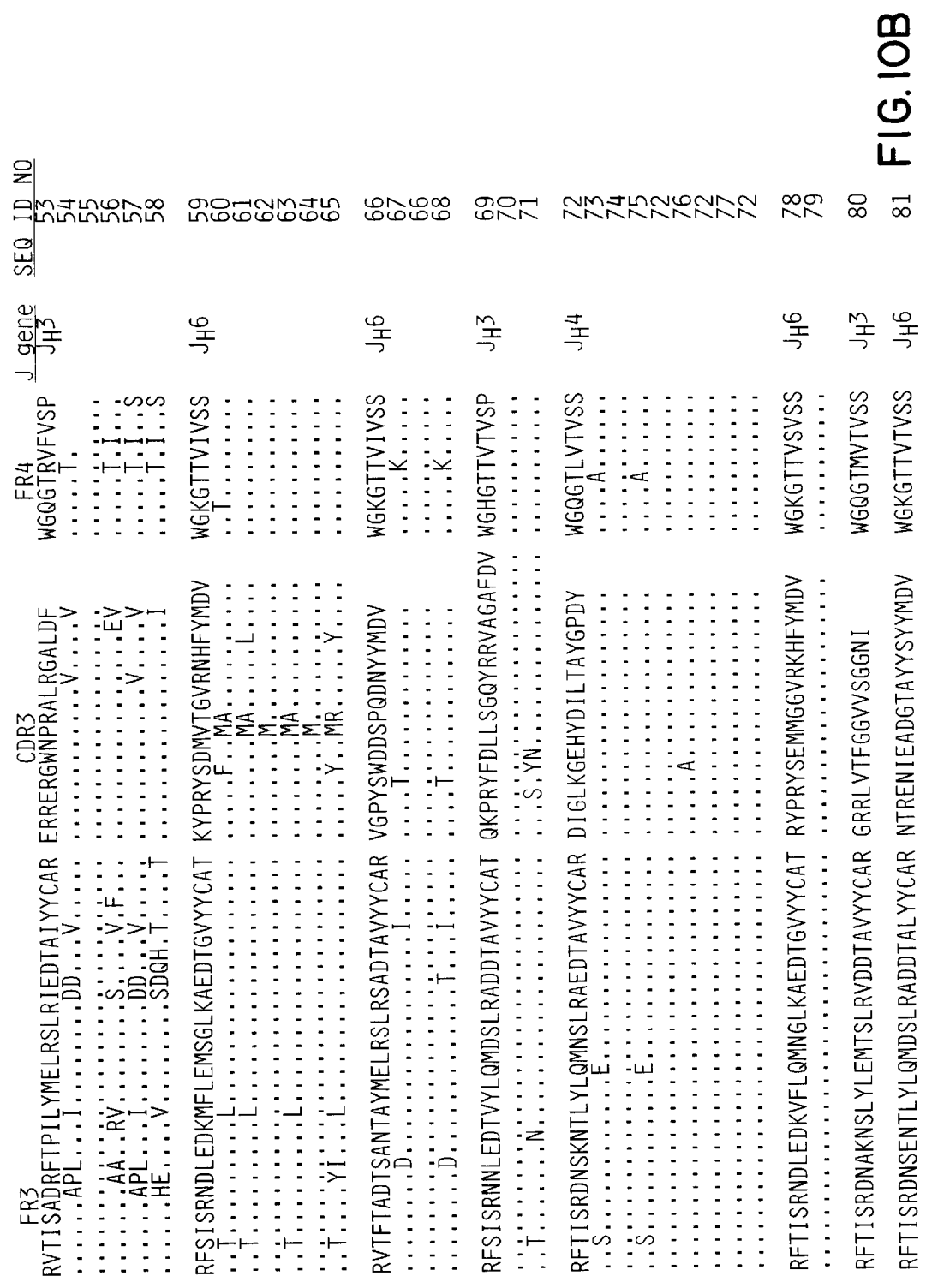
Figure 11A:
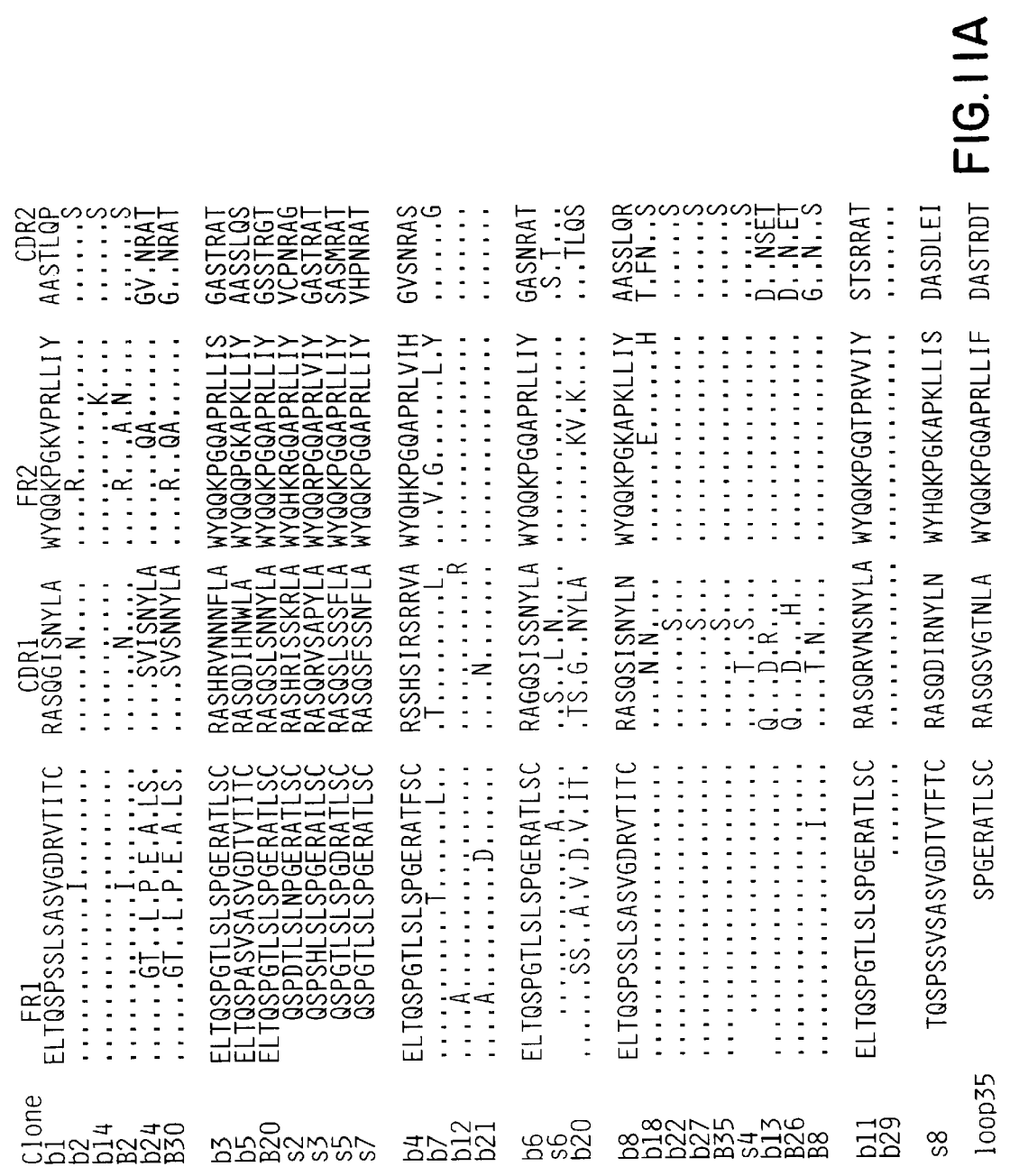
Figure 11B:
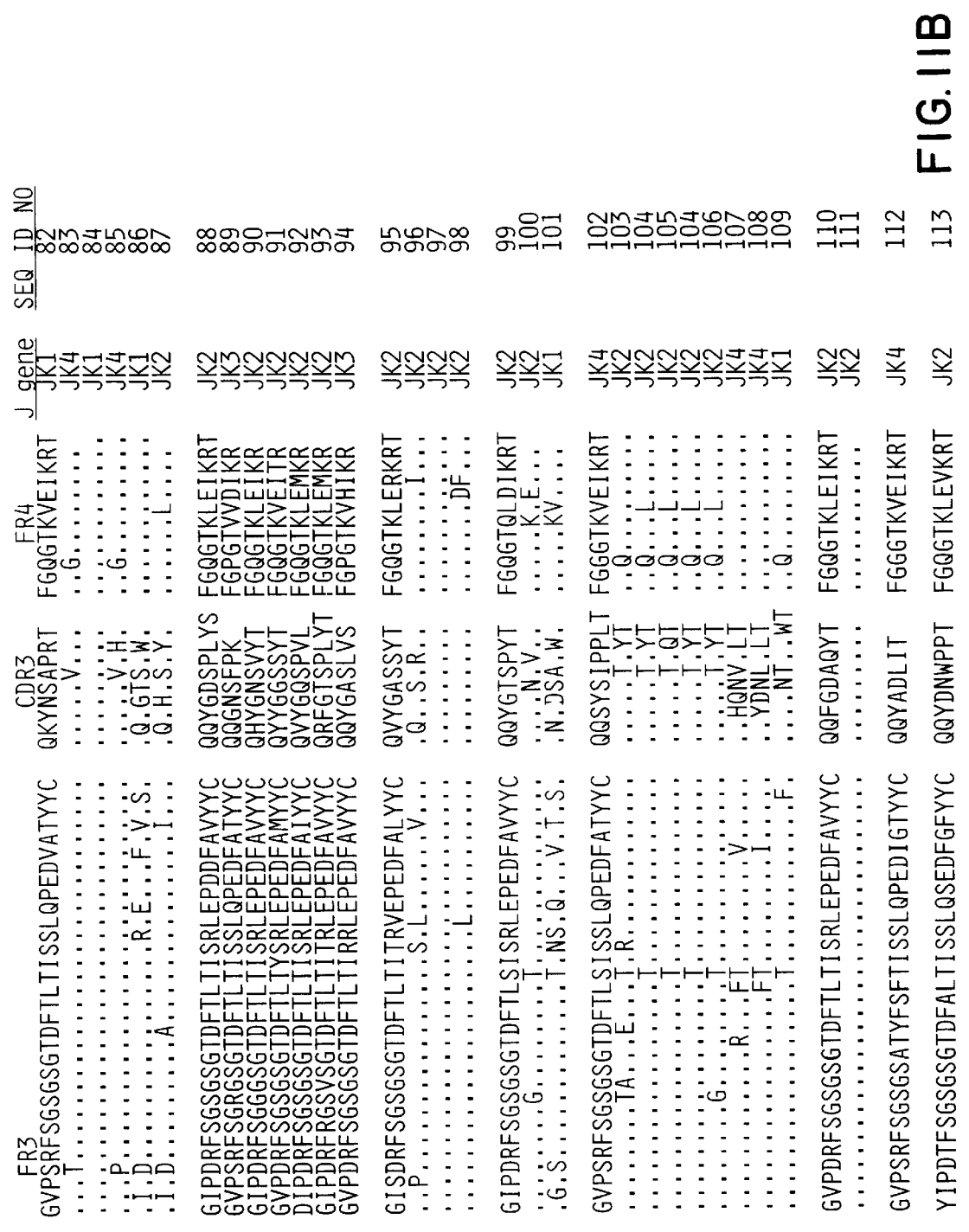

The amino acid residue sequences of the variable heavy and light chains derived from the nucleic acid sequences of the 32 gp120-specific clones are shown respectively in FIGS. 10 and 11. Groupings are made on the basis of similarities in heavy chain sequences. Dots indicate identity with the first sequence in each section. The SEQ ID NOs are listed to the right of the corresponding derived heavy and light chain ($V_H$ from SEQ ID NO 53–81 and VL from SEQ ID NO 82–113) amino acid residue sequences in the Figures themselves.

Alignment of derived sequences with one another and with the Genbank database made use of the MacVector suite of programs. For analysis of heavy chain CDR3 sequences as described by Sanz, *J. Immunol.*, 147:1720–1729 (1991), the most 5' nucleotide was considered to be the first nucleotide after codon 95 of the H chain variable region according to Kabat et al, Sequences of Proteins of Immunological Interest, U.S. Dept. of Health and Human Services, Washington, D.C. (1991). The most 3' nucleotide was assigned to the last unidentified nucleotide before the sequence matched with the published germline JH genes. The CDR3 sequences were analyzed using the DNASTAR software. Sequence comparisons were performed with both the ALIGN and COMPARE programs in order to determine the germline D gene which provided the best homology throughout. In a second step, the SEQCOMP program was used to find sequence identity of at least six nucleotides with either the coding strand or the reverse complement of germline D genes.

The heavy and light chain sequences of the gp41-specific Fabs are shown in FIGS. 18 and 19, respectively. The amino acid residue sequence of the CDR3 heavy chain exhibits the most variation between the Fabs than any other region of the variable domain.

a. Organization of Antibodies into Groups According to Heavy Chain Sequence $V_H$ and $V_L$ domains of 32 gp120 clones were sequenced and the $V_H$ domains compared using MacVector software. This analysis immediately established that a number of the clones, including those selected by panning against different antigens, are closely related to one another. The exception to this is the Fabs selected by panning against the V3 loop peptide which are not related to the Fabs selected by panning against the gp120/160 antigens. FIG. 10 shows that the VH sequences derived from gp120/160 panning can be organized into 7 groups. The broad features apparent from a comparison of amino acid sequences are discussed herein.

The relatedness of sequences within a group varies considerably. For instance, in the group beginning with clone number b8 the amino acid sequences are very similar. Six clones were identical and the remainder showed a maximum of 5 differences from the predominant sequence (the EQ difference due to the 5' primer excluded). Only one clone showed a single difference in the CDR3 region. The average discrepancy over all the sequences in this group from the predominant sequence is 1.1 amino acid residues/variable domain. This amount corresponds to the order of magnitude of discrepancies which could arise from the PCR. Sequencing of constant domains indicated a PCR error frequency of about 1 base change per domain.

In contrast, in the group headed by clone b3, no two clones were absolutely identical. The average difference from the consensus group sequence is 3.3 residues per sequence and determination for the CDR3 alone is 1.3. Therefore, it seems likely that the heavy chains in this group are somatic variants of one another.

The group headed by clone 1 presents a third pattern. Clones b1 and b14 are identical as are clones b2 and B2. However, 23 amino acid differences exist between the two sets of clones. Clones b24 and B30 are approximately equally well differentiated (13–25 differences) from either of these two sets of clones or one another. Still the CDR3 regions are very similar. A number of explanations can be suggested for this pattern: 1) all clones in this group originate from the same germline gene which has undergone extensive somatic mutation, 2) cross-over events have occurred to essentially recombine different germline genes with the same DJ combination, 3) a "convergent evolution" process has led to the selection of different germline genes associated with the same DJ combination.

b. Sequences of the $V_L$ Domains from the gp120 Binders

The $V_L$ sequences of the Fabs were organized into the groups defined in FIG. 10 are shown in FIG. 11. Immediately apparent was the extensive chain promiscuity as evidenced by the pairing of different light chains with the same or a very similar heavy chain with retention of antigen binding capability and indeed, for the most part, antigen affinity as compared with FIG. 10. This promiscuity can be explored further by reference to the groups considered above.

The clone b8 group, in which the heavy chain members were identical or very similar, also produced 4 light chains which are identical or very similar (less than 3 amino acid differences). Therefore a predominant heavy-light chain combination can be described for this group. One member (clone b8) had the same or very closely related $V_L$ gene but appeared to use a different Jk gene. Two other members (clones B8 and b18) were more distantly related to the major sequence (7–12 differences). Two further clones (b13 and B26) used a Vk gene from a different family, Vk3 compared to Vk1, and therefore were unrelated to the major sequence.

The clone b3 group, suggested to contain somatic variants of a single heavy chain, showed considerable light chain diversity with no two members being closely related to one another. Vk3–Jk2 combinations predominated but Vk3–Jk3 and Vk1–Jk3 combinations also occurred.

On the other hand, in the clone by group evidence existed for the heavy chains being more choosy about their light chain partner. Thus, closely related heavy chains appeared to be paired with related light chains. The identical heavy chain pairs (b1 and b14; b2 and B2) had very similar light chains (2 and 4 amino acid differences respectively) whereas the distinct heavy chains (b24 and B30) had distinct light chains which were unrelated to one another or the other group members. The clone 4 group provides another example of this phenomenon in that 4 closely related heavy chains were paired with 3 closely related light chains (a predominant heavy-light chain combination), except for the clone b7 light chain that was distinct.

In summary, the heavy chain ($V_H$) sequences was organized into 7 groups where each member of a group has an identical or very similar CDR3 region with a limited number of differences elsewhere. When the light chains ($V_L$) were constrained into the groupings defined by their heavy chain partners, considerable light chain sequence variation was observed. This phenomenon of chain promiscuity has been observed previously and can be appreciated by reference to FIG. 11. Marked neutralizing ability was confined to two groups of sequences. The first group consisted of Fabs 4, 7, 12 and 21 which have very similar heavy and light chains. The second group consisted of Fabs 13, 8, 18, 22 and 27. Only Fab 13 showed marked neutralizing ability, although the others showed some weaker activity. Interestingly in this group Fab 13 did have a light chain distinct from the other members of the group.

9. Shuffling of the Heavy and Light Chain of a Sinale Clone Against the Library

To further explore possible functional heavy-light chain combinations, the heavy chain of clone b12 (also referred to as Fab 12 for the corresponding soluble Fab preparation) shown in FIG. 10 was recombined with the original light chain library prepared in Example 2 to construct a new library H12-LCn. In addition, the b12 light chain was recombined with the original heavy chain library to construct a library Hn-L12. These two libraries were taken through 3 rounds of panning against gp120 (IIIB) as described in Example 2b5). The Fabs expressed from the resultant immunoreactant clones were analyzed as described in Example 3 above. Clone b12 was chosen as this Fab neutralized HIV-1 in vitro as shown in Example 3.

To accomplish the preparation of a shuffled library from the Fd gene of clone b12 with the original light chain library, the b12 heavy chain was first subcloned into a tetanus toxoid binding clone expressed in pComb2-3. The light chain library was then cloned into this construction to give a library of $1 \times 10^7$ members. The subcloning step was used to avoid contamination with and over-representation of the original light chain. A similar procedure was adopted for shuffling of heavy chains against the light chain from clone b12 to give a library of 3×10⁶ members. Cloning and panning procedures were carried out as described above for the original library.

Eleven light chains which recombined with the b12 heavy chain and bound gp120 by panning were randomly chosen for subsequent competition ELISA and sequence analysis. The apparent affinities of these shuffled combinations were similar with an $IC_{50}$ of approximately $10^{-8}$ to $10^{-9}$M. The sequences were organized where a set of 3 were very similar to the original b12 light chain and the other 8 showing many differences from the original with some sub-grouping possible.

The sequences of the light chains which bound to the b12 heavy chain clone are shown in FIG. 12. The sequences are compared to the sequence for the original light chain from clone b12. The light chains are identified by numbers which do not correspond to the original light chain clones; the assigned numbers of the newly selected clones having new light chains are thus arbitrary. The sequences of these light chains are also listed in the Sequence Listing from SEQ ID NO 114 to 122. Some light chain sequences are identical. In addition to immunoreactivity with gp120, the new Fabs isolated from these shuffled clones were tested in the syncytia assay for neutralization of HIV-1 infection as described in Example 3. Four shuffled monoclonal Fab antibodies, each having the heavy chain from clone b12, a known HIV-1 neutralizing clone, and new light chains designated L28, L25, L26 and L22, all exhibited approximately 60% neutralization in a syncytia assay with 0.4 μg/ml purified Fab. This effect was equivalent to that obtained with the original clone b12 heavy and light chain pair. Maximum neutralization of approximately 80% was obtained with the H12/L28 and H12/L25 Fabs at 0.7 μg/ml which was equivalent to that seen with the original clone b12 heavy and light pair. The neutralization resulting from the H12/L22 and H12/L26 Fabs plateaued at 60% with Fab concentrations of 0.4 μg/ml up to 1.0 μg/ml. Thus, in addition to the gp120 immunoreactive and HIV neutralizing Fabs obtained in the original library prepared as described in Example 2, by shuffling a known neutralizing heavy chain with a library of light chains, new HIV-1 neutralizing Fab monoclonal antibodies have been obtained.

Ten heavy chains which recombined with the b12 light chain were also randomly chosen. One was very similar to the original b12 heavy chain but the others have many differences. Nevertheless, the V-D and D-J junctions were essentially identical indicating the clones had probably arisen from the same rearranged B-cell clone by somatic modification. Competition ELISA failed to reveal any clear difference in affinity between the variants selected from those originally analyzed.

The sequences of the heavy chains which bound to the b12 light chain clone are shown in FIG. 13. The sequences are compared to the sequence for the original heavy chain from clone b12. The heavy chains are identified by numbers which do not correspond to the original light chain clones; the assigned numbers of the newly selected clones having new heavy chains are thus arbitrary. The sequences of these light chains are also listed in the Sequence Listing from SEQ ID NO 123 to 132. Some light chain sequences are identical. In addition to immunoreactivity with gp120, the new clones were tested in the syncytia assay for neutralization of HIV-1 infection as described in Example 3. Two shuffled monoclonal Fab antibodies, each having the light chain from clone b12, a known HIV-1 neutralizing clone, and new heavy chains designated H2 and H14, exhibited approximately 40% neutralization in a syncytia assay with 1.0 and 0.5 μg/ml purified Fab, respectively. This effect was equivalent to that obtained with the original clone b12 heavy and light chain pair at a concentration of 2 μg/ml. Maximum neutralization of approximately 50% was obtained with the Fab having the new H14 chain at 1.0 μg/ml compared to 80% neutralization with 0.7 μg/ml with the original clone b12 heavy and light pair. Thus, in addition to the gp120 immunoreactive and HIV neutralizing Fabs obtained in the original library prepared as described in Example 2, by shuffling a known neutralizing light chain with a library of heavy chains, new HIV-1 neutralizing Fab monoclonal antibodies have been obtained.

Thus, this shuffling process revealed many more heavy and light chain partners that bound to gp120 that were equal in affinity to those obtained from the original library prepared in Example 2. With this approach, additional HIV-1 neutralizing antibodies can easily be obtained over those present in an original library. The complexity of the clones arising from the heavy chain shuffling also suggests that this approach may be used to map the course of somatic diversification.

Combinatorial libraries randomly recombine heavy and light chains so to what extent antibodies derived from such libraries represent those produced in a response in vivo can be determined. In principle, a heavy-light chain combination binding antigen could arise fortuitously, i.e., neither chain is involved in binding antigen in vivo but the combination does bind antigen in vitro.

The available data suggests, however, that heavy chains, from immune libraries, involved in binding antigen tightly in vitro arise from antigen-specific clones in vivo. First, studies have generally failed to identify high-affinity binders in non-immunized IgG libraries. See, Persson et al. *Proc. Natl. Acad. Sci., USA*, 88:2432–2436 (1991) and Marks et al. *Eur. J. Immunol.*, 21:985–991 (1991).

Further, as described above, gp120 binders were not observed in panning a bone marrow IgG library from an HIV seronegative donor against gp120. Second, heavy chains associated with binders from immunized libraries were typically at relatively high frequency in the library indicating they were strongly represented in the mRNA isolated from immunized animals. See, Caton et al., *Proc. Natl. Acad. Sci., USA,* 87:6450–6454 (1990) and Persson et al., supra. Third, heavy chains from immunized libraries appeared to dictate specificity when recombined with various unrelated light chains as described in Example 10. Fourth, the isolation of intraclonal heavy chain variants as here indicated that an active antibody response was cloned. Thus, the shuffling of a known heavy chain with a light chain binder and vice versa is preferred for use in this invention as new neutralizing Fabs can be obtained beyond those generated in vivo.

Heavy chain promiscuity, i.e., the ability of a heavy chain to pair with different light chains with retention of antigen affinity, presents serious problems for identifying in vivo light chain partners. This applies not only to the strict definition of partners as having arisen from the same B-cell but also to one which would encompass somatic variants of either partner. The existence of predominant heavy-light chain combinations, particularly involving intraclonal light chain variants, suggests that the light chains concerned are well represented in the library and probably are associated with antigen binding in vivo. However, promiscuity means that, although some combinations probably do occur in vivo, one cannot be certain that one is not shuffling immune partner chains in the recombination. For instance, the occurrence of a virtually identical light chain (b6, B20) in 2 out of 33 clones suggests that it is probably over-represented in the library consistent with an in vivo involvement in antigen-stimulated clones. However, there is no way of knowing whether the in vivo partner of the light chain is the b6 or B20 heavy chain or indeed another heavy chain arising from a stimulated clone.

The light chains arising from the combinatorial library may not be those employed in vivo. Nevertheless it is interesting to note that some heavy chains appear relatively choosy about light chain partner whereas others appear almost indifferent. This observation needs to be tempered by the finding that apparently choosy heavy chains from this analysis will accept diverse light chains with maintenance of a antigen binding in a binary plasmid system where pairings are forced as shown below in Example 11 rather than selected in a competitive situation.

Two reports compare heavy-light chain combinations arising from combinatorial libraries and hybridomas in immunized mice. The library approach begins with mRNA and is therefore probably reflecting plasma cell populations. In contrast, hybridomas are thought to reflect activated but not terminally differentiated B cell populations and EBV transformation to reflect resting B cell populations.

Whatever the arguments about light chain authenticity, the heavy chains of FIG. 10 present many features of interest. The most frequently used heavy chain is of the clone b8 type. It could be argued that this usage simply represents bias in PCR amplification. However, the occurrence of approximately equal numbers of clones in this group amplified by VH1a and VH3a primers argues against this notion. Furthermore, the existence of intraclonal variants in some groups indicates that one is at least sampling different genes from the initial library.

The antibodies cloned here do bear qualitative relationship with the polyclonal antibodies present in the serum of the asymptomatic donor. The titer of anti-gp120 (IIIB) antibodies was approximately 1:3000, with greater than 50% of the reactivity being inhibited by CD4 or a cocktail of Fabs from clones 12, 13 and 14. The titer of anti-gp120 (SF2) antibodies was approximately 1:800. Further, the titer of serum against the short constrained V3 loop peptide was 1:500 and against the full length MN V3 loop peptide was only 1:300. The importance of "anti-CD4 site antibodies" seems general in donors with longer term HIV infection in that the cocktail of Fabs 12, 13 and 14 was able to inhibit binding of a large fraction of serum antibody reactivity with gp120 (IIIB) in 26 of 28 donors tested.

The ability of Fabs to neutralize viruses has been a controversial area. One of the problems has been that Fabs are classically generated by papain digestion of IgG. If the Fab, as is often the case, shows reduced activity relative to the parent IgG then it may be difficult to rule out IgG contamination in the Fab preparation. Recombinant Fabs, however, as shown herein definitively neutralize virus.

The mechanism of neutralization of HIV-1 appears to neither require virion aggregation nor gp120 cross-linking. In addition, there is no correlation with blocking of the CD4-gp120 interaction to neutralization. The existence of the cloned neutralizing Fabs of this invention should allow the molecular features that confer neutralizing potential to be explored. For instance, in the case of the group of clones containing Fab 13, the unique character of the light chain of that neutralizing clone suggests that chain shuffling experiments in which the 13 light chain was recombined with the other heavy chains in that group, might be revealing. Heavy chains paired with two dissimilar light chains have been shown to retain antigen affinity but exhibit altered fine specificity as shown in Example 11.

The observation here of a large number of Fabs with only a limited number being strongly neutralizing may have important consequences. If the pattern is repeated for whole antibodies then it would seem that much of the gp120 structure may be in a sense a "decoy", i.e., the immune system may invest considerable effort in producing antibodies of high affinity but limited anti-viral function. To exacerbate the situation the ineffective antibodies may bind to gp120 and inhibit the binding of strongly neutralizing antibodies. This has obvious consequences for vaccination which should be primarily designed to elicit neutralizing antibodies of this invention.

10. Shuffling of Selected Heavy and Light Chain DNA Sequences of a Combinatorial Library in a Binary Plasmid System A binary system of replicon-compatible plasmids has been developed to test the potential for promiscuous recombination of heavy and light chains within sets of human Fab fragments isolated from combinatorial antibody libraries. The efficiency of the system is demonstrated for the combinatorial library of this invention derived from the bone marrow library of an asymptomatic HIV donor.

a. Construction of the Binary Plasmid System

The binary plasmids pTAC01H and pTC01 for use in this invention contain the pelB leader region and multiple cloning sites from Lambda Hc2 and Lambda Lc3, respectively, and the set of replicon-compatible expression vectors pFL281 and pFL261. Both pFL281 and pFL261 have been described by Larimer et al., *Prot. Eng.*, 3:227–231 (1990), the disclosure of which is hereby incorporated by reference. The nucleotide sequences of pFL261 and pFL281 are in the EMBL, GenBank and DDBJ Nucleotide Sequence Databases under the accession numbers M29363 and M68946. The plasmid pFL281 is based on the plasmid pFL260 also described by Larimer et al., supra, and having the accession number M29362. The only distinction between the plasmids pFL260 and pFl281 is that pFL281 lacks a 60 bp sequence of pFL260 between the Eag I site and the Xma III site resulting in the loss of one of the two BamH I sites. This deletion is necessary to allow for cloning of the BamH I Hc2 fragment into the expression vector as described herein.

The replicon-compatible expression vectors share three common elements: (i) the f1 single-stranded DNA page intergenic IG regions; (ii) the tightly regulated tac promoter and lac operator; and (iii) an rbs-ATG region with specific cloning sites. The plasmid vectors differ in their antibiotic resistance markers and plasmid replicons: pFL261 carries a gene encoding chloramphenicol acetyltransferase (cat), conferring chloramphenicol resistance,a nd the p15A replicon; pFL281 carries a gene encoding beta-lactamase (bla), conferring ampicillin resistance, and the ColE1 replicon (ori) from pMB1. The p15A and ColE1 replicons permit the coincident maintenance of both plasmids in the same *E. coli* host.

The Hc2 and Lc2 vectors prepared in Examples 1a2) and 1a3), respectively, were converted into the plasmid form using standard methods familiar to one of ordinary skill in the art and as described by Sambrook et al., *Molecular Cloning: A Laboratory Manual,* 2nd ed., Cold Spring Harbor Laboratory Press, New York (1989) and subsequently digested with Xho I-Spe I (pHc2) and Sac I-Xba I for (pLc2). The synthetic linkers for insertion into the digested pHc2 and Lc2 plasmids were prepared by American Synthesis. The linkers were inserted to increase the distance between cloning sites so as to increase the effectiveness of the digestions. The 5' and 3' linkers for preparing the double-stranded linker insert into pHc2 were 5'

TCGAGGGTCGGTCGGTCTCTAGACG-
GTCGGTCGGTCA 3' (SEQ ID NO 133) and 5' CTAGT-
GACCGACCGACCGTCTAGAGACCGACCGACCC 3'
(SEQ ID NO 134), respectively. The 5' and 3' linkers for
preparing the double-stranded linker insert into pLc2 were 5'
CGGTCGGTCGGTCCTCGAGGGTCGGTCGGTCT 3'
(SEQ ID NO 135) and 5' CTAGAGACCGACCGACCCTC-
GAGGACCGACCGACCGAGCT 3' (SEQ ID NO 136),
respectively. The pairs of linker oligonucleotides were separately ligated to their respective digested, calf intestinal phosphatase-treated vectors.

Subsequently, the multiple cloning sites of pHc2 and pLc2 were transferred into the expression vectors, pFL281 and pFL261, respectively. To accomplish this process, the multiple cloning regions of both Lc2 and Hc2 were separately amplified by PCR as described by Gram et al., *Proc. Natl. Acad. Sci. USA*, 89:3576–3580 (1992) and as described in Example 2b using Vent Polymerase (New England Biolabs) according to the manufacturer's recommendations. The forward primer, 5' CAAGGAGACAGGATCCATGAAATAC 3' (SEQ ID NO 137) was designed to provide a flush fusion of the pelB leader sequence to the ribosome binding sites of the cloning vectors pFL261 and pFL281 via its internal BamH I site indicated by the underlined nucleotides. The reverse primer 5' AGGGCGAATTGGATCCCGGGCCCCC 3' (SEQ ID NO 138) was designed to anneal downstream of the region of interest in the parent vector of pHc2/pLc2 and create a second BamH I site. The resultant Hc2 and Lc2 PCR amplification products were then digested with BamH I to provide for BamH I overhangs for subsequent ligation into BamH I linearized pFL281 and pFL261 vectors, respectively. The resulting light chain vector containing the Lc2 insert, designated pTC01, was used in this form, whereas the heavy chain vector was further modified with a histidine tail to allow purification of Fab fragments by immobilized metal affinity chromatography as described by Skerra et al., *Bio/Technology*, 9:273–278 (1991). For this purpose, the synthetic linker oligonucleotides, respectively the 5' and 3' linkers, 5' CTAGTCATCATCATCATCATTAAGCTAGC 3' (SEQ ID NO 139) and 5' CTAGGCTAGCTTAATGATGATGAT-GATGA '3 (SEQ ID NO 140) was inserted into the Spe I site, in effect removing the decapeptide tag sequence to generate the heavy chain vector designated as pTAC01H. The expression of Fab fragment in all subsequent cloning experiments was suppressed by adding 1% (w/v) glucose to all media and plates.

b. Construction of Expression Plasmids

For expression of the light chain variable domain, pTC01 prepared above was first digested with Sac I and Xba I; individual light chain inserts were then obtained by separately digesting 22 of the pComb2-3 plasmids prepared and screened as described in Example 2 and listed in FIG. 7 that bind to gp120 with the same combination of enzymes and isolating the 0.7 kb fragment using low melting point agarose gel electrophoresis followed by b-agarose digestion. For the chain-shuffling experiments, the following representative members of each of the seven groups shown in FIG. 7 were chosen: b11; b6; b4-b12-b7-b21; b3; s8; b1-b14-b24; b13-b22-B26-b8-b18-b27-B8-B35-s4; and one loop peptide-binding clone, p35. The different groups are indicated by semicolon separations while members of the same group are dashed. The resultant isolated light chains were separately ligated into PTC01 overnight at 16° C. under standard conditions using a 5:1 molar insert-to-vector ratio to form 21 light chain pTC01 expression vectors. For expression of the heavy chain variable domain, pTAC01H prepared above was first digested with Xho I and Spe I; heavy chain inserts were then obtained by separately PCR amplification reactions of the 20 pComb2-3 plasmids from which light chain inserts were obtained. PCR was used to isolate the heavy chain inserts instead of restriction digestion in order to obtain heavy chain without the cpIII gene anchor sequence in the vector. For the PCR reaction, the respective 5' and 3' primers, 5' CAGGTGCAGCTCGAG-CAGTCTGGG 3' (VHla) (SEQ ID NO 42) and 5' GCAT-GTACTAGTTTTGTCACAAGATTTGGG 3' (CGlz) (SEQ ID NO 44) were used to amplify the region corresponding to the heavy chain as described in Examples 2a1) and 2a2). The resultant PCR products were purified by low-melting point electrophoresis, digested with Xho I and Spe I, re-purified, and separately ligated to the similarly prepared heavy chain pTAC01H vector using a 1:2 molar vector-to-insert ratio to form 21 heavy chain pTAC01H expression vectors.

c. Co-transformation of Binary Plasmids $CaCl_2$-competent XL1-Blue cells (Stratagene; recA1, endA1, gyrA96, thi, hsdR17, supE44, relA1, lac, {F' proAB, lacI$^q$, ZDM15, Tn10(tet$^R$)) were prepared and transformed with approximately 0.5 μg purified DNA of each plasmid in directed crosses of each of the 20 light chain vectors with each of the 20 heavy chain vectors. The presence of both plasmids and the episome was selected for by plating transformants on triple-antibiotic agar plates (100 μg/ml carbenicillin, 30 μg/ml chloramphenicol, 10 μg/ml tetracycline, 32 g/l LB agar) containing 1% glucose.

A binary plasmid system consisting of two replicon-compatible plasmids was constructed as shown in 14. The pTAC01H heavy chain vector schematic is shown in FIG. 14A and the pTC01 light chain vector schematic is shown in FIG. 14B. Both expression vectors feature similar cloning sites including pel B leader sequences fused to the ribosome binding sites and the tac promoters via BamH I sites as shown in FIG. 15. The nucleotide sequences of the multiple cloning sites along with the tac promoter, ribosome binding sites (rbs) and the underlined relevant restriction sites for the light chain vector, pTC01, and heavy chain vector, pTAC01H, are respectively shown in FIG. 15A and FIG. 15B. The sequences are also listed in the Sequence Listing as described in the Brief Description of the Drawings. The heavy chain vector pTAC01H also contains a (His)$_5$-tail to allow purification of the recombinant Fab fragments by immobilized metal affinity chromatography. The presence of both plasmids in the same bacterial cell is selected for by the presence of both antibiotics in the media. Expression is partially suppressed during growth by addition of glucose and induced by the addition of IPTG at room temperature. Under these conditions, both plasmids are stable within the cell and support expression of the Fab fragment as assayed by ELISA using goat anti-human kappa and goat anti-human IgG1 antibodies.

d. Preparation of Recombinant Fab Fragments

Bacterial cultures for determination of antigen-binding activity were grown in 96 well-tissue culture plates (Costar #3596). 250 μl Superbroth [SB had the following ingredients per liter: 10 g 3-(N-morpholino)propanesulfonic acid, 30 g tryptone, 20 g yeast extract at pH 7.0 at 25° C.) containing 30 μg/ml chloramphenicol, 100 μg/ml carbenicillin, and 1% (w/v)] glucose were admixed per well and inoculated with a single double-transformant prepared in Example 11c above. The inoculated plates were then maintained with moderate shaking (200 rpm) on a horizontal shaker for 7–9 hours at 37° C., until the $A_{550}$ was approximately 1–1.5. The cells were collected by centrifugation of the microtiter plate (1,500×g for 30 minutes at 4° C.), the supernatants were discarded, and the cells were resuspended and induced overnight at room temperature in fresh media containing 1 mM IPTG, but no glucose. Cells were harvested by centrifugation, resuspended in 175 μl PBS (10 mM sodium phosphate, 160 mM NaCl at pH 7.4 at 25° C.) containing 34 μg/ml phenylmethylsulfonyl fluoride (PMSF) and 1.5% (w/v) streptomycin sulfate, and lysed by 3 freeze-thaw cycles between −80° C. and 37° C. The resultant crude extracts were partially cleared by centrifugation as above before analysis by antigen-binding ELISA.

e. Assay and Determination of Relative Affinities

Relative affinities were determined as described in Example 2b6) after coating wells with 0.1 μg of antigen. The selected antigens included tetanus toxoid and recombinant gp120 (strain IIIB) and gp120 (strain SF2). For each antigen, a negative control extract of XL1-Blue cells co-transformed with pTC01 and pTAC01H was tested to determine whether other components in *E. coli* had any affinity for the antigens in the assay. Each extract was assayed for BSA-binding activity and BSA-positive clones were considered negative. All possible single-transformants expressing one chain only were prepared as described for the double-transformants and were found to have no affinity for any of the antigens used. Because of the nature of the assay, whether this was due to a lack of binding by the individual chains itself or due to a lack of expression or folding could not be determined.

f. Results of Direct Crosses of Heavy and Light Chains within a Set of gp120/gp160 Binding Antibodies The Fab fragments derived from the bone marrow of the same asymptomatic HIV donor but panned against gp120 (IIIB), gp160 (IIIB), and gp120 (SF2), were assigned to one of seven groups based on the amino acid sequences of the CDR3 of their heavy chains as described in Example 9. From the same library, antibodies to the constrained hypervariable v3-loop-like peptide JSISIGPGRAFYTGZC (SEQ ID NO 141) were isolated. For the chain-shuffling experiments, the following representative members of each of the seven groups shown in FIG. 7 were chosen: b11; b6; b4-b12-b7-b21; b3; s8; b1-b14-b24; b13-b22-B26-b8-b18-b27-B8-B35-s4; and one loop peptide-binding clone, p35. Clones b4, b7, b12, and b21 showed neutralization activity against HIV when monitoring inhibition of infection by syncytia formation and clones b13, b12, and b4 when monitoring p24 production as shown in Example 3. Light and heavy chains were cloned from the original constructs and cotransformed in all possible binary combinations into XL1-Blue cells as described above.

Figure 17:
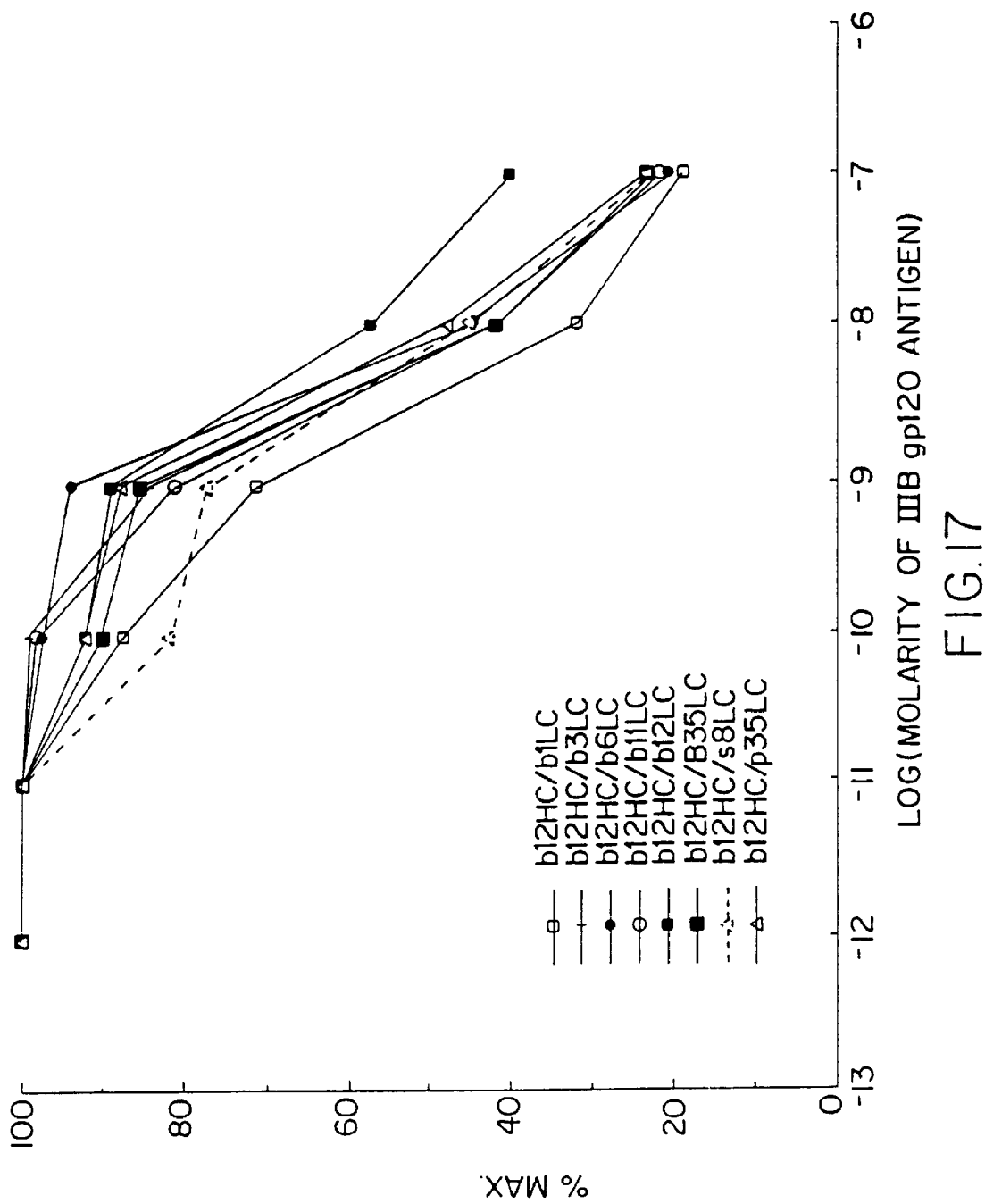
FIG. 17 illustrates the affinity of antibody-antigen interaction for b12 heavy chain crosses with light chains from all pannings analyzed by competitive ELISA using soluble IIIB gp120 as competing antigen as described in Example 10. The data is plotted as the percent age of maximum binding on the Y-axis against increasing concentrations of soluble gp120 (IIIB) ($10^{-12}$M to $10^{-7}$M) on the X-axis.

The results of the complete cross are shown in FIG. 16. As is to be expected, identical chains derived from different Fab fragments had similar binding properties e.g., b18HC, b27HC, B8HC, B35HC, s4HC. The crosses of the original heavy chains with the original light chains in each case clearly recapitulated binding activity. Minor differences existed between some heavy chains with identical variable domain sequences, e.g., b4 and b12 (constant domains were not sequenced for any of the constructs). The exception is b8HC, which was identical in its variable domain to b18HC, b27HC, B8HC, B35HC, s4HC, yet shows more cross reactivity. Presumably, this is due to differences in expression levels in the cell or differences in the constant domain sequences. Clear differences existed between heavy chains in their tendency to accept different light chains and still bind antigen, but even the least promiscuous heavy chain in the set panned against gp120 (IIIB), b1HC, still did so in 43% of its crosses. On the other side of the spectrum, 5 heavy chains, b11HC, b6HC, b12HC, b7HC, and b8HC, crossed productively with all light chains in this set. For the heavy chain crosses examined in detail (all of s4HC, B35HC, B26HC; most of b12HC, b12HC), no significant differences in apparent binding affinity were found between Fab fragments using the same heavy chain but different light chains as shown in FIG. 17 where the $IC_{50}$ from competition with soluble gp120 (IIB) was approximately $10^{-8}$M.

Within the original seven groups that were established according to the sequence of the CDR3 of the heavy chains and that are indicated by horizontal and vertical lines in FIG. 16, complete promiscuity was present, i.e., heavy and light chains within these CDR3-determined groups were completely promiscuous with each other. However, there was a lack of promiscuity between other groups, e.g., between b1HC-b24HC and b13LC-s4LC. In the analysis of these sequence-based groups, the protein antigen against which the phage display library was panned was not a critical factor. The exception to this case was the cross of p35HC with all light chains; the only cross that bound either to gp120 (SF2 strain) or the original antigen, the loop peptide, was the cross containing the original heavy and light chains.

Unlike the heavy chains, no light chains crossed productively with all heavy chains nor were any distinguishable from the other light chains by unusually low promiscuity.

In the neutralization assays performed as described in Example 3, the directed cross resulting from the pairing of the heavy chain from clone b12 with the light chain from clone b21, was effective at neutralizing HIV-1.

g. Interantigenic Crosses of Heavy and Light Chains

To determine whether conclusions derived from the crosses between high affinity Fab fragments originating from the same library can be extended to unrelated libraries, a non-related gammalk-Fab fragment (P3–13) specific for tetanus toxoid from a different donor was chosen for a new set of crosses [clone 3 in Persson et al., *Proc. Natl. Acad. Sci. USA*, 88:2432–2436 (1991)]. Extracts were probed with tetanus toxoid or with gp120 (IIIB). The data confirm the results from the gp120 cross experiment in that the binding activity towards the antigen was determined by the heavy chain. The heavy chain of clone P3-13 paired with the light chains b4, b12, b21, and b14 to yield an Fab fragment with an affinity towards tetanus toxoid; the light chain of P3-13 paired with the heavy chains of b3, b6, b11, and b14 to yield an Fab fragment with an affinity towards gp120 (IIIB). None of the light chains originating from the gp120 binders was able to confer gp120 specificity in combination with the P3-13 heavy chain.

Similarly, the P3-13 light chain was unable to generate tetanus toxoid specificity in combination with any of the heavy chains originating from the gp120 binders, confirming the dominance of the heavy chain in the antibody-antigen interaction.

Interestingly, all three light chains that showed a strong signal against tetanus toxoid (b4, b12, b21) were members of the same group when sorted by the CDR3's of their original heavy chains. As might be expected from crosses between unrelated libraries, not only was there a lower degree of promiscuity, i.e., chains paired productively with far fewer complementary chains, but the range of apparent affinity constants determined by competition ELISA was much broader ($6.3\times10^6$–$6.3\times10^{-8}$M). The replacement of the original P3-13 light chain in the P3-13 Fab fragment with another light chain lowered the affinity of the Fab towards tetanus toxoid 10 to 100-fold (from $6.3\times10^{-8}$M to $6.3\times10^{-6}$M). In the crosses of the light chain of P3-13 with all the heavy chains of the HIV pannings, the productive crosses had similar affinities to gp120 (IIIB) ($2.5\times10^7$–$6.3\times10^{-7}$M), with the exception of b14HC/P3-13Lc, whose signal was too weak for a definite determination of the apparent binding constant. These affinities were approximately five-fold lower than those of the gp120-heavy chains with their original light chains.

Thus, the results show that chain shuffling is yet another maneuver allowed in vitro but not in vivo which can be expected to help extend antibody diversity beyond that of Nature. The overriding feature of the binary system of this invention is its ability to create large numbers (several hundred) of directed crosses between characterized light and heavy chains without the need for recloning individual chains for each cross after the initial vector construction. When used in combination with the phage-display method and biological assays, it allows the rapid analysis of the most interesting subset of the pool of antigen-binding clones by chain shuffling, with the aim of finding biologically or chemically active antibodies. For the set of antigens studied here, most heavy chains recombined with a number of light chains to yield an antigen-binding Fab fragment.

These results have important implications for the diversity of combinatorial antibody libraries. While it is not possible to predict reliably the original in vivo combinations of light and heavy chains due to the surprising promiscuity of individual chains, recombinant antibody libraries take advantage of the fact that even distantly related Fabs against the same antigen can recombine in vitro to give chain combinations not found in vivo. In fact, after the identification of a certain number of antibodies that have been shown to possess some biological or chemical activity, it may be better to shuffle their individual chains in a directed fashion than to continue sampling randomly from the same pool of binders. By extension, the promiscuity observed in this system indicates that in libraries constructed using degenerate, chemically synthesized oligonucleotides, there should be considerable flexibility in which separate synthetic heavy chains can pair with separate synthetic light chains to generate separate antigen-binding Fab fragments. The diversity of combinatorial libraries coupled with chain-shuffling should allow wide exploration of three dimensional space thereby solving the problem of how to approximate molecules in the ternary complex of antibody, substrate and cofactor.

11. Deposit of Materials

The following cell lines have been deposited on Sep. 30, 1992, with the American Type Culture Collection (ATCC), 1301 Parklawn Drive, Rockville, Md., U.S.A.:

| Cell Line | ATCC Accession No. |
| --- | --- |
| E. coli MT11 | ATCC 69078 |
| E. coli MT12 | ATCC 69079 |
| E. coli MT13 | ATCC 69080 |

The deposits listed above, MT11, MT12 and MT13 are bacterial cells (E. coli) containing the expression vector pComb2-3 for the respective expression of the Fabs designated b11 (clone b11), b12 (clone b12), and b13 (clone b13) prepared in Example 2b. The sequences of the heavy and light chain variable domains are listed in FIGS. 10 and 11, respectively. This deposit was made with the ATCC under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organisms will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the culture deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

SEQUENCE LISTING ( 1 ) GENERAL INFORMATION:

( i i i ) NUMBER OF SEQUENCES: 170

( 2 ) INFORMATION FOR SEQ ID NO:1:

( i ) SEQUENCE CHARACTERISTICS:
        ( A ) LENGTH: 173 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (i v) ANTI-SENSE: NO (x i) SEQUENCE DESCRIPTION: SEQ ID NO:1:

| GGCCGCAAAT | TCTATTTCAA | GGAGACAGTC | ATAATGAAAT | ACCTATTGCC | TACGGCAGCC | 60 |
| GCTGGATTGT | TATTACTCGC | TGCCCAACCA | GCCATGGCCC | AGGTGAAACT | GCTCGAGATT | 120 |
| TCTAGACTAG | TTACCCGTAC | GACGTTCCGG | ACTACGGTTC | TTAATAGAAT | TCG | 173 |

(2) INFORMATION FOR SEQ ID NO:2:

(i) SEQUENCE CHARACTERISTICS:
        (A) LENGTH: 173 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:2:

| TCGACGAATT | CTATTAAGAA | CCGTAGTCCG | GAACGTCGTA | CGGGTAACTA | GTCTAGAAAT | 60 |
| CTCGAGCAGT | TTCACCTGGG | CCATGGCTGG | TTGGGCAGCG | AGTAATAACA | ATCCAGCGGC | 120 |
| TGCCGTAGGC | AATAGGTATT | TCATTATGAC | TGTCTCCTTG | AAATAGAATT | TGC | 173 |

(2) INFORMATION FOR SEQ ID NO:3:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:3:

| TGAATTCTAA | ACTAGTCGCC | AAGGAGACAG | TCATAATGAA | ATACCTATTG | CCTACGGCAG | 60 |
| CCGCTGGATT | GTTATTACTC | GCTGCCCAAC | CAGCCATGGC | CGAGCTCGTC | AGTTCTAGAG | 120 |
| TTAAGCGGCC | G | | | | | 131 |

(2) INFORMATION FOR SEQ ID NO:4:

(i) SEQUENCE CHARACTERISTICS:
        (A) LENGTH: 139 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:4:

| TCGACGGCCG | CTTAACTCTA | GAACTGACGA | GCTCGGCCAT | GGCTGGTTGG | GCAGCGAGTA | 60 |
| ATAACAATCC | AGCGGCTGCC | GTAGGCAATA | GGTATTTCAT | TATGACTGTC | TCCTTGGCGA | 120 |
| CTAGTTTAGA | ATTCAAGCT | | | | | 139 |

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:5:

```
Tyr Pro Tyr Asp Val Pro Asp Tyr Ala Ser
1               5                   10
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:6:

```
Met Lys Tyr Leu Leu Pro Thr Ala Ala Ala Gly Leu Leu Leu Leu Ala
1               5                   10                      15
Ala Gln Pro Ala Met Ala Gln Val Lys Leu
                20              25
```

( 2 ) INFORMATION FOR SEQ ID NO:7:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:7:

```
Met Lys Tyr Leu Leu Pro Thr Ala Ala Ala Gly Leu Leu Leu Leu Ala
1               5                   10                      15
Ala Gln Pro Ala Met Ala Glu
                20
```

( 2 ) INFORMATION FOR SEQ ID NO:8:

( i ) SEQUENCE CHARACTERISTICS:
        ( A ) LENGTH: 198 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

```
TGTTGACAAT TAATCATCGG CTCGTATAAT GTGTGGAATT GTGAGCGGAT AACAATTTCA      60
CACAGGAGGA AGGATCCATG AAATACCTAT TGCCTACGGC AGCCGCTGGA TTGTTATTAC     120
TCGCTGCCCA ACCAGCCATG GCCGAGCTCG GTCGGTCGGT CCTCGAGGGT CGGTCGGTCT     180
```

CTAGAGTTAA GCGGCCGC 198

( 2 ) INFORMATION FOR SEQ ID NO:9:

( i ) SEQUENCE CHARACTERISTICS:
        ( A ) LENGTH: 198 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GCGGCCGCTT AACTCTAGAG ACCGACCGAC CCTCGAGGAC CGACCGACCG AGCTCGGCCA 60

TGGCTGGTTG GGCAGCGAGT AATAACAATC CAGCGGCTGC CGTAGGCAAT AGGTATTTCA 120

TGGATCCTTC CTCCTGTGTG AAATTGTTAT CCGCTCACAA TTCCACACAT TATACGAGCC 180

GATGATTAAT TGTCAACA 198

( 2 ) INFORMATION FOR SEQ ID NO:10:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:10:

Met Lys Thr Leu Leu Pro Thr Ala Ala Ala Gly Leu Leu Leu Leu Ala
1               5                     10               15

Ala Gln Pro Ala Met Ala Glu Leu
          20

( 2 ) INFORMATION FOR SEQ ID NO:11:

( i ) SEQUENCE CHARACTERISTICS:
        ( A ) LENGTH: 220 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

TGTTGACAAT TAATCATCGG CTCGTATAAT GTGTGGAATT GTGAGCGGAT AACAATTTCA 60

CACAGGAGGA AGGATCCATG AAATACCTAT TGCCTACGGC AGCCGCTGGA TTGTTATTAC 120

TCGCTGCCCA ACCAGCCATG GCCCAGGTGA AACTGCTCGA GGGTCGGTCG GTCTCTAGAC 180

GGTCGGTCGG TCACTAGTCA TCATCATCAT CATTAAGCTA 220

( 2 ) INFORMATION FOR SEQ ID NO:12:

( i ) SEQUENCE CHARACTERISTICS:
        ( A ) LENGTH: 220 base pairs
        ( B ) TYPE: nucleic acid
        ( C ) STRANDEDNESS: double
        ( D ) TOPOLOGY: circular (i i) MOLECULE TYPE: DNA (genomic)

(i i i) HYPOTHETICAL: NO (i v) ANTI-SENSE: NO (x i) SEQUENCE DESCRIPTION: SEQ ID NO:12:

| | | | | | |
|---|---|---|---|---|---|
| TAGCTTAATG | ATGATGATGA | TGACTAGTGA | CCGACCGACC | GTCTAGAGAC | CGACCGACCC | 60 |
| TCGAGCAGTT | TCACCTGGGC | CATGGCTGGT | TGGGCAGCGA | GTAATAACAA | TCCAGCGGCT | 120 |
| GCCGTAGGCA | ATAGGTATTT | CATGGATCCT | TCCTCCTGTG | TGAAATTGTT | ATCCGCTCAC | 180 |
| AATTCCACAC | ATTATACGAG | CCGATGATTA | ATTGTCAACA | | | 220 |

(2) INFORMATION FOR SEQ ID NO:13:

(i) SEQUENCE CHARACTERISTICS:
  (A) LENGTH: 28 amino acids
  (B) TYPE: amino acid
  (D) TOPOLOGY: linear (i i) MOLECULE TYPE: peptide (v) FRAGMENT TYPE: N-terminal (x i) SEQUENCE DESCRIPTION: SEQ ID NO:13:

Met Lys Thr Leu Leu Pro Thr Ala Ala Ala Gly Leu Leu Leu Leu Ala
1               5                   10                  15

Ala Gln Pro Ala Met Ala Gln Val Lys Leu Leu Glu
            20              25

(2) INFORMATION FOR SEQ ID NO:14:

(i) SEQUENCE CHARACTERISTICS:
  (A) LENGTH: 7 amino acids
  (B) TYPE: amino acid
  (D) TOPOLOGY: linear (i i) MOLECULE TYPE: peptide (v) FRAGMENT TYPE: C-terminal (x i) SEQUENCE DESCRIPTION: SEQ ID NO:14:

Thr Ser His His His His His
1               5

(2) INFORMATION FOR SEQ ID NO:15:

(i) SEQUENCE CHARACTERISTICS:
  (A) LENGTH: 32 base pairs
  (B) TYPE: nucleic acid
  (C) STRANDEDNESS: single
  (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:15:

GGCCGCAAAT TCTATTTCAA GGAGACAGTC AT                                    32

(2) INFORMATION FOR SEQ ID NO:16:

(i) SEQUENCE CHARACTERISTICS:
  (A) LENGTH: 36 base pairs
  (B) TYPE: nucleic acid
  (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

AATGAAATAC CTATTGCCTA CGGCAGCCGC TGGATT                     36

(2) INFORMATION FOR SEQ ID NO:17:

(i) SEQUENCE CHARACTERISTICS:
                (A) LENGTH: 32 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

GTTATTACTC GCTGCCCAAC CAGCCATGGC CC                          32

(2) INFORMATION FOR SEQ ID NO:18:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

CAGTTTCACC TGGGCCATGG CTGGTTGGG                              29

(2) INFORMATION FOR SEQ ID NO:19:

(i) SEQUENCE CHARACTERISTICS:
                (A) LENGTH: 40 base pairs
                (B) TYPE: nucleic acid
                (C) STRANDEDNESS: single
                (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

CAGCGAGTAA TAACAATCCA GCGGCTGCCG TAGGCAATAG                  40

(2) INFORMATION FOR SEQ ID NO:20:

(i) SEQUENCE CHARACTERISTICS:
                (A) LENGTH: 38 base pairs
                (B) TYPE: nucleic acid
                (C) STRANDEDNESS: single
                (D) TOPOLOGY: linear (ii) MOLECULE TYPE: DNA (genomic)

( i i i ) HYPOTHETICAL: NO ( i v ) ANTI-SENSE: NO ( x i ) SEQUENCE DESCRIPTION: SEQ ID NO:20:

GTATTTCATT ATGACTGTCT CCTTGAAATA GAATTTGC                38

( 2 ) INFORMATION FOR SEQ ID NO:21:

( i ) SEQUENCE CHARACTERISTICS:
                ( A ) LENGTH: 40 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:21:

AGGTGAAACT GCTCGAGATT TCTAGACTAG TTACCCGTAC                40

( 2 ) INFORMATION FOR SEQ ID NO:22:

( i ) SEQUENCE CHARACTERISTICS:
                ( A ) LENGTH: 38 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

CGGAACGTCG TACGGGTAAC TAGTCTAGAA ATCTCGAG                38

( 2 ) INFORMATION FOR SEQ ID NO:23:

( i ) SEQUENCE CHARACTERISTICS:
                ( A ) LENGTH: 33 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

GACGTTCCGG ACTACGGTTC TTAATAGAAT TCG                33

( 2 ) INFORMATION FOR SEQ ID NO:24:

( i ) SEQUENCE CHARACTERISTICS:
                ( A ) LENGTH: 28 base pairs
                ( B ) TYPE: nucleic acid
                ( C ) STRANDEDNESS: single
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

TCGACGAATT CTATTAAGAA CCGTAGTC 28

( 2 ) INFORMATION FOR SEQ ID NO:25:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

TGAATTCTAA ACTAGTCGCC AAGGAGACAG TCAT 34

( 2 ) INFORMATION FOR SEQ ID NO:26:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

AATGAAATAC CTATTGCCTA CGGCAGCCGC TGGATT 36

( 2 ) INFORMATION FOR SEQ ID NO:27:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

GTTATTACTC GCTGCCCAAC CAGCCATGGC C 31

( 2 ) INFORMATION FOR SEQ ID NO:28:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:28:

GAGCTCGTCA GTTCTAGAGT TAAGCGGCCG 30

( 2 ) INFORMATION FOR SEQ ID NO:29:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:29:

GTATTTCATT ATGACTGTCT CCTTGGCGAC TAGTTTAGAA TTCAAGCT 48

( 2 ) INFORMATION FOR SEQ ID NO:30:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:30:

CAGCGAGTAA TAACAATCCA GCGGCTGCCG TAGGCAATAG 40

( 2 ) INFORMATION FOR SEQ ID NO:31:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:31:

TGACGAGCTC GGCCATGGCT GGTTGGG 27

( 2 ) INFORMATION FOR SEQ ID NO:32:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:32:

TCGACGGCCG CTTAACTCTA GAAC 24

( 2 ) INFORMATION FOR SEQ ID NO:33:

( i ) SEQUENCE CHARACTERISTICS:

(A) LENGTH: 666 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

| | | | | | |
|---|---|---|---|---|---|
| CCATTCGTTT | GTGAATATCA | AGGCCAAGGC | CAATCGTCTG | ACCTGCCTCA | ACCTCCTGTC | 60
| AATGCTGGCG | GCGGCTCTGG | TGGTGGTTCT | GGTGGCGGCT | CTGAGGGTGG | TGGCTCTGAG | 120
| GGTGGCGGTT | CTGAGGGTGG | CGGCTCTGAG | GGAGGCGGTT | CCGGTGGTGG | CTCTGGTTCC | 180
| GGTGATTTTG | ATTATGAAAA | GATGGCAAAC | GCTAATAAGG | GGGCTATGAC | CGAAAATGCC | 240
| GATGAAAACG | CGCTACAGTC | TGACGCTAAA | GGCAAACTTG | ATTCTGTCGC | TACTGATTAC | 300
| GGTGCTGCTA | TCGATGGTTT | CATTGGTGAC | GTTTCCGGCC | TTGCTAATGG | TAATGGTGCT | 360
| ACTGGTGATT | TTGCTGGCTC | TAATTCCCAA | ATGGCTCAAG | TCGGTGACGG | TGATAATTCA | 420
| CCTTTAATGA | ATAATTTCCG | TCAATATTTA | CCTTCCCTCC | CTCAATCGGT | TGAATGTCGC | 480
| CCTTTTGTCT | TTAGCGCTGG | TAAACCATAT | GAATTTTCTA | TTGATTGTGA | CAAAATAAAC | 540
| TTATTCGGTG | TCTTTGCGTT | TCTTTTATAT | GTTGCCACCT | TTATGTATGT | ATTTTCTACG | 600
| TTTGCTAACA | TACTGCGTAA | TAAGGAGTCT | TAATCATGCC | AGTTCTTTTG | GGTATTCCGT | 660
| TATTAT | | | | | | 666

(2) INFORMATION FOR SEQ ID NO:34:

(i) SEQUENCE CHARACTERISTICS:
(A) LENGTH: 211 amino acids
(B) TYPE: amino acid
(D) TOPOLOGY: unknown (ii) MOLECULE TYPE: protein (iii) HYPOTHETICAL: NO (v) FRAGMENT TYPE: internal (xi) SEQUENCE DESCRIPTION: SEQ ID NO:34:

Pro Phe Val Cys Glu Tyr Gln Gly Gln Gly Gln Ser Ser Asp Leu Pro
1               5                   10                  15

Gln Pro Pro Val Asn Ala Gly Gly Gly Ser Gly Gly Gly Ser Gly Gly
                20                  25                  30

Gly Ser Glu Gly Gly Gly Ser Glu Gly Gly Gly Ser Glu Gly Gly Gly
            35                  40                  45

Ser Glu Gly Gly Gly Ser Gly Gly Ser Gly Ser Gly Asp Phe Asp
        50                  55                  60

Tyr Glu Lys Met Ala Asn Ala Asn Lys Gly Ala Met Thr Glu Asn Ala
65                  70                  75                  80

Asp Glu Asn Ala Leu Gln Ser Asp Ala Lys Gly Lys Leu Asp Ser Val
                85                  90                  95

Ala Thr Asp Tyr Gly Ala Ala Ile Asp Gly Phe Ile Gly Asp Val Ser
                100                 105                 110

Gly Leu Ala Asn Gly Asn Gly Ala Thr Gly Asp Phe Ala Gly Ser Asn
            115                 120                 125

Ser Gln Met Ala Gln Val Gly Asp Gly Asp Asn Ser Pro Leu Met Asn
            130                 135                 140

| | | | | | | | | | | | | | | | |
|---|---|---|---|---|---|---|---|---|---|---|---|---|---|---|---|
| Asn | Phe | Arg | Gln | Tyr | Leu | Pro | Ser | Leu | Pro | Gln | Ser | Val | Glu | Cys | Arg |
| 145 | | | | 150 | | | | | | 155 | | | | | 160 |
| Pro | Phe | Val | Phe | Ser | Ala | Gly | Lys | Pro | Tyr | Glu | Phe | Ser | Ile | Asp | Cys |
| | | | | 165 | | | | | 170 | | | | | 175 | |
| Asp | Lys | Ile | Asn | Leu | Phe | Arg | Gly | Val | Phe | Ala | Phe | Leu | Leu | Tyr | Val |
| | | | 180 | | | | | 185 | | | | | 190 | | |
| Ala | Thr | Phe | Met | Tyr | Val | Phe | Ser | Thr | Phe | Ala | Asn | Ile | Leu | Arg | Asn |
| | | 195 | | | | | 200 | | | | | 205 | | | |
| Lys | Glu | Ser | | | | | | | | | | | | | |
| | | 210 | | | | | | | | | | | | | |

(2) INFORMATION FOR SEQ ID NO:35:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:35:

GAGACGACTA GTGGTGGCGG TGGCTCTCCA TTCGTTTGTG AATATCAA     48

(2) INFORMATION FOR SEQ ID NO:36:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

TTACTAGCTA GCATAATAAC GGAATACCCA AAAGAACTGG     40

(2) INFORMATION FOR SEQ ID NO:37:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

TATGCTAGCT AGTAACACGA CAGGTTTCCC GACTGG     36

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:38:

ACCGAGCTCG AATTCGTAAT CATGGTC 27

(2) INFORMATION FOR SEQ ID NO:39:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:39:

AGCTGTTGAA TTCGTGAAAT TGTTATCCGC T 31

(2) INFORMATION FOR SEQ ID NO:40:

(i) SEQUENCE CHARACTERISTICS:
        (A) LENGTH: 708 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:40:

GAGACGACTA GTGGTGGCGG TGGCTCTCCA TTCGTTTGTG AATATCAAGG CCAAGGCCAA 60
TCGTCTGACC TGCCTCAACC TCCTGTCAAT GCTGGCGGCG GCTCTGGTGG TGGTTCTGGT 120
GGCGGCTCTG AGGGTGGTGG CTCTGAGGGT GGCGGTTCTG AGGGTGGCGG CTCTGAGGGA 180
GGCGGTTCCG GTGGTGGCTC TGGTTCCGGT GATTTTGATT ATGAAAAGAT GGCAAACGCT 240
AATAAGGGGG CTATGACCGA AAATGCCGAT GAAACGCGC TACAGTCTGA CGCTAAAGGC 300
AAACTTGATT CTGTCGCTAC TGATTACGGT GCTGCTATCG ATGGTTTCAT TGGTGACGTT 360
TCCGGCCTTG CTAATGGTAA TGGTGCTACT GGTGATTTTG CTGGCTCTAA TTCCCAAATG 420
GCTCAAGTCG GTGACGGTGA TAATTCACCT TTAATGAATA ATTTCCGTCA ATATTTACCT 480
TCCCTCCCTC AATCGGTTGA ATGTCGCCCT TTTGTCTTTA GCGCTGGTAA ACCATATGAA 540
TTTTCTATTG ATTGTGACAA AATAAACTTA TTCCGTGGTG TCTTTGCGTT TCTTTTATAT 600
GTTGCCACCT TTATGTATGT ATTTTCTACG TTTGCTAACA TACTGCGTAA TAAGGAGTCT 660
TAATCATGCC AGTTCTTTTG GGTATTCCGT TATTATGCTA GCTAGTAA 708

(2) INFORMATION FOR SEQ ID NO:41:

(i) SEQUENCE CHARACTERISTICS:
        (A) LENGTH: 201 base pairs
        (B) TYPE: nucleic acid
        (C) STRANDEDNESS: double
        (D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:41:

| TATGCTAGCT | AGTAACACGA | CAGGTTTCCC | GACTGGAAAG | CGGGCAGTGA | GCGCAACGCA | 60 |
| ATTAATGTGA | GTTAGCTCAC | TCATTAGGCA | CCCCAGGCTT | TACACTTTAT | GCTTCCGGCT | 120 |
| CGTATGTTGT | GTGGAATTGT | GAGCGGATAA | CAATTTCACA | CAGGAAACAG | CTATGACCAT | 180 |
| GATTACGAAT | TCGAGCTCGG | T | | | | 201 |

( 2 ) INFORMATION FOR SEQ ID NO:42:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:42:

CAGGTGCAGC TCGAGCAGTC TGGG                                  24

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:43:

GAGGTGCAGC TCGAGGAGTC TGGG                                  24

( 2 ) INFORMATION FOR SEQ ID NO:44:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:44:

GCATGTACTA GTTTTGTCAC AAGATTTGGG                            30

( 2 ) INFORMATION FOR SEQ ID NO:45:

( i ) SEQUENCE CHARACTERISTICS:
        ( A ) LENGTH: 24 base pairs
        ( B ) TYPE: nucleic acid
        ( C ) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:45:

GACATCGAGC TCACCCAGTC TCCA 24

(2) INFORMATION FOR SEQ ID NO:46:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

GAAATTGAGC TCACGCAGTC TCCA 24

(2) INFORMATION FOR SEQ ID NO:47:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:47:

GCGCCGTCTA GAACTAACAC TCTCCCCTGT TGAAGCTCTT TGTGACGGGC AAG 53

(2) INFORMATION FOR SEQ ID NO:48:

(i) SEQUENCE CHARACTERISTICS:
        (A) LENGTH: 12 amino acids
        (B) TYPE: amino acid
        (C) STRANDEDNESS: single
        (D) TOPOLOGY: circular (ii) MOLECULE TYPE: peptide (v) FRAGMENT TYPE: internal (xi) SEQUENCE DESCRIPTION: SEQ ID NO:48:

Ser Ile Ser Gly Pro Gly Arg Ala Phe Tyr Thr Gly
1              5                      10

(2) INFORMATION FOR SEQ ID NO:49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:49:

GTCGTTGACC AGGCAGCCCA G     21

(2) INFORMATION FOR SEQ ID NO:50:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:50:

ATAGAAGTTG TTCAGCAGGC A     21

(2) INFORMATION FOR SEQ ID NO:51:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:51:

ATTAACCCTC ACTAAAG     17

(2) INFORMATION FOR SEQ ID NO:52:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:52:

GAATTCTAAA CTAGCTAGTT CG     22

(2) INFORMATION FOR SEQ ID NO:53:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:53:

Leu Glu Glu Ser Gly Thr Glu Phe Lys Pro Pro Gly Ser Ser Val Lys
1               5                   10                  15

|   |   |   |   |   |   |   |   |   |   |   |   |   |   |   |
|---|---|---|---|---|---|---|---|---|---|---|---|---|---|---|
| Val | Ser | Cys | Lys<br>20 | Ala | Ser | Gly | Gly | Thr<br>25 | Phe | Gly | Asp | Tyr | Ala<br>30 | Ser | Asn |
| Tyr | Ala | Ile<br>35 | Ser | Trp | Val | Arg | Gln<br>40 | Ala | Pro | Gly | Gln | Gly<br>45 | Leu | Glu | Tyr |
| Ile | Gly<br>50 | Gly | Ile | Thr | Pro | Thr<br>55 | Ser | Gly | Ser | Ala | Asp<br>60 | Tyr | Ala | Gln | Lys |
| Phe<br>65 | Gln | Gly | Arg | Val | Thr<br>70 | Ile | Ser | Ala | Asp | Arg<br>75 | Phe | Thr | Pro | Ile | Leu<br>80 |
| Tyr | Met | Glu | Leu | Arg<br>85 | Ser | Leu | Arg | Ile | Glu<br>90 | Asp | Thr | Ala | Ile | Tyr<br>95 | Tyr |
| Cys | Ala | Arg | Glu | Arg<br>100 | Arg | Glu | Arg | Gly | Trp<br>105 | Asn | Pro | Arg | Ala<br>110 | Leu | Arg |
| Gly | Ala | Leu<br>115 | Asp | Phe | Trp | Gly | Gln<br>120 | Gly | Thr | Arg | Val | Phe<br>125 | Val | Ser | Pro |

(2) INFORMATION FOR SEQ ID NO:54:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:54:

|   |   |   |   |   |   |   |   |   |   |   |   |   |   |   |   |
|---|---|---|---|---|---|---|---|---|---|---|---|---|---|---|---|
| Leu<br>1 | Glu | Glu | Ser | Gly<br>5 | Ala | Ala | Val | Gln | Lys<br>10 | Pro | Gly | Ser | Ser | Val<br>15 | Arg |
| Val | Ser | Cys | Gln<br>20 | Ala | Ser | Gly | Gly | Thr<br>25 | Phe | Asp | Asn | Phe | Ala<br>30 | Ser | Asn |
| Tyr | Ala | Val<br>35 | Ser | Trp | Val | Arg | Gln<br>40 | Ala | Pro | Gly | Gln | Gly<br>45 | Leu | Glu | Trp |
| Met | Gly<br>50 | Gly | Ile | Thr | Pro | Thr<br>55 | Ser | Gly | Thr | Ala | Thr<br>60 | Tyr | Ser | Gln | Lys |
| Phe<br>65 | Gln | Gly | Arg | Val | Thr<br>70 | Ile | Ser | Ala | Ala | Pro<br>75 | Leu | Thr | Pro | Ile | Ile<br>80 |
| Tyr | Met | Glu | Leu | Arg<br>85 | Ser | Leu | Arg | Asp | Asp<br>90 | Asp | Thr | Ala | Val | Tyr<br>95 | Tyr |
| Cys | Ala | Arg | Glu | Arg<br>100 | Arg | Glu | Arg | Gly | Trp<br>105 | Asn | Pro | Arg | Ala<br>110 | Leu | Val |
| Gly | Ala | Leu<br>115 | Asp | Val | Trp | Gly | Gln<br>120 | Gly | Thr | Thr | Val |

(2) INFORMATION FOR SEQ ID NO:55:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:55:

|   |   |   |   |   |   |   |   |   |   |   |   |   |   |   |   |
|---|---|---|---|---|---|---|---|---|---|---|---|---|---|---|---|
| Leu<br>1 | Glu | Glu | Ser | Gly<br>5 | Thr | Glu | Phe | Lys | Pro<br>10 | Pro | Gly | Ser | Ser | Val<br>15 | Lys |
| Val | Ser | Cys | Lys<br>20 | Ala | Ser | Gly | Gly | Thr<br>25 | Phe | Gly | Asp | Tyr | Ala<br>30 | Ser | Asn |
| Tyr | Ala | Ile<br>35 | Ser | Trp | Val | Arg | Gln<br>40 | Ala | Pro | Gly | Gln | Gly<br>45 | Leu | Glu | Tyr |
| Ile | Gly<br>50 | Gly | Ile | Thr | Pro | Thr<br>55 | Ser | Gly | Ser | Ala | Asp<br>60 | Tyr | Ala | Gln | Lys |

| Phe | Gln | Gly | Arg | Val | Thr | Ile | Ser | Ala | Asp | Arg | Phe | Thr | Pro | Ile | Leu |
| 65 | | | | | 70 | | | | | 75 | | | | | 80 |

| Tyr | Met | Glu | Leu | Arg | Ser | Leu | Arg | Ile | Glu | Asp | Thr | Ala | Ile | Tyr | Tyr |
| | | | | 85 | | | | | 90 | | | | | 95 | |

| Cys | Ala | Arg | Glu | Arg | Arg | Glu | Arg | Gly | Trp | Asn | Pro | Arg | Ala | Leu | Arg |
| | | | 100 | | | | | 105 | | | | | 110 | | |

| Gly | Ala | Leu | Asp | Phe | Trp | Gly | Gln | Gly | Thr | Arg | Val | Phe | Val | Ser | Pro |
| | | | 115 | | | | | 120 | | | | | 125 | | |

( 2 ) INFORMATION FOR SEQ ID NO:56:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

| Leu | Glu | Glu | Ser | Gly | Ala | Glu | Val | Lys | Lys | Pro | Gly | Ser | Ser | Val | Lys |
| 1 | | | | 5 | | | | | 10 | | | | | 15 | |

| Val | Ser | Cys | Lys | Ala | Ser | Gly | Gly | Ile | Phe | Ser | Asp | Phe | Ala | Ser | Asn |
| | | | 20 | | | | | 25 | | | | | 30 | | |

| Tyr | Ala | Ile | Ser | Trp | Val | Arg | Gln | Ala | Pro | Gly | Gln | Gly | Leu | Glu | Tyr |
| | | | 35 | | | | | 40 | | | | | 45 | | |

| Met | Gly | Gly | Ile | Thr | Pro | Thr | Ser | Gly | Ser | Ala | Asp | Tyr | Ala | Gln | Lys |
| | | | 50 | | | | | 55 | | | | | 60 | | |

| Phe | Gln | Gly | Arg | Val | Thr | Ile | Ser | Ala | Asp | Ala | Ala | Thr | Pro | Arg | Val |
| 65 | | | | | 70 | | | | | 75 | | | | | 80 |

| Tyr | Met | Glu | Leu | Arg | Ile | Leu | Arg | Ser | Glu | Asp | Thr | Ala | Val | Tyr | Phe |
| | | | | 85 | | | | | 90 | | | | | 95 | |

| Cys | Ala | Arg | Glu | Arg | Arg | Glu | Arg | Gly | Trp | Asn | Pro | Arg | Ala | Leu | Arg |
| | | | 100 | | | | | 105 | | | | | 110 | | |

| Gly | Ala | Leu | Glu | Val | Trp | Gly | Gln | Gly | Thr | Thr | Val | Ile | Val | Ser | Pro |
| | | | 115 | | | | | 120 | | | | | 125 | | |

( 2 ) INFORMATION FOR SEQ ID NO:57:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

| Leu | Glu | Glu | Ser | Gly | Ala | Ala | Val | Gln | Lys | Pro | Gly | Ser | Ser | Val | Arg |
| 1 | | | | 5 | | | | | 10 | | | | | 15 | |

| Val | Ser | Cys | Gln | Ala | Ser | Gly | Gly | Thr | Phe | Asp | Asn | Phe | Ala | Ser | Asn |
| | | | 20 | | | | | 25 | | | | | 30 | | |

| Tyr | Ala | Val | Ser | Trp | Val | Arg | Gln | Ala | Pro | Gly | Gln | Gly | Leu | Glu | Trp |
| | | | 35 | | | | | 40 | | | | | 45 | | |

| Met | Gly | Gly | Ile | Thr | Pro | Thr | Ser | Gly | Thr | Ala | Thr | Tyr | Ser | Gln | Lys |
| | | | 50 | | | | | 55 | | | | | 60 | | |

| Phe | Gln | Gly | Arg | Val | Thr | Ile | Ser | Ala | Ala | Pro | Leu | Thr | Pro | Ile | Ile |
| 65 | | | | | 70 | | | | | 75 | | | | | 80 |

| Tyr | Met | Glu | Leu | Arg | Ser | Leu | Arg | Asp | Asp | Asp | Thr | Ala | Val | Tyr | Tyr |
| | | | | 85 | | | | | 90 | | | | | 95 | |

Cys  Ala  Arg  Glu  Arg  Arg  Glu  Arg  Gly  Trp  Asn  Pro  Arg  Ala  Leu  Val
                       100                           105                      110

Gly  Ala  Leu  Asp  Val  Trp  Gly  Gln  Gly  Thr  Thr  Val  Ile  Val  Ser  Ser
                       115                           120                      125

( 2 ) INFORMATION FOR SEQ ID NO:58:

( i ) SEQUENCE CHARACTERISTICS:
         ( A ) LENGTH: 128 amino acids
         ( B ) TYPE: amino acid
         ( D ) TOPOLOGY: linear ( i i ) MOLECULE TYPE: protein ( x i ) SEQUENCE DESCRIPTION: SEQ ID NO:58:

Leu  Glu  Gln  Ser  Gly  Ala  Glu  Val  Lys  Lys  Pro  Gly  Ser  Ser  Val  Lys
        1                    5                            10                       15

Val  Ser  Cys  Lys  Thr  Ser  Gly  Gly  Thr  Phe  Ser  Asp  Tyr  Ala  Ser  Asn
                       20                           25                       30

His  Ala  Ile  Ser  Trp  Val  Arg  Gln  Ala  Pro  Gly  Gln  Gly  Leu  Glu  Tyr
                       35                           40                       45

Met  Gly  Gly  Ile  Thr  Pro  Thr  Ser  Gly  Thr  Ala  Asp  Tyr  Ala  Gln  Lys
                  50                      55                       60

Phe  Gln  Ala  Arg  Val  Thr  Ile  Ser  Ala  His  Glu  Phe  Thr  Pro  Ile  Val
        65                           70                       75                       80

Tyr  Met  Glu  Leu  Arg  Ser  Leu  Arg  Ser  Asp  Gln  His  Ala  Thr  Tyr  Tyr
                            85                           90                       95

Cys  Ala  Thr  Glu  Arg  Arg  Glu  Arg  Gly  Trp  Asn  Pro  Arg  Ala  Leu  Arg
                       100                           105                      110

Gly  Ala  Leu  Asp  Ile  Trp  Gly  Gln  Gly  Thr  Thr  Val  Ile  Val  Ser  Ser
                       115                           120                      125

( 2 ) INFORMATION FOR SEQ ID NO:59:

( i ) SEQUENCE CHARACTERISTICS:
         ( A ) LENGTH: 128 amino acids
         ( B ) TYPE: amino acid
         ( D ) TOPOLOGY: linear ( i i ) MOLECULE TYPE: protein ( x i ) SEQUENCE DESCRIPTION: SEQ ID NO:59:

Leu  Glu  Glu  Ser  Gly  Gly  Arg  Leu  Val  Lys  Pro  Gly  Gly  Ser  Leu  Arg
        1                    5                            10                       15

Leu  Ser  Cys  Glu  Gly  Ser  Gly  Phe  Thr  Phe  Thr  Asn  Ala  Trp  Met  Thr
                       20                           25                       30

Trp  Val  Arg  Gln  Ser  Pro  Gly  Lys  Gly  Leu  Glu  Trp  Val  Ala  Ser  Ile
                       35                           40                       45

Lys  Ser  Lys  Phe  Asp  Gly  Gly  Ser  Pro  His  Tyr  Ala  Ala  Pro  Val  Glu
                  50                      55                       60

Gly  Arg  Phe  Ser  Ile  Ser  Arg  Asn  Asp  Leu  Glu  Asp  Lys  Met  Phe  Leu
        65                           70                       75                       80

Glu  Met  Ser  Gly  Leu  Lys  Ala  Glu  Asp  Thr  Gly  Val  Tyr  Tyr  Cys  Ala
                            85                           90                       95

Thr  Lys  Tyr  Pro  Arg  Tyr  Ser  Asp  Met  Val  Thr  Gly  Val  Arg  Asn  His
                       100                           105                      110

Phe  Tyr  Met  Asp  Val  Trp  Gly  Lys  Gly  Thr  Thr  Val  Ile  Val  Ser  Ser
                       115                           120                      125

( 2 ) INFORMATION FOR SEQ ID NO:60:

(i) SEQUENCE CHARACTERISTICS:
(A) LENGTH: 128 amino acids
(B) TYPE: amino acid
(D) TOPOLOGY: linear (ii) MOLECULE TYPE: protein (xi) SEQUENCE DESCRIPTION: SEQ ID NO:60:

| Leu | Glu | Gln | Ser | Gly | Gly | Gly | Leu | Val | Lys | Pro | Gly | Gly | Ser | Leu | Arg |
|---|---|---|---|---|---|---|---|---|---|---|---|---|---|---|---|
| 1 | | | | 5 | | | | | 10 | | | | | 15 | |
| Leu | Ser | Cys | Glu | Gly | Ser | Gly | Phe | Thr | Phe | Thr | Asn | Ala | Trp | Met | Thr |
| | | | 20 | | | | | 25 | | | | | 30 | | |
| Trp | Val | Arg | Gln | Ser | Pro | Gly | Lys | Gly | Leu | Glu | Trp | Val | Ala | Ser | Ile |
| | | | 35 | | | | 40 | | | | | 45 | | | |
| Lys | Ser | Lys | Phe | Asp | Gly | Gly | Ser | Pro | His | Tyr | Ala | Ala | Pro | Val | Glu |
| | | 50 | | | | 55 | | | | | 60 | | | | |
| Gly | Arg | Phe | Thr | Ile | Ser | Arg | Asn | Asp | Leu | Glu | Asp | Lys | Leu | Phe | Leu |
| 65 | | | | | 70 | | | | | 75 | | | | | 80 |
| Glu | Met | Ser | Gly | Leu | Lys | Ala | Glu | Asp | Thr | Gly | Val | Tyr | Tyr | Cys | Ala |
| | | | | 85 | | | | | 90 | | | | | 95 | |
| Thr | Lys | Tyr | Pro | Arg | Tyr | Phe | Asp | Met | Met | Ala | Gly | Val | Arg | Asn | His |
| | | | 100 | | | | | 105 | | | | | 110 | | |
| Phe | Tyr | Met | Asp | Val | Trp | Gly | Thr | Gly | Thr | Thr | Val | Ile | Val | Ser | Ser |
| | | | 115 | | | | | 120 | | | | | 125 | | |

(2) INFORMATION FOR SEQ ID NO:61:

(i) SEQUENCE CHARACTERISTICS:
(A) LENGTH: 128 amino acids
(B) TYPE: amino acid
(D) TOPOLOGY: linear (ii) MOLECULE TYPE: protein (xi) SEQUENCE DESCRIPTION: SEQ ID NO:61:

| Leu | Glu | Glu | Ser | Gly | Gly | Gly | Leu | Val | Lys | Pro | Gly | Gly | Ser | Leu | Arg |
|---|---|---|---|---|---|---|---|---|---|---|---|---|---|---|---|
| 1 | | | | 5 | | | | | 10 | | | | | 15 | |
| Leu | Ser | Cys | Glu | Gly | Ser | Gly | Phe | Thr | Phe | Thr | Asn | Ala | Trp | Met | Thr |
| | | | 20 | | | | | 25 | | | | | 30 | | |
| Trp | Val | Arg | Gln | Ser | Pro | Gly | Lys | Gly | Leu | Glu | Trp | Val | Ala | Ser | Ile |
| | | | 35 | | | | 40 | | | | | 45 | | | |
| Lys | Ser | Lys | Phe | Asp | Gly | Gly | Ser | Pro | His | Tyr | Ala | Ala | Pro | Val | Glu |
| | | 50 | | | | 55 | | | | | 60 | | | | |
| Gly | Arg | Phe | Thr | Ile | Ser | Arg | Asn | Asp | Leu | Glu | Asp | Lys | Leu | Phe | Leu |
| 65 | | | | | 70 | | | | | 75 | | | | | 80 |
| Glu | Met | Ser | Gly | Leu | Lys | Ala | Glu | Asp | Thr | Gly | Val | Tyr | Tyr | Cys | Ala |
| | | | | 85 | | | | | 90 | | | | | 95 | |
| Thr | Lys | Tyr | Pro | Arg | Tyr | Ser | Asp | Met | Met | Ala | Gly | Val | Arg | Asn | His |
| | | | 100 | | | | | 105 | | | | | 110 | | |
| Leu | Tyr | Met | Asp | Val | Trp | Gly | Lys | Gly | Thr | Thr | Val | Ile | Val | Ser | Ser |
| | | | 115 | | | | | 120 | | | | | 125 | | |

(2) INFORMATION FOR SEQ ID NO:62:

(i) SEQUENCE CHARACTERISTICS:
(A) LENGTH: 128 amino acids
(B) TYPE: amino acid
(D) TOPOLOGY: linear (ii) MOLECULE TYPE: protein ( x i ) SEQUENCE DESCRIPTION: SEQ ID NO:62:

| Leu | Glu | Glu | Ser | Gly | Gly | Arg | Leu | Val | Lys | Pro | Gly | Gly | Ser | Leu | Arg |
|---|---|---|---|---|---|---|---|---|---|---|---|---|---|---|---|
| 1 | | | | 5 | | | | | 10 | | | | | 15 | |

| Leu | Ser | Cys | Glu | Ala | Ser | Gly | Phe | Thr | Phe | Thr | Asn | Ser | Trp | Met | Thr |
|---|---|---|---|---|---|---|---|---|---|---|---|---|---|---|---|
| | | | 20 | | | | | 25 | | | | | | 30 | |

| Trp | Val | Arg | Gln | Ser | Pro | Gly | Lys | Gly | Leu | Glu | Trp | Val | Ala | Ser | Ile |
|---|---|---|---|---|---|---|---|---|---|---|---|---|---|---|---|
| | | | 35 | | | | | 40 | | | | | 45 | | |

| Lys | Arg | Lys | Phe | Asp | Gly | Gly | Ser | Pro | His | Tyr | Ala | Ala | Pro | Val | Glu |
|---|---|---|---|---|---|---|---|---|---|---|---|---|---|---|---|
| | | 50 | | | | | 55 | | | | | 60 | | | |

| Gly | Arg | Phe | Ser | Ile | Ser | Arg | Asn | Asp | Leu | Glu | Asp | Lys | Met | Phe | Leu |
|---|---|---|---|---|---|---|---|---|---|---|---|---|---|---|---|
| 65 | | | | | 70 | | | | | 75 | | | | | 80 |

| Glu | Met | Ser | Gly | Leu | Lys | Ala | Glu | Asp | Thr | Gly | Val | Tyr | Tyr | Cys | Ala |
|---|---|---|---|---|---|---|---|---|---|---|---|---|---|---|---|
| | | | | 85 | | | | | 90 | | | | | 95 | |

| Thr | Lys | Tyr | Pro | Arg | Tyr | Ser | Asp | Met | Met | Thr | Gly | Val | Arg | Asn | His |
|---|---|---|---|---|---|---|---|---|---|---|---|---|---|---|---|
| | | | 100 | | | | | 105 | | | | | 110 | | |

| Phe | Tyr | Met | Asp | Val | Trp | Gly | Lys | Gly | Thr | Thr | Val | Ile | Val | Ser | Ser |
|---|---|---|---|---|---|---|---|---|---|---|---|---|---|---|---|
| | | | 115 | | | | | 120 | | | | | 125 | | |

( 2 ) INFORMATION FOR SEQ ID NO:63:

( i ) SEQUENCE CHARACTERISTICS:
( A ) LENGTH: 128 amino acids
( B ) TYPE: amino acid
( D ) TOPOLOGY: linear ( i i ) MOLECULE TYPE: protein ( x i ) SEQUENCE DESCRIPTION: SEQ ID NO:63:

| Leu | Glu | Glu | Ser | Gly | Gly | Gly | Leu | Val | Lys | Pro | Gly | Gly | Ser | Leu | Arg |
|---|---|---|---|---|---|---|---|---|---|---|---|---|---|---|---|
| 1 | | | | 5 | | | | | 10 | | | | | 15 | |

| Leu | Ser | Cys | Glu | Ser | Ser | Gly | Phe | Thr | Phe | Thr | Asn | Ala | Trp | Met | Thr |
|---|---|---|---|---|---|---|---|---|---|---|---|---|---|---|---|
| | | | 20 | | | | | 25 | | | | | | 30 | |

| Trp | Val | Arg | Gln | Ser | Pro | Gly | Lys | Gly | Leu | Glu | Trp | Val | Ala | Ser | Ile |
|---|---|---|---|---|---|---|---|---|---|---|---|---|---|---|---|
| | | | 35 | | | | | 40 | | | | | 45 | | |

| Lys | Ser | Lys | Phe | Asp | Gly | Gly | Ser | Pro | His | Tyr | Ala | Ala | Pro | Val | Glu |
|---|---|---|---|---|---|---|---|---|---|---|---|---|---|---|---|
| | | 50 | | | | | 55 | | | | | 60 | | | |

| Gly | Arg | Phe | Thr | Ile | Ser | Arg | Asn | Asp | Leu | Glu | Asp | Lys | Leu | Phe | Leu |
|---|---|---|---|---|---|---|---|---|---|---|---|---|---|---|---|
| 65 | | | | | 70 | | | | | 75 | | | | | 80 |

| Glu | Met | Ser | Gly | Leu | Lys | Ala | Glu | Asp | Thr | Gly | Val | Tyr | Tyr | Cys | Ala |
|---|---|---|---|---|---|---|---|---|---|---|---|---|---|---|---|
| | | | | 85 | | | | | 90 | | | | | 95 | |

| Thr | Lys | Tyr | Pro | Arg | Tyr | Ser | Asp | Met | Met | Ala | Gly | Val | Arg | Asn | His |
|---|---|---|---|---|---|---|---|---|---|---|---|---|---|---|---|
| | | | 100 | | | | | 105 | | | | | 110 | | |

| Phe | Tyr | Met | Asp | Val | Trp | Gly | Lys | Gly | Thr | Thr | Val | Ile | Val | Ser | Ser |
|---|---|---|---|---|---|---|---|---|---|---|---|---|---|---|---|
| | | | 115 | | | | | 120 | | | | | 125 | | |

( 2 ) INFORMATION FOR SEQ ID NO:64:

( i ) SEQUENCE CHARACTERISTICS:
( A ) LENGTH: 128 amino acids
( B ) TYPE: amino acid
( D ) TOPOLOGY: linear ( i i ) MOLECULE TYPE: protein ( x i ) SEQUENCE DESCRIPTION: SEQ ID NO:64:

| Leu | Glu | Glu | Ser | Gly | Gly | Arg | Leu | Val | Lys | Pro | Gly | Gly | Ser | Leu | Arg |
|---|---|---|---|---|---|---|---|---|---|---|---|---|---|---|---|
| 1 | | | | 5 | | | | | 10 | | | | | 15 | |

| Leu | Ser | Cys | Glu | Gly | Ser | Gly | Phe | Thr | Phe | Thr | Asn | Ala | Trp | Met | Thr |
|---|---|---|---|---|---|---|---|---|---|---|---|---|---|---|---|
| | | | 20 | | | | | 25 | | | | | | 30 | |

| Trp | Val | Arg | Gln | Ser | Pro | Gly | Lys | Gly | Leu | Glu | Trp | Val | Ala | Ser | Ile |
|||35|||||40||||||45|||

| Lys | Ser | Lys | Phe | Asp | Gly | Gly | Ser | Pro | His | Tyr | Ala | Ala | Pro | Val | Glu |
||50|||||55|||||60|||||

| Gly | Arg | Phe | Ser | Ile | Ser | Arg | Asn | Asp | Leu | Glu | Asp | Lys | Met | Phe | Leu |
|65|||||70|||||75||||||80|

| Glu | Met | Ser | Gly | Leu | Lys | Ala | Glu | Asp | Thr | Gly | Val | Tyr | Tyr | Cys | Ala |
|||||85|||||90|||||95||

| Thr | Lys | Tyr | Pro | Arg | Tyr | Ser | Asp | Met | Met | Thr | Gly | Val | Arg | Asn | His |
||||100||||||105||||110|||

| Phe | Tyr | Met | Asp | Val | Trp | Gly | Lys | Gly | Thr | Thr | Val | Ile | Val | Ser | Ser |
||||115||||||120||||125|||

( 2 ) INFORMATION FOR SEQ ID NO:65:

( i ) SEQUENCE CHARACTERISTICS:
        ( A ) LENGTH: 128 amino acids
        ( B ) TYPE: amino acid
        ( D ) TOPOLOGY: linear ( i i ) MOLECULE TYPE: protein ( x i ) SEQUENCE DESCRIPTION: SEQ ID NO:65:

| Leu | Glu | Glu | Ser | Gly | Gly | Gly | Leu | Val | Lys | Pro | Gly | Gly | Ser | Leu | Arg |
|1||||5|||||10|||||15||

| Leu | Ser | Cys | Ala | Gly | Ser | Gly | Phe | Thr | Phe | Thr | Asn | Ala | Trp | Met | Thr |
|||||20|||||25|||||30||

| Trp | Val | Arg | Gln | Ser | Pro | Gly | Lys | Gly | Leu | Glu | Trp | Val | Ala | Ser | Ile |
|||35|||||40||||||45|||

| Lys | Ser | Lys | Phe | Asp | Gly | Gly | Ser | Ser | His | Tyr | Pro | Gly | Pro | Val | Glu |
||50|||||55|||||60|||||

| Gly | Arg | Phe | Thr | Ile | Ser | Arg | Asn | Tyr | Ile | Glu | Asp | Lys | Leu | Phe | Leu |
|65|||||70|||||75||||||80|

| Glu | Met | Ser | Gly | Leu | Lys | Ala | Glu | Asp | Thr | Gly | Val | Tyr | Tyr | Cys | Ala |
|||||85|||||90|||||95||

| Thr | Lys | Tyr | Pro | Arg | Tyr | Tyr | Asp | Met | Met | Arg | Gly | Val | Arg | Asn | His |
||||100||||||105||||110|||

| Tyr | Tyr | Met | Asp | Val | Trp | Gly | Lys | Gly | Thr | Thr | Val | Ile | Val | Ser | Ser |
||||115||||||120||||125|||

( 2 ) INFORMATION FOR SEQ ID NO:66:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:66:

| Leu | Glu | Gln | Ser | Gly | Ala | Glu | Val | Lys | Lys | Pro | Gly | Ala | Ser | Val | Lys |
|1||||5|||||10|||||15||

| Val | Ser | Cys | Gln | Ala | Ser | Gly | Tyr | Arg | Phe | Ser | Asn | Phe | Val | Ile | His |
|||||20|||||25|||||30||

| Trp | Val | Arg | Gln | Ala | Pro | Gly | Gln | Arg | Phe | Glu | Trp | Met | Gly | Trp | Ile |
|||35|||||40||||||45|||

| Asn | Pro | Tyr | Asn | Gly | Asn | Lys | Glu | Phe | Ser | Ala | Lys | Phe | Gln | Asp | Arg |
||50|||||55|||||60|||||

| Val | Thr | Phe | Thr | Ala | Asp | Thr | Ser | Ala | Asn | Thr | Ala | Tyr | Met | Glu | Leu |
|65|||||70|||||75||||||80|

```
          Arg  Ser  Leu  Arg  Ser  Ala  Asp  Thr  Ala  Val  Tyr  Tyr  Cys  Ala  Arg  Val
                              85                      90                          95

Gly  Pro  Tyr  Ser  Trp  Asp  Asp  Ser  Pro  Gln  Asp  Asn  Tyr  Tyr  Met  Asp
                         100                      105                         110

Val  Trp  Gly  Lys  Gly  Thr  Thr  Val  Ile  Val  Ser  Ser
                         115                      120
```

( 2 ) INFORMATION FOR SEQ ID NO:67:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:67:

```
          Leu  Glu  Gln  Ser  Gly  Ala  Glu  Val  Lys  Lys  Pro  Gly  Ala  Ser  Val  Lys
          1                   5                       10                          15

Val  Ser  Cys  Gln  Ala  Ser  Gly  Tyr  Arg  Phe  Ser  Asn  Phe  Val  Ile  His
                         20                      25                          30

Trp  Val  Arg  Gln  Ala  Pro  Gly  Gln  Arg  Phe  Glu  Trp  Met  Gly  Trp  Ile
                         35                      40                          45

Asn  Pro  Tyr  Asn  Gly  Asn  Lys  Glu  Phe  Ser  Ala  Lys  Phe  Gln  Asp  Arg
                    50                      55                      60

Val  Thr  Phe  Thr  Ala  Asp  Thr  Asp  Ala  Asn  Thr  Ala  Tyr  Met  Glu  Leu
          65                       70                      75                              80

Arg  Ser  Leu  Arg  Ser  Ala  Asp  Thr  Ala  Ile  Tyr  Tyr  Cys  Ala  Arg  Val
                              85                      90                          95

Gly  Pro  Tyr  Thr  Trp  Asp  Asp  Ser  Pro  Gln  Asp  Asn  Tyr  Tyr  Met  Asp
                         100                     105                         110

Val  Trp  Gly  Lys  Gly  Thr  Lys  Val  Ile  Val  Ser  Ser
                         115                     120
```

( 2 ) INFORMATION FOR SEQ ID NO:68:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:68:

```
          Leu  Glu  Gln  Ser  Gly  Ala  Glu  Val  Lys  Lys  Pro  Gly  Ala  Ser  Val  Lys
          1                   5                       10                          15

Val  Ser  Cys  Gln  Ala  Ser  Gly  Tyr  Arg  Phe  Ser  Asn  Phe  Val  Ile  His
                         20                      25                          30

Trp  Val  Arg  Gln  Ala  Pro  Gly  Gln  Arg  Phe  Glu  Trp  Met  Gly  Trp  Ile
                         35                      40                          45

Asn  Pro  Tyr  Asn  Gly  Asn  Lys  Glu  Phe  Ser  Ala  Lys  Phe  Gln  Asp  Arg
                    50                      55                      60

Val  Thr  Phe  Thr  Ala  Asp  Thr  Asp  Ala  Asn  Thr  Ala  Tyr  Met  Glu  Leu
          65                       70                      75                              80

Arg  Ser  Leu  Arg  Ser  Thr  Asp  Thr  Ala  Ile  Tyr  Tyr  Cys  Ala  Arg  Val
                              85                      90                          95

Gly  Pro  Tyr  Thr  Trp  Asp  Asp  Ser  Pro  Gln  Asp  Asn  Tyr  Tyr  Met  Asp
                         100                     105                         110
```

-continued

```
Val Trp Gly Lys Gly Thr Lys Val Ile Val Ser Ser
            115                 120
```

( 2 ) INFORMATION FOR SEQ ID NO:69:

( i ) SEQUENCE CHARACTERISTICS:
        ( A ) LENGTH: 130 amino acids
        ( B ) TYPE: amino acid
        ( D ) TOPOLOGY: linear ( i i ) MOLECULE TYPE: protein ( x i ) SEQUENCE DESCRIPTION: SEQ ID NO:69:

```
Leu Glu Glu Ser Gly Gly Gly Leu Val Lys Pro Gly Gly Ser Leu Arg
1                 5                   10                  15
Leu Ser Cys Val Gly Ser Gly Phe Thr Phe Ser Ser Ala Trp Met Ala
            20                  25                  30
Trp Val Arg Gln Ala Pro Gly Arg Gly Leu Glu Trp Val Gly Leu Ile
            35                  40                  45
Lys Ser Lys Ala Asp Gly Glu Thr Thr Asp Tyr Ala Thr Pro Val Lys
50                  55                  60
Gly Arg Phe Ser Ile Ser Arg Asn Asn Leu Glu Asp Thr Val Tyr Leu
65                  70                  75                  80
Gln Met Asp Ser Leu Arg Ala Asp Asp Thr Ala Val Tyr Tyr Cys Ala
                85                  90                  95
Thr Gln Lys Pro Arg Tyr Phe Asp Leu Leu Ser Gly Gln Tyr Arg Arg
            100                 105                 110
Val Ala Gly Ala Phe Asp Val Trp Gly His Gly Thr Thr Val Thr Val
            115                 120                 125
Ser Pro
130
```

( 2 ) INFORMATION FOR SEQ ID NO:70:

( i ) SEQUENCE CHARACTERISTICS:
        ( A ) LENGTH: 130 amino acids
        ( B ) TYPE: amino acid
        ( D ) TOPOLOGY: linear ( i i ) MOLECULE TYPE: protein ( x i ) SEQUENCE DESCRIPTION: SEQ ID NO:70:

```
Leu Glu Glu Ser Gly Gly Gly Leu Val Lys Ala Gly Gly Ser Leu Arg
1                 5                   10                  15
Leu Ser Cys Val Gly Ser Gly Phe Thr Phe Ser Ser Ala Trp Met Ala
            20                  25                  30
Trp Val Gly Gln Ala Pro Gly Arg Gly Leu Glu Trp Val Gly Leu Ile
            35                  40                  45
Lys Ser Lys Ala Asp Gly Glu Thr Thr Asp Tyr Ala Thr Pro Val Lys
50                  55                  60
Gly Arg Phe Ser Ile Ser Arg Asn Asn Leu Glu Asp Thr Val Tyr Leu
65                  70                  75                  80
Gln Met Asp Ser Leu Arg Ala Asp Asp Thr Ala Val Tyr Tyr Cys Ala
                85                  90                  95
Thr Gln Lys Pro Arg Tyr Phe Asp Leu Leu Ser Gly Gln Tyr Arg Arg
            100                 105                 110
Val Ala Gly Ala Phe Asp Val Trp Gly His Gly Thr Thr Val Thr Val
            115                 120                 125
Ser Pro
130
```

( 2 ) INFORMATION FOR SEQ ID NO:71:

( i ) SEQUENCE CHARACTERISTICS:
        ( A ) LENGTH: 130 amino acids
        ( B ) TYPE: amino acid
        ( D ) TOPOLOGY: linear ( i i ) MOLECULE TYPE: protein ( x i ) SEQUENCE DESCRIPTION: SEQ ID NO:71:

```
Leu  Glu  Glu  Ser  Gly  Gly  Gly  Leu  Ile  Lys  Pro  Gly  Gly  Ser  Leu  Arg
 1              5                        10                         15
Leu  Ser  Cys  Val  Gly  Ser  Gly  Phe  Thr  Phe  Ser  Ser  Ala  Trp  Met  Thr
              20                        25                        30
Trp  Val  Arg  Gln  Ala  Pro  Gly  Lys  Gly  Leu  Glu  Trp  Ile  Gly  Leu  Ile
             35                        40                        45
Lys  Ser  Lys  Ala  Asp  Gly  Glu  Thr  Thr  Asp  Tyr  Ala  Thr  Pro  Val  Lys
     50                        55                        60
Gly  Arg  Phe  Thr  Ile  Ser  Arg  Asn  Asn  Leu  Glu  Asn  Thr  Val  Tyr  Leu
 65                       70                        75                        80
Gln  Met  Asp  Ser  Leu  Arg  Ala  Asp  Asp  Thr  Ala  Val  Tyr  Tyr  Cys  Ala
                    85                        90                        95
Thr  Gln  Lys  Pro  Ser  Tyr  Tyr  Asn  Leu  Leu  Ser  Gly  Gln  Tyr  Arg  Arg
               100                       105                       110
Val  Ala  Gly  Ala  Phe  Asp  Val  Trp  Gly  His  Gly  Thr  Thr  Val  Thr  Val
               115                       120                       125
Ser  Pro
```

( 2 ) INFORMATION FOR SEQ ID NO:72:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:72:

```
Leu  Glu  Glu  Ser  Gly  Glu  Ala  Val  Val  Gln  Pro  Gly  Arg  Ser  Leu  Arg
 1              5                        10                         15
Leu  Ser  Cys  Ala  Ala  Ser  Gly  Phe  Ile  Phe  Arg  Asn  Tyr  Ala  Met  His
              20                        25                        30
Trp  Val  Arg  Gln  Ala  Pro  Gly  Lys  Gly  Leu  Glu  Trp  Val  Ala  Leu  Ile
             35                        40                        45
Lys  Tyr  Asp  Gly  Arg  Asn  Lys  Tyr  Tyr  Ala  Asp  Ser  Val  Lys  Gly  Arg
     50                        55                        60
Phe  Thr  Ile  Ser  Arg  Asp  Asn  Ser  Lys  Asn  Thr  Leu  Tyr  Leu  Gln  Met
 65                       70                        75                        80
Asn  Ser  Leu  Arg  Ala  Glu  Asp  Thr  Ala  Val  Tyr  Tyr  Cys  Ala  Arg  Asp
                    85                        90                        95
Ile  Gly  Leu  Lys  Gly  Glu  His  Tyr  Asp  Ile  Leu  Thr  Ala  Tyr  Gly  Pro
               100                       105                       110
Asp  Tyr  Trp  Gly  Gln  Gly  Thr  Leu  Val  Thr  Val  Ser  Ser
               115                       120                       125
```

( 2 ) INFORMATION FOR SEQ ID NO:73:

( i ) SEQUENCE CHARACTERISTICS:
        ( A ) LENGTH: 125 amino acids (B) TYPE: amino acid
(D) TOPOLOGY: linear (ii) MOLECULE TYPE: protein (xi) SEQUENCE DESCRIPTION: SEQ ID NO:73:

| Leu | Glu | Gln | Ser | Gly | Glu | Ala | Val | Val | Gln | Pro | Gly | Thr | Ser | Leu | Arg |
|---|---|---|---|---|---|---|---|---|---|---|---|---|---|---|---|
| 1 | | | | 5 | | | | | 10 | | | | | 15 | |
| Leu | Ser | Cys | Ala | Ala | Ser | Gly | Phe | Thr | Phe | Arg | Asn | Tyr | Ala | Met | His |
| | | | 20 | | | | | 25 | | | | | 30 | | |
| Trp | Val | Arg | Gln | Ala | Pro | Gly | Lys | Gly | Leu | Glu | Trp | Val | Ala | Leu | Ile |
| | | 35 | | | | | 40 | | | | | 45 | | | |
| Lys | Tyr | Asp | Gly | Arg | Asn | Lys | Tyr | Tyr | Ala | Asp | Ser | Val | Lys | Gly | Arg |
| | | 50 | | | | 55 | | | | | 60 | | | | |
| Phe | Ser | Ile | Ser | Arg | Asp | Asn | Ser | Lys | Asn | Thr | Leu | Tyr | Leu | Glu | Met |
| 65 | | | | | 70 | | | | | 75 | | | | | 80 |
| Asn | Ser | Leu | Arg | Ala | Glu | Asp | Thr | Ala | Val | Tyr | Tyr | Cys | Ala | Arg | Asp |
| | | | | 85 | | | | | 90 | | | | | 95 | |
| Ile | Gly | Leu | Lys | Gly | Glu | His | Tyr | Asp | Ile | Leu | Thr | Ala | Tyr | Gly | Pro |
| | | | 100 | | | | | 105 | | | | | 110 | | |
| Asp | Tyr | Trp | Gly | Gln | Gly | Ala | Leu | Val | Thr | Val | Ser | Ser | | | |
| | | 115 | | | | | 120 | | | | | 125 | | | |

(2) INFORMATION FOR SEQ ID NO:74:

(i) SEQUENCE CHARACTERISTICS:
(A) LENGTH: 125 amino acids
(B) TYPE: amino acid
(D) TOPOLOGY: linear (ii) MOLECULE TYPE: protein (xi) SEQUENCE DESCRIPTION: SEQ ID NO:74:

| Leu | Glu | Gln | Ser | Gly | Glu | Ala | Val | Val | Gln | Pro | Gly | Arg | Ser | Leu | Arg |
|---|---|---|---|---|---|---|---|---|---|---|---|---|---|---|---|
| 1 | | | | 5 | | | | | 10 | | | | | 15 | |
| Leu | Ser | Cys | Ala | Ala | Ser | Gly | Phe | Ile | Phe | Arg | Asn | Tyr | Ala | Met | His |
| | | | 20 | | | | | 25 | | | | | 30 | | |
| Trp | Val | Arg | Gln | Ala | Pro | Gly | Lys | Gly | Leu | Glu | Trp | Val | Ala | Leu | Ile |
| | | 35 | | | | | 40 | | | | | 45 | | | |
| Lys | Tyr | Asp | Gly | Arg | Asn | Lys | Tyr | Tyr | Ala | Asp | Ser | Val | Lys | Gly | Arg |
| | | 50 | | | | 55 | | | | | 60 | | | | |
| Phe | Thr | Ile | Ser | Arg | Asp | Asn | Ser | Lys | Asn | Thr | Leu | Tyr | Leu | Gln | Met |
| 65 | | | | | 70 | | | | | 75 | | | | | 80 |
| Asn | Ser | Leu | Arg | Ala | Glu | Asp | Thr | Ala | Val | Tyr | Tyr | Cys | Ala | Arg | Asp |
| | | | | 85 | | | | | 90 | | | | | 95 | |
| Ile | Gly | Leu | Lys | Gly | Glu | His | Tyr | Asp | Ile | Leu | Thr | Ala | Tyr | Gly | Pro |
| | | | 100 | | | | | 105 | | | | | 110 | | |
| Asp | Tyr | Trp | Gly | Gln | Gly | Thr | Leu | Val | Thr | Val | Ser | Ser | | | |
| | | 115 | | | | | 120 | | | | | 125 | | | |

(2) INFORMATION FOR SEQ ID NO:75:

(i) SEQUENCE CHARACTERISTICS:
(A) LENGTH: 125 amino acids
(B) TYPE: amino acid
(D) TOPOLOGY: linear (ii) MOLECULE TYPE: protein (xi) SEQUENCE DESCRIPTION: SEQ ID NO:75:

| Leu<br>1 | Glu | Glu | Ser | Gly<br>5 | Glu | Ala | Val | Val | Gln<br>10 | Pro | Gly | Thr | Ser | Leu<br>15 | Arg |
|---|---|---|---|---|---|---|---|---|---|---|---|---|---|---|---|
| Leu | Ser | Cys | Ala<br>20 | Ala | Ser | Gly | Phe | Thr<br>25 | Phe | Arg | Asn | Tyr | Ala<br>30 | Met | His |
| Trp | Val | Arg<br>35 | Gln | Ala | Pro | Gly | Lys<br>40 | Gly | Leu | Glu | Trp | Val<br>45 | Ala | Leu | Ile |
| Lys | Tyr<br>50 | Asp | Gly | Arg | Asn | Lys<br>55 | Tyr | Tyr | Ala | Asp | Ser<br>60 | Val | Lys | Gly | Arg |
| Phe<br>65 | Ser | Ile | Ser | Arg | Asp<br>70 | Asn | Ser | Lys | Asn | Thr<br>75 | Leu | Tyr | Leu | Glu | Met<br>80 |
| Asn | Ser | Leu | Arg | Ala<br>85 | Glu | Asp | Thr | Ala | Val<br>90 | Tyr | Tyr | Cys | Ala | Arg<br>95 | Asp |
| Ile | Gly | Leu | Lys<br>100 | Gly | Glu | His | Tyr | Asp<br>105 | Ile | Leu | Thr | Ala | Tyr<br>110 | Gly | Pro |
| Asp | Tyr | Trp<br>115 | Gly | Gln | Gly | Ala | Leu<br>120 | Val | Thr | Val | Ser | Ser<br>125 | | | |

( 2 ) INFORMATION FOR SEQ ID NO:76:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:76:

| Leu<br>1 | Glu | Gln | Ser | Gly<br>5 | Glu | Ala | Val | Val | Gln<br>10 | Pro | Gly | Arg | Ser | Leu<br>15 | Arg |
|---|---|---|---|---|---|---|---|---|---|---|---|---|---|---|---|
| Leu | Ser | Cys | Ala<br>20 | Ala | Ser | Gly | Phe | Thr<br>25 | Phe | Arg | Asn | Tyr | Ala<br>30 | Met | His |
| Trp | Val | Arg<br>35 | Gln | Ala | Pro | Gly | Lys<br>40 | Gly | Leu | Glu | Trp | Val<br>45 | Ala | Leu | Ile |
| Lys | Tyr<br>50 | Asp | Gly | Arg | Asn | Lys<br>55 | Tyr | Tyr | Ala | Asp | Ser<br>60 | Val | Lys | Gly | Arg |
| Phe<br>65 | Thr | Ile | Ser | Arg | Asp<br>70 | Asn | Ser | Lys | Asn | Thr<br>75 | Leu | Tyr | Leu | Gln | Met<br>80 |
| Asn | Ser | Leu | Arg | Ala<br>85 | Glu | Asp | Thr | Ala | Val<br>90 | Tyr | Tyr | Cys | Ala | Arg<br>95 | Asp |
| Ile | Gly | Leu | Lys<br>100 | Ala | Glu | His | Tyr | Asp<br>105 | Ile | Leu | Thr | Ala | Tyr<br>110 | Gly | Pro |
| Asp | Tyr | Trp<br>115 | Gly | Gln | Gly | Thr | Leu<br>120 | Val | Thr | Val | Ser | Ser<br>125 | | | |

( 2 ) INFORMATION FOR SEQ ID NO:77:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:77:

| Leu<br>1 | Glu | Gln | Ser | Gly<br>5 | Glu | Ala | Val | Val | Gln<br>10 | Pro | Gly | Arg | Ser | Leu<br>15 | Arg |
|---|---|---|---|---|---|---|---|---|---|---|---|---|---|---|---|
| Leu | Ser | Cys | Ala<br>20 | Ala | Ser | Gly | Phe | Ile<br>25 | Phe | Arg | Asn | Tyr | Ala<br>30 | Met | His |
| Trp | Val | Arg<br>35 | Gln | Ala | Pro | Gly | Lys<br>40 | Gly | Leu | Glu | Trp | Val<br>45 | Ala | Leu | Ile |

|     | Lys | Tyr | Asp   | Gly | Arg | Asn   | Lys | Tyr | Ala | Asp   | Ser | Val | Lys   | Gly | Arg |
|-----|-----|-----|-------|-----|-----|-------|-----|-----|-----|-------|-----|-----|-------|-----|-----|
|     |     | 50  |       |     |     |       | 55  |     |     |       | 60  |     |       |     |     |

| Phe | Thr | Ile | Ser | Arg | Asp | Asn | Ser | Lys | Asn | Thr | Leu | Tyr | Leu | Gln | Met |
| 65  |     |     |     |     | 70  |     |     |     |     | 75  |     |     |     |     | 80  |

| Asn | Ser | Leu | Arg | Ala | Glu | Asp | Thr | Ala | Val | Tyr | Tyr | Cys | Ala | Arg | Asp |
|     |     |     |     | 85  |     |     |     |     | 90  |     |     |     |     | 95  |     |

| Ile | Gly | Leu | Lys | Gly | Glu | His | Tyr | Asp | Ile | Leu | Thr | Ala | Tyr | Gly | Pro |
|     |     |     | 100 |     |     |     |     | 105 |     |     |     |     | 110 |     |     |

| Asp | Tyr | Trp | Gly | Gln | Gly | Thr | Leu | Val | Thr | Val | Ser | Ser |
|     |     | 115 |     |     |     |     | 120 |     |     |     |     | 125 |

(2) INFORMATION FOR SEQ ID NO:78:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:78:

| Leu | Glu | Gln | Ser | Gly | Gly | Gly | Val | Val | Lys | Pro | Gly | Gly | Ser | Leu | Arg |
| 1   |     |     |     | 5   |     |     |     |     | 10  |     |     |     |     | 15  |     |

| Leu | Ser | Cys | Glu | Gly | Ser | Gly | Phe | Thr | Phe | Pro | Asn | Ala | Trp | Met | Thr |
|     |     |     | 20  |     |     |     |     | 25  |     |     |     |     | 30  |     |     |

| Trp | Val | Arg | Gln | Ser | Pro | Gly | Lys | Gly | Leu | Glu | Trp | Val | Ala | Ser | Ile |
|     |     |     | 35  |     |     |     |     | 40  |     |     |     |     | 45  |     |     |

| Lys | Ser | Lys | Phe | Asp | Gly | Gly | Ser | Pro | His | Tyr | Ala | Ala | Pro | Val | Glu |
|     |     | 50  |     |     |     |     | 55  |     |     |     |     | 60  |     |     |     |

| Gly | Arg | Phe | Thr | Ile | Ser | Arg | Asn | Asp | Leu | Glu | Asp | Lys | Val | Phe | Leu |
| 65  |     |     |     |     | 70  |     |     |     |     | 75  |     |     |     |     | 80  |

| Gln | Met | Asn | Gly | Leu | Lys | Ala | Glu | Asp | Thr | Gly | Val | Tyr | Tyr | Cys | Ala |
|     |     |     |     | 85  |     |     |     |     | 90  |     |     |     |     | 95  |     |

| Thr | Arg | Tyr | Pro | Arg | Tyr | Ser | Glu | Met | Met | Gly | Gly | Val | Arg | Lys | His |
|     |     |     | 100 |     |     |     |     | 105 |     |     |     |     | 110 |     |     |

| Phe | Tyr | Met | Asp | Val | Trp | Gly | Lys | Gly | Thr | Thr | Val | Ser | Val | Ser | Ser |
|     |     | 115 |     |     |     |     | 120 |     |     |     |     | 125 |     |     |     |

(2) INFORMATION FOR SEQ ID NO:79:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO:79:

| Leu | Glu | Glu | Ser | Gly | Gly | Gly | Val | Val | Lys | Pro | Gly | Gly | Ser | Leu | Arg |
| 1   |     |     |     | 5   |     |     |     |     | 10  |     |     |     |     | 15  |     |

| Leu | Ser | Cys | Glu | Gly | Ser | Gly | Phe | Thr | Phe | Pro | Asn | Ala | Trp | Met | Thr |
|     |     |     | 20  |     |     |     |     | 25  |     |     |     |     | 30  |     |     |

| Trp | Val | Arg | Gln | Ser | Pro | Gly | Lys | Gly | Leu | Glu | Trp | Val | Ala | Ser | Ile |
|     |     |     | 35  |     |     |     |     | 40  |     |     |     |     | 45  |     |     |

| Lys | Ser | Lys | Phe | Asp | Gly | Gly | Ser | Pro | His | Tyr | Ala | Ala | Pro | Val | Glu |
|     |     | 50  |     |     |     |     | 55  |     |     |     |     | 60  |     |     |     |

| Gly | Arg | Phe | Thr | Ile | Ser | Arg | Asn | Asp | Leu | Glu | Asp | Lys | Val | Phe | Leu |
| 65  |     |     |     |     | 70  |     |     |     |     | 75  |     |     |     |     | 80  |

```
            Gln  Met  Asn  Gly  Leu  Lys  Ala  Glu  Asp  Thr  Gly  Val  Tyr  Tyr  Cys  Ala
                           85                           90                           95

Thr  Arg  Tyr  Pro  Arg  Tyr  Ser  Glu  Met  Met  Gly  Gly  Val  Arg  Lys  His
                           100                          105                          110

Phe  Tyr  Met  Asp  Val  Trp  Gly  Lys  Gly  Thr  Thr  Val  Ser  Val  Ser  Ser
                           115                          120                          125
```

( 2 ) INFORMATION FOR SEQ ID NO:80:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:80:

```
            Leu  Glu  Glu  Ser  Gly  Gly  Gly  Leu  Val  Gln  Pro  Gly  Arg  Ser  Leu  Arg
            1                   5                            10                       15

Val  Ser  Cys  Glu  Ala  Ser  Gly  Phe  Thr  Phe  Ser  Ser  Tyr  Glu  Met  Asn
                           20                           25                           30

Trp  Val  Arg  Gln  Ala  Pro  Gly  Lys  Gly  Leu  Glu  Trp  Val  Ser  Gln  Ile
                           35                           40                           45

Ser  Ser  Ser  Gly  Ser  Arg  Thr  Tyr  Tyr  Ala  Asp  Ser  Val  Lys  Gly  Arg
                 50                           55                           60

Phe  Thr  Ile  Ser  Arg  Asp  Asn  Ala  Lys  Asn  Ser  Leu  Tyr  Leu  Glu  Met
            65                           70                           75                   80

Thr  Ser  Leu  Arg  Val  Asp  Asp  Thr  Ala  Val  Tyr  Tyr  Cys  Ala  Arg  Gly
                           85                           90                           95

Arg  Arg  Leu  Val  Thr  Phe  Gly  Gly  Val  Val  Ser  Gly  Gly  Asn  Ile  Trp
                           100                          105                          110

Gly  Gln  Gly  Thr  Met  Val  Thr  Val  Ser  Ser
                           115                          120
```

( 2 ) INFORMATION FOR SEQ ID NO:81:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:81:

```
            Leu  Glu  Gln  Ser  Gly  Gly  Gly  Val  Val  Gln  Pro  Gly  Arg  Ser  Leu  Arg
            1                   5                            10                       15

Leu  Ser  Cys  Ala  Gly  Ser  Gly  Phe  Asn  Phe  Ser  Asp  Asp  Thr  Met  His
                           20                           25                           30

Trp  Val  Arg  Gln  Ala  Pro  Gly  Lys  Gly  Leu  Glu  Trp  Val  Ala  Val  Ile
                           35                           40                           45

Ser  Tyr  Glu  Gly  Ser  Asp  Lys  Tyr  Tyr  Ala  Asp  Ser  Val  Lys  Gly  Arg
                 50                           55                           60

Phe  Thr  Ile  Ser  Arg  Asp  Asn  Ser  Glu  Asn  Thr  Leu  Tyr  Leu  Gln  Met
            65                           70                           75                   80

Asp  Ser  Leu  Arg  Ala  Asp  Asp  Thr  Ala  Leu  Tyr  Tyr  Cys  Ala  Arg  Asn
                           85                           90                           95

Thr  Arg  Glu  Asn  Ile  Glu  Ala  Asp  Gly  Thr  Ala  Tyr  Tyr  Ser  Tyr  Tyr
                           100                          105                          110

Met  Asp  Val  Trp  Gly  Lys  Gly  Thr  Thr  Val  Thr  Val  Ser  Ser
                           115                          120                          125
```

( 2 ) INFORMATION FOR SEQ ID NO:82:

( i ) SEQUENCE CHARACTERISTICS:
    ( A ) LENGTH: 107 amino acids
    ( B ) TYPE: amino acid
    ( D ) TOPOLOGY: linear ( i i ) MOLECULE TYPE: protein ( x i ) SEQUENCE DESCRIPTION: SEQ ID NO:82:

| Glu | Leu | Thr | Gln | Ser | Pro | Ser | Ser | Leu | Ser | Ala | Ser | Val | Gly | Asp | Arg |
|---|---|---|---|---|---|---|---|---|---|---|---|---|---|---|---|
| 1 | | | | 5 | | | | | 10 | | | | | 15 | |
| Val | Thr | Ile | Thr | Cys | Arg | Ala | Ser | Gln | Gly | Ile | Ser | Asn | Tyr | Leu | Ala |
| | | | 20 | | | | | 25 | | | | | 30 | | |
| Trp | Tyr | Gln | Gln | Lys | Pro | Gly | Lys | Val | Pro | Arg | Leu | Leu | Ile | Tyr | Ala |
| | | | 35 | | | | 40 | | | | | 45 | | | |
| Ala | Ser | Thr | Leu | Gln | Pro | Gly | Val | Pro | Ser | Arg | Phe | Ser | Gly | Ser | Gly |
| | 50 | | | | | 55 | | | | | 60 | | | | |
| Ser | Gly | Thr | Asp | Phe | Thr | Leu | Thr | Ile | Ser | Ser | Leu | Gln | Pro | Glu | Asp |
| 65 | | | | | 70 | | | | | 75 | | | | | 80 |
| Val | Ala | Thr | Tyr | Tyr | Cys | Gln | Lys | Tyr | Asn | Ser | Ala | Pro | Arg | Thr | Phe |
| | | | | 85 | | | | | 90 | | | | | 95 | |
| Gly | Gln | Gly | Thr | Lys | Val | Glu | Ile | Lys | Arg | Thr | | | | | |
| | | | 100 | | | | | 105 | | | | | | | |

( 2 ) INFORMATION FOR SEQ ID NO:83:

( i ) SEQUENCE CHARACTERISTICS:
    ( A ) LENGTH: 106 amino acids
    ( B ) TYPE: amino acid
    ( D ) TOPOLOGY: linear ( i i ) MOLECULE TYPE: protein ( x i ) SEQUENCE DESCRIPTION: SEQ ID NO:83:

| Glu | Leu | Thr | Gln | Ser | Pro | Ser | Ser | Leu | Ser | Ala | Ser | Ile | Gly | Asp | Arg |
|---|---|---|---|---|---|---|---|---|---|---|---|---|---|---|---|
| 1 | | | | 5 | | | | | 10 | | | | | 15 | |
| Val | Thr | Ile | Thr | Cys | Arg | Ala | Ser | Gln | Gly | Ile | Asn | Asn | Tyr | Leu | Ala |
| | | | 20 | | | | | 25 | | | | | 30 | | |
| Trp | Tyr | Gln | Gln | Arg | Pro | Gly | Lys | Val | Pro | Arg | Leu | Leu | Ile | Tyr | Ala |
| | | | 35 | | | | 40 | | | | | 45 | | | |
| Ala | Ser | Thr | Leu | Gln | Ser | Gly | Val | Pro | Thr | Arg | Phe | Ser | Gly | Ser | Gly |
| | 50 | | | | | 55 | | | | | 60 | | | | |
| Ser | Gly | Thr | Asp | Phe | Thr | Leu | Thr | Ile | Ser | Ser | Leu | Gln | Pro | Glu | Asp |
| 65 | | | | | 70 | | | | | 75 | | | | | 80 |
| Val | Ala | Thr | Tyr | Tyr | Cys | Gln | Lys | Tyr | Asn | Ser | Val | Pro | Arg | Thr | Phe |
| | | | | 85 | | | | | 90 | | | | | 95 | |
| Gly | Gly | Gly | Thr | Lys | Val | Glu | Ile | Lys | Arg | | | | | | |
| | | | 100 | | | | | 105 | | | | | | | |

( 2 ) INFORMATION FOR SEQ ID NO:84:

( i ) SEQUENCE CHARACTERISTICS:
    ( A ) LENGTH: 107 amino acids
    ( B ) TYPE: amino acid
    ( D ) TOPOLOGY: linear ( i i ) MOLECULE TYPE: protein ( x i ) SEQUENCE DESCRIPTION: SEQ ID NO:84:

```
Glu  Leu  Thr  Gln  Ser  Pro  Ser  Ser  Leu  Ser  Ala  Ser  Val  Gly  Asp  Arg
 1              5                    10                      15

Val  Thr  Ile  Thr  Cys  Arg  Ala  Ser  Gln  Gly  Ile  Ser  Asn  Tyr  Leu  Ala
               20                   25                      30

Trp  Tyr  Gln  Gln  Lys  Pro  Gly  Lys  Val  Pro  Lys  Leu  Leu  Ile  Tyr  Ala
               35                   40                      45

Ala  Ser  Thr  Leu  Gln  Ser  Gly  Val  Pro  Ser  Arg  Phe  Ser  Gly  Ser  Gly
      50                   55                        60

Ser  Gly  Thr  Asp  Phe  Thr  Leu  Thr  Ile  Ser  Ser  Leu  Gln  Pro  Glu  Asp
 65                        70                   75                            80

Val  Ala  Thr  Tyr  Tyr  Cys  Gln  Lys  Tyr  Asn  Ser  Ala  Pro  Arg  Thr  Phe
                    85                   90                            95

Gly  Gln  Gly  Thr  Lys  Val  Glu  Ile  Lys  Arg  Thr
               100                   105
```

( 2 ) INFORMATION FOR SEQ ID NO:85:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:85:

```
Glu  Leu  Thr  Gln  Ser  Pro  Ser  Ser  Leu  Ser  Ala  Ser  Ile  Gly  Asp  Arg
 1              5                    10                      15

Val  Thr  Ile  Thr  Cys  Arg  Ala  Ser  Gln  Gly  Ile  Asn  Asn  Tyr  Leu  Ala
               20                   25                      30

Trp  Tyr  Gln  Gln  Arg  Pro  Gly  Lys  Ala  Pro  Asn  Leu  Leu  Ile  Tyr  Ala
               35                   40                      45

Ala  Ser  Thr  Leu  Gln  Ser  Gly  Val  Pro  Pro  Arg  Phe  Ser  Gly  Ser  Gly
      50                   55                        60

Ser  Gly  Thr  Asp  Phe  Thr  Leu  Thr  Ile  Ser  Ser  Leu  Gln  Pro  Glu  Asp
 65                        70                   75                            80

Val  Ala  Thr  Tyr  Tyr  Cys  Gln  Lys  Tyr  Asn  Ser  Val  Pro  His  Thr  Phe
                    85                   90                            95

Gly  Gly  Gly  Thr  Lys  Val  Glu  Ile  Lys  Arg
               100                   105
```

( 2 ) INFORMATION FOR SEQ ID NO:86:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:86:

```
Glu  Leu  Thr  Gln  Ser  Pro  Gly  Thr  Leu  Ser  Leu  Ser  Pro  Gly  Glu  Arg
 1              5                    10                      15

Ala  Thr  Leu  Ser  Cys  Arg  Ala  Ser  Gln  Ser  Val  Ile  Ser  Asn  Tyr  Leu
               20                   25                      30

Ala  Trp  Tyr  Gln  Gln  Lys  Pro  Gly  Gln  Ala  Pro  Arg  Leu  Leu  Ile  Tyr
               35                   40                      45

Gly  Val  Ser  Asn  Arg  Ala  Thr  Gly  Ile  Pro  Asp  Arg  Phe  Ser  Gly  Ser
      50                   55                        60

Gly  Ser  Gly  Thr  Asp  Phe  Thr  Leu  Thr  Ile  Ser  Arg  Leu  Glu  Pro  Glu
 65                        70                   75                            80
```

```
            Asp  Phe  Ala  Val  Tyr  Ser  Cys  Gln  Gln  Tyr  Gly  Thr  Ser  Pro  Trp  Thr
                           8 5                      9 0                     9 5

Phe  Gly  Gln  Gly  Thr  Lys  Val  Glu  Ile  Lys  Arg  Thr
                           1 0 0                    1 0 5
```

( 2 ) INFORMATION FOR SEQ ID NO:87:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:87:

```
            Glu  Leu  Thr  Gln  Ser  Pro  Gly  Thr  Leu  Ser  Leu  Ser  Pro  Gly  Glu  Arg
            1                  5                    1 0                     1 5

Ala  Thr  Leu  Ser  Cys  Arg  Ala  Ser  Gln  Ser  Val  Ser  Asn  Asn  Tyr  Leu
                           2 0                      2 5                     3 0

Ala  Trp  Tyr  Gln  Gln  Arg  Pro  Gly  Gln  Ala  Pro  Arg  Leu  Leu  Ile  Tyr
                           3 5                      4 0                     4 5

Gly  Ala  Ser  Asn  Arg  Ala  Thr  Gly  Ile  Pro  Asp  Arg  Phe  Ser  Gly  Ser
            5 0                               5 5                     6 0

Gly  Ser  Gly  Thr  Ala  Phe  Thr  Leu  Thr  Ile  Ser  Ser  Leu  Gln  Pro  Glu
            6 5                               7 0                     7 5                    8 0

Asp  Val  Ala  Ile  Tyr  Tyr  Cys  Gln  Gln  Tyr  His  Ser  Ser  Pro  Tyr  Thr
                           8 5                      9 0                     9 5

Phe  Gly  Gln  Gly  Thr  Lys  Leu  Glu  Ile  Lys  Arg
                           1 0 0                    1 0 5
```

( 2 ) INFORMATION FOR SEQ ID NO:88:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:88:

```
            Glu  Leu  Thr  Gln  Ser  Pro  Gly  Thr  Leu  Ser  Leu  Ser  Pro  Gly  Glu  Arg
            1                  5                    1 0                     1 5

Ala  Thr  Leu  Ser  Cys  Arg  Ala  Ser  His  Arg  Val  Asn  Asn  Asn  Phe  Leu
                           2 0                      2 5                     3 0

Ala  Trp  Tyr  Gln  Gln  Lys  Pro  Gln  Ala  Pro  Arg  Leu  Leu  Ile  Ser  Gly
                           3 5                      4 0                     4 5

Ala  Ser  Thr  Arg  Ala  Thr  Gly  Ile  Pro  Asp  Arg  Phe  Ser  Gly  Ser  Gly
            5 0                               5 5                     6 0

Ser  Gly  Thr  Asp  Phe  Thr  Leu  Thr  Ile  Ser  Arg  Leu  Glu  Pro  Asp  Asp
            6 5                               7 0                     7 5                    8 0

Phe  Ala  Val  Tyr  Tyr  Cys  Gln  Gln  Tyr  Gly  Asp  Ser  Pro  Leu  Tyr  Ser
                           8 5                      9 0                     9 5

Phe  Gly  Gln  Gly  Thr  Lys  Leu  Glu  Ile  Lys  Arg  Thr
                           1 0 0                    1 0 5
```

( 2 ) INFORMATION FOR SEQ ID NO:89:

( i ) SEQUENCE CHARACTERISTICS:
        ( A ) LENGTH: 105 amino acids
        ( B ) TYPE: amino acid
        ( D ) TOPOLOGY: linear ( i i ) MOLECULE TYPE: protein ( x i ) SEQUENCE DESCRIPTION: SEQ ID NO:89:

| Glu | Leu | Thr | Gln | Ser | Pro | Ala | Ser | Val | Ser | Ala | Ser | Val | Gly | Asp | Thr |
|---|---|---|---|---|---|---|---|---|---|---|---|---|---|---|---|
| 1 | | | | 5 | | | | | 10 | | | | | 15 | |
| Val | Thr | Ile | Thr | Cys | Arg | Ala | Ser | Gln | Asp | Ile | His | Asn | Trp | Leu | Ala |
| | | | 20 | | | | | 25 | | | | | 30 | | |
| Trp | Tyr | Gln | Gln | Gln | Pro | Gly | Lys | Ala | Pro | Lys | Leu | Leu | Ile | Tyr | Ala |
| | | | 35 | | | | 40 | | | | | 45 | | | |
| Ala | Ser | Ser | Leu | Gln | Ser | Gly | Val | Pro | Ser | Arg | Phe | Ser | Gly | Arg | Gly |
| | 50 | | | | | 55 | | | | | 60 | | | | |
| Ser | Gly | Thr | Asp | Phe | Thr | Leu | Thr | Ile | Ser | Ser | Leu | Gln | Pro | Glu | Asp |
| 65 | | | | | 70 | | | | | 75 | | | | | 80 |
| Phe | Ala | Thr | Tyr | Tyr | Cys | Gln | Gln | Gly | Asn | Ser | Phe | Pro | Lys | Phe | Gly |
| | | | | 85 | | | | | 90 | | | | | 95 | |
| Pro | Gly | Thr | Val | Val | Asp | Ile | Lys | Arg | | | | | | | |
| | | | 100 | | | | | 105 | | | | | | | |

( 2 ) INFORMATION FOR SEQ ID NO:90:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:90:

| Glu | Leu | Thr | Gln | Ser | Pro | Gly | Thr | Leu | Ser | Leu | Ser | Pro | Gly | Glu | Arg |
|---|---|---|---|---|---|---|---|---|---|---|---|---|---|---|---|
| 1 | | | | 5 | | | | | 10 | | | | | 15 | |
| Ala | Thr | Leu | Ser | Cys | Arg | Ala | Ser | Gln | Ser | Leu | Ser | Asn | Asn | Tyr | Leu |
| | | | 20 | | | | | 25 | | | | | 30 | | |
| Ala | Trp | Tyr | Gln | Gln | Lys | Pro | Gly | Gln | Ala | Pro | Arg | Leu | Leu | Ile | Tyr |
| | | | 35 | | | | 40 | | | | | 45 | | | |
| Gly | Ser | Ser | Thr | Arg | Gly | Thr | Gly | Ile | Pro | Asp | Arg | Phe | Ser | Gly | Gly |
| | 50 | | | | | 55 | | | | | 60 | | | | |
| Gly | Ser | Gly | Thr | Asp | Phe | Thr | Leu | Thr | Ile | Ser | Arg | Leu | Glu | Pro | Glu |
| 65 | | | | | 70 | | | | | 75 | | | | | 80 |
| Asp | Phe | Ala | Val | Tyr | Tyr | Cys | Gln | His | Tyr | Gly | Asn | Ser | Val | Tyr | Thr |
| | | | | 85 | | | | | 90 | | | | | 95 | |
| Phe | Gly | Gln | Gly | Thr | Lys | Leu | Glu | Ile | Lys | Arg | | | | | |
| | | | 100 | | | | | 105 | | | | | | | |

( 2 ) INFORMATION FOR SEQ ID NO:91:

( i ) SEQUENCE CHARACTERISTICS:
        ( A ) LENGTH: 104 amino acids
        ( B ) TYPE: amino acid
        ( D ) TOPOLOGY: linear ( i i ) MOLECULE TYPE: protein ( x i ) SEQUENCE DESCRIPTION: SEQ ID NO:91:

| Gln | Ser | Pro | Asp | Thr | Leu | Ser | Leu | Asn | Pro | Gly | Glu | Arg | Ala | Thr | Leu |
|---|---|---|---|---|---|---|---|---|---|---|---|---|---|---|---|
| 1 | | | | 5 | | | | | 10 | | | | | 15 | |
| Ser | Cys | Arg | Ala | Ser | His | Arg | Ile | Ser | Ser | Lys | Arg | Leu | Ala | Trp | Tyr |
| | | | 20 | | | | | 25 | | | | | 30 | | |
| Gln | His | Lys | Arg | Gly | Gln | Ala | Pro | Arg | Leu | Leu | Ile | Tyr | Val | Cys | Pro |
| | | | 35 | | | | 40 | | | | | 45 | | | |

```
            Asn  Arg  Ala  Gly  Gly  Val  Pro  Asp  Arg  Phe  Ser  Gly  Ser  Gly
            50                        55                       60

Thr  Asp  Phe  Thr  Leu  Thr  Tyr  Ser  Arg  Leu  Glu  Pro  Glu  Asp  Phe  Ala
            65                        70                       75                        80

Met  Tyr  Tyr  Cys  Gln  Tyr  Tyr  Gly  Gly  Ser  Ser  Tyr  Thr  Phe  Gly  Gln
                                 85                        90                        95

Gly  Thr  Lys  Val  Glu  Ile  Thr  Arg
                           100
```

( 2 ) INFORMATION FOR SEQ ID NO:92:

( i ) SEQUENCE CHARACTERISTICS:
        ( A ) LENGTH: 104 amino acids
        ( B ) TYPE: amino acid
        ( D ) TOPOLOGY: linear ( i i ) MOLECULE TYPE: protein ( x i ) SEQUENCE DESCRIPTION: SEQ ID NO:92:

```
            Gln  Ser  Pro  Ser  His  Leu  Ser  Leu  Ser  Pro  Gly  Glu  Arg  Ala  Ile  Leu
            1                   5                        10                       15

Ser  Cys  Arg  Ala  Ser  Gln  Arg  Val  Ser  Ala  Pro  Tyr  Leu  Ala  Trp  Tyr
                            20                        25                       30

Gln  Gln  Arg  Pro  Gly  Gln  Ala  Pro  Arg  Leu  Val  Ile  Tyr  Gly  Ala  Ser
                            35                        40                       45

Thr  Arg  Ala  Thr  Asp  Ile  Pro  Asp  Arg  Phe  Ser  Gly  Ser  Gly  Ser  Gly
                            50                        55                       60

Thr  Asp  Phe  Thr  Leu  Thr  Ile  Ser  Arg  Leu  Glu  Pro  Glu  Asp  Phe  Ala
            65                        70                       75                        80

Ile  Tyr  Tyr  Cys  Gln  Val  Tyr  Gly  Gln  Ser  Pro  Val  Leu  Phe  Gly  Gln
                                 85                        90                       95

Gly  Thr  Lys  Leu  Glu  Met  Lys  Arg
                           100
```

( 2 ) INFORMATION FOR SEQ ID NO:93:

( i ) SEQUENCE CHARACTERISTICS:
        ( A ) LENGTH: 105 amino acids
        ( B ) TYPE: amino acid
        ( D ) TOPOLOGY: linear ( i i ) MOLECULE TYPE: protein ( x i ) SEQUENCE DESCRIPTION: SEQ ID NO:93:

```
            Gln  Ser  Pro  Gly  Thr  Leu  Ser  Leu  Ser  Pro  Gly  Asp  Arg  Ala  Thr  Leu
            1                   5                        10                       15

Ser  Cys  Arg  Ala  Ser  Gln  Ser  Leu  Ser  Ser  Ser  Phe  Leu  Ala  Trp  Tyr
                            20                        25                       30

Gln  Gln  Lys  Pro  Gly  Gln  Ala  Pro  Arg  Leu  Leu  Ile  Tyr  Ser  Ala  Ser
                            35                        40                       45

Met  Arg  Ala  Thr  Gly  Ile  Pro  Asp  Arg  Phe  Arg  Gly  Ser  Val  Ser  Gly
                            50                        55                       60

Thr  Asp  Phe  Thr  Leu  Thr  Ile  Thr  Arg  Leu  Glu  Pro  Glu  Asp  Phe  Ala
            65                        70                       75                        80

Val  Tyr  Tyr  Cys  Gln  Arg  Phe  Gly  Thr  Ser  Pro  Leu  Tyr  Thr  Phe  Gly
                                 85                        90                       95

Gln  Gly  Thr  Lys  Leu  Glu  Met  Lys  Arg
                            100                       105
```

( 2 ) INFORMATION FOR SEQ ID NO:94:

( i ) SEQUENCE CHARACTERISTICS:
  ( A ) LENGTH: 104 amino acids
  ( B ) TYPE: amino acid
  ( D ) TOPOLOGY: linear ( i i ) MOLECULE TYPE: protein ( x i ) SEQUENCE DESCRIPTION: SEQ ID NO:94:

Gln Ser Pro Gly Thr Leu Ser Leu Ser Pro Gly Glu Arg Ala Thr Leu
1               5                   10                  15

Ser Cys Arg Ala Ser Gln Ser Phe Ser Ser Asn Phe Leu Ala Trp Tyr
            20                  25                  30

Gln Gln Lys Pro Gly Gln Ala Pro Arg Leu Leu Ile Tyr Val His Pro
        35                  40                  45

Asn Arg Ala Thr Gly Val Pro Asp Arg Phe Ser Gly Ser Gly Ser Gly
    50                  55                  60

Thr Asp Phe Thr Leu Thr Ile Arg Arg Leu Glu Pro Glu Asp Phe Ala
65                  70                  75                  80

Val Tyr Tyr Cys Gln Gln Tyr Gly Ala Ser Leu Val Ser Phe Gly Pro
                85                  90                  95

Gly Thr Lys Val His Ile Lys Arg
            100

( 2 ) INFORMATION FOR SEQ ID NO:95:

( i ) SEQUENCE CHARACTERISTICS:
    ( A ) LENGTH: 108 amino acids
    ( B ) TYPE: amino acid
    ( D ) TOPOLOGY: linear ( i i ) MOLECULE TYPE: protein ( x i ) SEQUENCE DESCRIPTION: SEQ ID NO:95:

Glu Leu Thr Gln Ser Pro Gly Thr Leu Ser Leu Ser Pro Gly Glu Arg
1               5                   10                  15

Ala Thr Phe Ser Cys Arg Ser Ser His Ser Ile Arg Ser Arg Arg Val
            20                  25                  30

Ala Trp Tyr Gln His Lys Pro Gly Gln Ala Pro Arg Leu Val Ile His
        35                  40                  45

Gly Val Ser Asn Arg Ala Ser Gly Ile Ser Asp Arg Phe Ser Gly Ser
    50                  55                  60

Gly Ser Gly Thr Asp Phe Thr Leu Thr Ile Thr Arg Val Glu Pro Glu
65                  70                  75                  80

Asp Phe Ala Leu Tyr Tyr Cys Gln Val Tyr Gly Ala Ser Ser Tyr Thr
                85                  90                  95

Phe Gly Gln Gly Thr Lys Leu Glu Arg Lys Arg Thr
            100                 105

( 2 ) INFORMATION FOR SEQ ID NO:96:

( i ) SEQUENCE CHARACTERISTICS:
    ( A ) LENGTH: 108 amino acids
    ( B ) TYPE: amino acid
    ( D ) TOPOLOGY: linear ( i i ) MOLECULE TYPE: protein ( x i ) SEQUENCE DESCRIPTION: SEQ ID NO:96:

Glu Leu Thr Gln Ser Pro Gly Thr Leu Ser Leu Thr Pro Gly Glu Arg
1               5                   10                  15

-continued

```
            Ala  Thr  Leu  Ser  Cys  Arg  Thr  Ser  His  Ser  Ile  Arg  Ser  Arg  Arg  Leu
                           20                       25                      30

Ala  Trp  Tyr  Gln  Val  Lys  Gly  Gly  Gln  Ala  Pro  Arg  Leu  Leu  Ile  Tyr
                           35                       40                      45

Gly  Val  Ser  Asn  Arg  Ala  Gly  Ile  Pro  Asp  Arg  Phe  Ser  Gly  Ser
                           50                       55                      60

Gly  Ser  Gly  Thr  Asp  Phe  Thr  Leu  Thr  Ile  Ser  Arg  Leu  Glu  Pro  Glu
            65                            70                      75                      80

Asp  Phe  Ala  Val  Tyr  Tyr  Cys  Gln  Gln  Tyr  Gly  Ser  Ser  Arg  Tyr  Thr
                                     85                       90                      95

Phe  Gly  Gln  Gly  Thr  Lys  Leu  Glu  Ile  Lys  Arg  Thr
                           100                      105
```

( 2 ) INFORMATION FOR SEQ ID NO:97:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:97:

```
            Glu  Leu  Thr  Gln  Ala  Pro  Gly  Thr  Leu  Ser  Leu  Ser  Pro  Gly  Glu  Arg
            1                        5                       10                      15

Ala  Thr  Phe  Ser  Cys  Arg  Ser  Ser  His  Ser  Ile  Arg  Ser  Arg  Arg  Val
                           20                       25                      30

Arg  Trp  Tyr  Gln  His  Lys  Pro  Gly  Gln  Ala  Pro  Arg  Leu  Val  Ile  His
                           35                       40                      45

Gly  Val  Ser  Asn  Arg  Ala  Ser  Gly  Ile  Ser  Asp  Arg  Phe  Ser  Gly  Ser
                           50                       55                      60

Gly  Ser  Gly  Thr  Asp  Phe  Thr  Leu  Thr  Ile  Thr  Arg  Val  Glu  Pro  Glu
            65                            70                      75                      80

Asp  Phe  Ala  Leu  Tyr  Tyr  Cys  Gln  Val  Tyr  Gly  Ala  Ser  Ser  Tyr  Thr
                                     85                       90                      95

Phe  Gly  Gln  Gly  Thr  Lys  Leu  Glu  Arg  Lys  Arg
                           100                      105
```

( 2 ) INFORMATION FOR SEQ ID NO:98:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:98:

```
            Glu  Leu  Thr  Gln  Ala  Pro  Gly  Thr  Leu  Ser  Leu  Ser  Pro  Gly  Asp  Arg
            1                        5                       10                      15

Ala  Thr  Phe  Ser  Cys  Arg  Ser  Ser  His  Asn  Ile  Arg  Ser  Arg  Arg  Val
                           20                       25                      30

Ala  Trp  Tyr  Gln  His  Lys  Pro  Gly  Gln  Ala  Pro  Arg  Leu  Val  Ile  His
                           35                       40                      45

Gly  Val  Ser  Asn  Arg  Ala  Ser  Gly  Ile  Ser  Asp  Arg  Phe  Ser  Gly  Ser
                           50                       55                      60

Gly  Ser  Gly  Thr  Asp  Phe  Thr  Leu  Thr  Ile  Thr  Arg  Leu  Glu  Pro  Glu
            65                            70                      75                      80

Asp  Phe  Ala  Leu  Tyr  Tyr  Cys  Gln  Val  Tyr  Gly  Ala  Ser  Ser  Tyr  Thr
                                     85                       90                      95
```

Phe  Gly  Gln  Gly  Thr  Lys  Leu  Asp  Phe  Lys  Arg  Thr
                               100                      105

( 2 ) INFORMATION FOR SEQ ID NO:99:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:99:

Glu  Leu  Thr  Gln  Ser  Pro  Gly  Thr  Leu  Ser  Leu  Ser  Pro  Gly  Glu  Arg
        1                    5                        10                       15

Ala  Thr  Leu  Ser  Cys  Arg  Ala  Gly  Gln  Ser  Ile  Ser  Ser  Asn  Tyr  Leu
                       20                        25                       30

Ala  Trp  Tyr  Gln  Gln  Lys  Pro  Gly  Gln  Ala  Pro  Arg  Leu  Leu  Ile  Tyr
                  35                        40                       45

Gly  Ala  Ser  Asn  Arg  Ala  Thr  Gly  Ile  Pro  Asp  Arg  Phe  Ser  Gly  Ser
             50                        55                       60

Gly  Ser  Gly  Thr  Asp  Phe  Thr  Leu  Ser  Ile  Ser  Arg  Leu  Glu  Pro  Glu
        65                        70                       75                       80

Asp  Phe  Ala  Val  Tyr  Tyr  Cys  Gln  Gln  Tyr  Gly  Thr  Ser  Pro  Tyr  Thr
                            85                        90                       95

Phe  Gly  Gln  Gly  Thr  Gln  Leu  Asp  Ile  Lys  Arg  Thr
                            100                      105

( 2 ) INFORMATION FOR SEQ ID NO:100:

( i ) SEQUENCE CHARACTERISTICS:
        ( A ) LENGTH: 104 amino acids
        ( B ) TYPE: amino acid
        ( D ) TOPOLOGY: linear ( i i ) MOLECULE TYPE: protein ( x i ) SEQUENCE DESCRIPTION: SEQ ID NO:100:

Gln  Ser  Pro  Gly  Thr  Leu  Ser  Leu  Ser  Pro  Gly  Glu  Arg  Ala  Thr  Leu
        1                    5                        10                       15

Ser  Cys  Arg  Ala  Ser  Gln  Ser  Leu  Ser  Asn  Asn  Tyr  Leu  Ala  Trp  Tyr
                       20                        25                       30

Gln  Gln  Lys  Pro  Gly  Gln  Ala  Pro  Arg  Leu  Leu  Ile  Tyr  Gly  Ser  Ser
                  35                        40                       45

Thr  Arg  Ala  Thr  Gly  Ile  Pro  Asp  Arg  Phe  Ser  Gly  Gly  Gly  Ser  Gly
             50                        55                       60

Thr  Asp  Phe  Thr  Leu  Thr  Ile  Ser  Arg  Leu  Glu  Pro  Glu  Asp  Phe  Ala
        65                        70                       75                       80

Val  Tyr  Tyr  Cys  Gln  Gln  Tyr  Gly  Asn  Ser  Val  Tyr  Thr  Phe  Gly  Gln
                            85                        90                       95

Gly  Thr  Lys  Leu  Glu  Ile  Lys  Arg
                            100

( 2 ) INFORMATION FOR SEQ ID NO:101:

( i ) SEQUENCE CHARACTERISTICS:
        ( A ) LENGTH: 106 amino acids
        ( B ) TYPE: amino acid
        ( D ) TOPOLOGY: linear ( i i ) MOLECULE TYPE: protein ( x i ) SEQUENCE DESCRIPTION: SEQ ID NO:101:

| Glu | Leu | Thr | Gln | Ser | Pro | Ser | Ser | Leu | Ser | Ala | Ser | Val | Gly | Asp | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Thr | Ile | Thr | Cys | Arg | Thr | Ser | Gln | Gly | Ile | Ser | Asn | Tyr | Leu | Ala |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Trp | Tyr | Gln | Gln | Lys | Pro | Gly | Lys | Val | Pro | Lys | Leu | Leu | Ile | Tyr | Gly |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Ser | Thr | Leu | Gln | Ser | Gly | Gly | Pro | Ser | Arg | Phe | Ser | Gly | Ser | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Gly | Thr | Asp | Phe | Thr | Leu | Thr | Ile | Asn | Ser | Leu | Gln | Pro | Glu | Asp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Val | Ala | Thr | Tyr | Ser | Cys | Gln | Asn | Tyr | Asp | Ser | Ala | Pro | Trp | Thr | Phe |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gly | Gln | Gly | Thr | Lys | Val | Asp | Ile | Lys | Arg |
|-----|-----|-----|-----|-----|-----|-----|-----|-----|-----|
|     |     |     | 100 |     |     |     |     | 105 |     |

( 2 ) INFORMATION FOR SEQ ID NO:102:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: protein ( x i ) SEQUENCE DESCRIPTION: SEQ ID NO:102:

| Glu | Leu | Thr | Gln | Ser | Pro | Ser | Ser | Leu | Ser | Ala | Ser | Val | Gly | Asp | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Thr | Ile | Thr | Cys | Arg | Ala | Ser | Gln | Ser | Ile | Ser | Asn | Tyr | Leu | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Trp | Tyr | Gln | Gln | Lys | Pro | Gly | Lys | Ala | Pro | Lys | Leu | Leu | Ile | Tyr | Ala |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Ser | Ser | Leu | Gln | Arg | Gly | Val | Pro | Ser | Arg | Phe | Ser | Gly | Ser | Gly |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Gly | Thr | Asp | Phe | Thr | Leu | Ser | Ile | Ser | Ser | Leu | Gln | Pro | Glu | Asp |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Phe | Ala | Thr | Tyr | Tyr | Cys | Gln | Gln | Ser | Tyr | Ser | Ile | Pro | Pro | Leu | Thr |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Phe | Gly | Gly | Gly | Thr | Lys | Val | Glu | Ile | Lys | Arg | Thr |
|-----|-----|-----|-----|-----|-----|-----|-----|-----|-----|-----|-----|
|     |     |     | 100 |     |     |     |     | 105 |     |     |     |

( 2 ) INFORMATION FOR SEQ ID NO:103:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:103:

| Glu | Leu | Thr | Gln | Ser | Pro | Ser | Ser | Leu | Ser | Ala | Ser | Val | Gly | Asp | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Thr | Ile | Thr | Cys | Arg | Ala | Ser | Gln | Asn | Ile | Asn | Asn | Tyr | Leu | Asn |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Trp | Tyr | Gln | Gln | Lys | Pro | Gly | Glu | Ala | Pro | Lys | Leu | Leu | Ile | His | Thr |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Phe | Asn | Leu | Gln | Ser | Gly | Val | Pro | Ser | Arg | Phe | Ser | Gly | Thr | Ala |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

-continued

Ser Gly Thr Glu Phe Thr Leu Thr Ile Arg Ser Leu Gln Pro Glu Asp
65                  70                  75                  80

Phe Ala Thr Tyr Tyr Cys Gln Gln Ser Tyr Ser Thr Pro Tyr Thr Phe
                85                  90                  95

Gly Gln Gly Thr Lys Val Glu Ile Lys Arg Thr
            100             105

( 2 ) INFORMATION FOR SEQ ID NO:104:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:104:

Glu Leu Thr Gln Ser Pro Ser Ser Leu Ser Ala Ser Val Gly Asp Arg
1               5                   10                  15

Val Thr Ile Thr Cys Arg Ala Ser Gln Ser Ile Ser Ser Tyr Leu Asn
            20                  25                  30

Trp Tyr Gln Gln Lys Pro Gly Lys Ala Pro Lys Leu Leu Ile Tyr Ala
            35                  40                  45

Ala Ser Ser Leu Gln Ser Gly Val Pro Ser Arg Phe Ser Gly Ser Gly
        50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Ser Thr Pro Tyr Thr Phe
                85                  90                  95

Gly Gln Gly Thr Lys Leu Glu Ile Lys Arg Thr
            100             105

( 2 ) INFORMATION FOR SEQ ID NO:105:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:105:

Glu Leu Thr Gln Ser Pro Ser Ser Leu Ser Ala Ser Val Gly Asp Arg
1               5                   10                  15

Val Thr Ile Thr Cys Arg Ala Ser Gln Ser Ile Ser Ser Tyr Leu Asn
            20                  25                  30

Trp Tyr Gln Gln Lys Pro Gly Lys Ala Pro Lys Leu Leu Ile Tyr Ala
            35                  40                  45

Ala Ser Ser Leu Gln Ser Gly Val Pro Ser Arg Phe Ser Gly Ser Gly
        50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Ser Thr Pro Gln Thr Phe
                85                  90                  95

Gly Gln Gly Thr Lys Leu Glu Ile Lys Arg Thr
            100             105

( 2 ) INFORMATION FOR SEQ ID NO:106:

( i ) SEQUENCE CHARACTERISTICS:
        ( A ) LENGTH: 104 amino acids ( B ) TYPE: amino acid
( D ) TOPOLOGY: linear ( i i ) MOLECULE TYPE: protein ( x i ) SEQUENCE DESCRIPTION: SEQ ID NO:106:

| Gln | Ser | Pro | Ser | Ser | Leu | Ser | Ala | Ser | Val | Gly | Asp | Arg | Val | Thr | Ile |
|---|---|---|---|---|---|---|---|---|---|---|---|---|---|---|---|
| 1 | | | | 5 | | | | | 10 | | | | | 15 | |

| Thr | Cys | Arg | Ala | Ser | Gln | Thr | Ile | Ser | Ser | Tyr | Leu | Asn | Trp | Tyr | Gln |
|---|---|---|---|---|---|---|---|---|---|---|---|---|---|---|---|
| | | | 20 | | | | | 25 | | | | | 30 | | |

| Gln | Lys | Pro | Gly | Lys | Ala | Pro | Lys | Leu | Leu | Ile | Tyr | Ala | Ala | Ser | Ser |
|---|---|---|---|---|---|---|---|---|---|---|---|---|---|---|---|
| | | 35 | | | | | 40 | | | | | 45 | | | |

| Leu | Gln | Ser | Gly | Val | Pro | Ser | Arg | Phe | Ser | Gly | Gly | Ser | Gly | Thr |
|---|---|---|---|---|---|---|---|---|---|---|---|---|---|---|
| | 50 | | | | | 55 | | | | | 60 | | | |

| Asp | Phe | Thr | Leu | Thr | Ile | Ser | Ser | Leu | Gln | Pro | Glu | Asp | Phe | Ala | Thr |
|---|---|---|---|---|---|---|---|---|---|---|---|---|---|---|---|
| 65 | | | | | 70 | | | | | 75 | | | | | 80 |

| Tyr | Tyr | Cys | Gln | Gln | Ser | Tyr | Ser | Thr | Pro | Tyr | Thr | Phe | Gly | Gln | Gly |
|---|---|---|---|---|---|---|---|---|---|---|---|---|---|---|---|
| | | | | 85 | | | | | 90 | | | | | 95 | |

| Thr | Lys | Leu | Glu | Ile | Lys | Arg | Thr |
|---|---|---|---|---|---|---|---|
| | | | 100 | | | | |

( 2 ) INFORMATION FOR SEQ ID NO:107:

( i ) SEQUENCE CHARACTERISTICS:
( A ) LENGTH: 107 amino acids
( B ) TYPE: amino acid
( D ) TOPOLOGY: linear ( i i ) MOLECULE TYPE: protein ( x i ) SEQUENCE DESCRIPTION: SEQ ID NO:107:

| Glu | Leu | Thr | Gln | Ser | Pro | Ser | Ser | Leu | Ser | Ala | Ser | Val | Gly | Asp | Arg |
|---|---|---|---|---|---|---|---|---|---|---|---|---|---|---|---|
| 1 | | | | 5 | | | | | 10 | | | | | 15 | |

| Val | Thr | Ile | Thr | Cys | Gln | Ala | Ser | Gln | Asp | Ile | Arg | Asn | Tyr | Leu | Asn |
|---|---|---|---|---|---|---|---|---|---|---|---|---|---|---|---|
| | | | 20 | | | | | 25 | | | | | 30 | | |

| Trp | Tyr | Gln | Gln | Lys | Pro | Gly | Lys | Ala | Pro | Lys | Leu | Leu | Ile | Tyr | Asp |
|---|---|---|---|---|---|---|---|---|---|---|---|---|---|---|---|
| | | 35 | | | | | 40 | | | | | 45 | | | |

| Ala | Ser | Asn | Ser | Glu | Thr | Gly | Val | Pro | Ser | Arg | Phe | Ser | Gly | Ser | Gly |
|---|---|---|---|---|---|---|---|---|---|---|---|---|---|---|---|
| | 50 | | | | | 55 | | | | | 60 | | | | |

| Ser | Gly | Arg | Asp | Phe | Thr | Phe | Thr | Ile | Ser | Ser | Leu | Gln | Pro | Glu | Asp |
|---|---|---|---|---|---|---|---|---|---|---|---|---|---|---|---|
| 65 | | | | | 70 | | | | | 75 | | | | | 80 |

| Val | Ala | Thr | Tyr | Tyr | Cys | Gln | Gln | His | Gln | Asn | Val | Pro | Leu | Thr | Phe |
|---|---|---|---|---|---|---|---|---|---|---|---|---|---|---|---|
| | | | | 85 | | | | | 90 | | | | | 95 | |

| Gly | Gly | Gly | Thr | Lys | Val | Glu | Ile | Lys | Arg | Thr |
|---|---|---|---|---|---|---|---|---|---|---|
| | | | 100 | | | | | 105 | | |

( 2 ) INFORMATION FOR SEQ ID NO:108:

( i ) SEQUENCE CHARACTERISTICS:
( A ) LENGTH: 107 amino acids
( B ) TYPE: amino acid
( D ) TOPOLOGY: linear ( i i ) MOLECULE TYPE: protein ( x i ) SEQUENCE DESCRIPTION: SEQ ID NO:108:

| Glu | Leu | Thr | Gln | Ser | Pro | Ser | Ser | Leu | Ser | Ala | Ser | Val | Gly | Asp | Arg |
|---|---|---|---|---|---|---|---|---|---|---|---|---|---|---|---|
| 1 | | | | 5 | | | | | 10 | | | | | 15 | |

| Val | Thr | Ile | Thr | Cys | Gln | Ala | Ser | Gln | Asp | Ile | Ser | Asn | His | Leu | Asn |
|---|---|---|---|---|---|---|---|---|---|---|---|---|---|---|---|
| | | | 20 | | | | | 25 | | | | | 30 | | |

-continued

```
Trp Tyr Gln Gln Lys Pro Gly Lys Ala Pro Lys Leu Leu Ile Tyr Asp
        35              40              45

Ala Ser Asn Leu Glu Thr Gly Val Pro Ser Arg Phe Ser Gly Ser Gly
    50              55              60

Ser Gly Thr Asp Phe Thr Phe Thr Ile Ser Ser Leu Gln Pro Glu Asp
65              70              75              80

Ile Ala Thr Tyr Tyr Cys Gln Gln Tyr Asp Asn Leu Pro Leu Thr Phe
            85              90              95

Gly Gly Gly Thr Lys Val Glu Ile Lys Arg Thr
            100             105
```

(2) INFORMATION FOR SEQ ID NO:109:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:109:

```
Glu Leu Thr Gln Ser Pro Ser Ser Leu Ser Ala Ser Val Gly Asp Arg
1               5               10              15

Ile Thr Ile Thr Cys Arg Ala Ser Gln Thr Ile Asn Asn Tyr Leu Asn
            20              25              30

Trp Tyr Gln Gln Lys Pro Gly Lys Ala Pro Lys Leu Leu Ile Tyr Gly
        35              40              45

Ala Ser Asn Leu Gln Ser Gly Val Pro Ser Arg Phe Ser Gly Ser Gly
    50              55              60

Ser Gly Thr Asp Phe Thr Leu Thr Ile Ser Ser Leu Gln Pro Glu Asp
65              70              75              80

Phe Ala Thr Tyr Phe Cys Gln Gln Ser Tyr Asn Thr Pro Pro Trp Thr
            85              90              95

Phe Gly Gln Gly Thr Lys Val Glu Ile Lys Arg Thr
            100             105
```

(2) INFORMATION FOR SEQ ID NO:110:

(i) SEQUENCE CHARACTERISTICS:
        (A) LENGTH: 108 amino acids
        (B) TYPE: amino acid
        (D) TOPOLOGY: linear (ii) MOLECULE TYPE: protein (xi) SEQUENCE DESCRIPTION: SEQ ID NO:110:

```
Glu Leu Thr Gln Ser Pro Gly Thr Leu Ser Leu Ser Pro Gly Glu Arg
1               5               10              15

Ala Thr Leu Ser Cys Arg Ala Ser Gln Arg Val Asn Ser Asn Tyr Leu
            20              25              30

Ala Trp Tyr Gln Gln Lys Pro Gly Gln Thr Pro Arg Val Val Ile Tyr
        35              40              45

Ser Thr Ser Arg Arg Ala Thr Gly Val Pro Asp Arg Phe Ser Gly Ser
    50              55              60

Gly Ser Gly Thr Asp Phe Thr Leu Thr Ile Ser Arg Leu Glu Pro Glu
65              70              75              80

Asp Phe Ala Val Tyr Tyr Cys Gln Gln Phe Gly Asp Ala Gln Tyr Thr
            85              90              95

Phe Gly Gln Gly Thr Lys Leu Glu Ile Lys Arg Thr
            100             105
```

( 2 ) INFORMATION FOR SEQ ID NO:111:

( i ) SEQUENCE CHARACTERISTICS:
        ( A ) LENGTH: 93 amino acids
        ( B ) TYPE: amino acid
        ( D ) TOPOLOGY: linear ( i i ) MOLECULE TYPE: protein ( x i ) SEQUENCE DESCRIPTION: SEQ ID NO:111:

```
Glu Arg Ala Thr Leu Ser Cys Arg Ala Ser Gln Arg Val Asn Ser Asn
 1               5                  10                  15
Tyr Leu Ala Trp Tyr Gln Gln Lys Pro Gly Gln Thr Pro Arg Val Val
            20                  25                  30
Ile Tyr Ser Thr Ser Arg Arg Ala Thr Gly Val Pro Asp Arg Phe Ser
        35                  40                  45
Gly Ser Gly Ser Gly Thr Asp Phe Thr Leu Thr Ile Ser Arg Leu Glu
    50                  55                  60
Pro Glu Asp Phe Ala Val Tyr Tyr Cys Gln Gln Phe Gly Asp Ala Gln
65                  70                  75                  80
Tyr Thr Phe Gly Gln Gly Thr Lys Leu Glu Ile Lys Arg
                85                  90
```

( 2 ) INFORMATION FOR SEQ ID NO:112:

( i ) SEQUENCE CHARACTERISTICS:
        ( A ) LENGTH: 104 amino acids
        ( B ) TYPE: amino acid
        ( D ) TOPOLOGY: linear ( i i ) MOLECULE TYPE: protein ( x i ) SEQUENCE DESCRIPTION: SEQ ID NO:112:

```
Thr Gln Ser Pro Ser Ser Val Ser Ala Ser Val Gly Asp Thr Val Thr
 1               5                  10                  15
Phe Thr Cys Arg Ala Ser Gln Asp Ile Arg Asn Tyr Leu Asn Trp Tyr
            20                  25                  30
His Gln Lys Pro Gly Lys Ala Pro Lys Leu Leu Ile Ser Asp Ala Ser
        35                  40                  45
Asp Leu Glu Ile Gly Val Pro Ser Arg Phe Ser Gly Ser Gly Ser Ala
    50                  55                  60
Thr Tyr Phe Ser Phe Thr Ile Ser Ser Leu Gln Pro Glu Asp Ile Gly
65                  70                  75                  80
Thr Tyr Tyr Cys Gln Gln Tyr Ala Asp Leu Ile Thr Phe Gly Gly Gly
                85                  90                  95
Thr Lys Val Glu Ile Lys Arg Thr
            100
```

( 2 ) INFORMATION FOR SEQ ID NO:113:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:113:

```
Ser Pro Gly Glu Arg Ala Thr Leu Ser Cys Arg Ala Ser Gln Ser Val
 1               5                  10                  15
```

```
Gly  Thr  Asn  Leu  Ala  Trp  Tyr  Gln  Gln  Lys  Pro  Gly  Gln  Ala  Pro  Arg
               20                       25                       30

Leu  Leu  Ile  Phe  Asp  Ala  Ser  Thr  Arg  Asp  Thr  Tyr  Ile  Pro  Asp  Thr
               35                  40                       45

Phe  Ser  Gly  Ser  Gly  Ser  Gly  Thr  Asp  Phe  Ala  Leu  Thr  Ile  Ser  Ser
     50                       55                       60

Leu  Gln  Ser  Glu  Asp  Phe  Gly  Phe  Tyr  Tyr  Cys  Gln  Gln  Tyr  Asp  Asn
65                       70                  75                            80

Trp  Pro  Pro  Thr  Phe  Gly  Gln  Gly  Thr  Lys  Leu  Glu  Val  Lys  Arg  Thr
                    85                  90                            95
```

( 2 ) INFORMATION FOR SEQ ID NO:114:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:114:

```
Glu  Leu  Thr  Gln  Ser  Pro  Gly  Thr  Leu  Ser  Leu  Ser  Pro  Gly  Asp  Arg
1                   5                        10                       15

Ala  Thr  Phe  Ser  Cys  Arg  Ser  Ser  His  Asn  Ile  Arg  Ser  Arg  Arg  Val
               20                       25                       30

Ala  Trp  Tyr  Gln  His  Lys  Pro  Gly  Gln  Ala  Pro  Arg  Leu  Val  Ile  His
               35                       40                       45

Gly  Val  Ser  Asn  Arg  Ala  Ser  Gly  Ile  Ser  Asp  Arg  Phe  Ser  Gly  Ser
     50                       55                       60

Gly  Ser  Gly  Thr  Asp  Phe  Thr  Leu  Thr  Ile  Thr  Arg  Leu  Glu  Pro  Glu
65                       70                       75                        80

Asp  Phe  Ala  Leu  Tyr  Tyr  Cys  Gln  Val  Tyr  Gly  Ala  Ser  Ser  Tyr  Thr
                    85                       90                       95

Phe  Gly  Gln  Gly  Thr  Lys  Leu  Asp  Phe  Lys  Arg
               100                 105
```

( 2 ) INFORMATION FOR SEQ ID NO:115:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:115:

```
Glu  Leu  Thr  Gln  Ser  Pro  Gly  Thr  Leu  Ser  Leu  Ser  Pro  Gly  Glu  Arg
1                   5                        10                       15

Ala  Thr  Phe  Ser  Cys  Arg  Ser  Ser  His  Asn  Ile  Arg  Ser  Arg  Arg  Val
               20                       25                       30

Ala  Trp  Tyr  Gln  His  Lys  Pro  Gly  Gln  Ala  Pro  Arg  Leu  Val  Ile  His
               35                       40                       45

Gly  Val  Ser  Asn  Arg  Ala  Thr  Gly  Ile  Ser  Asp  Arg  Phe  Ser  Gly  Ser
     50                       55                       60

Gly  Ser  Gly  Thr  Asp  Phe  Thr  Leu  Thr  Ile  Thr  Arg  Leu  Glu  Pro  Glu
65                       70                       75                        80

Asp  Phe  Ala  Leu  Tyr  Tyr  Cys  Gln  Val  Tyr  Gly  Ala  Ser  Ser  Tyr  Thr
                    85                       90                       95

Phe  Gly  Gln  Gly  Thr  Lys  Leu  Asp  Phe  Lys  Arg
               100                 105
```

(2) INFORMATION FOR SEQ ID NO:116:

(i) SEQUENCE CHARACTERISTICS:
(A) LENGTH: 107 amino acids
(B) TYPE: amino acid
(D) TOPOLOGY: linear (ii) MOLECULE TYPE: protein (xi) SEQUENCE DESCRIPTION: SEQ ID NO:116:

```
Glu Leu Thr Gln Ser Pro Asp Thr Leu Ser Leu Asn Val Gly Glu Arg
1               5                   10                  15
Ala Thr Leu Ser Cys Arg Ala Ser His Arg Ile Ser Ser Arg Arg Leu
                20                  25                  30
Ala Trp Tyr Gln His Lys Arg Gly Gln Ala Pro Arg Leu Leu Ile Tyr
            35                  40                  45
Gly Val Ser Ser Arg Ala Gly Gly Val Pro Asp Arg Phe Ser Gly Ser
        50                  55                  60
Gly Ser Gly Thr Asp Phe Ser Leu Thr Ile Ser Arg Leu Glu Pro Glu
65                  70                  75                  80
Asp Phe Ala Met Tyr Tyr Cys Gln Thr Tyr Gly Gly Ser Ser Tyr Thr
                85                  90                  95
Phe Gly Gln Gly Thr Lys Val Asp Ile Lys Arg
                100                 105
```

(2) INFORMATION FOR SEQ ID NO:117:

(i) SEQUENCE CHARACTERISTICS:
(A) LENGTH: 107 amino acids
(B) TYPE: amino acid
(D) TOPOLOGY: linear (ii) MOLECULE TYPE: protein (xi) SEQUENCE DESCRIPTION: SEQ ID NO:117:

```
Glu Leu Thr Gln Ser Pro Asp Thr Leu Ser Leu Asn Ala Gly Glu Arg
1               5                   10                  15
Ala Thr Leu Ser Cys Arg Ala Ser His Arg Ile Ser Ser Arg Arg Leu
                20                  25                  30
Ala Trp Tyr Gln His Lys Arg Gly Gln Ala Pro Arg Leu Leu Ile Tyr
            35                  40                  45
Gly Val Ser Asn Arg Ala Gly Gly Val Pro Asp Arg Phe Ser Gly Ser
        50                  55                  60
Gly Ser Gly Thr Asp Phe Ser Leu Thr Ile Ser Arg Leu Glu Pro Glu
65                  70                  75                  80
Asp Phe Ala Ile Tyr Tyr Cys Gln Thr Tyr Gly Gly Ser Ser Tyr Thr
                85                  90                  95
Phe Gly Gln Gly Thr Thr Val Asp Ile Lys Arg
                100                 105
```

(2) INFORMATION FOR SEQ ID NO:118:

(i) SEQUENCE CHARACTERISTICS:
(A) LENGTH: 107 amino acids
(B) TYPE: amino acid
(D) TOPOLOGY: linear (ii) MOLECULE TYPE: protein (xi) SEQUENCE DESCRIPTION: SEQ ID NO:118:

-continued

```
Glu Leu Thr Gln Ser Pro Asp Thr Leu Ser Leu Asn Thr Gly Glu Arg
1               5                   10                  15

Ala Thr Leu Ser Cys Arg Ala Ser His Arg Ile Gly Ser Arg Arg Leu
                20                  25                  30

Ala Trp Tyr Gln His Arg Arg Gly Gln Ala Pro Arg Leu Leu Ile Tyr
            35                  40                  45

Gly Val Ser Asn Arg Ala Gly Gly Val Pro Asp Arg Phe Ser Gly Ser
        50                  55                  60

Gly Ser Gly Thr Asp Phe Thr Leu Thr Ile Ser Arg Leu Glu Pro Glu
65                  70                  75                  80

Asp Phe Ala Ile Tyr Tyr Cys Gln Thr Tyr Gly Gly Ser Ser Tyr Thr
                85                  90                  95

Phe Gly Gln Gly Thr Lys Val Asp Ile Lys Arg
                100                 105
```

( 2 ) INFORMATION FOR SEQ ID NO:119:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:119:

```
Glu Leu Thr Gln Ser Pro Gly Thr Leu Ser Leu Thr Pro Gly Glu Arg
1               5                   10                  15

Ala Ile Leu Ser Cys Lys Thr Ser His Asn Ile Trp Ser Arg Arg Leu
                20                  25                  30

Ala Trp Tyr Gln Leu Lys Ser Gly Gln Ala Pro Arg Leu Leu Ile Tyr
            35                  40                  45

Gly Val Ser Lys Arg Ala Gly Gly Ile Pro Asp Arg Phe Ser Gly Ser
        50                  55                  60

Gly Ser Ala Thr Asp Phe Thr Leu Thr Ile Ser Arg Val Glu Pro Glu
65                  70                  75                  80

Asp Phe Ala Val Tyr Tyr Cys Gln Thr Tyr Gly Gly Ser Ala Tyr Thr
                85                  90                  95

Phe Gly Gln Gly Thr Lys Leu Asp Ile Lys Arg
                100                 105
```

( 2 ) INFORMATION FOR SEQ ID NO:120:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:120:

```
Glu Leu Thr Gln Ser Pro Gly Thr Leu Ser Leu Thr Pro Gly Glu Arg
1               5                   10                  15

Ala Ile Leu Ser Cys Lys Thr Ser His Asn Ile Trp Ser Arg Arg Leu
                20                  25                  30

Ala Trp Tyr Gln Leu Lys Ser Gly Gln Ala Pro Arg Leu Leu Ile Tyr
            35                  40                  45

Gly Val Ser Lys Arg Ala Gly Gly Ile Pro Asp Arg Phe Ser Gly Ser
        50                  55                  60

Gly Ser Ala Thr Asp Phe Thr Leu Thr Ile Ser Arg Val Glu Pro Glu
65                  70                  75                  80
```

```
        Asp  Phe  Ala  Val  Tyr  Tyr  Cys  Gln  Thr  Tyr  Gly  Gly  Ser  Ala  Tyr  Thr
                            85                      90                          95

Phe  Gly  Gln  Gly  Thr  Lys  Leu  Glu  Ile  Lys  Arg
                       100                 105
```

( 2 ) INFORMATION FOR SEQ ID NO:121:

( i ) SEQUENCE CHARACTERISTICS:
    ( A ) LENGTH: 107 amino acids
    ( B ) TYPE: amino acid
    ( D ) TOPOLOGY: linear ( i i ) MOLECULE TYPE: protein ( x i ) SEQUENCE DESCRIPTION: SEQ ID NO:121:

```
        Glu  Leu  Thr  Gln  Ser  Pro  Gly  Thr  Leu  Ser  Ser  Thr  Pro  Gly  Glu  Arg
        1                   5                        10                       15

Ala  Ile  Leu  Ser  Cys  Lys  Thr  Ser  His  Asn  Ile  Trp  Ser  Arg  Arg  Leu
                            20                      25                       30

Ala  Trp  Tyr  Gln  Val  Lys  Ser  Gly  Leu  Pro  Pro  Arg  Leu  Leu  Ile  His
                       35                       40                  45

Gly  Val  Ser  Arg  Arg  Ala  Gly  Gly  Ile  Pro  Asp  Arg  Phe  Ser  Gly  Ser
             50                      55                       60

Gly  Ser  Ala  Arg  Asp  Phe  Thr  Leu  Thr  Ile  Ser  Arg  Leu  Glu  Pro  Ala
        65                       70                       75                       80

Asp  Phe  Ala  Val  Tyr  Tyr  Cys  Gln  Thr  Tyr  Gly  Gly  Ser  Ser  Tyr  Ser
                            85                      90                       95

Phe  Gly  Gln  Gly  Thr  Lys  Leu  Asp  Phe  Asn  Arg
                       100                 105
```

( 2 ) INFORMATION FOR SEQ ID NO:122:

( i ) SEQUENCE CHARACTERISTICS:
    ( A ) LENGTH: 107 amino acids
    ( B ) TYPE: amino acid
    ( D ) TOPOLOGY: linear ( i i ) MOLECULE TYPE: protein ( x i ) SEQUENCE DESCRIPTION: SEQ ID NO:122:

```
        Glu  Leu  Thr  Gln  Ser  Pro  Gly  Thr  Leu  Ser  Leu  Asn  Pro  Gly  Glu  Arg
        1                   5                        10                       15

Ala  Val  Leu  Ser  Cys  Arg  Thr  Ser  Arg  Asn  Ile  Trp  Ser  Arg  Arg  Leu
                            20                      25                       30

Ala  Trp  Tyr  Gln  Val  Arg  Arg  Gly  Gln  Ala  Pro  Arg  Leu  Leu  Ile  His
                       35                       40                  45

Gly  Val  Ser  Lys  Arg  Ala  Gly  Gly  Val  Pro  Asp  Arg  Phe  Ser  Gly  Ser
             50                      55                       60

Gly  Ser  Ala  Arg  Asp  Phe  Thr  Leu  Thr  Ile  Ser  Arg  Leu  Glu  Pro  Glu
        65                       70                       75                       80

Asp  Phe  Ala  Val  Tyr  Phe  Cys  Gln  Thr  Tyr  Gly  Gly  Ser  Ser  Tyr  Thr
                            85                      90                       95

Phe  Gly  Gln  Gly  Asn  Lys  Leu  Asp  Ile  Arg  Arg
                       100                 105
```

( 2 ) INFORMATION FOR SEQ ID NO:123:

( i ) SEQUENCE CHARACTERISTICS:
    ( A ) LENGTH: 126 amino acids
    ( B ) TYPE: amino acid
    ( D ) TOPOLOGY: linear ( i i ) MOLECULE TYPE: protein ( x i ) SEQUENCE DESCRIPTION: SEQ ID NO:123:

| Gln | Val | Lys | Leu | Leu | Glu | Gln | Ser | Gly | Ala | Glu | Val | Lys | Lys | Pro | Gly |
|---|---|---|---|---|---|---|---|---|---|---|---|---|---|---|---|
| 1 | | | | 5 | | | | | 10 | | | | | 15 | |

| Ala | Ser | Val | Lys | Val | Ser | Cys | Gln | Ala | Ser | Gly | Tyr | Arg | Phe | Ser | Asn |
|---|---|---|---|---|---|---|---|---|---|---|---|---|---|---|---|
| | | | 20 | | | | | 25 | | | | | 30 | | |

| Phe | Val | Leu | His | Trp | Ala | Arg | Gln | Ala | Pro | Gly | His | Arg | Pro | Glu | Trp |
|---|---|---|---|---|---|---|---|---|---|---|---|---|---|---|---|
| | | 35 | | | | | 40 | | | | | 45 | | | |

| Met | Gly | Trp | Ile | Asn | Pro | Ala | Asn | Gly | Val | Thr | Glu | Ile | Pro | Pro | Lys |
|---|---|---|---|---|---|---|---|---|---|---|---|---|---|---|---|
| | 50 | | | | | 55 | | | | | 60 | | | | |

| Phe | Gln | Asp | Arg | Val | Ser | Leu | Thr | Arg | Asp | Thr | Ser | Ala | Gly | Thr | Val |
|---|---|---|---|---|---|---|---|---|---|---|---|---|---|---|---|
| 65 | | | | | 70 | | | | | 75 | | | | | 80 |

| Tyr | Leu | Glu | Leu | Thr | Asn | Leu | Arg | Phe | Ala | Asp | Thr | Ala | Val | Tyr | Tyr |
|---|---|---|---|---|---|---|---|---|---|---|---|---|---|---|---|
| | | | | 85 | | | | | 90 | | | | | 95 | |

| Cys | Ala | Arg | Val | Gly | Glu | Trp | Thr | Trp | Asp | Asp | Ser | Pro | Gln | Asp | Asn |
|---|---|---|---|---|---|---|---|---|---|---|---|---|---|---|---|
| | | | 100 | | | | | 105 | | | | | 110 | | |

| Tyr | Tyr | Met | Asp | Val | Trp | Gly | Lys | Gly | Thr | Thr | Val | Thr | Val | | |
|---|---|---|---|---|---|---|---|---|---|---|---|---|---|---|---|
| | | 115 | | | | | 120 | | | | | 125 | | | |

( 2 ) INFORMATION FOR SEQ ID NO:124:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:124:

| Gln | Val | Lys | Leu | Leu | Glu | Gln | Ser | Gly | Ala | Glu | Val | Lys | Lys | Pro | Gly |
|---|---|---|---|---|---|---|---|---|---|---|---|---|---|---|---|
| 1 | | | | 5 | | | | | 10 | | | | | 15 | |

| Ala | Ser | Val | Lys | Val | Ser | Cys | Gln | Ala | Ser | Gly | Tyr | Arg | Phe | Ser | Asn |
|---|---|---|---|---|---|---|---|---|---|---|---|---|---|---|---|
| | | | 20 | | | | | 25 | | | | | 30 | | |

| Phe | Val | Leu | His | Trp | Ala | Arg | Gln | Ala | Pro | Gly | His | Arg | Pro | Glu | Trp |
|---|---|---|---|---|---|---|---|---|---|---|---|---|---|---|---|
| | | 35 | | | | | 40 | | | | | 45 | | | |

| Met | Gly | Trp | Ile | Asn | Pro | Ala | Asn | Gly | Val | Thr | Glu | Ile | Ser | Pro | Lys |
|---|---|---|---|---|---|---|---|---|---|---|---|---|---|---|---|
| | 50 | | | | | 55 | | | | | 60 | | | | |

| Phe | Gln | Asp | Arg | Val | Ser | Leu | Thr | Gly | Asp | Thr | Ser | Ala | Ser | Thr | Val |
|---|---|---|---|---|---|---|---|---|---|---|---|---|---|---|---|
| 65 | | | | | 70 | | | | | 75 | | | | | 80 |

| Tyr | Leu | Glu | Leu | Arg | Asn | Leu | Arg | Phe | Ala | Asp | Thr | Ala | Val | Tyr | Tyr |
|---|---|---|---|---|---|---|---|---|---|---|---|---|---|---|---|
| | | | | 85 | | | | | 90 | | | | | 95 | |

| Cys | Ala | Arg | Val | Gly | Glu | Trp | Thr | Trp | Asp | Asp | Ser | Pro | Gln | Asp | Asn |
|---|---|---|---|---|---|---|---|---|---|---|---|---|---|---|---|
| | | | 100 | | | | | 105 | | | | | 110 | | |

| Tyr | Tyr | Met | Asp | Val | Trp | Gly | Arg | Gly | Thr | Thr | Val | Thr | | | |
|---|---|---|---|---|---|---|---|---|---|---|---|---|---|---|---|
| | | 115 | | | | | 120 | | | | | 125 | | | |

( 2 ) INFORMATION FOR SEQ ID NO:125:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:125:

| Gln | Val | Lys | Leu | Leu | Glu | Gln | Ser | Gly | Ala | Glu | Val | Lys | Lys | Pro | Gly |
|---|---|---|---|---|---|---|---|---|---|---|---|---|---|---|---|
| 1 | | | | 5 | | | | | 10 | | | | | 15 | |

|   |   |   |   |   |   |   |   |   |   |   |   |   |   |   |
|---|---|---|---|---|---|---|---|---|---|---|---|---|---|---|
| Ala | Ser | Val | Lys<br>20 | Val | Ser | Cys | Gln | Ala<br>25 | Ser | Gly | Tyr | Arg | Phe<br>30 | Ser | Asn |
| Phe | Val | Leu<br>35 | His | Trp | Ala | Arg | Gln<br>40 | Ala | Pro | Gly | His | Arg<br>45 | Pro | Glu | Trp |
| Met | Gly<br>50 | Trp | Ile | Asn | Pro | Ala<br>55 | Asn | Gly | Val | Thr | Glu<br>60 | Ile | Ser | Pro | Lys |
| Phe<br>65 | Gln | Asp | Arg | Val | Ser<br>70 | Leu | Thr | Gly | Asp | Thr<br>75 | Ser | Ala | Ser | Thr | Val<br>80 |
| Tyr | Leu | Glu | Leu | Arg<br>85 | Ser | Leu | Arg | Phe | Ala<br>90 | Asp | Thr | Ala | Val | Tyr<br>95 | Tyr |
| Cys | Ala | Arg | Val<br>100 | Gly | Glu | Trp | Thr | Trp<br>105 | Asp | Asp | Ser | Pro | Gln<br>110 | Asp | Asn |
| Tyr | Tyr | Met<br>115 | Asp | Val | Trp | Gly | Lys<br>120 | Gly | Thr | Thr | Val |

( 2 ) INFORMATION FOR SEQ ID NO:126:

( i ) SEQUENCE CHARACTERISTICS:
    ( A ) LENGTH: 124 amino acids
    ( B ) TYPE: amino acid
    ( D ) TOPOLOGY: linear ( i i ) MOLECULE TYPE: protein ( x i ) SEQUENCE DESCRIPTION: SEQ ID NO:126:

|   |   |   |   |   |   |   |   |   |   |   |   |   |   |   |
|---|---|---|---|---|---|---|---|---|---|---|---|---|---|---|
| Gln<br>1 | Val | Lys | Leu | Leu<br>5 | Glu | Gln | Ser | Gly | Ala<br>10 | Glu | Val | Lys | Lys | Pro<br>15 | Gly |
| Ala | Ser | Val | Lys<br>20 | Ile | Ser | Cys | Gln | Ala<br>25 | Ser | Gly | Tyr | Arg | Phe<br>30 | Thr | Asn |
| Phe | Val | Leu<br>35 | His | Trp | Ala | Arg | Gln<br>40 | Ala | Pro | Gly | Gln | Arg<br>45 | Pro | Glu | Trp |
| Met | Gly<br>50 | Trp | Phe | Asn | Pro | Ala<br>55 | Asn | Gly | Ile | Lys | Glu<br>60 | Ile | Ser | Pro | Lys |
| Phe<br>65 | Gln | Asp | Arg | Val | Ser<br>70 | Phe | Thr | Gly | Asp | Thr<br>75 | Ser | Ala | Ser | Thr | Ala<br>80 |
| Tyr | Val | Glu | Leu | Arg<br>85 | Asn | Leu | Arg | Ser | Ala<br>90 | Asp | Thr | Ala | Val | Tyr<br>95 | Tyr |
| Cys | Ala | Arg | Val<br>100 | Gly | Pro | Trp | Thr | Trp<br>105 | Asp | Asp | Ser | Pro | Gln<br>110 | Asp | Asn |
| Tyr | Tyr | Met<br>115 | Asp | Val | Trp | Gly | Lys<br>120 | Gly | Thr | Thr | Val |

( 2 ) INFORMATION FOR SEQ ID NO:127:

( i ) SEQUENCE CHARACTERISTICS:
    ( A ) LENGTH: 124 amino acids
    ( B ) TYPE: amino acid
    ( D ) TOPOLOGY: linear ( i i ) MOLECULE TYPE: protein ( x i ) SEQUENCE DESCRIPTION: SEQ ID NO:127:

|   |   |   |   |   |   |   |   |   |   |   |   |   |   |   |
|---|---|---|---|---|---|---|---|---|---|---|---|---|---|---|
| Gln<br>1 | Val | Lys | Leu | Leu<br>5 | Glu | Gln | Ser | Gly | Ala<br>10 | Glu | Val | Lys | Lys | Pro<br>15 | Gly |
| Ala | Ser | Val | Lys<br>20 | Val | Ser | Cys | Gln | Ala<br>25 | Ser | Gly | Tyr | Arg | Phe<br>30 | Ser | Asn |
| Phe | Val | Leu<br>35 | His | Trp | Ala | Arg | Gln<br>40 | Ala | Pro | Gly | His | Arg<br>45 | Pro | Glu | Trp |
| Met | Gly<br>50 | Trp | Ile | Asn | Pro | Ala<br>55 | Asn | Gly | Val | Thr | Glu<br>60 | Ile | Ser | Pro | Lys |

```
            Phe   Gln   Asp   Arg   Val   Ser   Leu   Thr   Gly   Asp   Thr   Ser   Ala   Ser   Thr   Val
            65                            70                            75                                  80

Tyr   Leu   Glu   Leu   Arg   Asn   Leu   Arg   Phe   Ala   Asp   Thr   Ala   Val   Tyr   Tyr
                                    85                            90                            95

Cys   Ala   Arg   Val   Gly   Glu   Trp   Thr   Trp   Asp   Asp   Phe   Pro   Gln   Asp   Asn
                                    100                           105                           110

Tyr   Tyr   Met   Asp   Val   Trp   Gly   Lys   Gly   Thr   Thr   Val
                              115                           120
```

( 2 ) INFORMATION FOR SEQ ID NO:128:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:128:

```
            Gln   Val   Lys   Leu   Leu   Glu   Gln   Ser   Gly   Ala   Glu   Val   Lys   Lys   Pro   Gly
            1                             5                             10                            15

Ala   Ser   Val   Lys   Leu   Ser   Cys   Gln   Ala   Ser   Gly   Tyr   Arg   Phe   Ser   Asn
                                    20                            25                            30

Phe   Val   Leu   His   Trp   Ala   Arg   Gln   Ala   Pro   Gly   His   Arg   Pro   Glu   Trp
                              35                            40                            45

Met   Gly   Trp   Ile   Asn   Pro   Ala   Asn   Gly   Val   Thr   Glu   Ile   Ser   Pro   Lys
                        50                            55                            60

Phe   Gln   Asp   Arg   Val   Ser   Leu   Thr   Gly   Asp   Thr   Ser   Ala   Ser   Thr   Val
            65                            70                            75                                  80

Tyr   Leu   Glu   Leu   Arg   Asn   Leu   Arg   Phe   Ala   Asp   Thr   Ala   Val   Tyr   Tyr
                                    85                            90                            95

Cys   Ala   Arg   Val   Gly   Glu   Trp   Thr   Trp   Asp   Asp   Ser   Pro   Gln   Asp   Asn
                                    100                           105                           110

Tyr   Tyr   Met   Asp   Val   Trp   Gly   Lys   Gly   Thr   Thr   Val   Thr
                              115                           120                           125
```

( 2 ) INFORMATION FOR SEQ ID NO:129:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:129:

```
            Gln   Val   Lys   Leu   Leu   Glu   Gln   Ser   Gly   Thr   Glu   Val   Lys   Lys   Pro   Gly
            1                             5                             10                            15

Ala   Ser   Val   Lys   Ile   Ser   Cys   Lys   Ala   Ser   Gly   Tyr   Arg   Phe   Thr   Asn
                                    20                            25                            30

Phe   Pro   Leu   His   Trp   Val   Arg   Gln   Ala   Pro   Gly   Gln   Arg   Pro   Glu   Trp
                              35                            40                            45

Met   Gly   Trp   Ile   Lys   Ile   Val   Asn   Gly   Glu   Lys   Lys   Tyr   Ser   Gln   Lys
                        50                            55                            60

Phe   Val   Asp   Arg   Val   Thr   Phe   Thr   Gly   Asp   Thr   Ser   Ala   Asn   Thr   Ala
            65                            70                            75                                  80

Tyr   Met   Glu   Val   Arg   Gly   Leu   Arg   Ser   Ala   Asp   Thr   Ala   Thr   Tyr   Tyr
                                    85                            90                            95
```

```
              Cys  Ala  Arg  Val  Gly  Glu  Trp  Thr  Trp  Asp  Met  Asp  Pro  Gln  Ala  Asn
                             100                 105                      110

Tyr  Tyr  Met  Asp  Val  Trp  Gly  Lys  Gly  Thr  Thr  Val  Thr
                             115                 120                      125
```

( 2 ) INFORMATION FOR SEQ ID NO:130:

( i ) SEQUENCE CHARACTERISTICS:
      ( A ) LENGTH: 124 amino acids
      ( B ) TYPE: amino acid
      ( D ) TOPOLOGY: linear ( i i ) MOLECULE TYPE: protein ( x i ) SEQUENCE DESCRIPTION: SEQ ID NO:130:

```
              Gln  Val  Lys  Leu  Leu  Glu  Gln  Ser  Gly  Ala  Glu  Val  Lys  Lys  Pro  Gly
              1                    5                        10                      15

Ala  Ser  Val  Lys  Val  Ser  Cys  Gln  Ala  Ser  Gly  Tyr  Arg  Phe  Ser  Asn
                             20                      25                      30

Phe  Val  Ile  His  Trp  Val  Arg  Gln  Ala  Pro  Gly  Gln  Arg  Phe  Glu  Trp
                             35                      40                      45

Met  Gly  Trp  Ile  Asn  Pro  Tyr  Asn  Gly  Asn  Lys  Glu  Phe  Ser  Ala  Lys
                   50                         55                      60

Phe  Arg  Asp  Arg  Val  Thr  Phe  Thr  Ala  Asp  Thr  Asp  Ala  Asn  Thr  Ala
              65                            70                      75                      80

Tyr  Met  Glu  Leu  Arg  Ser  Leu  Arg  Ser  Ala  Asp  Thr  Ala  Ile  Tyr  Tyr
                                  85                      90                      95

Cys  Ala  Arg  Val  Gly  Pro  Tyr  Thr  Trp  Asp  Asp  Ser  Pro  Gln  Asp  Asn
                             100                 105                      110

Tyr  Tyr  Met  Asp  Val  Trp  Gly  Lys  Gly  Thr  Thr  Val
                             115                 120
```

( 2 ) INFORMATION FOR SEQ ID NO:131:

( i ) SEQUENCE CHARACTERISTICS:
      ( A ) LENGTH: 124 amino acids
      ( B ) TYPE: amino acid
      ( D ) TOPOLOGY: linear ( i i ) MOLECULE TYPE: protein ( x i ) SEQUENCE DESCRIPTION: SEQ ID NO:131:

```
              Gln  Val  Lys  Leu  Leu  Glu  Gln  Ser  Gly  Ala  Glu  Val  Lys  Lys  Pro  Gly
              1                    5                        10                      15

Ala  Ser  Val  Lys  Val  Ser  Cys  Gln  Ala  Ser  Gly  Tyr  Arg  Phe  Ser  Asn
                             20                      25                      30

Phe  Val  Leu  His  Trp  Ala  Arg  Gln  Ala  Pro  Thr  Gln  Asp  Leu  Glu  Trp
                             35                      40                      45

Met  Gly  Trp  Ile  Asn  Pro  Ala  Asn  Gly  Val  Lys  Glu  Ile  Ser  Pro  Lys
                   50                         55                      60

Phe  Gln  Asp  Arg  Val  Ser  Leu  Thr  Gly  Asp  Thr  Ser  Ala  Ser  Thr  Val
              65                            70                      75                      80

Tyr  Leu  Glu  Leu  Arg  Ser  Leu  Arg  Phe  Ala  Asp  Thr  Ala  Val  Tyr  Tyr
                                  85                      90                      95

Cys  Ala  Arg  Val  Gly  Glu  Trp  Thr  Trp  Asp  Asp  Ser  Pro  Gln  Asp  Asn
                             100                 105                      110

Tyr  Tyr  Met  Asp  Val  Trp  Gly  Lys  Gly  Thr  Thr  Val
                             115                 120
```

( 2 ) INFORMATION FOR SEQ ID NO:132:

( i ) SEQUENCE CHARACTERISTICS:
  ( A ) LENGTH: 124 amino acids
  ( B ) TYPE: amino acid
  ( D ) TOPOLOGY: linear ( i i ) MOLECULE TYPE: protein ( x i ) SEQUENCE DESCRIPTION: SEQ ID NO:132:

| Gln | Val | Lys | Leu | Leu | Glu | Gln | Ser | Gly | Ala | Glu | Val | Lys | Lys | Pro | Gly |
|---|---|---|---|---|---|---|---|---|---|---|---|---|---|---|---|
| 1 | | | | 5 | | | | | 10 | | | | | 15 | |
| Ala | Ser | Val | Lys | Val | Ser | Cys | Gln | Ala | Ser | Gly | Tyr | Arg | Phe | Ser | Asn |
| | | | 20 | | | | | 25 | | | | | 30 | | |
| Phe | Val | Leu | His | Trp | Ala | Arg | Gln | Ala | Pro | Gly | His | Arg | Pro | Glu | Trp |
| | | 35 | | | | | 40 | | | | | 45 | | | |
| Met | Gly | Trp | Ile | Asn | Pro | Ala | Asn | Gly | Val | Thr | Glu | Ile | Pro | Pro | Lys |
| | 50 | | | | | 55 | | | | | 60 | | | | |
| Phe | Gln | Asp | Arg | Val | Ser | Leu | Thr | Arg | Asp | Thr | Ser | Ala | Gly | Thr | Val |
| 65 | | | | | 70 | | | | | 75 | | | | | 80 |
| Tyr | Leu | Glu | Leu | Thr | Asn | Leu | Arg | Phe | Ala | Asp | Thr | Ala | Val | Tyr | Tyr |
| | | | | 85 | | | | | 90 | | | | | 95 | |
| Cys | Ala | Arg | Val | Gly | Glu | Trp | Thr | Trp | Asp | Asp | Ser | Pro | Gln | Asp | Asn |
| | | | 100 | | | | | 105 | | | | | 110 | | |
| Tyr | Tyr | Met | Asp | Val | Trp | Gly | Lys | Gly | Thr | Thr | Val | | | | |
| | | 115 | | | | | 120 | | | | | | | | |

( 2 ) INFORMATION FOR SEQ ID NO:133:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:133:

TCGAGGGTCG GTCGGTCTCT AGACGGTCGG TCGGTCA                37

( 2 ) INFORMATION FOR SEQ ID NO:134:

( i ) SEQUENCE CHARACTERISTICS:
    ( A ) LENGTH: 37 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:134:

CTAGTGACCG ACCGACCGTC TAGAGACCGA CCGACCC                37

( 2 ) INFORMATION FOR SEQ ID NO:135:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:135:

CGGTCGGTCG GTCCTCGAGG GTCGGTCGGT CT                                  32

(2) INFORMATION FOR SEQ ID NO:136:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:136:

CTAGAGACCG ACCGACCCTC GAGGACCGAC CGACCGAGCT                          40

(2) INFORMATION FOR SEQ ID NO:137:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:137:

CAAGGAGACA GGATCCATGA AATAC                                          25

(2) INFORMATION FOR SEQ ID NO:138:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:138:

AGGGCGAATT GGATCCCGGG CCCCC                                          25

(2) INFORMATION FOR SEQ ID NO:139:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO ( i v ) ANTI-SENSE: NO ( x i ) SEQUENCE DESCRIPTION: SEQ ID NO:139:

CTAGTCATCA TCATCATCAT TAAGCTAGC 29

( 2 ) INFORMATION FOR SEQ ID NO:140:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:140:

CTAGGCTAGC TTAATGATGA TGATGATGA 29

( 2 ) INFORMATION FOR SEQ ID NO:141:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Modified-site
        ( B ) LOCATION: 1
        ( D ) OTHER INFORMATION: /label=J ( i x ) FEATURE:
        ( A ) NAME/KEY: Modified-site
        ( B ) LOCATION: 13
        ( D ) OTHER INFORMATION: /label=ZC ( x i ) SEQUENCE DESCRIPTION: SEQ ID NO:141:

Ser Ile Ser Ile Gly Pro Gly Arg Ala Phe Tyr Thr Gly
1               5                   10

( 2 ) INFORMATION FOR SEQ ID NO:142:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:142:

Leu Leu Glu Ser Gly Pro Gly Leu Val Lys Pro Ser Glu Thr Leu Ser
1               5                   10                  15

Leu Thr Cys Thr Val Ser Gly Gly Ser Leu Ser Ser Phe Asp Trp Asn
                20                  25                  30

Trp Ile Arg Gln Pro Ala Gly Lys Gly Leu Glu Trp Ile Gly Arg Ile
            35                  40                  45

Tyr Pro Ser Gly Asn Thr His Tyr Asn Pro Ser Leu Arg Ser Arg Val
        50                  55                  60

Thr Met Ser Arg Asp Thr Ser Lys Asn Gln Phe Ser Val Lys Leu Thr
65                  70                  75                  80

```
      Ser  Val  Thr  Ala  Ala  Asp  Thr  Ala  Leu  Tyr  Tyr  Cys  Ala  Arg  Glu  Asn
                          85                      90                          95

Thr  Gly  Arg  Thr  Ile  Glu  Glu  Ile  Gly  Asn  Phe  Phe  Asp  Ile  Trp  Gly
                         100                     105                         110

Gln  Gly  Thr  Leu  Val  Thr  Val  Ser  Ser  Ala  Ser  Thr  Lys  Gly
                         115                     120                    125
```

( 2 ) INFORMATION FOR SEQ ID NO:143:

( i ) SEQUENCE CHARACTERISTICS:
        ( A ) LENGTH: 122 amino acids
        ( B ) TYPE: amino acid
        ( D ) TOPOLOGY: linear ( i i ) MOLECULE TYPE: protein ( x i ) SEQUENCE DESCRIPTION: SEQ ID NO:143:

```
      Leu  Leu  Lys  Ser  Gly  Gly  Gly  Leu  Val  Lys  Pro  Gly  Gly  Ser  Leu  Arg
      1                   5                       10                          15

Leu  Ser  Cys  Val  Ile  Ser  Ala  Phe  Ser  Phe  Ser  Gly  Tyr  Asn  Ile  Asn
                          20                      25                          30

Trp  Val  Arg  Gln  Ala  Pro  Gly  Lys  Gly  Leu  Glu  Trp  Val  Ser  Ser  Ile
                          35                      40                          45

Ser  Met  Ser  Thr  Gly  Ser  Leu  Ser  Tyr  Ala  Asp  Ser  Met  Lys  Gly  Arg
                50                      55                      60

Phe  Thr  Ile  Ser  Arg  Asp  Asn  Ala  Lys  Asn  Ser  Val  Tyr  Leu  Glu  Met
      65                      70                      75                          80

Ser  Ser  Leu  Thr  Ala  Glu  Asp  Thr  Ala  Met  Tyr  Tyr  Cys  Ala  Ala  Arg
                          85                      90                          95

Thr  Pro  Leu  Val  Gly  Arg  Ala  Leu  Asp  Ile  Trp  Gly  Gln  Gly  Thr  Val
                         100                     105                         110

Val  Thr  Val  Ser  Ser  Ala  Ser  Thr  Lys  Gly
                         115                     120
```

( 2 ) INFORMATION FOR SEQ ID NO:144:

( i ) SEQUENCE CHARACTERISTICS:
        ( A ) LENGTH: 132 amino acids
        ( B ) TYPE: amino acid
        ( D ) TOPOLOGY: linear ( i i ) MOLECULE TYPE: protein ( x i ) SEQUENCE DESCRIPTION: SEQ ID NO:144:

```
      Leu  Leu  Glu  Ser  Gly  Gly  Gly  Leu  Val  Lys  Pro  Gly  Gly  Ser  Leu  Arg
      1                   5                       10                          15

Leu  Ser  Cys  Ser  Ala  Ser  Gly  Phe  Thr  Phe  Ser  Ser  Tyr  Gly  Met  Asn
                          20                      25                          30

Trp  Val  Arg  Gln  Ala  Pro  Gly  Lys  Gly  Pro  Glu  Trp  Val  Ala  Tyr  Ile
                          35                      40                          45

Ser  Ser  Ser  Arg  Lys  Tyr  Thr  Glu  Tyr  Ala  Asp  Ser  Val  Lys  Gly  Arg
                50                      55                      60

Phe  Thr  Ile  Ser  Arg  Glu  Asn  Ala  Lys  Tyr  Ser  Val  Phe  Leu  Gln  Leu
      65                      70                      75                          80

Asp  Ser  Leu  Thr  Ala  Glu  Asp  Thr  Ala  Ile  Tyr  Tyr  Cys  Ala  Arg  Gly
                          85                      90                          95

Arg  Asp  Phe  Tyr  Ser  Gly  Phe  Gly  Arg  Arg  Asp  Asp  Phe  His  Leu  His
                         100                     105                         110

Tyr  Met  Asp  Val  Trp  Gly  Lys  Gly  Thr  Thr  Val  Thr  Val  Ser  Ser  Ala
                         115                     120                         125
```

Ser Thr Lys Gly
130

( 2 ) INFORMATION FOR SEQ ID NO:145:

( i ) SEQUENCE CHARACTERISTICS:
        ( A ) LENGTH: 126 amino acids
        ( B ) TYPE: amino acid
        ( D ) TOPOLOGY: linear ( i i ) MOLECULE TYPE: protein ( x i ) SEQUENCE DESCRIPTION: SEQ ID NO:145:

```
Leu Leu Glu Gln Ser Gly Gly Gly Leu Val Gln Pro Gly Gly Ser Leu
1               5                   10                  15
Arg Ile Ser Cys Val Ala Ser Gly Asp Ile Phe Tyr Ser Tyr Ala Met
                20                  25                  30
Ser Trp Val Arg Gln Ala Pro Gly Lys Gly Leu Glu Trp Val Ala Ser
            35                  40                  45
Ile Ser Gly Thr Gly Gly Ser Asn Tyr Tyr Ala Asp Ser Val Lys Gly
        50                  55                  60
Arg Phe Thr Ile Ser Arg Asp Asn Ser Lys Ser Thr Leu Tyr Leu Gln
65                  70                  75                  80
Met Asn Ser Leu Arg Ala Glu Asp Thr Ala Leu Tyr Tyr Cys Ala Arg
                85                  90                  95
Asp Arg Gly Pro Arg Ile Gly Ile Arg Gly Trp Phe Asp Ser Trp Gly
                100                 105                 110
Gln Gly Thr Leu Val Thr Val Ser Ser Ala Ser Thr Lys Gly
            115                 120                 125
```

( 2 ) INFORMATION FOR SEQ ID NO:146:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:146:

```
Leu Leu Glu Ser Gly Gly Gly Leu Val Gln Pro Gly Gly Ser Leu Arg
1               5                   10                  15
Leu Ser Cys Ala Ala Ser Gly Phe Leu Tyr Ser Ser Phe Ala Met Ser
                20                  25                  30
Trp Val Arg Gln Ala Pro Gly Lys Gly Leu Ala Trp Val Ser Thr Ile
            35                  40                  45
Ser Ala Ser Gly Gly Ser Thr Lys Tyr Ala Asp Ser Val Lys Gly Arg
        50                  55                  60
Phe Ile Ile Ser Arg Asp Asn Ser Lys Asn Thr Ile Tyr Leu Gln Met
65                  70                  75                  80
Asp Ser Leu Arg Ala Glu Asp Thr Ala Val Tyr Tyr Cys Ala Lys Asn
                85                  90                  95
Phe Arg Ala Phe Ala Arg Asp Pro Trp Gly Asp Trp Gly Gln Gly Thr
                100                 105                 110
Leu Val Thr Val Ser Ser Ala Ser Ala Ser Thr Lys
            115                 120
```

( 2 ) INFORMATION FOR SEQ ID NO:147:

( i ) SEQUENCE CHARACTERISTICS:

(A) LENGTH: 109 amino acids
(B) TYPE: amino acid
(D) TOPOLOGY: linear (ii) MOLECULE TYPE: protein (xi) SEQUENCE DESCRIPTION: SEQ ID NO:147:

Met Ala Glu Leu Thr Gln Ser Pro Gly Thr Leu Ser Leu Ser Pro Gly
1               5                   10                  15
Glu Arg Val Ile Val Ser Cys Arg Ala Ser Gln Ser Val Ser Ser Asn
                20                  25                  30
Tyr Leu Ala Trp Tyr Gln Gln Lys Pro Gly Gln Ala Pro Arg Leu Leu
            35                  40                  45
Ile Tyr Gly Ala Ser Asn Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Gly
                85                  90                  95
Thr Phe Gly Gln Gly Thr Lys Val Glu Ile Lys Arg Thr
                100                 105

(2) INFORMATION FOR SEQ ID NO:148:

(i) SEQUENCE CHARACTERISTICS:
(A) LENGTH: 112 amino acids
(B) TYPE: amino acid
(D) TOPOLOGY: linear (ii) MOLECULE TYPE: protein (xi) SEQUENCE DESCRIPTION: SEQ ID NO:148:

Met Ala Glu Leu Thr Gln Ser Pro Gly Thr Leu Ser Leu Ser Pro Gly
1               5                   10                  15
Glu Arg Ala Thr Phe Ser Cys Arg Ser Ser His Ser Ile His Thr Arg
                20                  25                  30
Arg Val Ala Trp Tyr Gln His Lys Pro Gly Gln Ala Pro Arg Leu Val
            35                  40                  45
Ile His Gly Val Ser Asn Arg Ala Ser Gly Ile Ser Asp Arg Phe Ser
        50                  55                  60
Gly Ser Gly Ser Gly Thr Asp Phe Thr Leu Thr Ile Thr Arg Val Glu
65                  70                  75                  80
Pro Glu Asp Phe Ala Leu Tyr Tyr Cys Gln Val Tyr Gly Ala Ser Ser
                85                  90                  95
Tyr Thr Phe Gly Gln Gly Thr Lys Leu Glu Arg Lys Arg Thr Val Val
                100                 105                 110

(2) INFORMATION FOR SEQ ID NO:149:

(i) SEQUENCE CHARACTERISTICS:
(A) LENGTH: 111 amino acids
(B) TYPE: amino acid
(D) TOPOLOGY: linear (ii) MOLECULE TYPE: protein (xi) SEQUENCE DESCRIPTION: SEQ ID NO:149:

Met Ala Glu Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Asn Gly
                20                  25                  30

|     | Tyr | Leu | Ala | Trp | Tyr | Gln | Gln | Lys | Pro | Gly | Gln | Ala | Pro | Arg | Leu | Leu |
|-----|-----|-----|-----|-----|-----|-----|-----|-----|-----|-----|-----|-----|-----|-----|-----|-----|
|     |     |     | 35  |     |     |     | 40  |     |     |     |     | 45  |     |     |     |     |

|     | Ile | Tyr | Gly | Ala | Ser | Thr | Arg | Ala | Thr | Asp | Ile | Pro | Asp | Arg | Phe | Ser |
|-----|-----|-----|-----|-----|-----|-----|-----|-----|-----|-----|-----|-----|-----|-----|-----|-----|
|     |     | 50  |     |     |     | 55  |     |     |     | 60  |     |     |     |     |     |     |

|     | Gly | Ser | Gly | Ser | Gly | Ala | Asp | Phe | Thr | Leu | Ala | Ile | Ser | Arg | Leu | Glu |
|-----|-----|-----|-----|-----|-----|-----|-----|-----|-----|-----|-----|-----|-----|-----|-----|-----|
|     | 65  |     |     |     |     | 70  |     |     |     | 75  |     |     |     |     |     | 80  |

|     | Pro | Glu | Asp | Phe | Ala | Val | Tyr | Tyr | Cys | Gln | Gln | Tyr | Ala | Gly | Ser | His |
|-----|-----|-----|-----|-----|-----|-----|-----|-----|-----|-----|-----|-----|-----|-----|-----|-----|
|     |     |     |     |     | 85  |     |     |     | 90  |     |     |     |     | 95  |     |     |

|     | Thr | Phe | Gly | Gln | Gly | Thr | Lys | Leu | Glu | Ile | Lys | Arg | Thr | Val | Ala |
|-----|-----|-----|-----|-----|-----|-----|-----|-----|-----|-----|-----|-----|-----|-----|-----|
|     |     |     |     | 100 |     |     |     | 105 |     |     |     |     | 110 |     |     |

( 2 ) INFORMATION FOR SEQ ID NO:150:

( i ) SEQUENCE CHARACTERISTICS:
( A ) LENGTH: 111 amino acids
( B ) TYPE: amino acid
( D ) TOPOLOGY: linear ( i i ) MOLECULE TYPE: protein ( x i ) SEQUENCE DESCRIPTION: SEQ ID NO:150:

|     | Met | Ala | Glu | Leu | Thr | Gln | Ser | Pro | Ser | Ser | Leu | Ser | Ala | Ser | Val | Gly |
|-----|-----|-----|-----|-----|-----|-----|-----|-----|-----|-----|-----|-----|-----|-----|-----|-----|
|     | 1   |     |     |     | 5   |     |     |     |     | 10  |     |     |     |     | 15  |     |

|     | Asp | Arg | Val | Thr | Ile | Thr | Cys | Arg | Pro | Ser | Gln | Gly | Ile | Gly | Arg | Phe |
|-----|-----|-----|-----|-----|-----|-----|-----|-----|-----|-----|-----|-----|-----|-----|-----|-----|
|     |     |     |     | 20  |     |     |     |     | 25  |     |     |     |     | 30  |     |     |

|     | Phe | Asn | Trp | Tyr | Gln | Gln | Lys | Pro | Gly | Lys | Ala | Pro | Asn | Leu | Leu | Ile |
|-----|-----|-----|-----|-----|-----|-----|-----|-----|-----|-----|-----|-----|-----|-----|-----|-----|
|     |     |     |     | 35  |     |     |     | 40  |     |     |     |     | 45  |     |     |     |

|     | Tyr | Ala | Ala | Asp | Ile | Leu | Gln | Ser | Gly | Val | Pro | Ser | Arg | Phe | Ser | Gly |
|-----|-----|-----|-----|-----|-----|-----|-----|-----|-----|-----|-----|-----|-----|-----|-----|-----|
|     |     | 50  |     |     |     | 55  |     |     |     | 60  |     |     |     |     |     |     |

|     | Ser | Gly | Ser | Gly | Thr | Asp | Phe | Thr | Leu | Thr | Ile | Ser | Ser | Leu | Gln | Pro |
|-----|-----|-----|-----|-----|-----|-----|-----|-----|-----|-----|-----|-----|-----|-----|-----|-----|
|     | 65  |     |     |     |     | 70  |     |     |     | 75  |     |     |     |     |     | 80  |

|     | Glu | Asp | Phe | Ala | Thr | Tyr | Tyr | Cys | Gln | Gln | Ser | Tyr | Ser | Thr | Pro | Tyr |
|-----|-----|-----|-----|-----|-----|-----|-----|-----|-----|-----|-----|-----|-----|-----|-----|-----|
|     |     |     |     |     | 85  |     |     |     | 90  |     |     |     |     | 95  |     |     |

|     | Thr | Phe | Gly | Gln | Gly | Thr | Arg | Leu | Asp | Ile | Lys | Arg | Thr | Val | Ala |
|-----|-----|-----|-----|-----|-----|-----|-----|-----|-----|-----|-----|-----|-----|-----|-----|
|     |     |     |     | 100 |     |     |     | 105 |     |     |     |     | 110 |     |     |

( 2 ) INFORMATION FOR SEQ ID NO:151:

( i ) SEQUENCE CHARACTERISTICS:
( A ) LENGTH: 112 amino acids
( B ) TYPE: amino acid
( D ) TOPOLOGY: linear ( i i ) MOLECULE TYPE: protein ( x i ) SEQUENCE DESCRIPTION: SEQ ID NO:151:

|     | Met | Ala | Glu | Leu | Thr | Gln | Ser | Pro | Ser | Ser | Leu | Ser | Ala | Ser | Val | Gly |
|-----|-----|-----|-----|-----|-----|-----|-----|-----|-----|-----|-----|-----|-----|-----|-----|-----|
|     | 1   |     |     |     | 5   |     |     |     |     | 10  |     |     |     |     | 15  |     |

|     | Asp | Arg | Val | Thr | Ile | Thr | Cys | Arg | Ala | Ser | Gln | Gly | Val | Ser | Ser | Ser |
|-----|-----|-----|-----|-----|-----|-----|-----|-----|-----|-----|-----|-----|-----|-----|-----|-----|
|     |     |     |     | 20  |     |     |     |     | 25  |     |     |     |     | 30  |     |     |

|     | Tyr | Leu | Ala | Trp | Tyr | Gln | Gln | Lys | Pro | Gly | Gln | Ala | Pro | Arg | Leu | Val |
|-----|-----|-----|-----|-----|-----|-----|-----|-----|-----|-----|-----|-----|-----|-----|-----|-----|
|     |     |     | 35  |     |     |     | 40  |     |     |     |     | 45  |     |     |     |     |

|     | Ile | Phe | Gly | Ala | Tyr | Ser | Arg | Ala | Thr | Gly | Ile | Pro | Asp | Arg | Phe | Ser |
|-----|-----|-----|-----|-----|-----|-----|-----|-----|-----|-----|-----|-----|-----|-----|-----|-----|
|     |     | 50  |     |     |     | 55  |     |     |     | 60  |     |     |     |     |     |     |

|     | Gly | Ser | Gly | Ser | Gly | Thr | Asp | Phe | Thr | Leu | Thr | Ile | Ser | Arg | Leu | Glu |
|-----|-----|-----|-----|-----|-----|-----|-----|-----|-----|-----|-----|-----|-----|-----|-----|-----|
|     | 65  |     |     |     |     | 70  |     |     |     | 75  |     |     |     |     |     | 80  |

|     | Pro | Glu | Asp | Phe | Ala | Val | Tyr | Tyr | Cys | Gln | Gln | Tyr | Gly | Ser | Ser | Pro |
|-----|-----|-----|-----|-----|-----|-----|-----|-----|-----|-----|-----|-----|-----|-----|-----|-----|
|     |     |     |     |     | 85  |     |     |     | 90  |     |     |     |     | 95  |     |     |

|     | Ile | Thr | Phe | Gly | Pro | Gly | Thr | Lys | Val | Asp | Ile | Lys | Arg | Thr | Val | Ala |
|-----|-----|-----|-----|-----|-----|-----|-----|-----|-----|-----|-----|-----|-----|-----|-----|-----|
|     |     |     |     | 100 |     |     |     | 105 |     |     |     |     | 110 |     |     |     |

( 2 ) INFORMATION FOR SEQ ID NO:152:

( i ) SEQUENCE CHARACTERISTICS:
        ( A ) LENGTH: 729 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 9..715

( x i ) SEQUENCE DESCRIPTION: SEQ ID NO:152:

```
AGCTTACC ATG GGT GTG CCC ACT CAG GTC CTG GGG TTG CTG CTG CTG TGG        50
         Met Gly Val Pro Thr Gln Val Leu Gly Leu Leu Leu Leu Trp
          1               5                       10

CTT ACA GAT GCC AGA TGT GAG ATC GTT CTC ACG CAG TCT CCA GGC ACC         98
Leu Thr Asp Ala Arg Cys Glu Ile Val Leu Thr Gln Ser Pro Gly Thr
 15              20                  25                      30

CTG TCT CTG TCT CCA GGG GAA AGA GCC ACC TTC TCC TGT AGG TCC AGT        146
Leu Ser Leu Ser Pro Gly Glu Arg Ala Thr Phe Ser Cys Arg Ser Ser
                 35                  40                  45

CAC AGC ATT CGC AGC CGC CGC GTA GCC TGG TAC CAG CAC AAA CCT GGC        194
His Ser Ile Arg Ser Arg Arg Val Ala Trp Tyr Gln His Lys Pro Gly
             50                  55                  60

CAG GCT CCA AGG CTG GTC ATA CAT GGT GTT TCC AAT AGG GCC TCT GGC        242
Gln Ala Pro Arg Leu Val Ile His Gly Val Ser Asn Arg Ala Ser Gly
         65                  70                  75

ATC TCA GAC AGG TTC AGC GGC AGT GGG TCT GGG ACA GAC TTC ACT CTC        290
Ile Ser Asp Arg Phe Ser Gly Ser Gly Ser Gly Thr Asp Phe Thr Leu
     80                  85                  90

ACC ATC ACC AGA GTG GAG CCT GAA GAC TTT GCA CTG TAC TAC TGT CAG        338
Thr Ile Thr Arg Val Glu Pro Glu Asp Phe Ala Leu Tyr Tyr Cys Gln
 95                 100                 105                 110

GTC TAT GGT GCC TCC TCG TAC ACT TTT GGC CAG GGG ACC AAA CTG GAG        386
Val Tyr Gly Ala Ser Ser Tyr Thr Phe Gly Gln Gly Thr Lys Leu Glu
                 115                 120                 125

AGG AAA CGA ACT GTG CCT GCA CCA TCT GTC TTC ATC TTC CCG CCA TCT        434
Arg Lys Arg Thr Val Pro Ala Pro Ser Val Phe Ile Phe Pro Pro Ser
         130                 135                 140

GAT GAG CAG TTG AAA TCT GGG ACT GCC TCT GTT GTG TGC CTG CTG AAT        482
Asp Glu Gln Leu Lys Ser Gly Thr Ala Ser Val Val Cys Leu Leu Asn
     145                 150                 155

AAC TTC TAT CCC AGA GAG GCC AAA GTA CAG TGG AAG GTG GAT AAC GCC        530
Asn Phe Tyr Pro Arg Glu Ala Lys Val Gln Trp Lys Val Asp Asn Ala
 160                 165                 170

CTC CAA TCG GGT AAC TCC CAG GAG AGT GTC ACA GAG CAG GAC AGC AAG        578
Leu Gln Ser Gly Asn Ser Gln Glu Ser Val Thr Glu Gln Asp Ser Lys
175                 180                 185                 190

GAC AGC ACC TAC AGC CTC AGC AGC ACC CTG ACG CTG AGC AAA GCA GAC        626
Asp Ser Thr Tyr Ser Leu Ser Ser Thr Leu Thr Leu Ser Lys Ala Asp
                 195                 200                 205

TAC GAG AAA CAC AAA GTC TAC GCC TGC GAA GTC ACC CAT CAG GGC CTG        674
Tyr Glu Lys His Lys Val Tyr Ala Cys Glu Val Thr His Gln Gly Leu
         210                 215                 220

AGT TCG CCC GTC ACA AAG AGC TTC AAC AGG GGA GAG TGT TA ATTCTAGAGA     725
Ser Ser Pro Val Thr Lys Ser Phe Asn Arg Gly Glu Cys
             225                 230                 235

ATTC                                                                   729
```

(2) INFORMATION FOR SEQ ID NO:153:

(i) SEQUENCE CHARACTERISTICS:
    (A) LENGTH: 235 amino acids
    (B) TYPE: amino acid
    (D) TOPOLOGY: linear (ii) MOLECULE TYPE: protein (xi) SEQUENCE DESCRIPTION: SEQ ID NO:153:

```
Met Gly Val Pro Thr Gln Val Leu Gly Leu Leu Leu Leu Trp Leu Thr
 1               5                  10                  15
Asp Ala Arg Cys Glu Ile Val Leu Thr Gln Ser Pro Gly Thr Leu Ser
             20                  25                  30
Leu Ser Pro Gly Glu Arg Ala Thr Phe Ser Cys Arg Ser Ser His Ser
         35                  40                  45
Ile Arg Ser Arg Arg Val Ala Trp Tyr Gln His Lys Pro Gly Gln Ala
     50                  55                  60
Pro Arg Leu Val Ile His Gly Val Ser Asn Arg Ala Ser Gly Ile Ser
 65                  70                  75                  80
Asp Arg Phe Ser Gly Ser Gly Ser Gly Thr Asp Phe Thr Leu Thr Ile
                 85                  90                  95
Thr Arg Val Glu Pro Glu Asp Phe Ala Leu Tyr Tyr Cys Gln Val Tyr
            100                 105                 110
Gly Ala Ser Ser Tyr Thr Phe Gly Gln Gly Thr Lys Leu Glu Arg Lys
        115                 120                 125
Arg Thr Val Pro Ala Pro Ser Val Phe Ile Phe Pro Pro Ser Asp Glu
    130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
        195                 200                 205
Lys His Lys Val Tyr Ala Cys Glu Val Thr His Gln Gly Leu Ser Ser
    210                 215                 220
Pro Val Thr Lys Ser Phe Asn Arg Gly Glu Cys
225                 230                 235
```

(2) INFORMATION FOR SEQ ID NO:154:

(i) SEQUENCE CHARACTERISTICS:
    (A) LENGTH: 3282 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: CDS
    (B) LOCATION: 15..452

(xi) SEQUENCE DESCRIPTION: SEQ ID NO:154:

```
AATTCGCCGC CACC ATG GAA TGG AGC TGG GTC TTT CTC TTC TTC CTG TCA          50
              Met Glu Trp Ser Trp Val Phe Leu Phe Phe Leu Ser
               1               5                  10

GTA ACT ACA GGT GTC CAC TCC CAG GTT CAG CTG GTT CAG TCC GGG GCT          98
```

```
                Val  Thr  Thr  Gly  Val  His  Ser  Gln  Val  Gln  Leu  Val  Gln  Ser  Gly  Ala
                          15                      20                        25

GAG  GTG  AAG  AAG  CCT  GGG  GCC  TCA  GTG  AAG  GTT  TCT  TGT  CAG  GCT  TCT                  146
Glu  Val  Lys  Lys  Pro  Gly  Ala  Ser  Val  Lys  Val  Ser  Cys  Gln  Ala  Ser
     30                       35                      40

GGA  TAC  AGA  TTC  AGT  AAC  TTT  GTT  ATT  CAT  TGG  GTG  CGC  CAG  GCC  CCC                  194
Gly  Tyr  Arg  Phe  Ser  Asn  Phe  Val  Ile  His  Trp  Val  Arg  Gln  Ala  Pro
45                       50                      55                            60

GGA  CAG  AGG  TTT  GAG  TGG  ATG  GGA  TGG  ATC  AAT  CCT  TAC  AAC  GGA  AAC                  242
Gly  Gln  Arg  Phe  Glu  Trp  Met  Gly  Trp  Ile  Asn  Pro  Tyr  Asn  Gly  Asn
                    65                       70                           75

AAA  GAA  TTT  TCA  GCG  AAG  TTC  CAG  GAC  AGA  GTC  ACC  TTT  ACC  GCG  GAC                  290
Lys  Glu  Phe  Ser  Ala  Lys  Phe  Gln  Asp  Arg  Val  Thr  Phe  Thr  Ala  Asp
               80                       85                           90

ACA  TCC  GCG  AAC  ACA  GCC  TAC  ATG  GAG  TTG  AGG  AGC  CTC  AGG  TCT  GCA                  338
Thr  Ser  Ala  Asn  Thr  Ala  Tyr  Met  Glu  Leu  Arg  Ser  Leu  Arg  Ser  Ala
          95                       100                     105

GAC  ACG  GCT  GTT  TAT  TAT  TGT  GCG  AGA  GTG  GGG  CCA  TAT  AGT  TGG  GAT                  386
Asp  Thr  Ala  Val  Tyr  Tyr  Cys  Ala  Arg  Val  Gly  Pro  Tyr  Ser  Trp  Asp
     110                      115                     120

GAT  TCT  CCC  CAG  GAC  AAT  TAT  TAT  ATG  GAC  GTC  TGG  GGC  AAA  GGA  ACC                  434
Asp  Ser  Pro  Gln  Asp  Asn  Tyr  Tyr  Met  Asp  Val  Trp  Gly  Lys  Gly  Thr
125                      130                     135                          140

ACG  GTC  ATC  GTG  AGC  TCA  GCTTCCACCA  AGGGCCCATC  GGTCTTCCCC                                 482
Thr  Val  Ile  Val  Ser  Ser
               145
```

| | |
|---|---|
| CTGGCACCCT CCTCCAAGAG CACCTCTGGG GGCACAGCGG CCCTGGGCTG CCTGGTCAAG | 542 |
| GACTACTTCC CCGAACCGGT GACGGTGTCG TGGAACTCAG GCGCCCTGAC CAGCGGCGTG | 602 |
| CACACCTTCC CGGCTGTCCT ACAGTCCTCA GGACTCTACT CCCTCAGCAG CGTGGTGACC | 662 |
| GTGCCCTCCA GCAGCTTGGG CACCCAGACC TACATCTGCA ACGTGAATCA CAAGCCCAGC | 722 |
| AACACCAAGG TGGACAAGAA AGTTGGTGAG AGGCCAGCAC AGGGAGGGAG GGTGTCTGCT | 782 |
| GGAAGCCAGG CTCAGCGCTC CTGCCTGGAC GCATCCGGC TATGCAGCCC CAGTCCAGGG | 842 |
| CAGCAAGGCA GGCCCCGTCT GCCTCTTCAC CCGGAGGCCT CTGCCCGCCC CACTCATGCT | 902 |
| CAGGGAGAGG GTCTTCTGGC TTTTTCCCCA GGCTCTGGGC AGGCACAGGC TAGGTGCCCC | 962 |
| TAACCCAGGC CCTGCACACA AAGGGGCAGG TGCTGGGCTC AGACCTGCCA AGAGCCATAT | 1022 |
| CCGGGAGGAC CCTGCCCCTG ACCTAAGCCC ACCCCAAAGG CCAAACTCTC CACTCCCTCA | 1082 |
| GCTCGGACAC CTTCTCTCCT CCCAGATTCG AGTAACTCCC AATCTTCTCT CTGCAGAGCC | 1142 |
| CAAATCTTGT GACAAAACTC ACACATGCCC ACCGTGCCCA GGTAAGCCAG CCCAGGCCTC | 1202 |
| GCCCTCCAGC TCAAGGCGGG ACAGGTGCCC TAGAGTAGCC TGCATCCAGG ACAGGCCCC | 1262 |
| AGCCGGGTGC TGACACGTCC ACCTCCATCT CTCCCTCAGC ACCTGAGGCC GCGGGAGGAC | 1322 |
| CATCAGTCTT CCTCTTCCCC CCAAAACCCA AGGACACCCT CATGATCTCC CGGACCCCTG | 1382 |
| AGGTCACATG CGTGGTGGTG GACGTGAGCC ACGAAGACCC TGAGGTCAAG TTCAACTGGT | 1442 |
| ACGTGGACGG CGTGGAGGTG CATAATGCCA AGACAAAGCC GCGGGAGGAG CAGTACAACA | 1502 |
| GCACGTACCG TGTGGTCAGC GTCCTCACCG TCCTGCACCA GGACTGGCTG AATGGCAAGG | 1562 |
| AGTACAAGTG CAAGGTCTCC AACAAAGCCC TCCCAGCCCC CATCGAGAAA ACCATCTCCA | 1622 |
| AAGCCAAAGG TGGGACCCGT GGGGTGCGAG GGCCACATGG ACAGAGGCCG GCTCGGCCCA | 1682 |
| CCCTCTGCCC TGAGAGTGAC CGCTGTACCA ACCTCTGTCC CTACAGGGCA GCCCCGAGAA | 1742 |
| CCACAGGTGT ACACCCTGCC CCCATCCCGG GATGAGCTGA CCAAGAACCA GGTCAGCCTG | 1802 |
| ACCTGCCTGG TCAAAGGCTT CTATCCCAGC GACATCGCCG TGGAGTGGGA GAGCAATGGG | 1862 |

```
CAGCCGGAGA    ACAACTACAA    GACCACGCCT    CCCGTGCTGG    ACTCCGACGG    CTCCTTCTTC    1922
CTCTACAGCA    AGCTCACCGT    GGACAAGAGC    AGGTGGCAGC    AGGGGAACGT    CTTCTCATGC    1982
TCCGTGATGC    ATGAGGCTCT    GCACAACCAC    TACACGCAGA    AGAGCCTCTC    CCTGTCTCCG    2042
GGTAAATGAG    TGCGACGGCC    GGCAAGCCCC    CGCTCCCCGG    GCTCTCGCGG    TCGCACGAGG    2102
ATGCTTGGCA    CGTACCCCCT    GTACATACTT    CCCGGGCGCC    CAGCATGGAA    ATAAAGCACC    2162
CAGCGCTGCC    CTGGGCCCCT    GCGAGACTGT    GATGGTTCTT    CCACGGGTC     AGGCCGAGTC    2222
TGAGGCCTGA    GTGGCATGAG    GGAGGCAGAG    CGGGTCCCAC    TGTCCCACA     CTGGCCCAGG    2282
CTGTGCAGGT    GTGCCTGGGC    CGCCTAGGGT    GGGGCTCAGC    CAGGGGCTGC    CCTCGGCAGG    2342
GTGGGGGATT    TGCCAGCGTT    GCCCTCCCTC    CAGCAGCACC    TGCCCTGGGC    TGGGCCACGG    2402
GAAGCCCTAG    GAGCCCCTGG    GGACAGACAC    ACAGCCCTG     CCTCTGTAGG    AGACTGTCCT    2462
GTTCTGTGAG    CGCCCTGTCC    TCCGACCTCC    ATGCCCACTC    GGGGGCATGC    CTAGTCCATG    2522
TGCGTAGGGA    CAGGCCCTCC    CTCACCCATC    TACCCCCACG    GCACTAACCC    CTGGCTGTCC    2582
TGCCCAGCCT    CGCACCCGCA    TGGGGACACA    ACCGACTCCG    GGGACATGCA    CTCTCGGGCC    2642
CTGTGGAGGG    ACTGGTGCAG    ATGCCCACAC    ACACACTCAG    TCCAGACCCG    TTCAACAAAA    2702
CCCCCGCACT    GAGGTTGGCC    GGCCACACGG    CCACCACACA    CACACGTGCA    CGCCTCACAC    2762
ACGGAGCCTC    ACCCGGGCGA    ACTGCACAGC    ACCAGACCA     GAGCAAGGTC    CTCGCACACG    2822
TGAACACTCC    TCGGACACAG    GCCCCACGA     GCCCCACGCG    GCACCTCAAG    GCCCACGAGC    2882
CTCTCGGCAG    CTTCTCCACA    TGCTGACCTG    CTCAGACAAA    CCCAGCCCTC    CTCTCACAAG    2942
GGTGCCCCTG    CAGCCGCCAC    ACACACACAG    GGGATCACAC    ACCACGTCAC    GTCCCTGGCC    3002
CTGGCCCACT    TCCCAGTGCC    GCCCTTCCCT    GCAGGGCGGA    TCATAATCAG    CCATACCACA    3062
TTTGTAGAGG    TTTTACTTGC    TTTAAAAAAC    CTCCCACACC    TCCCCCTGAA    CCTGAAACAT    3122
AAAATGAATG    CAATTGTTGT    TGTTAACTTG    TTTATTGCAG    CTTATAATGG    TTACAAATAA    3182
AGCAATAGCA    TCACAAATTT    CACAAATAAA    GCATTTTTTT    CACTGCATTC    TAGTTGTGGT    3242
TTGTCCAAAC    TCATCAATGT    ATCTTATCAT    GTCTAGATCC                                3282
```

( 2 ) INFORMATION FOR SEQ ID NO:155:

( i ) SEQUENCE CHARACTERISTICS:
( A ) LENGTH: 146 amino acids
( B ) TYPE: amino acid
( D ) TOPOLOGY: linear ( i i ) MOLECULE TYPE: protein ( x i ) SEQUENCE DESCRIPTION: SEQ ID NO:155:

```
Met  Glu  Trp  Ser  Trp  Val  Phe  Leu  Phe  Phe  Leu  Ser  Val  Thr  Thr  Gly
 1                  5                        10                       15

Val  His  Ser  Gln  Val  Gln  Leu  Val  Gln  Ser  Gly  Ala  Glu  Val  Lys  Lys
                20                       25                       30

Pro  Gly  Ala  Ser  Val  Lys  Val  Ser  Cys  Gln  Ala  Ser  Gly  Tyr  Arg  Phe
                35                       40                       45

Ser  Asn  Phe  Val  Ile  His  Trp  Val  Arg  Gln  Ala  Pro  Gly  Gln  Arg  Phe
           50                       55                       60

Glu  Trp  Met  Gly  Trp  Ile  Asn  Pro  Tyr  Asn  Gly  Asn  Lys  Glu  Phe  Ser
 65                      70                       75                       80

Ala  Lys  Phe  Gln  Asp  Arg  Val  Thr  Phe  Thr  Ala  Asp  Thr  Ser  Ala  Asn
                85                       90                       95
```

| Thr | Ala | Tyr | Met<br>100 | Glu | Leu | Arg | Ser | Leu<br>105 | Arg | Ser | Ala | Asp | Thr<br>110 | Ala | Val |
| Tyr | Tyr | Cys<br>115 | Ala | Arg | Val | Gly | Pro<br>120 | Tyr | Ser | Trp | Asp | Asp<br>125 | Ser | Pro | Gln |
| Asp | Asn<br>130 | Tyr | Tyr | Met | Asp | Val<br>135 | Trp | Gly | Lys | Gly | Thr<br>140 | Thr | Val | Ile | Val |
| Ser | Ser<br>145 |

( 2 ) INFORMATION FOR SEQ ID NO:156:

( i ) SEQUENCE CHARACTERISTICS:
        ( A ) LENGTH: 13254 base pairs
        ( B ) TYPE: nucleic acid
        ( C ) STRANDEDNESS: double
        ( D ) TOPOLOGY: circular ( i i ) MOLECULE TYPE: DNA (genomic)

( x i ) SEQUENCE DESCRIPTION: SEQ ID NO:156:

| | | | | | |
|---|---|---|---|---|---|
| TTCATTGATC | ATTAATCAGC | CATACCACAT | TTGTAGAGGT | TTTACTTGCT | TTAAAAAACC | 60 |
| TCCCACACCT | CCCCCTGAAC | CTGAAACATA | AAATGAATGC | AATTGTTGTT | GTTAACTTGT | 120 |
| TTATTGCAGC | TTATAATGGT | TACAAATAAA | GCAATAGCAT | CACAAATTTC | ACAAATAAAG | 180 |
| CATTTTTTTC | ACTGCATTCT | AGTTGTGGTT | TGTCCAAACT | CATCAATGTA | TCTTATCATG | 240 |
| TCTGGATCTC | TAGCTTCGTG | TCAAGGACGG | TGACTGCAGT | GAATAATAAA | ATGTGTGTTT | 300 |
| GTCCGAAATA | CGCGTTTTGA | GATTTCTGTC | GCCGACTAAA | TTCATGTCGC | GCGATAGTGG | 360 |
| TGTTTATCGC | CGATAGAGAT | GGCGATATTG | GAAAATCGA | TATTTGAAAA | TATGGCATAT | 420 |
| TGAAAATGTC | GCCGATGTGA | GTTTCTGTGT | AACTGATATC | GCCATTTTTC | CAAAAGTGAT | 480 |
| TTTTGGGCAT | ACGCGATATC | TGGCGATAGC | GCTTATATCG | TTTACGGGGG | ATGGCGATAG | 540 |
| ACGACTTTGG | TGACTTGGGC | GATTCTGTGT | GTCGCAAATA | TCGCAGTTTC | GATATAGGTG | 600 |
| ACAGACGATA | TGAGGCTATA | TCGCCGATAG | AGGCGACATC | AAGCTGGCAC | ATGGCCAATG | 660 |
| CATATCGATC | TATACATTGA | ATCAATATTG | GCCATTAGCC | ATATTATTCA | TTGGTTATAT | 720 |
| AGCATAAATC | AATATTGGCT | ATTGGCCATT | GCATACGTTG | TATCCATATC | ATAATATGTA | 780 |
| CATTTATATT | GGCTCATGTC | CAACATTACC | GCCATGTTGA | CATTGATTAT | TGACTAGTTA | 840 |
| TTAATAGTAA | TCAATTACGG | GGTCATTAGT | TCATAGCCCA | TATATGGAGT | TCCGCGTTAC | 900 |
| ATAACTTACG | GTAAATGGCC | CGCCTGGCTG | ACCGCCCAAC | GACCCCGCC | CATTGACGTC | 960 |
| AATAATGACG | TATGTTCCCA | TAGTAACGCC | AATAGGGACT | TTCCATTGAC | GTCAATGGGT | 1020 |
| GGAGTATTTA | CGGTAAACTG | CCCACTTGGC | AGTACATCAA | GTGTATCATA | TGCCAAGTAC | 1080 |
| GCCCCCTATT | GACGTCAATG | ACGGTAAATG | GCCCGCCTGG | CATTATGCCC | AGTACATGAC | 1140 |
| CTTATGGGAC | TTTCCTACTT | GGCAGTACAT | CTACGTATTA | GTCATCGCTA | TTACCATGGT | 1200 |
| GATGCGGTTT | TGGCAGTACA | TCAATGGGCG | TGGATAGCGG | TTTGACTCAC | GGGGATTTCC | 1260 |
| AAGTCTCCAC | CCCATTGACG | TCAATGGGAG | TTTGTTTTGG | CACCAAAATC | AACGGGACTT | 1320 |
| TCCAAAATGT | CGTAACAACT | CCGCCCCATT | GACGCAAATG | GGCGGTAGGC | GTGTACGGTG | 1380 |
| GGAGGTCTAT | ATAAGCAGAG | CTCGTTTAGT | GAACCGTCAG | ATCGCCTGGA | GACGCCATCC | 1440 |
| ACGCTGTTTT | GACCTCCATA | GAAGACACCG | GGACCGATCC | AGCCTCCGCG | GCCGGGAACG | 1500 |
| GTGCATTGGA | ACGCGGATTC | CCCGTGCCAA | GAGTGACGTA | AGTACCGCCT | ATAGAGTCTA | 1560 |
| TAGGCCCACC | CCCTTGGCTT | CTTATGCATG | CTATACTGTT | TTTGGCTTGG | GGTCTATACA | 1620 |
| CCCCCGCTTC | CTCATGTTAT | AGGTGATGGT | ATAGCTTAGC | CTATAGGTGT | GGGTTATTGA | 1680 |

| | | | | | |
|---|---|---|---|---|---|
| CCATTATTGA | CCACTCCCCT | ATTGGTGACG | ATACTTTCCA | TTACTAATCC | ATAACATGGC | 1740 |
| TCTTTGCCAC | AACTCTCTTT | ATTGGCTATA | TGCCAATACA | CTGTCCTTCA | GAGACTGACA | 1800 |
| CGGACTCTGT | ATTTTTACAG | GATGGGGTCT | CATTTATTAT | TTACAAATTC | ACATATACAA | 1860 |
| CACCACCGTC | CCCAGTGCCC | GCAGTTTTTA | TTAAACATAA | CGTGGGATCT | CCACGCGAAT | 1920 |
| CTCGGGTACG | TGTTCCGGAC | ATGGGCTCTT | CTCCGGTAGC | GGCGGAGCTT | CTACATCCGA | 1980 |
| GCCCTGCTCC | CATGCCTCCA | GCGACTCATG | GTCGCTCGGC | AGCTCCTTGC | TCCTAACAGT | 2040 |
| GGAGGCCAGA | CTTAGGCACA | GCACGATGCC | CACCACCACC | AGTGTGCCGC | ACAAGGCCGT | 2100 |
| GGCGGTAGGG | TATGTGTCTG | AAAATGAGCT | CGGGGAGCGG | GCTTGCACCG | CTGACGCATT | 2160 |
| TGGAAGACTT | AAGGCAGCGG | CAGAAGAAGA | TGCAGGCAGC | TGAGTTGTTG | TGTTCTGATA | 2220 |
| AGAGTCAGAG | GTAACTCCCG | TTGCGGTGCT | GTTAACGGTG | GAGGGCAGTG | TAGTCTGAGC | 2280 |
| AGTACTCGTT | GCTGCCGCGC | GCGCCACCAG | ACATAATAGC | TGACAGACTA | ACAGACTGTT | 2340 |
| CCTTTCCATG | GGTCTTTTCT | GCAGTCACCG | TCCTTGACAC | GAAGCTTGGG | CTGCAGGTCG | 2400 |
| ATCGACTCTA | GAGGATCGAT | CCCCGGGCGA | GCTCGAATTC | GCCGCCACCA | TGGAATGGAG | 2460 |
| CTGGGTCTTT | CTCTTCTTCC | TGTCAGTAAC | TACAGGTGTC | CACTCCCAGG | TTCAGCTGGT | 2520 |
| TCAGTCCGGG | GCTGAGGTGA | AGAAGCCTGG | GGCCTCAGTG | AAGGTTTCTT | GTCAGGCTTC | 2580 |
| TGGATACAGA | TTCAGTAACT | TTGTTATTCA | TTGGGTGCGC | CAGGCCCCCG | GACAGAGGTT | 2640 |
| TGAGTGGATG | GGATGGATCA | ATCCTTACAA | CGGAAACAAA | GAATTTTCAG | CGAAGTTCCA | 2700 |
| GGACAGAGTC | ACCTTTACCG | CGGACACATC | CGCGAACACA | GCCTACATGG | AGTTGAGGAG | 2760 |
| CCTCAGGTCT | GCAGACACGG | CTGTTTATTA | TTGTGCGAGA | GTGGGGCCAT | ATAGTTGGGA | 2820 |
| TGATTCTCCC | CAGGACAATT | ATTATATGGA | CGTCTGGGGC | AAAGGAACCA | CGGTCATCGT | 2880 |
| GAGCTCAGCT | TCCACCAAGG | GCCCATCGGT | CTTCCCCCTG | GCACCCTCCT | CCAAGAGCAC | 2940 |
| CTCTGGGGGC | ACAGCGGCCC | TGGGCTGCCT | GGTCAAGGAC | TACTTCCCCG | AACCGGTGAC | 3000 |
| GGTGTCGTGG | AACTCAGGCG | CCCTGACCAG | CGGCGTGCAC | ACCTTCCCGG | CTGTCCTACA | 3060 |
| GTCCTCAGGA | CTCTACTCCC | TCAGCAGCGT | GGTGACCGTG | CCCTCCAGCA | GCTTGGGCAC | 3120 |
| CCAGACCTAC | ATCTGCAACG | TGAATCACAA | GCCCAGCAAC | ACCAAGGTGG | ACAAGAAAGT | 3180 |
| TGGTGAGAGG | CCAGCACAGG | GAGGGAGGGT | GTCTGCTGGA | AGCCAGGCTC | AGCGCTCCTG | 3240 |
| CCTGGACGCA | TCCCGGCTAT | GCAGCCCCAG | TCCAGGGCAG | CAAGGCAGGC | CCCGTCTGCC | 3300 |
| TCTTCACCCG | GAGGCCTCTG | CCCGCCCCAC | TCATGCTCAG | GGAGAGGGTC | TTCTGGCTTT | 3360 |
| TTCCCCAGGC | TCTGGGCAGG | CACAGGCTAG | GTGCCCCTAA | CCCAGGCCCT | GCACACAAAG | 3420 |
| GGGCAGGTGC | TGGGCTCAGA | CCTGCCAAGA | GCCATATCCG | GGAGGACCCT | GCCCCTGACC | 3480 |
| TAAGCCCACC | CCAAAGGCCA | AACTCTCCAC | TCCCTCAGCT | CGGACACCTT | CTCTCCTCCC | 3540 |
| AGATTCGAGT | AACTCCCAAT | CTTCTCTCTG | CAGAGCCCAA | ATCTTGTGAC | AAAACTCACA | 3600 |
| CATGCCCACC | GTGCCCAGGT | AAGCCAGCCC | AGGCCTCGCC | CTCCAGCTCA | AGGCGGGACA | 3660 |
| GGTGCCCTAG | AGTAGCCTGC | ATCCAGGGAC | AGGCCCCAGC | CGGGTGCTGA | CACGTCCACC | 3720 |
| TCCATCTCTC | CCTCAGCACC | TGAGGCCGCG | GGAGGACCAT | CAGTCTTCCT | CTTCCCCCCA | 3780 |
| AAACCCAAGG | ACACCCTCAT | GATCTCCCGG | ACCCCTGAGG | TCACATGCGT | GGTGGTGGAC | 3840 |
| GTGAGCCACG | AAGACCCTGA | GGTCAAGTTC | AACTGGTACG | TGGACGGCGT | GGAGGTGCAT | 3900 |
| AATGCCAAGA | CAAAGCCGCG | GGAGGAGCAG | TACAACAGCA | CGTACCGTGT | GGTCAGCGTC | 3960 |
| CTCACCGTCC | TGCACCAGGA | CTGGCTGAAT | GGCAAGGAGT | ACAAGTGCAA | GGTCTCCAAC | 4020 |
| AAAGCCCTCC | CAGCCCCCAT | CGAGAAAACC | ATCTCCAAAG | CCAAAGGTGG | GACCCGTGGG | 4080 |

```
GTGCGAGGGC  CACATGGACA  GAGGCCGGCT  CGGCCCACCC  TCTGCCCTGA  GAGTGACCGC    4140

TGTACCAACC  TCTGTCCCTA  CAGGGCAGCC  CCGAGAACCA  CAGGTGTACA  CCCTGCCCCC    4200

ATCCCGGGAT  GAGCTGACCA  AGAACCAGGT  CAGCCTGACC  TGCCTGGTCA  AAGGCTTCTA    4260

TCCCAGCGAC  ATCGCCGTGG  AGTGGGAGAG  CAATGGGCAG  CCGGAGAACA  ACTACAAGAC    4320

CACGCCTCCC  GTGCTGGACT  CCGACGGCTC  CTTCTTCCTC  TACAGCAAGC  TCACCGTGGA    4380

CAAGAGCAGG  TGGCAGCAGG  GGAACGTCTT  CTCATGCTCC  GTGATGCATG  AGGCTCTGCA    4440

CAACCACTAC  ACGCAGAAGA  GCCTCTCCCT  GTCTCCGGGT  AAATGAGTGC  GACGGCCGGC    4500

AAGCCCCCGC  TCCCCGGGCT  CTCGCGGTCG  CACGAGGATG  CTTGGCACGT  ACCCCCTGTA    4560

CATACTTCCC  GGGCGCCCAG  CATGGAAATA  AAGCACCCAG  CGCTGCCCTG  GCCCCTGCG     4620

AGACTGTGAT  GGTTCTTTCC  ACGGGTCAGG  CCGAGTCTGA  GGCCTGAGTG  GCATGAGGGA    4680

GGCAGAGCGG  GTCCCACTGT  CCCCACACTG  GCCCAGGCTG  TGCAGGTGTG  CCTGGGCCGC    4740

CTAGGGTGGG  GCTCAGCCAG  GGGCTGCCCT  CGGCAGGGTG  GGGGATTTGC  CAGCGTTGCC    4800

CTCCCTCCAG  CAGCACCTGC  CCTGGGCTGG  GCCACGGGAA  GCCCTAGGAG  CCCCTGGGGA    4860

CAGACACACA  GCCCCTGCCT  CTGTAGGAGA  CTGTCCTGTT  CTGTGAGCGC  CCTGTCCTCC    4920

GACCTCCATG  CCCACTCGGG  GGCATGCCTA  GTCCATGTGC  GTAGGGACAG  GCCCTCCCTC    4980

ACCCATCTAC  CCCCACGGCA  CTAACCCCTG  GCTGTCCTGC  CCAGCCTCGC  ACCCGCATGG    5040

GGACACAACC  GACTCCGGGG  ACATGCACTC  TCGGGCCCTG  TGGAGGGACT  GGTGCAGATG    5100

CCCACACACA  CACTCAGTCC  AGACCCGTTC  AACAAACCC   CCGCACTGAG  GTTGGCCGGC    5160

CACACGGCCA  CCACACACAC  ACGTGCACGC  CTCACACACG  GAGCCTCACC  CGGGCGAACT    5220

GCACAGCACC  CAGACCAGAG  CAAGGTCCTC  GCACACGTGA  ACACTCCTCG  GACACAGGCC    5280

CCCACGAGCC  CCACGCGGCA  CCTCAAGGCC  CACGAGCCTC  TCGGCAGCTT  CTCCACATGC    5340

TGACCTGCTC  AGACAAACCC  AGCCCTCCTC  TCACAAGGGT  GCCCCTGCAG  CCGCCACACA    5400

CACACAGGGG  ATCACACACC  ACGTCACGTC  CCTGGCCCTG  GCCCACTTCC  CAGTGCCGCC    5460

CTTCCCTGCA  GGGCGGATCA  TAATCAGCCA  TACCACATTT  GTAGAGGTTT  TACTTGCTTT    5520

AAAAAACCTC  CCACACCTCC  CCCTGAACCT  GAAACATAAA  ATGAATGCAA  TTGTTGTTGT    5580

TAACTTGTTT  ATTGCAGCTT  ATAATGGTTA  CAAATAAAGC  AATAGCATCA  CAAATTTCAC    5640

AAATAAAGCA  TTTTTTTCAC  TGCATTCTAG  TTGTGGTTTG  TCCAAACTCA  TCAATGTATC    5700

TTATCATGTC  TAGATCCTCT  ACGCCGGACG  CATCGTGGCC  GGCATCACCG  GCGCCACAGG    5760

TGCGGTTGCT  GGCGCCTATA  TCGCCGACAT  CACCGATGGG  GAAGATCGGG  CTCGCCACTT    5820

CGGGCTCATG  AGCGCTTGTT  TCGGCGTGGG  TATGGTGGCA  GGCCCGTGGC  CGGGGGACTG    5880

TTGGGCGCCA  TCTCCTTGCA  TGCACCATTC  CTTGCGGCGG  CGGTGCTCAA  CGGCCTCAAC    5940

CTACTACTGG  GCTGCTTCCT  AATGCAGGAG  TCGCATAAGG  GAGAGCGTCG  ACCTCGGGCC    6000

GCGTTGCTGG  CGTTTTTCCA  TAGGCTCCGC  CCCCCTGACG  AGCATCACAA  AAATCGACGC    6060

TCAAGTCAGA  GGTGGCGAAA  CCCGACAGGA  CTATAAAGAT  ACCAGGCGTT  CCCCCTGGA     6120

AGCTCCCTCG  TGCGCTCTCC  TGTTCCGACC  CTGCCGCTTA  CCGGATACCT  GTCCGCCTTT    6180

CTCCCTTCGG  GAAGCGTGGC  GCTTTCTCAA  TGCTCACGCT  GTAGGTATCT  CAGTTCGGTG    6240

TAGGTCGTTC  GCTCCAAGCT  GGGCTGTGTG  CACGAACCCC  CCGTTCAGCC  CGACCGCTGC    6300

GCCTTATCCG  GTAACTATCG  TCTTGAGTCC  AACCCGGTAA  GACACGACTT  ATCGCCACTG    6360

GCAGCAGCCA  CTGGTAACAG  GATTAGCAGA  GCGAGGTATG  TAGGCGGTGC  TACAGAGTTC    6420

TTGAAGTGGT  GGCCTAACTA  CGGCTACACT  AGAAGGACAG  TATTTGGTAT  CTGCGCTCTG    6480
```

```
CTGAAGCCAG TTACCTTCGG AAAAAGAGTT GGTAGCTCTT GATCCGGCAA ACAAACCACC    6540
GCTGGTAGCG GTGGTTTTTT TGTTTGCAAG CAGCAGATTA CGCGCAGAAA AAAAGGATCT    6600
CAAGAAGATC CTTTGATCTT TTCTACGGGG TCTGACGCTC AGTGGAACGA AAACTCACGT    6660
TAAGGGATTT TGGTCATGAG ATTATCAAAA AGGATCTTCA CCTAGATCCT TTTAAATTAA    6720
AAATGAAGTT TTAAATCAAT CTAAAGTATA TATGAGTAAA CTTGGTCTGA CAGTTACCAA    6780
TGCTTAATCA GTGAGGCACC TATCTCAGCG ATCTGTCTAT TTCGTTCATC CATAGTTGCC    6840
TGACTCCCCG TCGTGTAGAT AACTACGATA CGGGAGGGCT TACCATCTGG CCCCAGTGCT    6900
GCAATGATAC CGCGAGACCC ACGCTCACCG GCTCCAGATT TATCAGCAAT AAACCAGCCA    6960
GCCGGAAGGG CCGAGCGCAG AAGTGGTCCT GCAACTTTAT CCGCCTCCAT CCAGTCTATT    7020
AATTGTTGCC GGGAAGCTAG AGTAAGTAGT TCGCCAGTTA ATAGTTTGCG CAACGTTGTT    7080
GCCATTGCTA CAGGCATCGT GGTGTCACGC TCGTCGTTTG GTATGGCTTC ATTCAGCTCC    7140
GGTTCCCAAC GATCAAGGCG AGTTACATGA TCCCCCATGT TGTGCAAAAA AGCGGTTAGC    7200
TCCTTCGGTC CTCCGATCGT TGTCAGAAGT AAGTTGGCCG CAGTGTTATC ACTCATGGTT    7260
ATGGCAGCAC TGCATAATTC TCTTACTGTC ATGCCATCCG TAAGATGCTT TTCTGTGACT    7320
GGTGAGTACT CAACCAAGTC ATTCTGAGAA TAGTGTATGC GGCGACCGAG TTGCTCTTGC    7380
CCGGCGTCAA CACGGGATAA TACCGCGCCA CATAGCAGAA CTTTAAAAGT GCTCATCATT    7440
GGAAAACGTT CTTCGGGGCG AAAACTCTCA AGGATCTTAC CGCTGTTGAG ATCCAGTTCG    7500
ATGTAACCCA CTCGTGCACC CAACTGATCT TCAGCATCTT TTACTTTCAC CAGCGTTTCT    7560
GGGTGAGCAA AAACAGGAAG GCAAAATGCC GCAAAAAAGG GAATAAGGGC GACACGGAAA    7620
TGTTGAATAC TCATACTCTT CCTTTTTCAA TATTATTGAA GCATTTATCA GGGTTATTGT    7680
CTCATGAGCG GATACATATT TGAATGTATT TAGAAAAATA AACAAATAGG GGTTCCGCGC    7740
ACATTTCCCC GAAAAGTGCC ACCTGACGTC TAAGAAACCA TTATTATCAT GACATTAACC    7800
TATAAAAATA GGCGTATCAC GAGGCCCTGA TGGCTCTTTG CGGCACCCAT CGTTCGTAAT    7860
GTTCCGTGGC ACCGAGGACA ACCCTCAAGA GAAAATGTAA TCACACTGGC TCACCTTCGG    7920
GTGGGCCTTT CTGCGTTTAT AAGGAGACAC TTTATGTTTA AGAAGGTTGG TAAATTCCTT    7980
GCGGCTTTGG CAGCCAAGCT AGATCCGGCT GTGGAATGTG TGTCAGTTAG GGTGTGGAAA    8040
GTCCCCAGGC TCCCCAGCAG GCAGAAGTAT GCAAAGCATG CATCTCAATT AGTCAGCAAC    8100
CAGGCTCCCC AGCAGGCAGA AGTATGCAAA GCATGCATCT CAATTAGTCA GCAACCATAG    8160
TCCCGCCCCT AACTCCGCCC ATCCCGCCCC TAACTCCGCC CAGTTCCGCC CATTCTCCGC    8220
CCCATGGCTG ACTAATTTTT TTATTTATG CAGAGGCCGA GGCCGCCTCG GCCTCTGAGC    8280
TATTCCAGAA GTAGTGAGGA GGCTTTTTTG GAGGCCTAGG CTTTTGCAAA AACTAGCTTG    8340
GGGCCACCGC TCAGAGCACC TTCCACCATG GCCACCTCAG CAAGTTCCCA CTTGAACAAA    8400
AACATCAAGC AAATGTACTT GTGCCTGCCC CAGGGTGAGA AAGTCCAAGC CATGTATATC    8460
TGGGTTGATG GTACTGGAGA AGGACTGCGC TGCAAAACCC GCACCTGGA CTGTGAGCCC    8520
AAGTGTGTAG AAGAGTTACC TGAGTGGAAT TTTGATGGCT CTAGTACCTT TCAGTCTGAG    8580
GGCTCCAACA GTGACATGTA TCTCAGCCCT GTTGCCATGT TCGGGACCC CTTCCGCAGA    8640
GATCCCAACA AGCTGGTGTT CTGTGAAGTT TTCAAGTACA ACCGGAAGCC TGCAGAGACC    8700
AATTTAAGGC ACTCGTGTAA ACGGATAATG GACATGGTGA GCAACCAGCA CCCCTGGTTT    8760
GGAATGGAAC AGGAGTATAC TCTGATGGGA ACAGATGGGC ACCCTTTTGG TTGGCCTTCC    8820
AATGGCTTTC CTGGGCCCCA AGGTCCGTAT TACTGTGGTG TGGGCGCAGA CAAAGCCTAT    8880
```

| | | | | | | |
|---|---|---|---|---|---|---|
| GGCAGGGATA | TCGTGGAGGC | TCACTACCGC | GCCTGCTTGT | ATGCTGGGGT | CAAGATTACA | 8940 |
| GGAACAAATG | CTGAGGTCAT | GCCTGCCCAG | TGGGAACTCC | AAATAGGACC | CTGTGAAGGA | 9000 |
| ATCCGCATGG | GAGATCATCT | CTGGGTGGCC | CGTTTCATCT | TCATCGAGTA | TGTGAAGACT | 9060 |
| TTGGGGTAAT | AGCAACCTTT | GACCCCAAGC | CCATTCCTGG | GAACTGGAAT | GGTGCAGGCT | 9120 |
| GCCATACCAA | CTTTAGCACC | AAGGCCATGC | GGGAGGAGAA | TGGTCTGAAG | CACATCGAGG | 9180 |
| AGGCCATCGA | GAAACTAAGC | AAGCGGCACC | GGTACCACAT | TCGAGCCTAC | GATCCCAAGG | 9240 |
| GGGGCCTGGA | CAATGCCCGT | GGTCTGACTG | GGTTCCACGA | AACGTCCAAC | ATCAACGACT | 9300 |
| TTTCTGCTGG | TGTCGCCAAT | CGCAGTGCCA | GCATCCGCAT | TCCCCGGACT | GTCGGCCAGG | 9360 |
| AGAAGAAAGG | TTACTTTGAA | GACCGCGGCC | CCTCTGCCAA | TTGTGACCCC | TTTGCAGTGA | 9420 |
| CAGAAGCCAT | CGTCCGCACA | TGCCTTCTCA | ATGAGACTGG | CCACGAGCCC | TTCCAATACA | 9480 |
| AAAACTAATT | AGACTTTGAG | TGATCTTGAG | CCTTTCCTAG | TTCATCCCAC | CCCGCCCCAG | 9540 |
| AGAGATCTTT | GTGAAGGAAC | CTTACTTCTG | TGGTGTGACA | TAATTGGACA | AACTACCTAC | 9600 |
| AGAGATTTAA | AGCTCTAAGG | TAAATATAAA | ATTTTAAGT | GTATAATGTG | TTAAACTACT | 9660 |
| GATTCTAATT | GTTTGTGTAT | TTTAGATTCC | AACCTATGGA | ACTGATGAAT | GGGAGCAGTG | 9720 |
| GTGGAATGCC | TTTAATGAGG | AAAACCTGTT | TTGCTCAGAA | GAAATGCCAT | CTAGTGATGA | 9780 |
| TGAGGCTACT | GCTGACTCTC | AACATTCTAC | TCCTCCAAAA | AAGAAGAGAA | AGGTAGAAGA | 9840 |
| CCCCAAGGAC | TTTCCTTCAG | AATTGCTAAG | TTTTTGAGT | CATGCTGTGT | TTAGTAATAG | 9900 |
| AACTCTTGCT | TGCTTTGCTA | TTTACACCAC | AAAGGAAAAA | GCTGCACTGC | TATACAAGAA | 9960 |
| AATTATGGAA | AAATATTCTG | TAACCTTTAT | AAGTAGGCAT | AACAGTTATA | ATCATAACAT | 10020 |
| ACTGTTTTTT | CTTACTCCAC | ACAGGCATAG | AGTGTCTGCT | ATTAATAACT | ATGCTCAAAA | 10080 |
| ATTGTGTACC | TTTAGCTTTT | TAATTTGTAA | AGGGGTTAAT | AAGGAATATT | TGATGTATAG | 10140 |
| TGCCTTGACT | AGAGATCATA | ATCAGCCATA | CCACATTTGT | AGAGGTTTTA | CTTGCTTTAA | 10200 |
| AAAACCTCCC | ACACCTCCCC | CTGAACCTGA | AACATAAAAT | GAATGCAATT | GTTGTTGTTA | 10260 |
| ACTTGTTTAT | TGCAGCTTAT | AATGGTTACA | AATAAAGCAA | TAGCATCACA | AATTTCACAA | 10320 |
| ATAAAGCATT | TTTTTCACTG | CATTCTAGTT | GTGGTTTGTC | CAAACTCATC | AATGTATCTT | 10380 |
| ATCATGTCTG | GATCTCTAGC | TTCGTGTCAA | GGACGGTGAC | TGCAGTGAAT | AATAAAATGT | 10440 |
| GTGTTTGTCC | GAAATACGCG | TTTTGAGATT | TCTGTCGCCG | ACTAAATTCA | TGTCGCGCGA | 10500 |
| TAGTGGTGTT | TATCGCCGAT | AGAGATGGCG | ATATTGGAAA | AATCGATATT | TGAAAATATG | 10560 |
| GCATATTGAA | AATGTCGCCG | ATGTGAGTTT | CTGTGTAACT | GATATCGCCA | TTTTTCCAAA | 10620 |
| AGTGATTTTT | GGGCATACGC | GATATCTGGC | GATAGCGCTT | ATATCGTTTA | CGGGGGATGG | 10680 |
| CGATAGACGA | CTTTGGTGAC | TTGGGCGATT | CTGTGTGTCG | CAAATATCGC | AGTTTCGATA | 10740 |
| TAGGTGACAG | ACGATATGAG | GCTATATCGC | CGATAGAGGC | GACATCAAGC | TGGCACATGG | 10800 |
| CCAATGCATA | TCGATCTATA | CATTGAATCA | ATATTGGCCA | TTAGCCATAT | TATTCATTGG | 10860 |
| TTATATAGCA | TAAATCAATA | TTGGCTATTG | GCCATTGCAT | ACGTTGTATC | CATATCATAA | 10920 |
| TATGTACATT | TATATTGGCT | CATGTCCAAC | ATTACCGCCA | TGTTGACATT | GATTATTGAC | 10980 |
| TAGTTATTAA | TAGTAATCAA | TTACGGGGTC | ATTAGTTCAT | AGCCCATATA | TGGAGTTCCG | 11040 |
| CGTTACATAA | CTTACGGTAA | ATGGCCCGCC | TGGCTGACCG | CCCAACGACC | CCCGCCCATT | 11100 |
| GACGTCAATA | ATGACGTATG | TTCCCATAGT | AACGCCAATA | GGGACTTTCC | ATTGACGTCA | 11160 |
| ATGGGTGGAG | TATTTACGGT | AAACTGCCCA | CTTGGCAGTA | CATCAAGTGT | ATCATATGCC | 11220 |
| AAGTACGCCC | CCTATTGACG | TCAATGACGG | TAAATGGCCC | GCCTGGCATT | ATGCCCAGTA | 11280 |

| | | | | | | |
|---|---|---|---|---|---|---|
| CATGACCTTA | TGGGACTTTC | CTACTTGGCA | GTACATCTAC | GTATTAGTCA | TCGCTATTAC | 11340 |
| CATGGTGATG | CGGTTTTGGC | AGTACATCAA | TGGGCGTGGA | TAGCGGTTTG | ACTCACGGGG | 11400 |
| ATTTCCAAGT | CTCCACCCCA | TTGACGTCAA | TGGGAGTTTG | TTTTGGCACC | AAAATCAACG | 11460 |
| GGACTTTCCA | AAATGTCGTA | ACAACTCCGC | CCCATTGACG | CAAATGGGCG | GTAGGCGTGT | 11520 |
| ACGGTGGGAG | GTCTATATAA | GCAGAGCTCG | TTTAGTGAAC | CGTCAGATCG | CCTGGAGACG | 11580 |
| CCATCCACGC | TGTTTTGACC | TCCATAGAAG | ACACCGGGAC | CGATCCAGCC | TCCGCGGCCG | 11640 |
| GGAACGGTGC | ATTGAACGC | GGATTCCCCG | TGCCAAGAGT | GACGTAAGTA | CCGCCTATAG | 11700 |
| AGTCTATAGG | CCCACCCCCT | TGGCTTCTTA | TGCATGCTAT | ACTGTTTTTG | GCTTGGGGTC | 11760 |
| TATACACCCC | CGCTTCCTCA | TGTTATAGGT | GATGGTATAG | CTTAGCCTAT | AGGTGTGGGT | 11820 |
| TATTGACCAT | TATTGACCAC | TCCCCTATTG | GTGACGATAC | TTTCCATTAC | TAATCCATAA | 11880 |
| CATGGCTCTT | TGCCACAACT | CTCTTTATTG | GCTATATGCC | AATACACTGT | CCTTCAGAGA | 11940 |
| CTGACACGGA | CTCTGTATTT | TTACAGGATG | GGGTCTCATT | TATTATTTAC | AAATTCACAT | 12000 |
| ATACAACACC | ACCGTCCCCA | GTGCCCGCAG | TTTTTATTAA | ACATAACGTG | GGATCTCCAC | 12060 |
| GCGAATCTCG | GGTACGTGTT | CCGGACATGG | GCTCTTCTCC | GGTAGCGGCG | GAGCTTCTAC | 12120 |
| ATCCGAGCCC | TGCTCCCATG | CCTCCAGCGA | CTCATGGTCG | CTCGGCAGCT | CCTTGCTCCT | 12180 |
| AACAGTGGAG | GCCAGACTTA | GGCACAGCAC | GATGCCCACC | ACCACCAGTG | TGCCGCACAA | 12240 |
| GGCCGTGGCG | GTAGGGTATG | TGTCTGAAAA | TGAGCTCGGG | GAGCGGGCTT | GCACCGCTGA | 12300 |
| CGCATTTGGA | AGACTTAAGG | CAGCGGCAGA | AGAAGATGCA | GGCAGCTGAG | TTGTTGTGTT | 12360 |
| CTGATAAGAG | TCAGAGGTAA | CTCCCGTTGC | GGTGCTGTTA | ACGGTGGAGG | GCAGTGTAGT | 12420 |
| CTGAGCAGTA | CTCGTTGCTG | CCGCGCGCGC | CACCAGACAT | AATAGCTGAC | AGACTAACAG | 12480 |
| ACTGTTCCTT | TCCATGGGTC | TTTTCTGCAG | TCACCGTCCT | TGACACGAAG | CTTACCATGG | 12540 |
| GTGTGCCCAC | TCAGGTCCTG | GGGTTGCTGC | TGCTGTGGCT | TACAGATGCC | AGATGTGAGA | 12600 |
| TCGTTCTCAC | GCAGTCTCCA | GGCACCCTGT | CTCTGTCTCC | AGGGGAAAGA | GCCACCTTCT | 12660 |
| CCTGTAGGTC | CAGTCACAGC | ATTCGCAGCC | GCCGCGTAGC | CTGGTACCAG | CACAAACCTG | 12720 |
| GCCAGGCTCC | AAGGCTGGTC | ATACATGGTG | TTTCCAATAG | GGCCTCTGGC | ATCTCAGACA | 12780 |
| GGTTCAGCGG | CAGTGGGTCT | GGGACAGACT | TCACTCTCAC | CATCACCAGA | GTGGAGCCTG | 12840 |
| AAGACTTTGC | ACTGTACTAC | TGTCAGGTCT | ATGGTGCCTC | CTCGTACACT | TTTGGCCAGG | 12900 |
| GGACCAAACT | GGAGAGGAAA | CGAACTGTGC | CTGCACCATC | TGTCTTCATC | TTCCCGCCAT | 12960 |
| CTGATGAGCA | GTTGAAATCT | GGGACTGCCT | CTGTTGTGTG | CCTGCTGAAT | AACTTCTATC | 13020 |
| CCAGAGAGGC | CAAAGTACAG | TGGAAGGTGG | ATAACGCCCT | CCAATCGGGT | AACTCCCAGG | 13080 |
| AGAGTGTCAC | AGAGCAGGAC | AGCAAGGACA | GCACCTACAG | CCTCAGCAGC | ACCCTGACGC | 13140 |
| TGAGCAAAGC | AGACTACGAG | AAACACAAAG | TCTACGCCTG | CGAAGTCACC | CATCAGGGCC | 13200 |
| TGAGATCGCC | CGTCACAAAG | AGCTTCAACA | GGGGAGAGTG | TTAATTCTAG | AGAA | 13254 |

( 2 ) INFORMATION FOR SEQ ID NO:157:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:157:

CAGGTTCAGC TGGTTCAGTC CGGGGCT 27

( 2 ) INFORMATION FOR SEQ ID NO:158:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:158:

CCTTGGAGCT CACGATGACC GTGGTTCCTT GGCCCCAGAC GTCC 44

( 2 ) INFORMATION FOR SEQ ID NO:159:

( i ) SEQUENCE CHARACTERISTICS:
    ( A ) LENGTH: 60 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:159:

GGCCGCGAAT TCGCCGCCAC CATGGAATGG AGCTGGGTCT TTCTCTTCTT CCTGTCAGTA 60

( 2 ) INFORMATION FOR SEQ ID NO:160:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:160:

AGCCCCGGAC TGAACCAGCT GAACCTG 27

( 2 ) INFORMATION FOR SEQ ID NO:161:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:161:

GGAGTTGAGG AGCCTCAGGT CTGCAGACAC GG 32

( 2 ) INFORMATION FOR SEQ ID NO:162:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:162:

CCGTGTCTGC AGACCTGTGG CTCCTCAACT CC 32

( 2 ) INFORMATION FOR SEQ ID NO:163:

( i ) SEQUENCE CHARACTERISTICS:
　　　　( A ) LENGTH: 33 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:163:

GATGCCAGAT GTGAGATCGT TCTCACGCAG TCT　　　　　　　　　　　　33

( 2 ) INFORMATION FOR SEQ ID NO:164:

( i ) SEQUENCE CHARACTERISTICS:
　　　　( A ) LENGTH: 67 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:164:

GCGGGATCCG AATTCTCTAG AATTAACACT CTCCCTGTT GAAGCTCTTT GTGACGGGCG　　60

AACTCAG　　　　　　　　　　　　　　　　　　　　　　　　　　67

( 2 ) INFORMATION FOR SEQ ID NO:165:

( i ) SEQUENCE CHARACTERISTICS:
　　　　( A ) LENGTH: 51 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:165:

GCGCGAATTC ACCATGGGTG TGCCCACTCA GGTCCTGGGG GTTGCTGCTG C　　　51

( 2 ) INFORMATION FOR SEQ ID NO:166:

( i ) SEQUENCE CHARACTERISTICS:
　　　　( A ) LENGTH: 33 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:166:

AGACTGCGTG AGAACGATCT CACATCTGGC ATC　　　　　　　　　　　33

( 2 ) INFORMATION FOR SEQ ID NO:167:

( i ) SEQUENCE CHARACTERISTICS:
　　　　( A ) LENGTH: 50 base pairs
　　　　( B ) TYPE: nucleic acid
　　　　( C ) STRANDEDNESS: single
　　　　( D ) TOPOLOGY: linear ( i i ) MOLECULE TYPE: DNA (genomic)

( x i ) SEQUENCE DESCRIPTION: SEQ ID NO:167:

GCGCAAGCTT ACCATGGGTG TGCCCACTCA GGTCCTGGGG TTGCTGCTGC　　　50

( 2 ) INFORMATION FOR SEQ ID NO:168:

( i ) SEQUENCE CHARACTERISTICS:
　　　　( A ) LENGTH: 729 base pairs
　　　　( B ) TYPE: nucleic acid ( C ) STRANDEDNESS: double
( D ) TOPOLOGY: linear ( i i ) MOLECULE TYPE: DNA (genomic)

( x i ) SEQUENCE DESCRIPTION: SEQ ID NO:168:

| | | | | | | |
|---|---|---|---|---|---|---|
| GAATTCTCTA | GAATTAACAC | TCTCCCCTGT | TGAAGCTCTT | TGTGACGGGC | GAACTCAGGC | 60 |
| CCTGATGGGT | GACTTCGCAG | GCGTAGACTT | TGTGTTTCTC | GTAGTCTGCT | TTGCTCAGCG | 120 |
| TCAGGGTGCT | GCTGAGGCTG | TAGGTGCTGT | CCTTGCTGTC | CTGCTCTGTG | ACACTCTCCT | 180 |
| GGGAGTTACC | CGATTGGAGG | GCGTTATCCA | CCTTCCACTG | TACTTTGGCC | TCTCTGGGAT | 240 |
| AGAAGTTATT | CAGCAGGCAC | ACAACAGAGG | CAGTCCCAGA | TTTCAACTGC | TCATCAGATG | 300 |
| GCGGGAAGAT | GAAGACAGAT | GGTGCAGGCA | CAGTTCGTTT | CCTCTCCAGT | TTGGTCCCCT | 360 |
| GGCCAAAAGT | GTACGAGGAG | GCACCATAGA | CCTGACAGTA | GTACAGTGCA | AAGTCTTCAG | 420 |
| GCTCCACTCT | GGTGATGGTG | AGAGTGAAGT | CTGTCCCAGA | CCCACTGCCG | CTGAACCTGT | 480 |
| CTGAGATGCC | AGAGGCCCTA | TTGGAAACAC | CATGTATGAC | CAGCCTTGGA | GCCTGGCCAG | 540 |
| GTTTGTGCTG | GTACCAGGCT | ACGCGGCGGC | TGCGAATGCT | GTGACTGGAC | CTACAGGAGA | 600 |
| AGGTGGCTCT | TTCCCCTGGA | GACAGAGACA | GGGTGCCTGG | AGACTGCGTG | AGAACGATCT | 660 |
| CACATCTGGC | ATCTGTAAGC | CACAGCAGCA | GCAACCCCAG | GACCTGAGTG | GGCACACCCA | 720 |
| TGGTAAGCT | | | | | | 729 |

( 2 ) INFORMATION FOR SEQ ID NO:169:

( i ) SEQUENCE CHARACTERISTICS:
( A ) LENGTH: 3282 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:169:

| | | | | | | |
|---|---|---|---|---|---|---|
| GGATCTAGAC | ATGATAAGAT | ACATTGATGA | GTTGGACAA | ACCACAACTA | GAATGCAGTG | 60 |
| AAAAAAATGC | TTTATTTGTG | AAATTTGTGA | TGCTATTGCT | TTATTTGTAA | CCATTATAAG | 120 |
| CTGCAATAAA | CAAGTTAACA | ACAACAATTG | CATTCATTTT | ATGTTTCAGG | TTCAGGGGGA | 180 |
| GGTGTGGGAG | GTTTTTTAAA | GCAAGTAAAA | CCTCTACAAA | TGTGGTATGG | CTGATTATGA | 240 |
| TCCGCCCTGC | AGGGAAGGGC | GGCACTGGGA | AGTGGGCCAG | GGCCAGGGAC | GTGACGTGGT | 300 |
| GTGTGATCCC | CTGTGTGTGT | GTGGCGGCTG | CAGGGCACC | CTTGTGAGAG | GAGGGCTGGG | 360 |
| TTTGTCTGAG | CAGGTCAGCA | TGTGGAGAAG | CTGCCGAGAG | GCTCGTGGGC | CTTGAGGTGC | 420 |
| CGCGTGGGGC | TCGTGGGGGC | CTGTGTCCGA | GGAGTGTTCA | CGTGTGCGAG | GACCTTGCTC | 480 |
| TGGTCTGGGT | GCTGTGCAGT | TCGCCCGGGT | GAGGCTCCGT | GTGTGAGGCG | TGCACGTGTG | 540 |
| TGTGTGGTGG | CCGTGTGGCC | GGCCAACCTC | AGTGCGGGGG | TTTTGTTGAA | CGGGTCTGGA | 600 |
| CTGAGTGTGT | GTGTGGGCAT | CTGCACCAGT | CCCTCCACAG | GGCCCGAGAG | TGCATGTCCC | 660 |
| CGGAGTCGGT | TGTGTCCCCA | TGCGGGTGCG | AGGCTGGGCA | GGACAGCCAG | GGGTTAGTGC | 720 |
| CGTGGGGGTA | GATGGGTGAG | GGAGGGCCTG | TCCCTACGCA | CATGGACTAG | GCATGCCCCC | 780 |
| GAGTGGGCAT | GGAGGTCGGA | GGACAGGGCG | CTCACAGAAC | AGGACAGTCT | CCTACAGAGG | 840 |
| CAGGGGCTGT | GTGTCTGTCC | CCAGGGGCTC | CTAGGGCTTC | CCGTGGCCCA | GCCCAGGGCA | 900 |
| GGTGCTGCTG | GAGGGAGGGC | AACGCTGGCA | AATCCCCCAC | CCTGCCGAGG | GCAGCCCCTG | 960 |
| GCTGAGCCCC | ACCCTAGGCG | GCCCAGGCAC | ACCTGCACAG | CCTGGGCCAG | TGTGGGACA | 1020 |

-continued

| | | | | | | |
|---|---|---|---|---|---|---|
| GTGGGACCCG | CTCTGCCTCC | CTCATGCCAC | TCAGGCCTCA | GACTCGGCCT | GACCCGTGGA | 1080 |
| AAGAACCATC | ACAGTCTCGC | AGGGGCCCAG | GGCAGCGCTG | GGTGCTTTAT | TTCCATGCTG | 1140 |
| GGCGCCCGGG | AAGTATGTAC | AGGGGGTACG | TGCCAAGCAT | CCTCGTGCGA | CCGCGAGAGC | 1200 |
| CCGGGGAGCG | GGGGCTTGCC | GGCCGTCGCA | CTCATTTACC | CGGAGACAGG | GAGAGGCTCT | 1260 |
| TCTGCGTGTA | GTGGTTGTGC | AGAGCCTCAT | GCATCACGGA | GCATGAGAAG | ACGTTCCCCT | 1320 |
| GCTGCCACCT | GCTCTTGTCC | ACGGTGAGCT | TGCTGTAGAG | GAAGAAGGAG | CCGTCGGAGT | 1380 |
| CCAGCACGGG | AGGCGTGGTC | TTGTAGTTGT | TCTCCGGCTG | CCCATTGCTC | TCCCACTCCA | 1440 |
| CGGCGATGTC | GCTGGGATAG | AAGCCTTTGA | CCAGGCAGGT | CAGGCTGACC | TGGTTCTTGG | 1500 |
| TCAGCTCATC | CCGGGATGGG | GGCAGGGTGT | ACACCTGTGG | TTCTCGGGGC | TGCCCTGTAG | 1560 |
| GGACAGAGGT | TGGTACAGCG | GTCACTCTCA | GGGCAGAGGG | TGGGCCGAGC | CGGCCTCTGT | 1620 |
| CCATGTGGCC | CTCGCACCCC | ACGGGTCCCA | CCTTTGGCTT | TGGAGATGGT | TTTCTCGATG | 1680 |
| GGGGCTGGGA | GGGCTTTGTT | GGAGACCTTG | CACTTGTACT | CCTTGCCATT | CAGCCAGTCC | 1740 |
| TGGTGCAGGA | CGGTGAGGAC | GCTGACCACA | CGGTACGTGC | TGTTGTACTG | CTCCTCCCGC | 1800 |
| GGCTTTGTCT | TGGCATTATG | CACCTCCACG | CCGTCCACGT | ACCAGTTGAA | CTTGACCTCA | 1860 |
| GGGTCTTCGT | GGCTCACGTC | CACCACCACG | CATGTGACCT | CAGGGGTCCG | GGAGATCATG | 1920 |
| AGGGTGTCCT | TGGGTTTTGG | GGGGAAGAGG | AAGACTGATG | GTCCTCCCGC | GGCCTCAGGT | 1980 |
| GCTGAGGGAG | AGATGGAGGT | GGACGTGTCA | GCACCCGGCT | GGGGCCTGTC | CCTGGATGCA | 2040 |
| GGCTACTCTA | GGGCACCTGT | CCCGCCTTGA | GCTGGAGGGC | GAGGCCTGGG | CTGGCTTACC | 2100 |
| TGGGCACGGT | GGGCATGTGT | GAGTTTTGTC | ACAAGATTTG | GGCTCTGCAG | AGAGAAGATT | 2160 |
| GGGAGTTACT | CGAATCTGGG | AGGAGAGAAG | GTGTCCGAGC | TGAGGGAGTG | GAGAGTTTGG | 2220 |
| CCTTTGGGGT | GGGCTTAGGT | CAGGGCAGG | GTCCTCCCGG | ATATGGCTCT | TGGCAGGTCT | 2280 |
| GAGCCCAGCA | CCTGCCCCTT | TGTGTGCAGG | GCCTGGGTTA | GGGGCACCTA | GCCTGTGCCT | 2340 |
| GCCCAGAGCC | TGGGGAAAAA | GCCAGAAGAC | CCTCTCCCTG | AGCATGAGTG | GGGCGGGCAG | 2400 |
| AGGCCTCCGG | GTGAAGAGGC | AGACGGGGCC | TGCCTTGCTG | CCCTGGACTG | GGGCTGCATA | 2460 |
| GCCGGGATGC | GTCCAGGCAG | GAGCGCTGAG | CCTGGCTTCC | AGCAGACACC | CTCCCTCCCT | 2520 |
| GTGCTGGCCT | CTCACCAACT | TTCTTGTCCA | CCTTGGTGTT | GCTGGGCTTG | TGATTCACGT | 2580 |
| TGCAGATGTA | GGTCTGGGTG | CCCAAGCTGC | TGGAGGGCAC | GGTCACCACG | CTGCTGAGGG | 2640 |
| AGTAGAGTCC | TGAGGACTGT | AGGACAGCCG | GGAAGGTGTG | CACGCCGCTG | GTCAGGGCGC | 2700 |
| CTGAGTTCCA | CGACACCGTC | ACCGGTTCGG | GGAAGTAGTC | CTTGACCAGG | CAGCCCAGGG | 2760 |
| CCGCTGTGCC | CCCAGAGGTG | CTCTTGGAGG | AGGGTGCCAG | GGGAAGACC | GATGGGCCCT | 2820 |
| TGGTGGAAGC | TGAGCTCACG | ATGACCGTGG | TTCCTTTGCC | CCAGACGTCC | ATATAATAAT | 2880 |
| TGTCCTGGGG | AGAATCATCC | CAACTATATG | GCCCCACTCT | CGCACAATAA | TAAACAGCCG | 2940 |
| TGTCTGCAGA | CCTGAGGCTC | CTCAACTCCA | TGTAGGCTGT | GTTCGCGGAT | GTGTCCGCGG | 3000 |
| TAAAGGTGAC | TCTGTCCTGG | AACTTCGCTG | AAAATTCTTT | GTTTCCGTTG | TAAGGATTGA | 3060 |
| TCCATCCCAT | CCACTCAAAC | CTCTGTCCGG | GGGCCTGGCG | CACCCAATGA | ATAACAAAGT | 3120 |
| TACTGAATCT | GTATCCAGAA | GCCTGACAAG | AAACCTTCAC | TGAGGCCCCA | GGCTTCTTCA | 3180 |
| CCTCAGCCCC | GGACTGAACC | AGCTGAACCT | GGGAGTGGAC | ACCTGTAGTT | ACTGACAGGA | 3240 |
| AGAAGAGAAA | GACCCAGCTC | CATTCCATGG | TGGCGGCGAA | TT | | 3282 |

( 2 ) INFORMATION FOR SEQ ID NO:170:

( i ) SEQUENCE CHARACTERISTICS:

(A) LENGTH: 13254 base pairs
(B) TYPE: nucleic acid
(C) STRANDEDNESS: double
(D) TOPOLOGY: circular (ii) MOLECULE TYPE: DNA (genomic)

(xi) SEQUENCE DESCRIPTION: SEQ ID NO:170:

```
TTCTCTAGAA  TTAACACTCT  CCCCTGTTGA  AGCTCTTTGT  GACGGGCGAT  CTCAGGCCCT    60
GATGGGTGAC  TTCGCAGGCG  TAGACTTTGT  GTTTCTCGTA  GTCTGCTTTG  CTCAGCGTCA   120
GGGTGCTGCT  GAGGCTGTAG  GTGCTGTCCT  TGCTGTCCTG  CTCTGTGACA  CTCTCCTGGG   180
AGTTACCCGA  TTGGAGGGCG  TTATCCACCT  TCCACTGTAC  TTTGGCCTCT  CTGGGATAGA   240
AGTTATTCAG  CAGGCACACA  ACAGAGGCAG  TCCAGATTT   CAACTGCTCA  TCAGATGGCG   300
GGAAGATGAA  GACAGATGGT  GCAGGCACAG  TTCGTTTCCT  CTCCAGTTTG  GTCCCCTGGC   360
CAAAAGTGTA  CGAGGAGGCA  CCATAGACCT  GACAGTAGTA  CAGTGCAAAG  TCTTCAGGCT   420
CCACTCTGGT  GATGGTGAGA  GTGAAGTCTG  TCCCAGACCC  ACTGCCGCTG  AACCTGTCTG   480
AGATGCCAGA  GGCCCTATTG  GAAACACCAT  GTATGACCAG  CCTTGGAGCC  TGGCCAGGTT   540
TGTGCTGGTA  CCAGGCTACG  CGGCGGCTGC  GAATGCTGTG  ACTGGACCTA  CAGGAGAAGG   600
TGGCTCTTTC  CCCTGGAGAC  AGAGACAGGG  TGCCTGGAGA  CTGCGTGAGA  ACGATCTCAC   660
ATCTGGCATC  TGTAAGCCAC  AGCAGCAGCA  ACCCCAGGAC  CTGAGTGGGC  ACACCCATGG   720
TAAGCTTCGT  GTCAAGGACG  GTGACTGCAG  AAAAGACCCA  TGGAAAGGAA  CAGTCTGTTA   780
GTCTGTCAGC  TATTATGTCT  GGTGGCGCGC  GCGGCAGCAA  CGAGTACTGC  TCAGACTACA   840
CTGCCCTCCA  CCGTTAACAG  CACCGCAACG  GGAGTTACCT  CTGACTCTTA  TCAGAACACA   900
ACAACTCAGC  TGCCTGCATC  TTCTTCTGCC  GCTGCCTTAA  GTCTTCCAAA  TGCGTCAGCG   960
GTGCAAGCCC  GCTCCCCGAG  CTCATTTTCA  GACACATACC  CTACCGCCAC  GGCCTTGTGC  1020
GGCACACTGG  TGGTGGTGGG  CATCGTGCTG  TGCCTAAGTC  TGGCCTCCAC  TGTTAGGAGC  1080
AAGGAGCTGC  CGAGCGACCA  TGAGTCGCTG  GAGGCATGGG  AGCAGGGCTC  GGATGTAGAA  1140
GCTCCGCCGC  TACCGGAGAA  GAGCCCATGT  CCGGAACACG  TACCCGAGAT  CGCGTGGAG   1200
ATCCACGTT   ATGTTTAATA  AAAACTGCGG  GCACTGGGGA  CGGTGGTGTT  GTATATGTGA  1260
ATTTGTAAAT  AATAAATGAG  ACCCCATCCT  GTAAAAATAC  AGAGTCCGTG  TCAGTCTCTG  1320
AAGGACAGTG  TATTGGCATA  TAGCCAATAA  AGAGAGTTGT  GGCAAAGAGC  CATGTTATGG  1380
ATTAGTAATG  GAAAGTATCG  TCACCAATAG  GGGAGTGGTC  AATAATGGTC  ATAACCCAC   1440
ACCTATAGGC  TAAGCTATAC  CATCACCTAT  AACATGAGGA  AGCGGGGTG   TATAGACCCC  1500
AAGCCAAAAA  CAGTATAGCA  TGCATAAGAA  GCCAAGGGGG  TGGGCCTATA  GACTCTATAG  1560
GCGGTACTTA  CGTCACTCTT  GGCACGGGGA  ATCCGCGTTC  CAATGCACCG  TTCCCGGCCG  1620
CGGAGGCTGG  ATCGGTCCCG  GTGTCTTCTA  TGGAGGTCAA  AACAGCGTGG  ATGGCGTCTC  1680
CAGGCGATCT  GACGGTTCAC  TAAACGAGCT  CTGCTTATAT  AGACCTCCCA  CCGTACACGC  1740
CTACCGCCCA  TTTGCGTCAA  TGGGGCGGAG  TTGTTACGAC  ATTTTGGAAA  GTCCGTTGA   1800
TTTTGGTGCC  AAAACAAACT  CCCATTGACG  TCAATGGGGT  GGAGACTTGG  AAATCCCCGT  1860
GAGTCAAACC  GCTATCCACG  CCCATTGATG  TACTGCCAAA  ACCGCATCAC  CATGGTAATA  1920
GCGATGACTA  ATACGTAGAT  GTACTGCCAA  GTAGGAAAGT  CCCATAAGGT  CATGTACTGG  1980
GCATAATGCC  AGGCGGGCCA  TTTACCGTCA  TTGACGTCAA  TAGGGGCGT   ACTTGGCATA  2040
TGATACACTT  GATGTACTGC  CAAGTGGGCA  GTTTACCGTA  AATACTCCAC  CCATTGACGT  2100
CAATGGAAAG  TCCCTATTGG  CGTTACTATG  GGAACATACG  TCATTATTGA  CGTCAATGGG  2160
```

```
CGGGGGTCGT  TGGGCGGTCA  GCCAGGCGGG  CCATTTACCG  TAAGTTATGT  AACGCGGAAC     2220

TCCATATATG  GGCTATGAAC  TAATGACCCC  GTAATTGATT  ACTATTAATA  ACTAGTCAAT     2280

AATCAATGTC  AACATGGCGG  TAATGTTGGA  CATGAGCCAA  TATAAATGTA  CATATTATGA     2340

TATGGATACA  ACGTATGCAA  TGGCCAATAG  CCAATATTGA  TTTATGCTAT  ATAACCAATG     2400

AATAATATGG  CTAATGGCCA  ATATTGATTC  AATGTATAGA  TCGATATGCA  TTGGCCATGT     2460

GCCAGCTTGA  TGTCGCCTCT  ATCGGCGATA  TAGCCTCATA  TCGTCTGTCA  CCTATATCGA     2520

AACTGCGATA  TTTGCGACAC  ACAGAATCGC  CCAAGTCACC  AAAGTCGTCT  ATCGCCATCC     2580

CCCGTAAACG  ATATAAGCGC  TATCGCCAGA  TATCGCGTAT  GCCCAAAAAT  CACTTTTGGA     2640

AAAATGGCGA  TATCAGTTAC  ACAGAAACTC  ACATCGGCGA  CATTTTCAAT  ATGCCATATT     2700

TTCAAATATC  GATTTTTCCA  ATATCGCCAT  CTCTATCGGC  GATAAACACC  ACTATCGCGC     2760

GACATGAATT  TAGTCGGCGA  CAGAAATCTC  AAAACGCGTA  TTTCGGACAA  ACACACATTT     2820

TATTATTCAC  TGCAGTCACC  GTCCTTGACA  CGAAGCTAGA  GATCCAGACA  TGATAAGATA     2880

CATTGATGAG  TTTGGACAAA  CCACAACTAG  AATGCAGTGA  AAAAAATGCT  TTATTTGTGA     2940

AATTTGTGAT  GCTATTGCTT  TATTTGTAAC  CATTATAAGC  TGCAATAAAC  AAGTTAACAA     3000

CAACAATTGC  ATTCATTTTA  TGTTTCAGGT  TCAGGGGGAG  GTGTGGGAGG  TTTTTTAAAG     3060

CAAGTAAAAC  CTCTACAAAT  GTGGTATGGC  TGATTATGAT  CTCTAGTCAA  GGCACTATAC     3120

ATCAAATATT  CCTTATTAAC  CCCTTTACAA  ATTAAAAGC   TAAAGGTACA  CAATTTTTGA     3180

GCATAGTTAT  TAATAGCAGA  CACTCTATGC  CTGTGTGGAG  TAAGAAAAA   CAGTATGTTA     3240

TGATTATAAC  TGTTATGCCT  ACTTATAAAG  GTTACAGAAT  ATTTTTCCAT  AATTTTCTTG     3300

TATAGCAGTG  CAGCTTTTTC  CTTTGTGGTG  TAAATAGCAA  AGCAAGCAAG  AGTTCTATTA     3360

CTAAACACAG  CATGACTCAA  AAAACTTAGC  AATTCTGAAG  GAAAGTCCTT  GGGGTCTTCT     3420

ACCTTTCTCT  TCTTTTTTGG  AGGAGTAGAA  TGTTGAGAGT  CAGCAGTAGC  CTCATCATCA     3480

CTAGATGGCA  TTTCTTCTGA  GCAAAACAGG  TTTTCCTCAT  TAAAGGCATT  CCACCACTGC     3540

TCCCATTCAT  CAGTTCCATA  GGTTGGAATC  TAAAATACAC  AAACAATTAG  AATCAGTAGT     3600

TTAACACATT  ATACACTTAA  AAATTTTATA  TTTACCTTAG  AGCTTTAAAT  CTCTGTAGGT     3660

AGTTTGTCCA  ATTATGTCAC  ACCACAGAAG  TAAGGTTCCT  TCACAAAGAT  CTCTCTGGGG     3720

CGGGGTGGGA  TGAACTAGGA  AAGGCTCAAG  ATCACTCAAA  GTCTAATTAG  TTTTTGTATT     3780

GGAAGGGCTC  GTGGCCAGTC  TCATTGAGAA  GGCATGTGCG  GACGATGGCT  TCTGTCACTG     3840

CAAAGGGGTC  ACAATTGGCA  GAGGGCCGC   GGTCTTCAAA  GTAACCTTTC  TTCTCCTGGC     3900

CGACAGTCCG  GGGAATGCGG  ATGCTGGCAC  TGCGATTGGC  GACACCAGCA  GAAAAGTCGT     3960

TGATGTTGGA  CGTTTCGTGG  AACCCAGTCA  GACCACGGGC  ATTGTCCAGG  CCCCCCTTGG     4020

GATCGTAGGC  TCGAATGTGG  TACCGGTGCC  GCTTGCTTAG  TTTCTCGATG  GCCTCCTCGA     4080

TGTGCTTCAG  ACCATTCTCC  TCCCGCATGG  CCTTGGTGCT  AAAGTTGGTA  TGGCAGCCTG     4140

CACCATTCCA  GTTCCCAGGA  ATGGGCTTGG  GGTCAAAGGT  TGCTATTACC  CCAAAGTCTT     4200

CACATACTCG  ATGAAGATGA  AACGGGCCAC  CCAGAGATGA  TCTCCCATGC  GGATTCCTTC     4260

ACAGGGTCCT  ATTTGGAGTT  CCCACTGGGC  AGGCATGACC  TCAGCATTTG  TTCCTGTAAT     4320

CTTGACCCCA  GCATACAAGC  AGGCGCGGTA  GTGAGCCTCC  ACGATATCCC  TGCCATAGGC     4380

TTTGTCTGCG  CCCACACCAC  AGTAATACGG  ACCTTGGGGC  CAGGAAAGC   CATTGGAAGG     4440

CCAACCAAAA  GGGTGCCCAT  CTGTTCCCAT  CAGAGTATAC  TCCTGTTCCA  TTCCAAACCA     4500

GGGGTGCTGG  TTGCTCACCA  TGTCCATTAT  CCGTTTACAC  GAGTGCCTTA  AATTGGTCTC     4560
```

```
TGCAGGCTTC CGGTTGTACT TGAAAACTTC ACAGAACACC AGCTTGTTGG GATCTCTGCG    4620
GAAGGGGTCC CGAAACATGG CAACAGGGCT GAGATACATG TCACTGTTGG AGCCCTCAGA    4680
CTGAAAGGTA CTAGAGCCAT CAAAATTCCA CTCAGGTAAC TCTTCTACAC ACTTGGGCTC    4740
ACAGTCCAGG GTGCGGGTTT TGCAGCGCAG TCCTTCTCCA GTACCATCAA CCCAGATATA    4800
CATGGCTTGG ACTTTCTCAC CCTGGGGCAG GCACAAGTAC ATTTGCTTGA TGTTTTTGTT    4860
CAAGTGGGAA CTTGCTGAGG TGGCCATGGT GGAAGGTGCT CTGAGCGGTG GCCCCAAGCT    4920
AGTTTTTGCA AAAGCCTAGG CCTCCAAAAA AGCCTCCTCA CTACTTCTGG AATAGCTCAG    4980
AGGCCGAGGC GGCCTCGGCC TCTGCATAAA TAAAAAAAT TAGTCAGCCA TGGGGCGGAG    5040
AATGGGCGGA ACTGGGCGGA GTTAGGGGCG GGATGGGCGG AGTTAGGGGC GGGACTATGG    5100
TTGCTGACTA ATTGAGATGC ATGCTTTGCA TACTTCTGCC TGCTGGGGAG CCTGGTTGCT    5160
GACTAATTGA GATGCATGCT TTGCATACTT CTGCCTGCTG GGAGCCTGG GGACTTTCCA    5220
CACCCTAACT GACACACATT CCACAGCCGG ATCTAGCTTG GCTGCCAAAG CCGCAAGGAA    5280
TTTACCAACC TTCTTAAACA TAAAGTGTCT CCTTATAAAC GCAGAAAGGC CCACCCGAAG    5340
GTGAGCCAGT GTGATTACAT TTTCTCTTGA GGGTTGTCCT CGGTGCCACG GAACATTACG    5400
AACGATGGGT GCCGCAAAGA GCCATCAGGG CCTCGTGATA CGCCTATTTT TATAGGTTAA    5460
TGTCATGATA ATAATGGTTT CTTAGACGTC AGGTGGCACT TTTCGGGGAA ATGTGCGCGG    5520
AACCCCTATT TGTTTATTTT CTAAATACA TTCAAATATG TATCCGCTCA TGAGACAATA    5580
ACCCTGATAA ATGCTTCAAT AATATTGAAA AAGGAAGAGT ATGAGTATTC AACATTTCCG    5640
TGTCGCCCTT ATTCCCTTTT TTGCGGCATT TTGCCTTCCT GTTTTGCTC ACCCAGAAAC    5700
GCTGGTGAAA GTAAAAGATG CTGAAGATCA GTTGGGTGCA CGAGTGGGTT ACATCGAACT    5760
GGATCTCAAC AGCGGTAAGA TCCTTGAGAG TTTTCGCCCC GAAGAACGTT TTCCAATGAT    5820
GAGCACTTTT AAAGTTCTGC TATGTGGCGC GGTATTATCC CGTGTTGACG CCGGGCAAGA    5880
GCAACTCGGT CGCCGCATAC ACTATTCTCA GAATGACTTG GTTGAGTACT CACCAGTCAC    5940
AGAAAAGCAT CTTACGGATG GCATGACAGT AAGAGAATTA TGCAGTGCTG CCATAACCAT    6000
GAGTGATAAC ACTGCGGCCA ACTTACTTCT GACAACGATC GGAGGACCGA AGGAGCTAAC    6060
CGCTTTTTTG CACAACATGG GGATCATGT AACTCGCCTT GATCGTTGGG AACCGGAGCT    6120
GAATGAAGCC ATACCAAACG ACGAGCGTGA CACCACGATG CCTGTAGCAA TGGCAACAAC    6180
GTTGCGCAAA CTATTAACTG GCGAACTACT TACTCTAGCT TCCCGGCAAC AATTAATAGA    6240
CTGGATGGAG GCGGATAAAG TTGCAGGACC ACTTCTGCGC TCGGCCCTTC CGGCTGGCTG    6300
GTTTATTGCT GATAAATCTG GAGCCGGTGA GCGTGGGTCT CGCGGTATCA TTGCAGCACT    6360
GGGGCCAGAT GGTAAGCCCT CCCGTATCGT AGTTATCTAC ACGACGGGGA GTCAGGCAAC    6420
TATGGATGAA CGAAATAGAC AGATCGCTGA GATAGGTGCC TCACTGATTA AGCATTGGTA    6480
ACTGTCAGAC CAAGTTTACT CATATATACT TTAGATTGAT TTAAAACTTC ATTTTTAATT    6540
TAAAAGGATC TAGGTGAAGA TCCTTTTTGA TAATCTCATG ACCAAAATCC CTTAACGTGA    6600
GTTTTCGTTC CACTGAGCGT CAGACCCCGT AGAAAAGATC AAAGGATCTT CTTGAGATCC    6660
TTTTTTTCTG CGCGTAATCT GCTGCTTGCA AACAAAAAAA CCACCGCTAC CAGCGGTGGT    6720
TTGTTTGCCG GATCAAGAGC TACCAACTCT TTTTCCGAAG GTAACTGGCT TCAGCAGAGC    6780
GCAGATACCA AATACTGTCC TTCTAGTGTA GCCGTAGTTA GGCCACCACT TCAAGAACTC    6840
TGTAGCACCG CCTACATACC TCGCTCTGCT AATCCTGTTA CCAGTGGCTG CTGCCAGTGG    6900
CGATAAGTCG TGTCTTACCG GGTTGGACTC AAGACGATAG TTACCGGATA AGGCGCAGCG    6960
```

```
GTCGGGCTGA ACGGGGGGTT CGTGCACACA GCCCAGCTTG GAGCGAACGA CCTACACCGA    7020

ACTGAGATAC CTACAGCGTG AGCATTGAGA AAGCGCCACG CTTCCCGAAG GGAGAAAGGC    7080

GGACAGGTAT CCGGTAAGCG GCAGGGTCGG AACAGGAGAG CGCACGAGGG AGCTTCCAGG    7140

GGGAAACGCC TGGTATCTTT ATAGTCCTGT CGGGTTTCGC CACCTCTGAC TTGAGCGTCG    7200

ATTTTTGTGA TGCTCGTCAG GGGGGCGGAG CCTATGGAAA AACGCCAGCA ACGCGGCCCG    7260

AGGTCGACGC TCTCCCTTAT GCGACTCCTG CATTAGGAAG CAGCCCAGTA GTAGGTTGAG    7320

GCCGTTGAGC ACCGCCGCCG CAAGGAATGG TGCATGCAAG GAGATGGCGC CCAACAGTCC    7380

CCCGGCCACG GGCCTGCCAC CATACCCACG CCGAAACAAG CGCTCATGAG CCCGAAGTGG    7440

CGAGCCCGAT CTTCCCCATC GGTGATGTCG GCGATATAGG CGCCAGCAAC CGCACCTGTG    7500

GCGCCGGTGA TGCCGGCCAC GATGCGTCCG GCGTAGAGGA TCTAGACATG ATAAGATACA    7560

TTGATGAGTT TGGACAAACC ACAACTAGAA TGCAGTGAAA AAAATGCTTT ATTTGTGAAA    7620

TTTGTGATGC TATTGCTTTA TTTGTAACCA TTATAAGCTG CAATAAACAA GTTAACAACA    7680

ACAATTGCAT TCATTTTATG TTTCAGGTTC AGGGGGAGGT GTGGGAGGTT TTTTAAAGCA    7740

AGTAAAACCT CTACAAATGT GGTATGGCTG ATTATGATCC GCCCTGCAGG GAAGGGCGGC    7800

ACTGGGAAGT GGGCCAGGGC CAGGGACGTG ACGTGGTGTG TGATCCCCTG TGTGTGTGTG    7860

GCGGCTGCAG GGGCACCCTT GTGAGAGGAG GGCTGGGTTT GTCTGAGCAG GTCAGCATGT    7920

GGAGAAGCTG CCGAGAGGCT CGTGGGCCTT GAGGTGCCGC GTGGGGCTCG TGGGGGCCTG    7980

TGTCCGAGGA GTGTTCACGT GTGCGAGGAC CTTGCTCTGG TCTGGGTGCT GTGCAGTTCG    8040

CCCGGGTGAG GCTCCGTGTG TGAGGCGTGC ACGTGTGTGT GTGGTGGCCG TGTGGCCGGC    8100

CAACCTCAGT GCGGGGGTTT TGTTGAACGG GTCTGGACTG AGTGTGTGTG TGGGCATCTG    8160

CACCAGTCCC TCCACAGGGC CCGAGAGTGC ATGTCCCCGG AGTCGGTTGT GTCCCCATGC    8220

GGGTGCGAGG CTGGGCAGGA CAGCCAGGGG TTAGTGCCGT GGGGGTAGAT GGGTGAGGGA    8280

GGGCCTGTCC CTACGCACAT GGACTAGGCA TGCCCCCGAG TGGGCATGGA GGTCGGAGGA    8340

CAGGGCGCTC ACAGAACAGG ACAGTCTCCT ACAGAGGCAG GGGCTGTGTG TCTGTCCCCA    8400

GGGGCTCCTA GGGCTTCCCG TGGCCCAGCC CAGGGCAGGT GCTGCTGGAG GGAGGGCAAC    8460

GCTGGCAAAT CCCCCACCCT GCCGAGGGCA GCCCTGGCT GAGCCCACC CTAGGCGGCC     8520

CAGGCACACC TGCACAGCCT GGGCCAGTGT GGGGACAGTG GGACCCGCTC TGCCTCCCTC    8580

ATGCCACTCA GGCCTCAGAC TCGGCCTGAC CCGTGGAAAG AACCATCACA GTCTCGCAGG    8640

GGCCCAGGGC AGCGCTGGGT GCTTTATTTC CATGCTGGGC GCCCGGGAAG TATGTACAGG    8700

GGGTACGTGC CAAGCATCCT CGTGCGACCG CGAGAGCCCG GGAGCGGGG GCTTGCCGGC     8760

CGTCGCACTC ATTTACCCGG AGACAGGGAG AGGCTCTTCT GCGTGTAGTG GTTGTGCAGA    8820

GCCTCATGCA TCACGGAGCA TGAGAAGACG TTCCCTGCT GCCACCTGCT CTTGTCCACG     8880

GTGAGCTTGC TGTAGAGGAA GAAGGAGCCG TCGGAGTCCA GCACGGGAGG CGTGGTCTTG    8940

TAGTTGTTCT CCGGCTGCCC ATTGCTCTCC CACTCCACGG CGATGTCGCT GGGATAGAAG    9000

CCTTTGACCA GGCAGGTCAG GCTGACCTGG TTCTTGGTCA GCTCATCCCG GGATGGGGC     9060

AGGGTGTACA CCTGTGGTTC TCGGGGCTGC CCTGTAGGGA CAGAGGTTGG TACAGCGGTC    9120

ACTCTCAGGG CAGAGGGTGG GCCGAGCCGG CCTCTGTCCA TGTGGCCCTC GCACCCCACG    9180

GGTCCCACCT TTGGCTTTGG AGATGGTTTT CTCGATGGGG GCTGGGAGGG CTTTGTTGGA    9240

GACCTTGCAC TTGTACTCCT TGCCATTCAG CCAGTCCTGG TGCAGGACGG TGAGGACGCT    9300

GACCACACGG TACGTGCTGT TGTACTGCTC CTCCCGCGGC TTTGTCTTGG CATTATGCAC    9360
```

```
CTCCACGCCG  TCCACGTACC  AGTTGAACTT  GACCTCAGGG  TCTTCGTGGC  TCACGTCCAC   9420
CACCACGCAT  GTGACCTCAG  GGGTCCGGGA  GATCATGAGG  GTGTCCTTGG  GTTTTGGGGG   9480
GAAGAGGAAG  ACTGATGGTC  CTCCCGCGGC  CTCAGGTGCT  GAGGGAGAGA  TGGAGGTGGA   9540
CGTGTCAGCA  CCCGGCTGGG  GCCTGTCCCT  GGATGCAGGC  TACTCTAGGG  CACCTGTCCC   9600
GCCTTGAGCT  GGAGGGCGAG  GCCTGGGCTG  GCTTACCTGG  GCACGGTGGG  CATGTGTGAG   9660
TTTTGTCACA  AGATTTGGGC  TCTGCAGAGA  GAAGATTGGG  AGTTACTCGA  ATCTGGGAGG   9720
AGAGAAGGTG  TCCGAGCTGA  GGGAGTGGAG  AGTTTGGCCT  TTGGGGTGGG  CTTAGGTCAG   9780
GGGCAGGGTC  CTCCCGGATA  TGGCTCTTGG  CAGGTCTGAG  CCCAGCACCT  GCCCCTTTGT   9840
GTGCAGGGCC  TGGGTTAGGG  GCACCTAGCC  TGTGCCTGCC  CAGAGCCTGG  GGAAAAAGCC   9900
AGAAGACCCT  CTCCCTGAGC  ATGAGTGGGG  CGGGCAGAGG  CCTCCGGGTG  AAGAGGCAGA   9960
CGGGGCCTGC  CTTGCTGCCC  TGGACTGGGG  CTGCATAGCC  GGGATGCGTC  CAGGCAGGAG  10020
CGCTGAGCCT  GGCTTCCAGC  AGACACCCTC  CCTCCCTGTG  CTGGCCTCTC  ACCAACTTTC  10080
TTGTCCACCT  TGGTGTTGCT  GGGCTTGTGA  TTCACGTTGC  AGATGTAGGT  CTGGGTGCCC  10140
AAGCTGCTGG  AGGGCACGGT  CACCACGCTG  CTGAGGGAGT  AGAGTCCTGA  GGACTGTAGG  10200
ACAGCCGGGA  AGGTGTGCAC  GCCGCTGGTC  AGGGCGCCTG  AGTTCCACGA  CACCGTCACC  10260
GGTTCGGGGA  AGTAGTCCTT  GACCAGGCAG  CCCAGGGCCG  CTGTGCCCCC  AGAGGTGCTC  10320
TTGGAGGAGG  GTGCCAGGGG  GAAGACCGAT  GGGCCCTTGG  TGGAAGCTGA  GCTCACGATG  10380
ACCGTGGTTC  CTTTGCCCCA  GACGTCCATA  TAATAATTGT  CCTGGGGAGA  ATCATCCCAA  10440
CTATATGGCC  CCACTCTCGC  ACAATAATAA  ACAGCCGTGT  CTGCAGACCT  GAGGCTCCTC  10500
AACTCCATGT  AGGCTGTGTT  CGCGGATGTG  TCCGCGGTAA  AGGTGACTCT  GTCCTGGAAC  10560
TTCGCTGAAA  ATTCTTTGTT  TCCGTTGTAA  GGATTGATCC  ATCCATCCA  CTCAAACCTC  10620
TGTCCGGGGG  CCTGGCGCAC  CCAATGAATA  ACAAAGTTAC  TGAATCTGTA  TCCAGAAGCC  10680
TGACAAGAAA  CCTTCACTGA  GGCCCCAGGC  TTCTTCACCT  CAGCCCCGGA  CTGAACCAGC  10740
TGAACCTGGG  AGTGGACACC  TGTAGTTACT  GACAGGAAGA  AGAGAAAGAC  CCAGCTCCAT  10800
TCCATGGTGG  CGGCGAATTC  GAGCTCGCCC  GGGGATCGAT  CCTCTAGAGT  CGATCGACCT  10860
GCAGCCCAAG  CTTCGTGTCA  AGGACGGTGA  CTGCAGAAAA  GACCCATGGA  AAGGAACAGT  10920
CTGTTAGTCT  GTCAGCTATT  ATGTCTGGTG  GCGCGCGCGG  CAGCAACGAG  TACTGCTCAG  10980
ACTACACTGC  CCTCCACCGT  TAACAGCACC  GCAACGGGAG  TTACCTCTGA  CTCTTATCAG  11040
AACACAACAA  CTCAGCTGCC  TGCATCTTCT  TCTGCCGCTG  CCTTAAGTCT  TCCAAATGCG  11100
TCAGCGGTGC  AAGCCCGCTC  CCCGAGCTCA  TTTTCAGACA  CATACCCTAC  CGCCACGGCC  11160
TTGTGCGGCA  CACTGGTGGT  GGTGGGCATC  GTGCTGTGCC  TAAGTCTGGC  CTCCACTGTT  11220
AGGAGCAAGG  AGCTGCCGAG  CGACCATGAG  TCGCTGGAGG  CATGGGAGCA  GGGCTCGGAT  11280
GTAGAAGCTC  CGCCGCTACC  GGAGAAGAGC  CCATGTCCGG  AACACGTACC  CGAGATTCGC  11340
GTGGAGATCC  CACGTTATGT  TTAATAAAAA  CTGCGGGCAC  TGGGACGGT  GGTGTTGTAT  11400
ATGTGAATTT  GTAAATAATA  AATGAGACCC  CATCCTGTAA  AAATACAGAG  TCCGTGTCAG  11460
TCTCTGAAGG  ACAGTGTATT  GGCATATAGC  CAATAAAGAG  AGTTGTGGCA  AAGAGCCATG  11520
TTATGGATTA  GTAATGGAAA  GTATCGTCAC  CAATAGGGGA  GTGGTCAATA  ATGGTCAATA  11580
ACCCACACCT  ATAGGCTAAG  CTATACCATC  ACCTATAACA  TGAGGAAGCG  GGGGTGTATA  11640
GACCCCAAGC  CAAAAACAGT  ATAGCATGCA  TAAGAAGCCA  AGGGGGTGGG  CCTATAGACT  11700
CTATAGGCGG  TACTTACGTC  ACTCTTGGCA  CGGGGAATCC  GCGTTCCAAT  GCACCGTTCC  11760
```

-continued

| | | | | | | |
|---|---|---|---|---|---|---|
| CGGCCGCGGA | GGCTGGATCG | GTCCCGGTGT | CTTCTATGGA | GGTCAAAACA | GCGTGGATGG | 11820 |
| CGTCTCCAGG | CGATCTGACG | GTTCACTAAA | CGAGCTCTGC | TTATATAGAC | CTCCCACCGT | 11880 |
| ACACGCCTAC | CGCCCATTTG | CGTCAATGGG | GCGGAGTTGT | TACGACATTT | TGGAAAGTCC | 11940 |
| CGTTGATTTT | GGTGCCAAAA | CAAACTCCCA | TTGACGTCAA | TGGGGTGGAG | ACTTGGAAAT | 12000 |
| CCCCGTGAGT | CAAACCGCTA | TCCACGCCCA | TTGATGTACT | GCCAAAACCG | CATCACCATG | 12060 |
| GTAATAGCGA | TGACTAATAC | GTAGATGTAC | TGCCAAGTAG | GAAAGTCCCA | TAAGGTCATG | 12120 |
| TACTGGGCAT | AATGCCAGGC | GGGCCATTTA | CCGTCATTGA | CGTCAATAGG | GGGCGTACTT | 12180 |
| GGCATATGAT | ACACTTGATG | TACTGCCAAG | TGGGCAGTTT | ACCGTAAATA | CTCCACCCAT | 12240 |
| TGACGTCAAT | GGAAAGTCCC | TATTGGCGTT | ACTATGGGAA | CATACGTCAT | TATTGACGTC | 12300 |
| AATGGGCGGG | GGTCGTTGGG | CGGTCAGCCA | GGCGGGCCAT | TTACCGTAAG | TTATGTAACG | 12360 |
| CGGAACTCCA | TATATGGGCT | ATGAACTAAT | GACCCCGTAA | TTGATTACTA | TTAATAACTA | 12420 |
| GTCAATAATC | AATGTCAACA | TGGCGGTAAT | GTTGGACATG | AGCCAATATA | AATGTACATA | 12480 |
| TTATGATATG | GATACAACGT | ATGCAATGGC | CAATAGCCAA | TATTGATTTA | TGCTATATAA | 12540 |
| CCAATGAATA | ATATGGCTAA | TGGCCAATAT | TGATTCAATG | TATAGATCGA | TATGCATTGG | 12600 |
| CCATGTGCCA | GCTTGATGTC | GCCTCTATCG | GCGATATAGC | CTCATATCGT | CTGTCACCTA | 12660 |
| TATCGAAACT | GCGATATTTG | CGACACACAG | AATCGCCCAA | GTCACCAAAG | TCGTCTATCG | 12720 |
| CCATCCCCCG | TAAACGATAT | AAGCGCTATC | GCCAGATATC | GCGTATGCCC | AAAAATCACT | 12780 |
| TTTGGAAAAA | TGGCGATATC | AGTTACACAG | AAACTCACAT | CGGCGACATT | TTCAATATGC | 12840 |
| CATATTTTCA | AATATCGATT | TTTCCAATAT | CGCCATCTCT | ATCGGCGATA | AACACCACTA | 12900 |
| TCGCGCGACA | TGAATTTAGT | CGGCGACAGA | AATCTCAAAA | CGCGTATTTC | GGACAAACAC | 12960 |
| ACATTTTATT | ATTCACTGCA | GTCACCGTCC | TTGACACGAA | GCTAGAGATC | CAGACATGAT | 13020 |
| AAGATACATT | GATGAGTTTG | GACAAACCAC | AACTAGAATG | CAGTGAAAAA | AATGCTTTAT | 13080 |
| TTGTGAAATT | TGTGATGCTA | TTGCTTTATT | TGTAACCATT | ATAAGCTGCA | ATAAACAAGT | 13140 |
| TAACAACAAC | AATTGCATTC | ATTTTATGTT | TCAGGTTCAG | GGGGAGGTGT | GGGAGGTTTT | 13200 |
| TTAAAGCAAG | TAAAACCTCT | ACAATGTGG | TATGGCTGAT | TAATGATCAA | TGAA | 13254 |

What is claimed is:

1. A polynucleotide encoding a heavy chain immunoglobulin variable region amino acid residue sequence portion of a human monoclonal antibody capable of immunoreacting with human immunodeficiency virus (HIV) glycoprotein gp120 and neutralizing HIV, wherein the amino acid sequence is SEQ ID NO:66.

2. The polynucleotide of claim 1 wherein said polynucleotide is a deoxyribonucleotide.

3. A polynucleotide encoding a light chain immunoglobulin variable region amino acid residue sequence portion of a human monoclonal antibody capable of immunoreacting with human immunodeficiency virus (HIV) glycoprotein gp120 and neutralizing HIV, wherein the amino acid sequence is SEQ ID NO:97.

4. The polynucleotide of claim 3 wherein said polynucleotide is a deoxyribonucleotide.

5. A DNA expression vector comprising the polynucleotide of claim 1 or claim 3.

6. A DNA expression vector comprising the polynucleotides of claim 1 and claim 3.

7. The DNA expression vector of claim 6 wherein said monoclonal antibody has a heavy and light chain immunoglobulin variable region amino acid residue sequence as shown in the pair of SEQ ID NOs 66:97.

8. A host cell comprising the DNA expression vector of claim 5.

* * * * *

UNITED STATES PATENT AND TRADEMARK OFFICE
CERTIFICATE OF CORRECTION

PATENT NO. : 5,804,440
DATED : September 8, 1998
INVENTOR(S) : Burton, et al.

It is certified that error appears in the above-identified patent and that said Letters Patent is hereby corrected as shown below:

In Column 1, line 5, insert:

--This invention was made with government support under Contract Nos. AI 33292, AI 27242, AI 35168 and AI 22541 by the National Institutes of Health. The government has certain rights in the invention.--

Signed and Sealed this

Twentieth Day of April, 1999

*Attest:*

Q. TODD DICKINSON

*Attesting Officer*   *Acting Commissioner of Patents and Trademarks*